US012630864B2

(12) United States Patent
Stahl et al.

(10) Patent No.: US 12,630,864 B2
(45) **Date of Patent: *May 19, 2026**

(54) METHODS OF NUCLEIC ACID SAMPLE PREPARATION

(71) Applicant: Laboratory Corporation of America Holdings, Burlington, NC (US)

(72) Inventors: Joshua Stahl, Boulder, CO (US); Jason Myers, Boulder, CO (US); Brady Culver, Aliso Viejo, CA (US); Brian Kudlow, Boulder, CO (US); Jens Eberlein, Boulder, CO (US)

(73) Assignee: Laboratory Corporation of America Holdings, Burlington, NC (US)

( * ) Notice: Subject to any disclaimer, the term of this patent is extended or adjusted under 35 U.S.C. 154(b) by 1038 days.

This patent is subject to a terminal disclaimer.

(21) Appl. No.: 17/746,191

(22) Filed: May 17, 2022

(65) Prior Publication Data

US 2022/0282305 A1 Sep. 8, 2022

Related U.S. Application Data

(63) Continuation-in-part of application No. 17/177,740, filed on Feb. 17, 2021, now abandoned, and a continuation-in-part of application No. 16/919,238, filed on Jul. 2, 2020, now Pat. No. 11,795,492, and a continuation-in-part of application No. 16/804,695, filed on Feb. 28, 2020, now Pat. No. 11,390,905, said application No. 17/177,740 is a continuation of application No. 15/802,408, filed on Nov. 2, 2017, now Pat. No. 10,947,582, said application No. 16/804,695 is a continuation of application No. 15/706,649, filed on Sep. 15, 2017, now Pat. No. 10,683,531, said application No. 16/919,238 is a continuation of application No. 15/706,642, filed on Sep. 15, 2017, now Pat. No. 10,704,082.

(60) Provisional application No. 62/416,677, filed on Nov. 2, 2016, provisional application No. 62/395,339, filed on Sep. 15, 2016, provisional application No. 62/395,347, filed on Sep. 15, 2016.

(51) Int. Cl.

| | |
|---|---|
| ***C12Q 1/68*** | (2018.01) |
| ***A61P 35/02*** | (2006.01) |
| ***C07K 16/28*** | (2006.01) |
| ***C12N 15/09*** | (2006.01) |
| ***C12Q 1/6806*** | (2018.01) |
| ***C12Q 1/6813*** | (2018.01) |
| *C07D 495/04* | (2006.01) |
| *C12Q 1/6869* | (2018.01) |

(52) U.S. Cl.

CPC ............ *C12Q 1/6813* (2013.01); *A61P 35/02* (2018.01); *C07K 16/2809* (2013.01); *C12N 15/09* (2013.01); *C12Q 1/6806* (2013.01); *C07D 495/04* (2013.01); *C07K 2319/32* (2013.01); *C12Q 1/6869* (2013.01)

(58) Field of Classification Search

CPC ........................................................ C12Q 1/68

See application file for complete search history.

(56) References Cited

U.S. PATENT DOCUMENTS

| | | | | |
|---|---|---|---|---|
| 4,868,104 | A | 9/1989 | Kurn et al. | |
| 5,157,032 | A | 10/1992 | Barton | |
| 5,374,524 | A | 12/1994 | Miller | |
| 5,565,340 | A | 10/1996 | Chenchik et al. | |
| 5,604,098 | A | 2/1997 | Mead et al. | |
| 5,824,518 | A | 10/1998 | Kacian et al. | |
| 5,827,658 | A * | 10/1998 | Liang | C12Q 1/6809 435/6.14 |
| 5,861,251 | A | 1/1999 | Park et al. | |
| 6,063,566 | A | 5/2000 | Joyce | |
| 6,087,101 | A | 7/2000 | Gruelich et al. | |
| 6,172,214 | B1 | 1/2001 | Brenner | |
| 6,197,554 | B1 | 3/2001 | Lin et al. | |
| 6,225,062 | B1 | 5/2001 | Dunn et al. | |
| 6,576,448 | B2 | 6/2003 | Weissman et al. | |
| 6,632,611 | B2 | 10/2003 | Su et al. | |
| 6,818,395 | B1 | 11/2004 | Quake et al. | |
| 6,833,246 | B2 | 12/2004 | Balasubramanian | |
| 6,911,345 | B2 | 6/2005 | Quake et al. | |
| 7,169,560 | B2 | 1/2007 | Lapidus et al. | |
| 7,214,490 | B2 | 5/2007 | Su et al. | |

(Continued)

FOREIGN PATENT DOCUMENTS

| | | |
|---|---|---|
| AU | 2005203617 A1 | 9/2005 |
| CN | 101270395 A | 9/2008 |

(Continued)

OTHER PUBLICATIONS

Forshew et al., 2012. Noninvasive identification and monitoring of cancer mutations by targeted deep sequencing of plasma DNA. Science translational medicine, 4(136), 36ra68, pp. 1-14. (Year: 2012).*

(Continued)

*Primary Examiner* — Gary Benzion
*Assistant Examiner* — Olayinka A Oyeyemi
(74) *Attorney, Agent, or Firm* — Wolf, Greenfield & Sacks, P.C.

(57) ABSTRACT

Aspects of the technology disclosed herein relate to methods of preparing and analyzing nucleic acids, e.g., cfDNA, and nucleic acids encoding immune receptors and immunoglobulins. In some embodiments, methods for preparing nucleic acids for sequence analysis (e.g., using next-generation sequencing) are provided herein.

20 Claims, 56 Drawing Sheets

Specification includes a Sequence Listing.

(56) References Cited

U.S. PATENT DOCUMENTS 7,220,549 B2 5/2007 Buzby
7,226,720 B2 6/2007 Wisnudel et al.
7,244,559 B2 7/2007 Rothberg et al.
7,273,730 B2 9/2007 Du Breuil Lastrucci
7,279,563 B2 10/2007 Kwiatkowski
7,282,337 B1 10/2007 Harris
7,741,463 B2 6/2010 Gromley et al.
7,824,856 B2 11/2010 Monforte
7,972,820 B2 7/2011 Mayer
8,067,434 B2 11/2011 Ibrahim et al.
9,074,204 B2 7/2015 Anderson et al.
9,297,014 B2 3/2016 Grabherr et al.
9,487,828 B2 11/2016 Iafrate et al.
9,546,399 B2 1/2017 Amorese et al.
9,650,628 B2 5/2017 Amorese et al.
10,017,810 B2 7/2018 Iafrate et al.
10,036,012 B2 7/2018 Amorese et al.
10,450,597 B2 10/2019 Iafrate et al.
10,570,448 B2 2/2020 Amorese et al.
10,683,531 B2 * 6/2020 Stahl .................... C12Q 1/6806
10,704,082 B2 * 7/2020 Stahl .................... C12Q 1/6855
10,718,009 B2 7/2020 Iafrate et al.
10,870,847 B2 12/2020 Finn et al.
10,876,108 B2 12/2020 Amorese et al.
10,947,582 B2 * 3/2021 Myers ................ C07K 16/2809
11,098,357 B2 8/2021 Amorese et al.
11,390,905 B2 * 7/2022 Stahl .................... C12Q 1/6853
11,725,241 B2 8/2023 Amorese et al.
11,781,179 B2 10/2023 Iafrate et al.
11,795,492 B2 * 10/2023 Stahl .................... C12Q 1/6806
11,807,897 B2 11/2023 Iafrate et al.
2002/0061532 A1 5/2002 Adams et al.
2002/0086317 A1 7/2002 Nagayama
2003/0022318 A1 1/2003 Lin et al.
2003/0104432 A1 6/2003 Xu et al.
2003/0143553 A1 7/2003 Sommer
2004/0053260 A1 3/2004 Gut et al.
2004/0058373 A1 3/2004 Winkler et al.
2004/0096853 A1 5/2004 Mayer
2004/0161792 A1 8/2004 Liao et al.
2005/0142577 A1 6/2005 Jones et al.
2005/0164226 A1 7/2005 Huang
2006/0252077 A1 11/2006 Buzby
2006/0257856 A1 11/2006 Kang et al.
2007/0070349 A1 3/2007 Harris et al.
2007/0172824 A1 7/2007 Chun
2007/0259348 A1 11/2007 Phadke et al.
2008/0021205 A1 1/2008 Blau et al.
2008/0300142 A1 12/2008 Getts et al.
2009/0011959 A1 1/2009 Costa et al.
2009/0093378 A1 * 4/2009 Bignell .............. C12N 15/1093 506/23
2009/0127589 A1 5/2009 Rothberg et al.
2009/0131275 A1 5/2009 Shimamoto et al.
2009/0203085 A1 8/2009 Kurn et al.
2010/0248310 A1 9/2010 Morley
2010/0279305 A1 11/2010 Kuersten
2010/0286143 A1 11/2010 Dias-Santagata et al.
2011/0104785 A1 5/2011 Vaidyanathan et al.
2011/0201507 A1 * 8/2011 Rava ...................... G16H 10/40 506/37
2011/0201598 A1 8/2011 Gujral et al.
2011/0224105 A1 9/2011 Kurn et al.
2011/0269631 A1 11/2011 Fu et al.
2011/0269647 A1 11/2011 Ule et al.
2011/0288780 A1 11/2011 Rabinowitz et al.
2012/0021460 A1 1/2012 Lowe et al.
2012/0071331 A1 3/2012 Casbon et al.
2012/0122701 A1 5/2012 Ryan et al.
2012/0220494 A1 8/2012 Samuels et al.
2012/0270212 A1 10/2012 Rabinowitz et al.
2012/0283145 A1 11/2012 Wang
2012/0309002 A1 12/2012 Link
2013/0005585 A1 1/2013 Anderson et al.
2013/0017960 A1 1/2013 Honisch et al.
2013/0040825 A1 * 2/2013 Queimado ........... C12Q 1/6853 506/9
2013/0231253 A1 9/2013 Amorese et al.
2013/0303461 A1 * 11/2013 Iafrate .................. C12Q 1/6806 514/183
2014/0227705 A1 8/2014 Vogelstein et al.
2015/0011396 A1 1/2015 Schroeder et al.
2015/0140553 A1 5/2015 Cushing et al.
2015/0211050 A1 * 7/2015 Iafrate ................ C12Q 1/6806 506/2
2015/0211061 A1 7/2015 Iafrate et al.
2015/0252361 A1 * 9/2015 Hayden ................ C12Q 1/6806 506/4
2015/0291953 A1 10/2015 Finn et al.
2015/0337364 A1 11/2015 Stahl et al.
2017/0037459 A1 2/2017 Godwin
2018/0127806 A1 * 5/2018 Stahl .................. C12N 15/1013
2018/0127807 A1 * 5/2018 Stahl .................... C12Q 1/6806
2018/0155767 A1 * 6/2018 Myers .................. C12Q 1/6806
2019/0078084 A1 3/2019 Finn et al.
2021/0017571 A1 * 1/2021 Stahl .................. C12N 15/1096
2021/0054435 A1 * 2/2021 Stahl .................... C12Q 1/6806
2021/0071171 A1 3/2021 Amorese et al.
2021/0171942 A1 6/2021 Finn et al.
2021/0180118 A1 6/2021 Stahl et al.
2022/0282305 A1 * 9/2022 Stahl ....................... C40B 50/08

FOREIGN PATENT DOCUMENTS

CN 104603287 A 5/2015
CN 104946737 A 9/2015
CN 105189748 A 12/2015
CN 105339507 A 2/2016
EP 356021 A2 2/1990
GB 2466379 A 6/2010
JP H04-500759 A 2/1992
JP 2001-333800 A 12/2001
JP 2002-537817 A 11/2002
JP 2005-245297 A 9/2005
JP 2015-517307 A 6/2015
WO WO 91/01384 A1 2/1991
WO WO 96/24664 A1 8/1996
WO WO 97/23646 A1 7/1997
WO WO 97/23647 A1 7/1997
WO WO 98/28443 A1 7/1998
WO WO 99/42618 A1 8/1999
WO WO 00/43543 A1 7/2000
WO WO 00/43544 A1 7/2000
WO WO 00/70095 A2 11/2000
WO WO 01/12859 A2 2/2001
WO WO 01/20035 A2 3/2001
WO WO 01/83696 A2 11/2001
WO WO 02/00938 A2 1/2002
WO WO 02/29117 A2 4/2002
WO WO 02/48402 A2 6/2002
WO WO 02/072772 A2 9/2002
WO WO 03/078645 A2 9/2003
WO WO 03/083435 A2 10/2003
WO WO 2004/011665 A2 2/2004
WO WO 2004/079326 A2 9/2004
WO WO 2004/092418 A2 10/2004
WO WO 2005/065321 A2 7/2005
WO WO 2006/034833 A1 4/2006
WO WO 2007/030759 A2 3/2007
WO WO 2007/057652 A1 5/2007
WO WO 2007/129778 A1 11/2007
WO WO 2007/136717 A1 11/2007
WO WO 2008/005459 A2 1/2008
WO WO 2008/093098 A2 8/2008
WO WO 2009/032167 A1 3/2009
WO WO 2009/102878 A2 8/2009
WO WO 2009/102896 A2 8/2009
WO WO 2009/117698 A2 9/2009
WO WO 2009/133466 A2 11/2009
WO WO 2009/148617 A2 12/2009
WO WO 2010/077288 A2 7/2010
WO WO 2010/083046 A2 7/2010
WO WO 2011/014811 A1 2/2011

(56) References Cited

FOREIGN PATENT DOCUMENTS

| | | | | |
|---|---|---|---|---|
| WO | WO 2011/019964 A1 | | 2/2011 | |
| WO | WO 2011/032053 A1 | | 3/2011 | |
| WO | WO 2011/053987 A1 | | 5/2011 | |
| WO | WO 2011/141754 A1 | | 11/2011 | |
| WO | WO 2011/156529 A2 | | 12/2011 | |
| WO | WO 2012/003374 A2 | | 1/2012 | |
| WO | WO 2012/024658 A2 | | 2/2012 | |
| WO | WO 2012/040387 A1 | | 3/2012 | |
| WO | WO 2012/044956 A1 | | 4/2012 | |
| WO | WO 2012/054873 A2 | | 4/2012 | |
| WO | WO 2012/064739 A2 | | 5/2012 | |
| WO | WO 2012/103154 A1 | | 8/2012 | |
| WO | WO 2012/166425 A2 | | 12/2012 | |
| WO | WO 2013/059746 A1 | | 4/2013 | |
| WO | WO 2013/074833 A1 | | 5/2013 | |
| WO | WO 2013/112923 A1 | | 8/2013 | |
| WO | WO 2013/122826 A1 | | 8/2013 | |
| WO | WO 2013/123442 A1 | | 8/2013 | |
| WO | WO 2013/169339 A1 | | 11/2013 | |
| WO | WO-2013177220 A1 | * | 11/2013 | .......... B01J 19/0046 |
| WO | WO 2013/191775 A2 | | 12/2013 | |
| WO | WO 2014/008447 A1 | | 1/2014 | |
| WO | WO 2014/047678 A1 | | 4/2014 | |
| WO | WO 2014/138385 A1 | | 9/2014 | |
| WO | WO 2014/144092 A1 | | 9/2014 | |
| WO | WO 2014/144495 A1 | | 9/2014 | |
| WO | WO 2014/150931 A1 | | 9/2014 | |
| WO | WO 2015/073711 A1 | | 5/2015 | |
| WO | WO 2015/089496 A1 | | 6/2015 | |
| WO | WO-2015112974 A1 | * | 7/2015 | ........... C12Q 1/6806 |
| WO | WO 2015/200334 A1 | | 12/2015 | |
| WO | WO 2016/044227 A1 | | 3/2016 | |
| WO | WO 2016/138500 A1 | | 9/2016 | |
| WO | WO 2017/177308 A1 | | 10/2017 | |
| WO | WO 2018/053365 A1 | | 3/2018 | |
| WO | WO-2018053362 A1 | * | 3/2018 | ........... C12Q 1/6855 |
| WO | WO-2018085599 A2 | * | 5/2018 | .............. A61P 35/02 |

OTHER PUBLICATIONS

Frenel et al., 2015. Serial next-generation sequencing of circulating cell-free DNA evaluating tumor clone response to molecularly targeted drug administration. Clinical Cancer Research, 21(20), pp. 4586-4596. (Year: 2015).*

Murtaza et al., 2013. Non-invasive analysis of acquired resistance to cancer therapy by sequencing of plasma DNA. Nature, 497(7447), pp. 108-112. (Year: 2013).*

Ruggiero, 2015. High-resolution analysis of the human T-cell receptor repertoire. Nature communications, 6(1), 8081, pp. 1-7. (Year : 2015).*

Stahlberg, et al., Epub Apr. 7, 2016. Simple, multiplexed, PCR-based barcoding of DNA enables sensitive mutation detection in liquid biopsies using sequencing. Nucleic acids research, 44(11), e105, pp. 1-7. (Year: 2016).*

Sterling et al., 2015. An efficient and sensitive method for preparing cDNA libraries from scarce biological samples. Nucleic acids research, 43(1), e1, pp. 1-19. (Year: 2015).*

Extended European Search Report for Application No. 17851671.2, mailed Apr. 6, 2020.

Extended European Search Report for Application No. EP 21193343.7, mailed Oct. 14, 2021.

International Search Report and Written Opinion for Application No. PCT/US2017/051924, mailed Dec. 11, 2017.

International Preliminary Report on Patentability for Application No. PCT/US2017/051924, mailed Mar. 28, 2019.

Extended European Search Report for Application No. 17851672.0, mailed May 13, 2020.

International Search Report and Written Opinion for Application No. PCT/US2017/051927, mailed Dec. 1, 2017.

International Preliminary Report on Patentability for Application No. PCT/US2017/051927, mailed Mar. 28, 2019.

Extended European Search Report for Application No. EP 17868046.8, mailed Jun. 15, 2020.

Extended European Search Report for Application No. 22209186.0, mailed Mar. 14, 2023.

International Search Report and Written Opinion for Application No. PCT/US2017/059804, mailed Apr. 24, 2018.

International Preliminary Report on Patentability for Application No. PCT/US2017/059804, mailed May 16, 2019.

Partial Supplementary European Search Report for Application No. EP 15739782.9, mailed Aug. 30, 2017.

Extended European Search Report for Application No. EP 15739782.9, mailed Dec. 12, 2017.

International Search Report and Written Opinion for Application No. PCT/US2015/012842 mailed May 18, 2015.

International Search Report and Written Opinion for Application No. PCT/US2013/068277 mailed Jan. 30, 2014.

International Preliminary Report on Patentability for Application No. PCT/US2013/068277 mailed May 14, 2015.

[No Author Listed], 16S Metagenomic Sequencing Library Preparation. Illumina. 2013. 28 pages.

[No Author Listed], APAgene™ GOLD-RT Genome Walking Kits. Bio S&T Inc. Sep. 2010. 14 pages.

[No Author Listed], Genomic Sequencing. Illumina. Jan. 2009. 6 pages.

[No Author Listed], Getting Started Guide Applied Biosystems 3130/3130x/Genetic Analyzers. Applied Biosystems. 2004. 196 pages.

[No Author Listed], High-Speed, Multiplexed 16S Amplicon Sequencing on the MiSeq® System. Illumina. 2013. 4 pages.

[No Author Listed], Illumina Sequencing Technology. Illumina. 2010. 5 pages.

[No Author Listed], Multiplexing Sample Preparation Guide. Illumina. Feb. 2010. 35 pages.

[No Author Listed], TruSeq™ RNA and DNA Library Preparation Kits v2. Illumina. 2011. 4 pages.

Akeno-Stuart et al., The RET kinase inhibitor NVP-AST487 blocks growth and calcitonin gene expression through distinct mechanisms in medullary thyroid cancer cells. Cancer Res. Jul. 15, 2007;67(14):6956-64.

Ali et al., Sequence analysis of TnphoA insertion sites in Vibrio cholerae mutants defective in rugose polysaccharide production. Infect Immun. Dec. 2000;68(12):6857-64.

Amsterdam et al., Retroviral-mediated Insertional Mutagenesis in Zebrafish. Methods Cell Biol. 2011;104:59-82. doi: 10.1016/B978-0-12-374814-0.00004-5. PMID: 21924157; PMCID: PMC3373308.

Baetens et al., Applying massive parallel sequencing to molecular diagnosis of Marfan and Loeys-Dietz syndromes. Hum Mutat. Sep. 2011;32(9):1053-62. doi: 10.1002/humu.21525. Epub Jul. 20, 2011.

Bentley, Whole-genome re-sequencing. Curr Opin Genet Dev. Dec. 2006;16(6):545-52. Epub Oct. 18, 2006.

Boers et al., High-throughput multilocus sequence typing: bringing molecular typing to the next level. PLoS One. 2012;7(7):e39630. doi:10.1371/journal.pone.0039630.

Bohmer et al., (2009). Novel application for isothermal nucleic acid sequence-based amplification (NASBA). Journal of Virological Methods 158 (1-2): 199-201. doi:10.1016/j.jviromet.2009.02.010. PMID 19428591.

Borodina et al., A strand-specific library preparation protocol for RNA sequencing. Methods Enzymol. 2011:500:79-98. doi: 10.1016/B978-0-12-385118-5.00005-0.

Bowman et al., Multiplexed Illumina sequencing libraries from picogram quantities of DNA. BMC Genomics. Jul. 9, 2013;14:466. doi: 10.1186/1471-2164-14-466.

Bronner et al., Improved Protocols for Illumina Sequencing. Curr Protoc Hum Genet. Author manuscript; available in PMC Dec. 4, 2013. Published in final edited form as: Curr Protoc Hum Genet. Jul. 2009; 0 18: 10.1002/0471142905.hg1802s62. doi: 10.1002/0471142905.hg1802s62. Author manuscript, 46 pages.

Callaway et al., A Sobemovirus coat protein gene complements long-distance movement of a coat protein-null Dianthovirus. Virology. Dec. 5, 2004;330(1):186-95. doi: 10.1016/j.virol.2004.09.037.

Carlomagno et al., BAY 43-9006 inhibition of oncogenic RET mutants. J Natl Cancer Inst. Mar. 1, 2006;98(5):326-34.

(56) References Cited

OTHER PUBLICATIONS

Chadwick et al., Comparison of three RNA amplification methods as sources of DNA for sequencing. Biotechniques. Nov. 1998;25(5):818-20, 822. doi: 10.2144/98255st02.
Chang et al., Identification of a biomarker panel using a multiplex proximity ligation assay improves accuracy of pancreatic cancer diagnosis. J Transl Med. Dec. 11, 2009;7:105. doi: 10.1186/1479-5876-7-105.
Chen et al., Allele-specific copy number profiling by next-generation DNA sequencing. Nucleic Acids Res. Feb. 27, 2015;43(4):e23. doi: 10.1093/nar/gku1252. Epub Dec. 3, 2014.
Chenchik et al., Full-length cDNA cloning and determination of mRNA 5' and 3' ends by amplification of adaptor-ligated cDNA. Biotechniques. Sep. 1996;21(3):526-34.
Chiarle et al., Genome-wide translocation sequencing reveals mechanisms of chromosome breaks and rearrangements in B cells. Cell. Sep. 30, 2011;147(1):107-19. doi: 10.1016/j.cell.2011.07.049. Erratum in: Cell. Dec. 23, 2011;147(7):1640. PMID: 21962511; PMCID: PMC3186939.
Compton, Nucleic acid sequence-based amplification. Nature. 1991;350 (6313): 91-2. doi:10.1038/350091a0. PMID 1706072.
Cornish-Bowden, Nomenclature for incompletely specified bases in nucleic acid sequences: recommendations 1984. Nucleic Acids Res. May 10, 1985;13(9):3021-30. doi: 10.1093/nar/13.9.3021. PMID: 2582368; PMCID: PMC341218.
Craig et al., Identification of genetic variants using bar-coded multiplexed sequencing. Nat Methods. Oct. 2008;5(10):887-93. doi: 10.1038/nmeth.1251. Epub Sep. 14, 2008. PMID: 18794863; PMCID: PMC3171277.
Cuccuru et al., Cellular effects and antitumor activity of RET inhibitor RPI-1 on MEN2A-associated medullary thyroid carcinoma. J Natl Cancer Inst. Jul. 7, 2004;96(13):1006-14.
Cushing et al., RVD: a command-line program for ultrasensitive rare single nucleotide variant detection using targeted next-generation DNA resequencing. BMC Res Notes. May 23, 2013;6:206. doi:10.1186/1756-0500-6-206.
Dafforn et al., Linear mRNA amplification from as little as 5 ng total RNA for global gene expression analysis. Biotechniques. Nov. 2004;37(5):854-7.
Dahl et al., Multigene amplification and massively parallel sequencing for cancer mutation discovery. Proc Natl Acad Sci U S A. May 29, 2007;104(22):9387-92. Epub May 17, 2007.
D'Amore et al., A comprehensive benchmarking study of protocols and sequencing platforms for 16S rRNA community profiling. BMC Genomics. Jan. 14, 2016;17:55. doi: 10.1186/s12864-015-2194-9.
Das et al., Full-length cDNAs: more than just reaching the ends. Physiol Genomics. Jul. 17, 2001;6(2):57-80.
Deiman et al., Characteristics and applications of nucleic acid sequence-based amplification (NASBA). Mol Biotechnol. Feb. 2002;20(2):163-79. doi: 10.1385/MB:20:2:163. PMID: 11876473.
Fadrosh et al., An improved dual-indexing approach for multiplexed 16S rRNA gene sequencing on the Illumina MiSeq platform. Microbiome. 2014;2(1):6. Published Feb. 24, 2014. doi:10.1186/2049-2618-2-6.
Fang et al., Quantitative T cell repertoire analysis by deep cDNA sequencing of T cell receptor α and β chains using next-generation sequencing (NGS). Oncoimmunology. Jan. 7, 2015;3(12):e968467. doi: 10.4161/21624011.2014.968467. PMID: 25964866; PMCID: PMC4368121.
Flaherty et al., Ultrasensitive detection of rare mutations using next-generation targeted resequencing. Nucleic Acids Res. Jan. 2012;40(1):e2. doi: 10.1093/nar/gkr861. Epub Oct. 19, 2011.
Fraiture et al., An innovative and integrated approach based on DNA walking to identify unauthorised GMOs. Food Chem. Mar. 15, 2014;147:60-9. doi: 10.1016/j.foodchem.2013.09.112. Epub Sep. 29, 2013. PMID: 24206686.
Fredriksson et al., Multiplex amplification of all coding sequences within 10 cancer genes by Gene-Collector. Nucleic Acids Res. 2007;35(7):e47. Epub Feb. 22, 2007.
Fredriksson et al., Multiplexed protein detection by proximity ligation for cancer biomarker validation. Nat Methods. Apr. 2007;4(4):327-9. Epub Mar. 18, 2007.
Freier et al., Improved free-energy parameters for predictions of RNA duplex stability. Proc Natl Acad Sci U S A. Dec. 1986; 83(24): 9373-9377. doi: 10.1073/pnas.83.24.9373.
Frohman et al., Rapid production of full-length cDNAs from rare transcripts: amplification using a single gene-specific oligonucleotide primer. Proc Natl Acad Sci U S A. Dec. 1988;85(23):8998-9002. doi: 10.1073/pnas.85.23.8998.
Fu et al., Molecular indexing enables quantitative targeted RNA sequencing and reveals poor efficiencies in standard library preparations. Proc Natl Acad Sci U S A. Feb. 4, 2014;111(5):1891-6. doi: 10.1073/pnas.1323732111. Epub Jan. 21, 2014.
Galkin et al., Identification of NVP-TAE684, a potent, selective, and efficacious inhibitor of NPM-ALK. Proc Natl Acad Sci U S A. Jan. 2, 2007;104(1):270-5. Epub Dec. 21, 2006. Erratum in: Proc Natl Acad Sci U S A. Feb. 6, 2007;104(6):2025.
Ganova-Raeva et al., Primer Extension Enrichment Reaction (PEER): a new subtraction method for identification of genetic differences between biological specimens. Nucleic Acids Res. Jun. 21, 2006;34(11):e76. doi: 10.1093/nar/gk1391. Erratum in: Nucleic Acids Res. 2007;35(10):3517.
Gazzola et al., The evolution of clonality testing in the diagnosis and monitoring of hematological malignancies [published correction appears in Ther Adv Hematol. Oct. 2014;5(5):181]. Ther Adv Hematol. 2014;5(2):35-47. doi:10.1177/2040620713519729.
Gillet et al., The host genomic environment of the provirus determines the abundance of HTLV-1-infected T-cell clones. Blood. Mar. 17, 2011;117(11):3113-22. doi: 10.1182/blood-2010-10-312926. Epub Jan. 12, 2011.
Gould et al., Analysis of sequence variation among smeDEF multi drug efflux pump genes and flanking DNA from defined 16S rRNA subgroups of clinical Stenotrophomonas maltophilia isolates. J Antimicrob Chemother. Aug. 2004;54(2):348-53. doi: 10.1093/jac/dkh367. Epub Jul. 14, 2004.
Grace et al., Degradable dUMP outer primers in merged tandem (M/T)-nested PCR: low- and single-copy DNA target amplification. Anal Biochem. Oct. 1, 1998;263(1):85-92.
Grazma et al., Activity of novel RET inhibitors against RET genotypes associated with medullary thyroid cancer. J Clin Oncol. 2010;28:15s:5559. Epub Sep. 22, 2016. doi: 10/1200/jco.1010.28.15_suppl.5559.
Green et al., Hierarchy in somatic mutations arising during genomic evolution and progression of follicular lymphoma. Blood. Feb. 28, 2013;121(9):1604-11. doi: 10.1182/blood-2012-09-457283. Epub Jan. 7, 2013.
Grimes et al., MendeLIMS: a web-based laboratory information management system for clinical genome sequencing. BMC Bioinformatics. Aug. 27, 2014;15:290. doi: 10.1186/1471-2105-15-290.
Grothues et al., PCR amplification of megabase DNA with tagged random primers (T-PCR). Nucleic Acids Res. Mar. 11, 1993;21(5):1321-2. doi: 10.1093/nar/21.5.1321.
Guled et al., Array comparative genomic hybridization analysis of olfactory neuroblastoma. Mod Pathol. Jun. 2008;21(6):770-8. doi: 10.1038/modpathol.2008.57. Epub Apr. 11, 2008.
Hallberg et al., ALK and NSCLC: Targeted therapy with ALK Inhibitors. F1000 Med Reports 2011;3:21. Epub Nov. 1, 2011. doi: 10.3410/M3-21. 9 pages.
Harrison et al., Polymer-stimulated ligation: enhanced ligation of oligo- and polynucleotides by T4 RNA ligase in polymer solutions. Nucleic Acids Res. Nov. 12, 1984;12(21):8235-51. doi: 10.1093/nar/12.21.8235.
Head et al., Method for improved Illumina sequencing library preparation using NuGEN Ovation RNA-Seq System. Biotechniques. Mar. 2011;50(3):177-80. doi:10.2144/000113613.
Hoeijmakers et al., Linear amplification for deep sequencing. Nat Protoc. Jun. 23, 2011;6(7):1026-36. doi: 10.1038/nprot.2011.345.
Hoon et al., Aptamer selection by high-throughput sequencing and informatic analysis. Biotechniques. Dec. 2011;51(6):413-6. doi: 10.2144/000113786.

(56) References Cited

OTHER PUBLICATIONS

Hopmans et al., A programmable method for massively parallel targeted sequencing. Nucleic Acids Res. Jun. 2014;42(10):e88. doi: 10.1093/nar/gku282. Epub Apr. 29, 2014.
Hou et al., High-Throughput Sequencing-Based Immune Repertoire Study during Infectious Disease. Front Immunol. Aug. 31, 2016;7:336. doi: 10.3389/fimmu.2016.00336.
Iskow et al., Natural mutagenesis of human genomes by endogenous retrotransposons. Cell. Jun. 25, 2010;141(7):1253-61. doi: 10.1016/j.cell.2010.05.020. PMID: 20603005; PMCID: PMC2943760.
Islam et al., Highly multiplexed and strand-specific single-cell RNA 5' end sequencing. Nat Protoc. Apr. 5, 2012;7(5):813-28. doi: 10.1038/nprot.2012.022.
Ji et al., Data quality in genomics and microarrays. Nat Biotechnol. Sep. 2006;24(9):1112-3.
Ji et al., Identification of a novel deletion mutant strain in *Saccharomyces cerevisiae* that results in a microsatellite instability phenotype. Biodiscovery. Jul. 23, 2012;(1). Author manuscript, 14 pages.
Ji et al., Molecular inversion probe analysis of gene copy alterations reveals distinct categories of colorectal carcinoma. Cancer Res. Aug. 15, 2006;66(16):7910-9.
Ji et al., Molecular inversion probe assay for allelic quantitation. Methods Mol Biol. 2009;556:67-87. doi: 10.1007/978-1-60327-192-9_6.
Ji, Improving bioinformatic pipelines for exome variant calling. Genome Med. Jan. 30, 2012;4(1):7. doi: 10.1186/gm306.
Kim et al., Genetic-based biomarkers and next-generation sequencing: the future of personalized care in colorectal cancer. Per Med. May 1, 2011;8(3):331-345.
Kinde et al., Detection and quantification of rare mutations with massively parallel sequencing. Proc Natl Acad Sci U S A. Jun. 7, 2011;108(23):9530-5. doi: 10.1073/pnas.1105422108.
Kircher et al., Double indexing overcomes inaccuracies in multiplex sequencing on the Illumina platform. Nucleic Acids Res. Jan. 2012;40(1):e3. doi: 10.1093/nar/gkr771. Epub Oct. 21, 2011. PMID: 22021376; PMCID: PMC3245947.
Kohno et al., KIF5B-RET fusions in lung adenocarcinoma. Nat Med. Feb. 12, 2012;18(3):375-7. doi: 10.1038/nm.2644. Author manuscript, 7 pages.
Kurn et al., Novel isothermal linear nucleic acid amplification systems for highly multiplexed applications. Clin Chem. Oct. 2005;51(10):1973-81.
Lam et al., Performance comparison of whole-genome sequencing platforms. Nat Biotechnol. Dec. 18, 2011;30(1):78-82. doi: 10.1038/nbt.2065. Erratum in: Nat Biotechnol. Jun. 2012;30(6):562.
Lamant et al., A new fusion gene TPM3-ALK in anaplastic large cell lymphoma created by a (1;2)(q25;p23) translocation. Blood. May 1, 1999;93(9):3088-95.
Lee et al., Systematic genomic identification of colorectal cancer genes delineating advanced from early clinical stage and metastasis. BMC Med Genomics. Dec. 5, 2013;6:54. doi: 10.1186/1755-8794-6-54.
Lennon et al., A scalable, fully automated process for construction of sequence-ready barcoded libraries for 454. Genome Biology. Feb. 2010;11:R15.
Leoni et al., Genome walking in eukaryotes. FEBS J. Nov. 2011;278(21):3953-77. doi: 10.1111/j.1742-4658.2011.08307.x. Epub Sep. 15, 2011. PMID: 21848672.
Li et al., Determination of tag density required for digital transcriptome analysis: application to an androgen-sensitive prostate cancer model. Proc Natl Acad Sci U S A. Dec. 23, 2008;105(51):20179-84. doi: 10.1073/pnas.0807121105. Epub Dec. 16, 2008.
Lin et al., Reproducibility Probability Score—incorporating measurement variability across laboratories for gene selection. Nat Biotechnol. Dec. 2006;24(12):1476-7.
Lishanski et al., Branch migration inhibition in PCR-amplified DNA: homogeneous mutation detection. Nucleic Acids Res. May 1, 2000;28(9):E42.
Liu et al., Comparison of next-generation sequencing systems. J Biomed Biotechnol. 2012;2012:251364. doi: 10.1155/2012/251364. Epub Jul. 5, 2012. PMID: 22829749; PMCID: PMC3398667.
Liu et al., High-efficiency thermal asymmetric interlaced PCR for amplification of unknown flanking sequences. Biotechniques. Nov. 2007;43(5):649-50, 652, 654 passim. doi: 10.2144/000112601.
Liu et al., Systematic Comparative Evaluation of Methods for Investigating the TCRβ Repertoire. PLoS One. 2016; 11(3): e0152464. EPub Mar. 28, 2016. doi: 10.1371/journal.pone.0152464. 18 pages.
Lovci et al., RNA-seq analysis of gene expression and alternative splicing by double-random priming strategy. Methods Mol Biol. 2011;729:247-55. doi: 10.1007/978-1-61779-065-2_16. Author Manuscript, 9 pages.
MAQC Consortium, The MicroArray Quality Control (MAQC) project shows inter- and intraplatform reproducibility of gene expression measurements. Nat Biotechnol. Sep. 2006;24(9):1151-61.
Mardis, The impact of next-generation sequencing technology on genetics. Trends Genet. Mar. 2008;24(3):133-41. doi: 10.1016/j.tig.2007.12.007. Epub Feb. 11, 2008.
Martin-Harris et al., Gene walking using sequential hybrid primer polymerase chain reaction. Anal Biochem. Apr. 15, 2010;399(2):308-10. doi: 10.1016/j.ab.2010.01.005. Epub Jan. 13, 2010. PMID: 20074545.
Mccarty et al., Mu-seq: sequence-based mapping and identification of transposon induced mutations. PLoS One. Oct. 23, 2013;8(10):e77172. doi: 10.1371/journal.pone.0077172. PMID: 24194867; PMCID: PMC3806735.
Metzker, Emerging technologies in DNA sequencing. Genome Res. Dec. 2005;15(12):1767-76. doi: 10.1101/gr.3770505. PMID: 16339375.
Metzker, Sequencing technologies—the next generation. Nat Rev Genet. Jan. 2010;11(1):31-46. doi: 10.1038/nrg2626. Epub Dec. 8, 2009. PMID: 19997069.
Meuzelaar et al., MegaPlex PCR: a strategy for multiplex amplification. Nat Methods. Oct. 2007;4(10):835-7. doi: 10.1038/nmeth1091. Epub Sep. 16, 2007. PMID: 17873887.
Miotke et al., High sensitivity detection and quantitation of DNA copy number and single nucleotide variants with single color droplet digital PCR. Anal Chem. Mar. 4, 2014;86(5):2618-24. doi: 10.1021/ac403843j. Epub Feb. 12, 2014. Erratum in: Anal Chem. May 6, 2014;86(9):4635. Anal Chem. Mar. 3, 2015;87(5):3114.
Miyoshi et al., Molecular crowding effects on structure and stability of DNA. Biochimie. 2008;90(7):1040-1051. doi:10.1016/j.biochi.2008.02.009.
Mologni et al., Inhibition of RET tyrosine kinase by SU5416. J Mol Endocrinol. Oct. 2006;37(2):199-212.
Mologni, Development of RET kinase inhibitors for targeted cancer therapy. Curr Med Chem. 2011;18(2):162-75.
Mugasa et al., (2009). Nucleic acid sequence-based amplification with oligochromatography for detection of Trypanosoma brucei in clinical samples. Journal of clinical microbiology 47 (3): 630-5. doi:10.1128/JCM.01430-08. PMC 2650916. PMID 19116352.
Muralidharan et al., A cross-sample statistical model for SNP detection in short-read sequencing data. Nucleic Acids Res. Jan. 2012;40(1):e5. doi: 10.1093/nar/gkr851. Epub Nov. 7, 2011.
Mussolin et al., Plasma Cell-Free DNA in Paediatric Lymphomas. J Cancer. 2013; 4(4): 323-329. EPub Apr. 16, 2013. doi: 10.7150/jca.6226.
Myll Ykangas et al., [Novel high-throughput sequencing strategies in genetic diagnostics]. Duodecim. 2013;129(2):141-8. Review. Finnish.
Myll Ykangas et al., Classification of human cancers based on DNA copy number amplification modeling. BMC Med Genomics. May 14, 2008;1:15. doi: 10.1186/1755-8794-1-15.
Myll Ykangas et al., DNA copy number amplification profiling of human neoplasms. Oncogene. Nov. 23, 2006;25(55):7324-32. Epub Jun. 5, 2006.
Myll Ykangas et al., Efficient targeted resequencing of human germline and cancer genomes by oligonucleotide-selective sequencing. Nat Biotechnol. Oct. 23, 2011;29(11):1024-7. doi: 10.1038/nbt.1996. Supplemental Information included.

(56) References Cited

OTHER PUBLICATIONS

Myll Ykangas et al., Integrated gene copy number and expression microarray analysis of gastric cancer highlights potential target genes. Int J Cancer. Aug. 15, 2008;123(4):817-25. doi: 10.1002/ijc.23574.
Myll Ykangas et al., Manifestation mechanisms and mysteries of gene amplifications. Cancer Lett. Jan. 28, 2006;232(1):79-89. Epub Nov. 8, 2005.
Myll Ykangas et al., Specificity selection and significance of gene amplifications in cancer. Semin Cancer Biol. Feb. 2007;17(1):42-55. Epub Oct. 26, 2006.
Myll Ykangas et al., Targeted deep resequencing of the human cancer genome using next-generation technologies. Biotechnol Genet Eng Rev. 2010;27:135-58.
Myll Ykangas et al., Targeted sequencing library preparation by genomic DNA circularization. BMC Biotechnol. Dec. 14, 2011;11:122. doi: 10.1186/1472-6750-11-122.
Nadauld et al., Quantitative and Sensitive Detection of Cancer Genome Amplifications from Formalin Fixed Paraffin Embedded Tumors with Droplet Digital PCR. Transl Med (Sunnyvale). 2012;2(2).
Natsoulis et al., A flexible approach for highly multiplexed candidate gene targeted resequencing. PLoS One. 2011;6(6):e21088. doi:10.1371/journal.pone.0021088. Epub Jun. 30, 2011.
Natsoulis et al., Identification of Insertion Deletion Mutations from Deep Targeted Resequencing. J Data Mining Genomics Proteomics. Jul. 2, 2013;4(3).
Newburger et al., The Human OligoGenome Resource: a database of oligonucleotide capture probes for resequencing target regions across the human genome. Nucleic Acids Res. Jan. 2012;40(Database issue):D1137-43. doi: 10.1093/nar/gkr973. Epub Nov. 18, 2011.
Newton et al., Analysis of any point mutation in DNA. The amplification refractory mutation system (ARMS). Nucleic Acids Res. Apr. 11, 1989;17(7):2503-16. doi: 10.1093/nar/17.7.2503. PMID: 2785681; PMCID: PMC317639.
Nyrén et al., Solid phase DNA minisequencing by an enzymatic luminometric inorganic pyrophosphate detection assay. Anal Biochem. Jan. 1993;208(1):171-5.
Ortlepp et al., Performing nucleic acid reactions using predispensed lyophilized reaction mixtures. Biotechniques. Nov.-Dec. 1989;7(10):1110-5. PMID: 2560929.
Patton et al., Development Of Room Temperature Stable Library Construction Kits For Next Generation Sequencing. Poster Associated With Product Information For The Spark DNA Sample Prep Kit Illumina Platform, Enzymatics, Inc. May 6, 2013. Retrieved on Dec. 17, 2013 from http://www.enzymatics.com/product_spk0001-v08.htm.
Quail et al., A tale of three next generation sequencing platforms: comparison of Ion Torrent, Pacific Biosciences and Illumina MiSeq sequencers. BMC Genomics. Jul. 24, 2012;13:341. doi: 10.1186/1471-2164-13-341. PMID: 22827831; PMCID: PMC3431227.
Rikova et al., Global survey of phosphotyrosine signaling identifies oncogenic kinases in lung cancer. Cell. Dec. 14, 2007;131(6):1190-203.
Ritchey et al., Structure-seq2: sensitive and accurate genome-wide profiling of RNA structure in vivo. Nucleic Acids Res. Aug. 21, 2017;45(14):e135. doi: 10.1093/nar/gkx533.
Rothberg et al., An integrated semiconductor device enabling non-optical genome sequencing. Nature. Jul. 20, 2011;475(7356):348-52. doi: 10.1038/nature10242. Supplementary Information included, 25 pages.
Ruggiero et al., High-resolution analysis of the human T-cell receptor repertoire. Nat Commun. Sep. 1, 2015;6:8081. doi: 10.1038/ncomms9081.
Ruggiero et al., High-resolution analysis of the human T-cell receptor repertoire. Nat Commun. 2015;6(Suppl Info). Published Sep. 1, 2015. doi:10.1038/ncomms9081.
Rumsby, An introduction to PCR techniques. Methods Mol Biol. 2006;324:75-89.
Sakamoto et al., CH5424802, a selective ALK inhibitor capable of blocking the resistant gatekeeper mutant. Cancer Cell. May 17, 2011;19(5):679-90. doi: 10.1016/j.ccr.2011.04.004.
Samadi et al., A novel RET inhibitor with potent efficacy against medullary thyroid cancer in vivo. Surgery. Dec. 2010;148(6):1228-36; discussion 1236. doi: 10.1016/j.surg.2010.09.026. Author manuscript, 14 pages.
Scheinin et al., CanGEM: mining gene copy number changes in cancer. Nucleic Acids Res. Jan. 2008;36(Database issue):D830-5. Epub Oct. 11, 2007.
Schiffman et al., Molecular inversion probes reveal patterns of 9p21 deletion and copy number aberrations in childhood leukemia. Cancer Genet Cytogenet. Aug. 2009;193(1):9-18. doi: 10.1016/j.cancergencyto.2009.03.005.
Schiffman et al., Oncogenic BRAF mutation with CDKN2A inactivation is characteristic of a subset of pediatric malignant astrocytomas. Cancer Res. Jan. 15, 2010;70(2):512-9. doi:10.1158/0008-5472.CAN-09-1851. Epub Jan. 12, 2010.
Shapero et al., MARA: a novel approach for highly multiplexed locus-specific SNP genotyping using high-density DNA oligonucleotide arrays. Nucleic Acids Res. Dec. 15, 2004;32(22):e181. doi: 10.1093/nar/gnh178.
Shendure et al., Next-generation DNA sequencing. Nat Biotechnol. Oct. 2008;26(10):1135-45. doi: 10.1038/nbt1486.
Siebert et al., An improved PCR method for walking in uncloned genomic DNA. Nucleic Acids Res. Mar. 25, 1995;23(6):1087-8. doi: 10.1093/nar/23.6.1087. PMID: 7731798; PMCID: PMC306810.
Singh et al., Microarray-based comparison of three amplification methods for nanogram amounts of total RNA. Am J Physiol Cell Physiol. May 2005;288(5):C1179-89.
Sinkkonen et al., Serial analysis of gene expression in the chicken otocyst. J Assoc Res Otolaryngol. Dec. 2011;12(6):697-710. doi: 10.1007/s10162-011-0286-z. Epub Aug. 19, 2011.
Skerra, Phosphorothioate primers improve the amplification of DNA sequences by DNA polymerases with proofreading activity. Nucleic Acids Res. Jul. 25, 1992;20(14):3551-4. doi: 10.1093/nar/20.14.3551. PMID: 1641322; PMCID: PMC334000.
Soda et al., Identification of the transforming EML4-ALK fusion gene in non-small-cell lung cancer. Nature. Aug. 2, 2007;448(7153):561-6. Epub Jul. 11, 2007.
Song et al., Elimination of Ligation Dependent Artifacts in T4 RNA Ligase to Achieve High Efficiency and Low Bias MicroRNA Capture. PLoS One. 2014; 9(4): e94619. EPub Apr. 10, 2014. doi: 10.1371/journal.pone.0094619.
Sooknanan et al., Detection and direct sequence identification of BCR-ABL mRNA in Ph+ chronic myeloid leukemia. Exp Hematol. Dec. 1993;21(13):1719-24.
Strausberg et al., Emerging DNA sequencing technologies for human genomic medicine. Drug Discov Today. Jul. 2008;13(13-14):569-77. doi: 10.1016/j.drudis.2008.03.025. Epub May 22, 2008.
Su et al., Next-generation sequencing and its applications in molecular diagnostics. Expert Rev Mol Diagn. Apr. 2011;11(3):333-43. doi: 10.1586/erm.11.3.
Tong et al., Genome-scale identification of conditionally essential genes in *E. coli* by DNA microarrays. Biochem Biophys Res Commun. Sep. 10, 2004;322(1):347-54.
Tucker et al., Massively parallel sequencing: the next big thing in genetic medicine. Am J Hum Genet. Aug. 2009;85(2):142-54. doi: 10.1016/j.ajhg.2009.06.022.
Turchaninova et al., High-quality full-length immunoglobulin profiling with unique molecular barcoding. Nat Protoc. Sep. 2016;11(9):1599-616. doi: 10.1038/nprot.2016.093. Epub Aug. 4, 2016.
Turner et al., Gene expression profiling of RNA extracted from FFPE tissues: NuGEN technologies' whole-transcriptome amplification system. Methods Mol Biol. 2011;724:269-80. doi: 10.1007/978-1-61779-055-3_17.
Van Berkum et al., Hi-C: A Method to Study the Three-dimensional Architecture of Genomes. J Vis Exp. 2010; (39):e1869. EPub May 6, 2010. doi: 10.3791/1869. Author Manuscript.

(56) References Cited

OTHER PUBLICATIONS

Verbeek et al., The Effects of Four Different Tyrosine Kinase Inhibitors on Medullary and Papillary Thyroid Cancer Cells. The Journal of Clinical Endocrinology & Metabolism. Jun. 2011;96(6):E991-5.
Wang et al., Efficient genome-wide mutagenesis of zebrafish genes by retroviral insertions. Proc Natl Acad Sci U S A. Jul. 24, 2007;104(30):12428-33. doi: 10.1073/pnas.0705502104. Epub Jul. 18, 2007. PMID: 17640903; PMCID: PMC1924792.
Wang et al., Fusion primer and nested integrated PCR (FPNI-PCR): a new high-efficiency strategy for rapid chromosome walking or flanking sequence cloning. BMC Biotechnology. Nov. 2011;11:109.
Wu et al., Transcription start regions in the human genome are favored targets for MLV integration. Science. Jun. 13, 2003;300(5626):1749-51. doi: 10.1126/science.1083413. PMID: 12805549. Supporting Online Material included.
Xiao et al., Sequential amplification of flanking sequences by Y-shaped adaptor dependent extension using multiple templates. Journal of Plant Physiology and Molecular Biology. Feb. 2007;33(1):85-90. Abstract.
Yates et al., Quantitative detection of hepatitis B virus DNA by real-time nucleic acid sequence-based amplification with molecular beacon detection. J Clin Microbiol. Oct. 2001;39(10):3656-65. doi: 10.1128/JCM.39.10.3656-3665.2001. PMID: 11574587; PMCID: PMC88403.
Ying, Complementary DNA libraries: an overview. Mol Biotechnol. Jul. 2004;27(3):245-52.
Yuanxin et al., T-linker-specific ligation PCR (T-linker PCR): an advanced PCR technique for chromosome walking or for isolation of tagged DNA ends. Nucleic Acids Research. Jun. 2003;31(12):e68.
Zhang et al., Detecting simultaneous changepoints in multiple sequences. Biometrika. Sep. 2010;97(3):631-645. Epub Jun. 16, 2010.
Zhang et al., Titration-free 454 sequencing using Y adapters. Nature Protocols (2011) 6(9): 1367-1376.
Zhang et al., The impact of next-generation sequencing on genomics. J Genet Genomics. Mar. 20, 2011;38(3):95-109. doi: 10.1016/j.jgg.2011.02.003. Epub Mar. 15, 2011. Author Manuscript, 27 pages.
Zheng et al., Anchored multiplex PCR for targeted next-generation sequencing. Nat Med. Dec. 2014;20(12):1479-84. doi: 10.1038/nm.3729. Epub Nov. 10, 2014.
Zou et al., An orally available small-molecule inhibitor of c-Met, PF-2341066, exhibits cytoreductive antitumor efficacy through antiproliferative and antiangiogenic mechanisms. Cancer Res. May 1, 2007;67(9):4408-17.
U.S. Appl. No. 18/478,870, filed Sep. 29, 2023, Johnson et al.
EP 17851671.2, Apr. 6, 2020, Extended European Search Report.
EP 21193343.7, Oct. 14, 2021, Extended European Search Report.
PCT/US2017/051924, Dec. 11, 2017, International Search Report and Written Opinion.
PCT/US2017/051924, Mar. 28, 2019, International Preliminary Report on Patentability.
EP 17851672.0, May 13, 2020, Extended European Search Report.
PCT/US2017/051927, Dec. 1, 2017, International Search Report and Written Opinion.
PCT/US2017/051927, Mar. 28, 2019, International Preliminary Report on Patentability.
EP 17868046.8, Jun. 15, 2020, Extended European Search Report.
EP 22209186.0, Mar. 14, 2023, Extended European Search Report.
PCT/US2017/059804, Apr. 24, 2018, International Search Report and Written Opinion.
PCT/US2017/059804, May 16, 2019, International Preliminary Report on Patentability.
EP 15739782.9, Aug. 30, 2017, Partial Supplementary European Search Report.
EP 15739782.9, Dec. 12, 2017, Extended European Search Report.
PCT/US2015/012842, May 18, 2015, International Search Report and Written Opinion.
PCT/US2013/068277, Jan. 30, 2014, International Search Report and Written Opinion.
PCT/US2013/068277, May 14, 2015, International Preliminary Report on Patentability.

* cited by examiner

Top to bottom:
SEQ ID NO: 119
SEQ ID NO: 120
SEQ ID NO: 121
SEQ ID NO: 122

Top to bottom:
SEQ ID NO: 124
SEQ ID NO: 124

| | Std Ampure® | Hi Ampure® |
|---|---|---|
| Mean Unique Coverage Depth Over Variant Position | 647.3 | 693.2 |
| Mean Variant Observations | 6.3 | 7.3 |

25 ng 100 ng 200 ng

SEQUENCE LISTING

<160> NUMBER OF SEQ ID NOS: 124

<210> SEQ ID NO 1
<211> LENGTH: 91
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (71)..(78)
<223> OTHER INFORMATION: n is a, c, g, or t
<220> FEATURE:
<221> NAME/KEY: misc_feature
<222> LOCATION: (90)..(91)
<223> OTHER INFORMATION: may be linked via phosphorothioate

<400> SEQUENCE: 1
aatgatacgg cgaccaccga gatctacaca tccgtacaca ctctttccct acacgacgct 60
cttccgatct nnnnnnnnaa ccgccaggag t 91

<210> SEQ ID NO 2
<211> LENGTH: 13
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (13)..(13)

<400> SEQUENCE: 2
ctcctggcgg ttt 13

<210> SEQ ID NO 3
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 3
aatgatacgg cgaccaccga gatcta 26

<210> SEQ ID NO 4
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 4
atgatacggc gaccaccgag atctacac 28

<210> SEQ ID NO 5
<211> LENGTH: 61
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (41)..(48)
<223> OTHER INFORMATION: n is a, c, g, or t
<220> FEATURE:
<221> NAME/KEY: misc_feature
<222> LOCATION: (60)..(61)
<223> OTHER INFORMATION: may be linked via phosphorothioate

<400> SEQUENCE: 5
ccatctcatc cctgcgtgtc tccgactcag ctaaggtaac nnnnnnnngc tcttccgatc 60
t 61

<210> SEQ ID NO 6
<211> LENGTH: 13
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (13)..(13)

<400> SEQUENCE: 6
gatcggaaga gct 13

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
ccatctcatc cctgcgtgtc 20

<210> SEQ ID NO 8
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 8
ccatctcatc cctgcgtgtc tccgactcag 30

<210> SEQ ID NO 9
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 9
atggccagcg 10

<210> SEQ ID NO 10
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 10
aggaattaag agaagc 16

<210> SEQ ID NO 11
<211> LENGTH: 23

<212> TYPE: DNA
<213> ORGANISM: Artificial Sequence
<220> FEATURE:
<223> OTHER INFORMATION: Synthetic Oligonucleotide

<400> SEQUENCE: 11
cactggattt agagtctctc agc 23

<210> SEQ ID NO 12
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: may be linked via phosphorothioate

<400> SEQUENCE: 12
cactggattt agagtctctc agc 23

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
gaacaccttg ttcaggtcct 20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: may be linked via phosphorothioate

<400> SEQUENCE: 14
gaacaccttg ttcaggtcct 20

<210> SEQ ID NO 15
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 15
gaacacgttt ttcaggtcct c 21

<210> SEQ ID NO 16
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: may be linked via phosphorothioate

<400> SEQUENCE: 16

-continued

```
gaacacgttt ttcaggtcct c                                              21


<210> SEQ ID NO 17
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 17

tcttatatcc ttggggtaga attcc                                          25


<210> SEQ ID NO 18
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: may be linked via phosphorothioate

<400> SEQUENCE: 18

tcttatatcc ttggggtaga attcc                                          25


<210> SEQ ID NO 19
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 19

gggaaacatc tgcatcaagt tg                                             22


<210> SEQ ID NO 20
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: may be linked via phosphorothioate

<400> SEQUENCE: 20

gggaaacatc tgcatcaagt tg                                             22


<210> SEQ ID NO 21
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 21

caggtcctct acaactgtga gtctgg                                         26


<210> SEQ ID NO 22
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 22
```

agacgtgtgc tcttccgatc tcaggtcctc tacaactgtg agtctgg 47

<210> SEQ ID NO 23
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 23
ggtcctctac aacggttaac ctggtc 26

<210> SEQ ID NO 24
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 24
agacgtgtgc tcttccgatc tggtcctcta caacggttaa cctggtc 47

<210> SEQ ID NO 25
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 25
ggtcctctac aacagtgagc caactt 26

<210> SEQ ID NO 26
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 26
agacgtgtgc tcttccgatc tggtcctcta caacagtgag ccaactt 47

<210> SEQ ID NO 27
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 27
ggtcctccaa gacagagagc tgg 23

<210> SEQ ID NO 28
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 28
agacgtgtgc tcttccgatc tggtcctcca agacagagag ctgg 44

<210> SEQ ID NO 29
<211> LENGTH: 26
<212> TYPE: DNA

<213> ORGANISM: Artificial Sequence
<220> FEATURE:
<223> OTHER INFORMATION: Synthetic Oligonucleotide

<400> SEQUENCE: 29
ggtcctctag gatggagagt cgagtc 26

<210> SEQ ID NO 30
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 30
agacgtgtgc tcttccgatc tggtcctcta ggatggagag tcgagtc 47

<210> SEQ ID NO 31
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 31
ggtcctctgt cacagtgagc ctg 23

<210> SEQ ID NO 32
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 32
agacgtgtgc tcttccgatc tggtcctctg tcacagtgag cctg 44

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
tctagcacgg tgagccgtgt 20

<210> SEQ ID NO 34
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 34
agacgtgtgc tcttccgatc ttctagcacg gtgagccgtg t 41

<210> SEQ ID NO 35
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 35
cagtacggtc agcctagagc cttc 24

-continued

<210> SEQ ID NO 36
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 36
agacgtgtgc tcttccgatc tcagtacggt cagcctagag ccttc 45

<210> SEQ ID NO 37
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 37
ttcaggtcct cgagcactgt cag 23

<210> SEQ ID NO 38
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 38
agacgtgtgc tcttccgatc tttcaggtcc tcgagcactg tcag 44

<210> SEQ ID NO 39
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 39
ttcaggtcct ccagcactga gag 23

<210> SEQ ID NO 40
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 40
agacgtgtgc tcttccgatc tttcaggtcc tccagcactg agag 44

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
caggtcctcg agcaccagga 20

<210> SEQ ID NO 42
<211> LENGTH: 41
<212> TYPE: DNA
<213> ORGANISM: Artificial Sequence
<220> FEATURE:

<223> OTHER INFORMATION: Synthetic Oligonucleotide

<400> SEQUENCE: 42
agacgtgtgc tcttccgatc tcaggtcctc gagcaccagg a 41

<210> SEQ ID NO 43
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 43
cagcacggtc agcctgct 18

<210> SEQ ID NO 44
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 44
agacgtgtgc tcttccgatc tcagcacggt cagcctgct 39

<210> SEQ ID NO 45
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 45
ttcaggtcct ctgtgaccgt gag 23

<210> SEQ ID NO 46
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 46
agacgtgtgc tcttccgatc tttcaggtcc tctgtgaccg tgag 44

<210> SEQ ID NO 47
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 47
acatctgcat caagttgttt atctgtgaca ac 32

<210> SEQ ID NO 48
<211> LENGTH: 53
<212> TYPE: DNA
<213> ORGANISM: Artificial Sequence
<220> FEATURE:
<223> OTHER INFORMATION: Synthetic Oligonucleotide

<400> SEQUENCE: 48
agacgtgtgc tcttccgatc tacatctgca tcaagttgtt tatctgtgac aac 53

-continued

<210> SEQ ID NO 49
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 49
tgtttatctg taatgataag ctttgttccg gga 33

<210> SEQ ID NO 50
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 50
agacgtgtgc tcttccgatc ttgtttatct gtaatgataa gctttgttcc ggga 54

<210> SEQ ID NO 51
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 51
tcaggtgaag ttactatgag cttagtccct 30

<210> SEQ ID NO 52
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 52
agacgtgtgc tcttccgatc ttcaggtgaa gttactatga gcttagtccc t 51

<210> SEQ ID NO 53
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 53
gcgaagttac tatgagccta gtccctt 27

<210> SEQ ID NO 54
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 54
agacgtgtgc tcttccgatc tgcgaagtta ctatgagcct agtccctt 48

<210> SEQ ID NO 55
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 55
tctctcagct ggtacacggc a 21

<210> SEQ ID NO 56
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 56
agacgtgtgc tcttccgatc ttctctcagc tggtacacgg ca 42

<210> SEQ ID NO 57
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 57
tcaccagaca agcgacattt gttcc 25

<210> SEQ ID NO 58
<211> LENGTH: 46
<212> TYPE: DNA
<213> ORGANISM: Artificial Sequence
<220> FEATURE:
<223> OTHER INFORMATION: Synthetic Oligonucleotide

<400> SEQUENCE: 58
agacgtgtgc tcttccgatc ttcaccagac aagcgacatt tgttcc 46

<210> SEQ ID NO 59
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 59
ggctcctggg ggaaga 16

<210> SEQ ID NO 60
<211> LENGTH: 16
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: may be linked via phosphorothioate

<400> SEQUENCE: 60
ggctcctggg ggaaga 16

<210> SEQ ID NO 61
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 61
gtacccagtt atcaagcatg c 21

<210> SEQ ID NO 62
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: may be linked via phosphorothioate

<400> SEQUENCE: 62
gtacccagtt atcaagcatg c 21

<210> SEQ ID NO 63
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 63
agtcacggag gtggcat 17

<210> SEQ ID NO 64
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: may be linked via phosphorothioate

<400> SEQUENCE: 64
agtcacggag gtggcat 17

<210> SEQ ID NO 65
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 65
gacaccgtca ccggttc 17

<210> SEQ ID NO 66
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: may be linked via phosphorothioate

<400> SEQUENCE: 66
gacaccgtca ccggttc 17

<210> SEQ ID NO 67
<211> LENGTH: 18
<212> TYPE: DNA
<213> ORGANISM: Artificial Sequence
<220> FEATURE:

<223> OTHER INFORMATION: Synthetic Oligonucleotide

<400> SEQUENCE: 67
gaaggaagtc ctgtgcga 18

<210> SEQ ID NO 68
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: may be linked via phosphorothioate

<400> SEQUENCE: 68
gaaggaagtc ctgtgcga 18

<210> SEQ ID NO 69
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 69
ttgacggggc tgctatct 18

<210> SEQ ID NO 70
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: may be linked via phosphorothioate

<400> SEQUENCE: 70
ttgacggggc tgctatct 18

<210> SEQ ID NO 71
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 71
acggggctgc catct 15

<210> SEQ ID NO 72
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: may be linked via phosphorothioate

<400> SEQUENCE: 72
acggggctgc catct 15

<210> SEQ ID NO 73
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 73
cagatttcaa ctgctcatca ga 22

<210> SEQ ID NO 74
<211> LENGTH: 22
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: may be linked via phosphorothioate

<400> SEQUENCE: 74
cagatttcaa ctgctcatca ga 22

<210> SEQ ID NO 75
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 75
gggaagtagt ccttgacca 19

<210> SEQ ID NO 76
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: may be linked via phosphorothioate

<400> SEQUENCE: 76
gggaagtagt ccttgacca 19

<210> SEQ ID NO 77
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 77
aggctcagcg ggaagacct 19

<210> SEQ ID NO 78
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 78
agacgtgtgc tcttccgatc taggctcagc gggaagacct 40

<210> SEQ ID NO 79
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 79
cagggctgtt atcctttggg tgtc 24

<210> SEQ ID NO 80
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 80
agacgtgtgc tcttccgatc tcagggctgt tatcctttgg gtgtc 45

<210> SEQ ID NO 81
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 81
gaggtggcat tggagggaat gt 22

<210> SEQ ID NO 82
<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 82
agacgtgtgc tcttccgatc tgaggtggca ttggagggaa tgt 43

<210> SEQ ID NO 83
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 83
ttcggggaag tagtccttga cca 23

<210> SEQ ID NO 84
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 84
agacgtgtgc tcttccgatc tttcggggaa gtagtccttg acca 44

<210> SEQ ID NO 85
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 85
ggttctggga agtagtcctt gacca 25

<210> SEQ ID NO 86
<211> LENGTH: 46
<212> TYPE: DNA
<213> ORGANISM: Artificial Sequence
<220> FEATURE:
<223> OTHER INFORMATION: Synthetic Oligonucleotide

<400> SEQUENCE: 86
agacgtgtgc tcttccgatc tggttctggg aagtagtcct tgacca 46

<210> SEQ ID NO 87
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 87
tcgtatccga cggggaattc tcac 24

<210> SEQ ID NO 88
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 88
agacgtgtgc tcttccgatc ttcgtatccg acggggaatt ctcac 45

<210> SEQ ID NO 89
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 89
tgctcatcag atggcgggaa gat 23

<210> SEQ ID NO 90
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 90
agacgtgtgc tcttccgatc ttgctcatca gatggcggga agat 44

<210> SEQ ID NO 91
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 91
ccttgttggc ttgaagctcc tca 23

<210> SEQ ID NO 92

<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 92
agacgtgtgc tcttccgatc tccttgttgg cttgaagctc ctca 44

<210> SEQ ID NO 93
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 93
cttgttggct tggagctcct ca 22

<210> SEQ ID NO 94
<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 94
agacgtgtgc tcttccgatc tcttgttggc ttggagctcc tca 43

<210> SEQ ID NO 95
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 95
cccagaggtg ctcttggagg ag 22

<210> SEQ ID NO 96
<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 96
agacgtgtgc tcttccgatc tcccagaggt gctcttggag gag 43

<210> SEQ ID NO 97
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 97
gctgtgctct cggaggtgct 20

<210> SEQ ID NO 98
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 98
agacgtgtgc tcttccgatc tgctgtgctc tcggaggtgc t 41

<210> SEQ ID NO 99
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 99
cggaggtgct cctggagca 19

<210> SEQ ID NO 100
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 100
agacgtgtgc tcttccgatc tcggaggtgc tcctggagca 40

<210> SEQ ID NO 101
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 101
gcgagaccac gttcccatct 20

<210> SEQ ID NO 102
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 102
agacgtgtgc tcttccgatc tgcgagacca cgttcccatc t 41

<210> SEQ ID NO 103
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 103
gcgatgacca cgttcccatc t 21

<210> SEQ ID NO 104
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 104
agacgtgtgc tcttccgatc tgcgatgacc acgttcccat ct 42

<210> SEQ ID NO 105
<211> LENGTH: 22
<212> TYPE: DNA

<213> ORGANISM: Artificial Sequence
<220> FEATURE:
<223> OTHER INFORMATION: Synthetic Oligonucleotide

<400> SEQUENCE: 105
gcgatgacca cgttcccatc tg 22

<210> SEQ ID NO 106
<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 106
agacgtgtgc tcttccgatc tgcgatgacc acgttcccat ctg 43

<210> SEQ ID NO 107
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 107
gcgacgacca cgttcccatc t 21

<210> SEQ ID NO 108
<211> LENGTH: 42
<212> TYPE: DNA
<213> ORGANISM: Artificial Sequence
<220> FEATURE:
<223> OTHER INFORMATION: Synthetic Oligonucleotide

<400> SEQUENCE: 108
agacgtgtgc tcttccgatc tgcgacgacc acgttcccat ct 42

<210> SEQ ID NO 109
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 109
gcgacgacca cgttcccatc 20

<210> SEQ ID NO 110
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 110
agacgtgtgc tcttccgatc tgcgacgacc acgttcccat c 41

<210> SEQ ID NO 111
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 111
ttcccatctg gctgggtgct 20

<210> SEQ ID NO 112
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 112
agacgtgtgc tcttccgatc tttcccatct ggctgggtgc t 41

<210> SEQ ID NO 113
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 113
ttcccatctt ggggggtgct 20

<210> SEQ ID NO 114
<211> LENGTH: 41
<212> TYPE: DNA
<213> ORGANISM: Artificial Sequence
<220> FEATURE:
<223> OTHER INFORMATION: Synthetic Oligonucleotide

<400> SEQUENCE: 114
agacgtgtgc tcttccgatc tttcccatct tggggggtgc t 41

<210> SEQ ID NO 115
<211> LENGTH: 115
<212> TYPE: PRT
<213> ORGANISM: Artificial Sequence
<220> FEATURE:
<223> OTHER INFORMATION: Synthetic

<400> SEQUENCE: 115

```
His Asn Cys Ala Ser Leu Trp Ser Phe Pro Gly Leu Leu Ser His Thr
1               5                   10                  15

Tyr Thr Glu Pro Leu Pro Gly Pro Asp Ser Ser Ser Asn Pro Ser Pro
            20                  25                  30

Ile Thr Ser Ser Leu Ser Arg Gly Pro Glu Lys Arg Val Pro Thr Arg
        35                  40                  45

Gly Arg Cys Val Ala Ile Arg Ser Arg Asp Leu Pro His Pro Lys Gly
    50                  55                  60

His Thr Gly Val Pro Gly His Arg Leu Leu Pro Arg Pro Arg Gly Ala
65                  70                  75                  80

Glu Leu Val Gly Glu Trp Glu Gly Gly Ala Gln Trp Gly Gln His Arg
                85                  90                  95

Pro Ala Ala Pro Gln Gly Ala Ala Arg Pro Gln Leu Gly Ile Leu Pro
            100                 105                 110

Glu Gln Pro
        115
```

<210> SEQ ID NO 116
<211> LENGTH: 120
<212> TYPE: PRT
<213> ORGANISM: Artificial Sequence
<220> FEATURE:
<223> OTHER INFORMATION: Synthetic

<400> SEQUENCE: 116

Ser Asn Ile Ile Val Leu His Tyr Gly Pro Phe Pro Ala Phe Ser Leu
1 5 10 15

Thr His Thr Gly Ser Pro Tyr Gln Asp Gln Thr Ala Leu Arg Ala Thr
20 25 30

Leu Ala Pro Leu Pro Leu Pro Phe Pro Glu Asp Leu Lys Asn Val Phe
35 40 45

Pro Pro Glu Val Ala Val Phe Glu Pro Ser Glu Ala Glu Ile Ser His
50 55 60

Thr Gln Lys Ala Thr Leu Val Cys Leu Ala Thr Gly Phe Tyr Pro Asp
65 70 75 80

His Met Glu Leu Ser Trp Trp Val Asn Gly Lys Glu Val His Ser Gly
85 90 95

Val Ser Thr Asp Pro Gln Pro Leu Lys Glu Gln Pro Ala Leu Asn Asp
100 105 110

Ser Arg Tyr Cys Leu Ser Ser Arg
115 120

<210> SEQ ID NO 117
<211> LENGTH: 113
<212> TYPE: PRT
<213> ORGANISM: Artificial Sequence
<220> FEATURE:
<223> OTHER INFORMATION: Synthetic

<400> SEQUENCE: 117

Val Thr Leu Cys Phe Ile Met Val Leu Ser Arg Pro Ser Leu Ser His
1 5 10 15

Ile His Arg Ala Pro Thr Arg Thr Arg Gln Leu Leu Glu Gln Pro Pro
20 25 30

His Tyr Leu Phe Pro Phe Gln Arg Thr Lys Thr Cys Ser His Pro Arg
35 40 45

Ser Leu Cys Leu Ser His Gln Lys Gln Arg Ser Pro Thr Pro Lys Arg
50 55 60

Pro His Trp Cys Ala Trp Pro Cys Ala Ser Thr Pro Thr Thr Trp Ser
65 70 75 80

Ala Cys Gly Met Gly Arg Arg Cys Thr Val Gly Ser Ala Gln Thr Arg
85 90 95

Ser Pro Ser Arg Ser Ser Pro Pro Ser Met Thr Pro Asp Thr Ala Ala
100 105 110

Ala

<210> SEQ ID NO 118
<211> LENGTH: 36
<212> TYPE: DNA
<213> ORGANISM: Artificial Sequence
<220> FEATURE:
<223> OTHER INFORMATION: Synthetic

<400> SEQUENCE: 118
ttcgccttgt gatgggacaa aaaaaaaaaa aaaaaa 36

<210> SEQ ID NO 119
<211> LENGTH: 136
<212> TYPE: DNA
<213> ORGANISM: Artificial Sequence
<220> FEATURE:
<223> OTHER INFORMATION: Synthetic

<400> SEQUENCE: 119
agcatctatt gaaaatatct gacaaactca tcttttattt tgatgtgtgt gtgtgtgtgt 60
gtgtgttttt ttaacaggga tttggggaat tatttgagaa agcaaaacaa aacaataaca 120
atagagaaaa cttcta 136

<210> SEQ ID NO 120
<211> LENGTH: 43
<212> TYPE: PRT
<213> ORGANISM: Artificial Sequence
<220> FEATURE:
<223> OTHER INFORMATION: Synthetic

<400> SEQUENCE: 120

Ser Ile Tyr Lys Tyr Leu Thr Asn Ser Ser Phe Ile Phe Asp Val Cys
1 5 10 15

Val Cys Val Cys Val Phe Phe Gln Gly Phe Gly Glu Leu Phe Glu Lys
20 25 30

Ala Lys Gln Asn Asn Asn Asn Arg Lys Thr Ser
35 40

<210> SEQ ID NO 121
<211> LENGTH: 44
<212> TYPE: PRT
<213> ORGANISM: Artificial Sequence
<220> FEATURE:
<223> OTHER INFORMATION: Synthetic

<400> SEQUENCE: 121

Ala Ser Ile Glu Asn Ile Gln Thr His Leu Leu Phe Leu Met Cys Val
1 5 10 15

Cys Val Cys Val Cys Phe Phe Asn Arg Asp Leu Gly Asn Tyr Leu Arg
20 25 30

Lys Gln Asn Lys Thr Ile Thr Ile Glu Lys Leu Leu
35 40

<210> SEQ ID NO 122
<211> LENGTH: 41
<212> TYPE: PRT
<213> ORGANISM: Artificial Sequence
<220> FEATURE:
<223> OTHER INFORMATION: Synthetic

<400> SEQUENCE: 122

Lys His Leu Leu Lys Ile Ser Asp Lys Leu Ile Phe Tyr Phe Cys Val
1 5 10 15

Cys Val Cys Val Cys Val Phe Leu Thr Gly Ile Trp Gly Ile Ile Glu
20 25 30

Ser Lys Thr Lys Gln Gln Lys Asn Phe
35 40

<210> SEQ ID NO 123
<211> LENGTH: 135
<212> TYPE: DNA
<213> ORGANISM: Artificial Sequence
<220> FEATURE:
<223> OTHER INFORMATION: Synthetic

<400> SEQUENCE: 123
agcatctatt gaaaatatct gacaaactca tcttttattt ttgatgtgtg tgtgtgtgtg 60
tgtgtgtttt tttaacaggg atttggggaa ttatttgaga aagcaaaaca aaacaataac 120

-continued

```
aatagaaaac ttcta                                                     135


<210> SEQ ID NO 124
<211> LENGTH: 37
<212> TYPE: PRT
<213> ORGANISM: Artificial Sequence
<220> FEATURE:
<223> OTHER INFORMATION: Synthetic

<400> SEQUENCE: 124

Glu Ile Thr Phe Asp Tyr Glu Asp Val Phe His Asn Gln Ile Leu Gln
1               5                   10                  15

Ile Thr Leu Ala Ser Lys Gly Val Gly Gly Ala Gly Val Val Val Leu
            20                  25                  30

Lys Tyr Glu Thr Met
        35
```

METHODS OF NUCLEIC ACID SAMPLE PREPARATION

RELATED APPLICATIONS

This application is a continuation-in-part of: (i) U.S. patent application Ser. No. 16/804,695, filed Feb. 28, 2020, now U.S. Pat. No. 11,390,905, which is a continuation of U.S. patent application Ser. No. 15/706,649, filed Sep. 15, 2017, now U.S. Pat. No. 10,683,531, which claims priority under 35 U.S.C. § 119 (e) to U.S. Provisional Patent Application No. 62/395,347, filed Sep. 15, 2016; (ii) U.S. patent application Ser. No. 16/919,238, filed Jul. 2, 2020, now U.S. Pat. No. 11,795,492, which is a continuation of U.S. patent application Ser. No. 15/706,642, filed Sep. 15, 2017, now U.S. Pat. No. 10,704,082, which claims priority under 35 U.S.C. § 119 (e) to U.S. Provisional Patent Application No. 62/395,339, filed Sep. 15, 2016 and (iii) U.S. patent application Ser. No. 17/177,740, filed Feb. 17, 2021, now abandoned, which is a continuation of U.S. patent application Ser. No. 15/802,408, filed Nov. 2, 2017, now U.S. Pat. No. 10,947,582, which claims priority under 35 U.S.C. § 119 (e) to U.S. Provisional Patent Application No. 62/416,677, filed Nov. 2, 2016. The entire content of each of the foregoing applications is incorporated herein by reference, including all text, tables and drawings.

TECHNICAL FIELD

The technology described herein relates to methods and compositions useful in the preparation of nucleic acid molecules for analysis.

REFERENCE TO SEQUENCE LISTING SUBMITTED AS A TEXT FILE VIA EFS-WEB

The instant application contains a sequence listing which has been submitted in ASCII format via EFS-Web and is hereby incorporated by reference in its entirety. Said ASCII copy, created on May 17, 2022, is named A110070018US00-SEQ-COB.txt and is 31,100 bytes in size.

BACKGROUND

Target enrichment prior to next-generation sequencing is more cost-effective than whole genome, whole exome, and whole transcriptome sequencing and therefore more practical for broad implementation; both for research discovery and clinical applications. For example, high coverage depth afforded by target enrichment approaches enables a wider dynamic range for allele counting (in gene expression and copy number assessment) and detection of low frequency mutations, which is advantageous for evaluating somatic mutations in cancer. Examples of current enrichment protocols for next generation sequencing include hybridization-based capture assays (TruSeq Capture, Illumina; SureSelect Hybrid Capture, Agilent) and polymerase chain reaction (PCR)-based assays (HaloPlex, Agilent; AmpliSeq, Ion Torrent: TruSeq Amplicon, Illumina; emulsion/digital PCR, Raindance). Hybridization-based approaches capture not only the targeted sequences covered by the capture probes but also near off-target bases that consume sequencing capacity. In addition, these methods are relatively time-consuming, labor-intensive, and suffer from a relatively low level of specificity.

SUMMARY

Aspects of the technology disclosed herein relate to methods of preparing and analyzing nucleic acids. Methods provided herein are useful, in some embodiments, for detecting ultra-low frequency nucleic acid variants (e.g., ultra-low allelic frequency variants, splice variants, fusions, single nucleotide variants, insertions and deletions, copy number variants, mRNAs from somatically recombined immune receptor loci, and expression level variants) in nucleic acid preparations, including cell-free DNA preparations (e.g., from urine or blood samples) as well as sequences representative of an immune repertoire comprising a diverse landscape of nucleic acid sequences encoding immune receptors and immunoglobulins. In some embodiments, the methods minimize carryover of adapter nucleic acid molecules into amplification and/or sequencing steps.

Methods provided herein, in some embodiments, involve ligation-based capture that enriches for highly fragmented material such that the methods are particularly useful for detecting variants in cell-free DNA preparations. In some embodiments, methods provided herein facilitate generation of high coverage (e.g., high unique coverage) sequencing libraries from fragmented input, including, e.g., from cell-free DNA preparations. Methods provided herein, in some embodiments, involve ligation-based capture that enriches for nucleic acid molecules having nucleotide sequences corresponding to transcribed nucleic acids that reflect previously occurring recombination and/or splicing events. In some embodiments, unique molecule depth or capture is vastly improved over conventional methods for nucleic acids extracted from individuals, e.g., tumor bearing individuals or immune-compromised individuals. In some embodiments, coverage depth or capture efficiency is at least doubled compared with conventional methods for nucleic acids extracted from individuals, e.g., tumor bearing individuals or immune-compromised individuals. In some embodiments, improved depth is accomplished as a result of improved front-end capture chemistry.

In some embodiments, methods provided herein are useful for evaluating RNA immune repertoires via sequencing. In some embodiments, methods and compositions useful in the preparation of nucleic acid samples for sequence analysis (e.g., using next-generating sequencing) are provided herein. In some embodiments, techniques described herein are related to methods of determining a nucleic acid sequence. In some embodiments, methods and compositions described herein relate to the enrichment of nucleic acids comprising one or more target nucleotide sequences prior to sequencing.

In some aspects, the disclosure provides methods of preparing nucleic acids (e.g., for use in a sequencing analysis) that involve adding one or more capture moiety modified nucleotides to a nucleic acid or the use of a capture moiety modified primer to synthesize a first nucleic acid strand. In some embodiments, the methods further involve ligating an adapter nucleic acid to the nucleic acid to which the capture moiety modified nucleotide has been added to produce a ligation product. In some embodiments, the methods further involve ligating an adapter nucleic acid to the nucleic acid to which the capture moiety modified primer has been used in synthesizing a first strand of the nucleic acid to produce a ligation product. In some embodiments, the methods further involve capturing the ligation product by contacting the ligation product with a binding partner of a capture moiety of the capture moiety modified nucleotide or a binding partner of a capture moiety of the capture moiety modified primer.

In some embodiments, the methods further involve amplifying the ligation product, e.g., by polymerase chain reaction or another suitable amplification approach. In some embodiments, methods are provided for preparing nucleic acids that involve adding one or more nucleotides to a 3' end of a nucleic acid (e.g., a double-stranded nucleic acid) comprising a target nucleotide sequence, in which at least one of the one or more nucleotides is a capture moiety modified nucleotide. In some embodiments, presence of the capture moiety modified nucleotide at the 3'-end of the nucleic acid facilitates isolation, purification and/or washing of the nucleic acid while avoiding incorporation of modified nucleotides (e.g., randomly) throughout the nucleic acid. In some embodiments, methods are provided for preparing nucleic acids that involve incorporating one or more nucleotides into a nucleic acid (e.g., a double-stranded nucleic acid) comprising a target nucleotide sequence, in which at least one of the one or more nucleotides is a capture moiety modified nucleotide. In some embodiments, the one or more nucleotides are incorporated using a primer (e.g., a reverse transcription primer). In some embodiments, the one or more nucleotides are incorporated during an earlier step of preparing the nucleic acids. For example, in some embodiments, the one or more nucleotides are incorporated during fragmentation, random priming, first strand synthesis, second strand synthesis, and/or end repair.

According to some aspects, methods of preparing nucleic acids for analysis are provided, wherein the methods comprise:

(a) adding one or more nucleotides to a 3' end of a double-stranded nucleic acid comprising a target nucleotide sequence, wherein at least one of the one or more nucleotides is a capture moiety modified nucleotide;
(b) ligating an adapter nucleic acid to at least one strand of the double-stranded nucleic acid to produce a ligation product comprising the one or more capture moiety modified nucleotides; and
(c) capturing the ligation product by contacting the ligation product with a binding partner of the capture moiety modified nucleotide.

In some embodiments, the method further comprises, after the capturing of (c): (d) amplifying the ligation product of (b). In some embodiments, the amplifying comprises linear amplification or a polymerase chain reaction. In some embodiments, the polymerase chain reaction comprises use of a first target-specific primer that specifically anneals to a portion of the target nucleotide sequence and a first adapter primer that specifically anneals to a complementary sequence of the adapter nucleic acid. In some embodiments, the first target-specific primer comprises a 5' tail portion comprising a nucleic acid sequence that does not anneal to the target nucleotide sequence.

In some embodiments, the method further comprises:

(e) amplifying a product of (d) by a second polymerase chain reaction that comprises (i) use of a second adapter primer that specifically anneals to a complementary sequence of the adapter nucleic acid, and (ii) use of a tail primer comprising a 3' sequence that is substantially identical to the 5' tail portion of the first target-specific primer.

In some embodiments, the first adapter primer and the second adapter primer are the same, and the amplifying of (d) and the amplifying of (e) takes place in a same reaction mixture or at the same time.

In some embodiments, the method further comprises, after the capturing of (c), determining a sequence of at least a portion of the double stranded nucleic acid.

In some embodiments, the double-stranded nucleic acid comprises genomic DNA, fragmented DNA, cell free DNA (cfDNA) or cDNA.

In some embodiments, after the adding of (a), the double-stranded nucleic acid comprises a 3'-overhang sequence. In some embodiments, the 3'-overhang sequence is complementary to one or more nucleotides at a 3' end of the adapter nucleic acid.

In some embodiments, each of the one or more nucleotides is a capture moiety modified nucleotide.

In some embodiments, only one nucleotide is added to the 3' end of the double-stranded nucleic acid in step (a), wherein the one nucleotide is a capture moiety modified nucleotide. In some embodiments, the one nucleotide comprises adenine.

In some embodiments, the capture moiety modified nucleotide comprises a biotin capture moiety.

In some embodiments, the capturing of (c) provides an immobilized ligation product, and the method further comprises washing the immobilized ligation product, releasing the immobilized ligation product, and amplifying at least a portion of the ligation product.

In some embodiments, the adapter nucleic acid comprises a barcode and a primer binding site.

In some embodiments, the adapter nucleic acid is double-stranded.

According to some aspects, a method of preparing nucleic acids for analysis provided herein comprises:

(a) adding one or more nucleotides to a 3' end of each of a plurality of double-stranded nucleic acids comprising a plurality of different target nucleotide sequences, wherein at least one of the one or more nucleotides is a capture moiety modified nucleotide;
(b) ligating an adapter nucleic acid to at least one strand of each of the plurality of double-stranded nucleic acids to produce a plurality of ligation products comprising the one or more capture moiety modified nucleotides;
(c) capturing the plurality of ligation products by contacting the plurality of ligation products with a binding partner of the capture moiety modified nucleotide; and
(d) amplifying the plurality of ligation products, thereby providing a plurality of amplicons.

In some embodiments, the plurality of double-stranded nucleic acids comprises 25 to 1,000 different target nucleotide sequences or 1,000 to 10,000 different target nucleotide sequences.

Other advantages and novel features of the present disclosure will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Among other aspects, the present disclosure provides improved techniques related to the preparation of nucleic acid sample libraries (e.g., cell free DNA (cfDNA) samples, mRNA samples) for analysis (e.g., DNA analysis, immune repertoire analysis). As described herein, an adapter nucleic acid may be ligated to a nucleic acid comprising a target nucleotide sequence. The use of adapter nucleic acids can be useful during library preparation and sequencing analysis, for example, by providing primer binding sites and molecular barcode or index sequences. In some aspects, the present disclosure relates to improvements in processes related to adapter ligation and adapter-ligated sample isolation that substantially improves molecular barcode fidelity.

In some aspects, the disclosure relates to the recognition that, following adapter ligation, carryover of unligated adapter into subsequent PCR reactions could result in an overabundance of molecular barcodes. This overabundance, or inflation, of molecular barcodes can result in false positives, as one molecule should only contain one barcode. It is appreciated that, in some embodiments, unligated adapter can, in some instances, prime off of a common region in existing fragments during PCR. Over multiple reaction cycles, additional copies of a barcode or other artificial sequence can be integrated into a single molecule. Accordingly, the inventors have recognized and appreciated the need for improved processes relating to the ligation of adapters and the isolation of adapter-ligated library fragments.

Adding Capture Moiety Modified Nucleotide to 3' End

In some aspects, the disclosure provides a method of preparing nucleic acids for analysis, comprising (a) adding a capture moiety modified nucleotide to a 3' end of a double-stranded nucleic acid (e.g., cDNA, gDNA, cfDNA, cfRNA), ligating an adapter nucleic acid to the double-stranded nucleic acid having the capture moiety modified nucleotide, and capturing the adapter-ligated nucleic acid with a binding partner of the capture moiety modified nucleotide.

Figure 1:
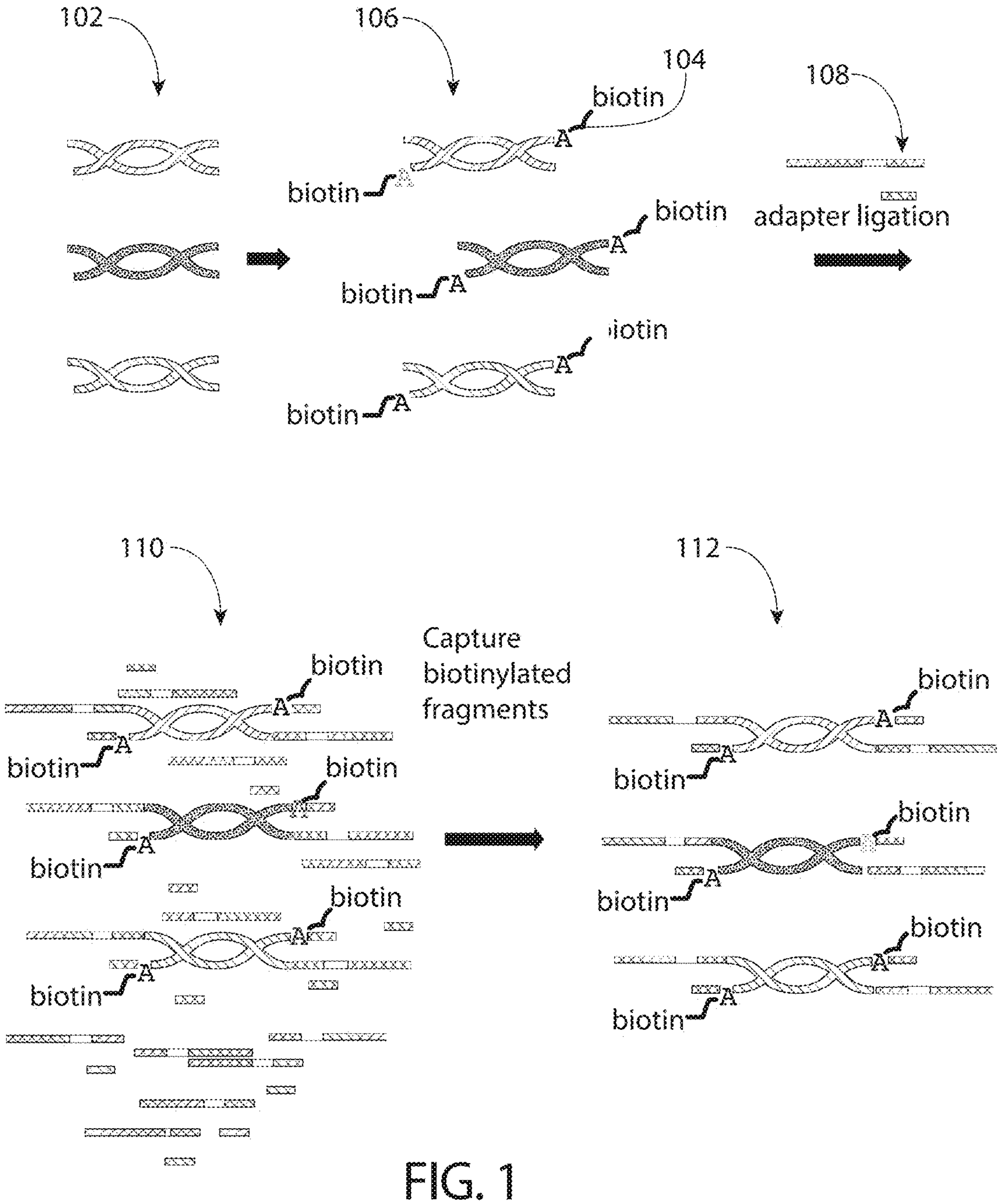
FIG. 1 is an illustration of a process that allows for the capture of an adapter-ligated nucleic acid library.

In some embodiments, the capture moiety modified nucleotide is a biotin moiety modified nucleotide. A general depiction of this method is shown in FIG. 1, which provides a non-limiting example of a method involving a biotin moiety modified nucleotide. In this embodiment, a library of blunt-ended, 5' phosphorylated double-stranded nucleic acids 102 is provided. Biotin-labeled ATP 104 is added to the 3' ends of the double-stranded nucleic acids to produce a library 106 comprising capture moiety modified nucleotides at the 3' ends of the fragments. The library fragments are ligated with an adapter 108 to produce a sample 110 having unligated adapter along with adapter-ligated library fragments. Ligated library fragments are captured, or isolated, from unligated adapter using a streptavidin coated surface to generate a library 112 that minimizes or eliminates the occurrence of unligated adapter carryover. Although this example utilizes a biotin capture moiety, any moiety that is capable of being specifically targeted for isolation (e.g., via an interaction with a binding partner) may be suitable in the techniques described herein.

Aspects of the disclosure provide improved methods of determining the nucleotide sequence contiguous to a known target nucleotide sequence (e.g., a known target nucleotide sequence of a cfDNA or an immune receptor). Traditional sequencing methods generate sequence information randomly (e.g., "shotgun" sequencing) or between two known sequences which are used to design primers. In contrast, certain of the methods described herein, in some embodiments, allow for determining the nucleotide sequence (e.g., sequencing) upstream or downstream of a single region of known sequence with a high level of specificity and sensitivity.

In some embodiments, the disclosure provides a method of enriching specific nucleotide sequences prior to determining the nucleotide sequence using a next-generation sequencing technology. In some embodiments, methods provided herein can relate to enriching samples comprising deoxyribonucleic acid (DNA). In some embodiments, methods provided herein comprise: (a) adding one or more nucleotides to a 3' end of a double-stranded nucleic acid comprising a target nucleotide sequence, wherein at least one (e.g., 1, 2, 3, 4, 5 or more) of the one or more nucleotides is a capture moiety modified nucleotide: (b) ligating an adapter nucleic acid to the double-stranded nucleic acid to which the capture moiety modified nucleotide has been added to produce a ligation product, wherein a sequence of one or more nucleotides at a 3' end of the adapter nucleic acid is complementary with the one or more nucleotides added to the 3' end of the double stranded nucleic acid in step (a); (c) capturing the ligation product by contacting the ligation product with a binding partner of a capture moiety of the capture moiety modified nucleotide; and (d) amplifying the ligation product by polymerase chain reaction using a first target-specific primer that specifically anneals to the target nucleotide sequence and a first adapter primer that specifically anneals to a complementary sequence of the adapter nucleic acid.

Figure 2:
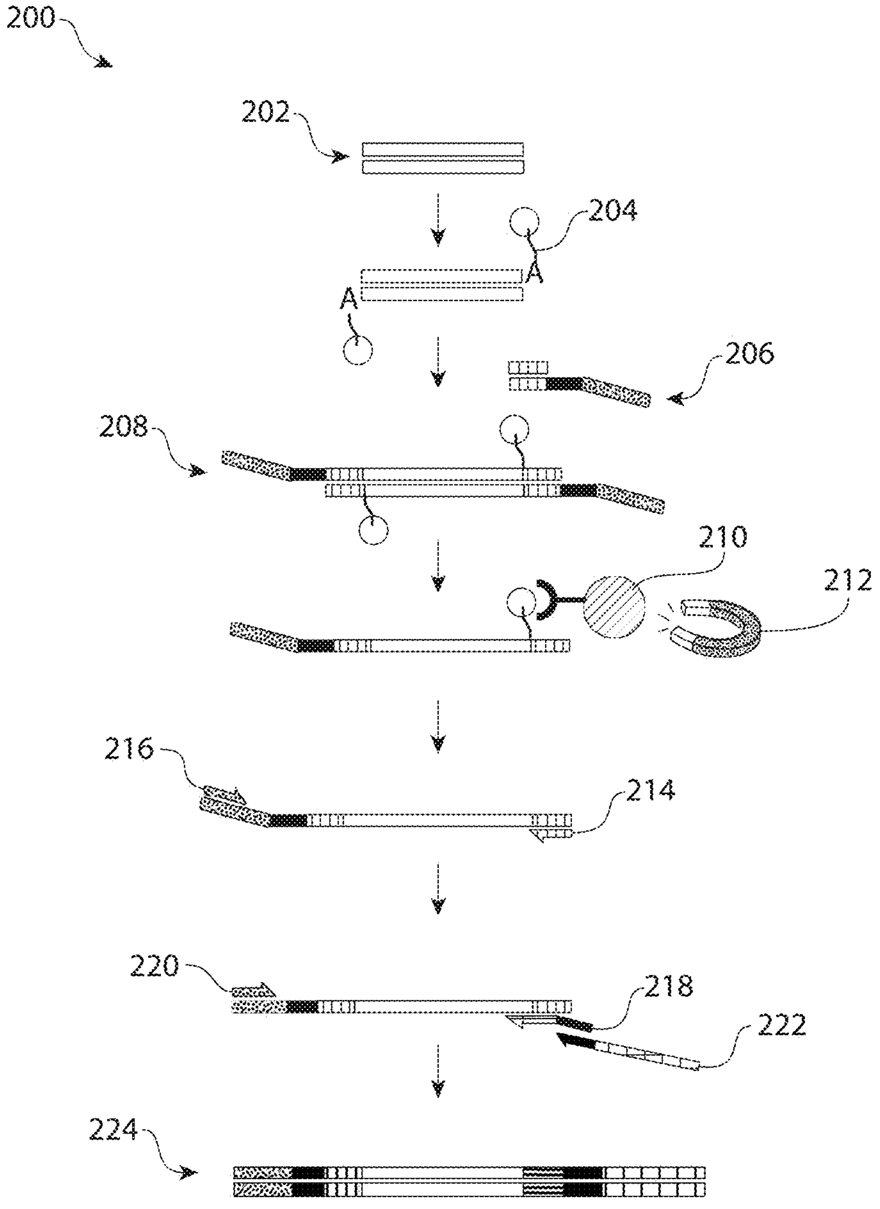
FIG. 2 is an illustration of a method of preparing a high-fidelity nucleic acid sample for analysis.

In some embodiments, the method further comprises: (e) amplifying an amplification product of step (d) by polymerase chain reaction using a second adapter primer and a second target-specific primer. For example, FIG. 2 depicts a non-limiting process 200 by which this embodiment can proceed. Double-stranded nucleic acid 202 comprising a target nucleotide sequence is tailed by adding one or more capture moiety modified nucleotides 204 to the 3' ends (e.g., 1, 2, 3, 4, 5 or more capture moiety modified nucleotides). The capture moiety labeled nucleic acid is ligated with an adapter 206 to generate an adapter-ligated library fragment 208. The adapter-ligated fragment is isolated by introducing a binding partner of the capture moiety, the former of which is attached to a magnetic support 210. Application of a magnetic field 212 isolated adapter-ligated nucleic acids from unligated adapter. The captured ligation product is subjected to a first round of PCR using a first target-specific primer 214 that specifically anneals to the target nucleotide sequence and a first adapter primer 216 that specifically anneals to a complementary sequence of the adapter nucleic acid. In this way, the first adapter primer 216 primes off of the strand generated by the first target-specific primer 214. A second round of PCR is conducted using a second target-specific primer 218 and a second adapter primer 220. As shown, the second target-specific primer 218 is nested relative to the first target-specific primer 214. Also as shown, the second target-specific primer is tailed with a 5' region that does not hybridize with the target nucleotide sequence. In a similar fashion to the first round of PCR, the second adapter primer 220 primes off of the strand generated by the second target-specific primer 218. In this second round of PCR, an additional primer 222 is included that contains (i) a 3' region that is identical to at least a portion of the tailed 5' region of the second target-specific primer 218 and (ii) a 5' region that can contain additional elements useful for sequencing, such as index or barcode sequences and primer binding sites. After the second adapter primer 220 generates a sense strand from the complementary strand generated by the second target-specific primer 218, the additional primer

222 then primes off of the now complementary sequence of the tailed region to generate the sequencing-ready product 224.

In some embodiments, the techniques described herein allow for the enrichment of target nucleotide sequences from a nucleic acid sample. In some embodiments, the nucleic acid sample comprises genomic DNA. In some embodiments, the nucleic acid sample comprises cDNA. In some embodiments, cDNA may be prepared by conducting a randomly-primed first strand synthesis reaction using a product of the randomly-primed first strand synthesis reaction as a template, wherein the RNA preparation comprises a target nucleotide sequence. In some embodiments, a nucleic acid sequencing library is prepared from an RNA preparation. For example, FIG. 3 generically depicts a process 300 by which a double-stranded nucleic acid library fragment is prepared from an RNA template.

As shown, an RNA template 302 is annealed with random primers 304 (e.g., random hexamers) under conditions suitable for hybridization. Following random priming, first strand cDNA synthesis is achieved by template-dependent extension using a reverse transcriptase enzyme to generate a DNA/RNA hybrid 306. The RNA strand of the DNA/RNA hybrid is enzymatically or chemically cleaved. The resulting fragments of RNA 308 that remain hybridized to the DNA strand 310 serve as primers for second strand cDNA synthesis via the action of a polymerase. In some embodiments, inactivation of the polymerase following second strand cDNA synthesis may be desirable, for example, to prevent 5'→3' and/or 3'→5' exonuclease activity during end repair. Following second strand cDNA synthesis, the double-stranded cDNA 312 is subjected to end repair to generate blunt ended, 5' phosphorylated cDNA 314. In some embodiments, SPRI cleanup (e.g., AMPure) is conducted following end repair. As subsequent steps in the process may involve adding a capture moiety modified nucleotide to a 3' end of the nucleic acid, it may be preferable to remove any residual dNTPs in the sample. Thus, any cleanup method capable of removing dNTPs from solution are envisioned to be suitable in this technique. In some embodiments, a capture moiety modified nucleotide may be added and/or incorporated into a nucleic acid at an earlier step of preparing the nucleic acids (e.g., fragmentation, random or specific priming, first strand synthesis, second strand synthesis, and/or end repair). In such embodiments, it may therefore be desirable to perform a cleanup step preceding the step of adding and/or incorporating the capture moiety modified nucleotide.

The blunt ended, 5' phosphorylated cDNA 314 is tailed with a biotin-labeled dATP 316 (biotin-11-ATP) comprising a thioate bond (e.g., a phosphorothioate bond) at its 3' ends and subjected to SPRI cleanup before being ligated with an adapter nucleic acid to generate an adapter-ligated library fragment 318. The inclusion of a crowding agent (20%) was shown to increase adapter ligation efficiency. The adapter-ligated fragment 318 is captured by introducing a streptavidin-coated paramagnetic bead 320. Once the non-covalent biotin-streptavidin complex has formed, application of a magnetic field 322 captures the adapter-ligated nucleic acids to isolate the desired product from unligated adapter.

Figure 3:
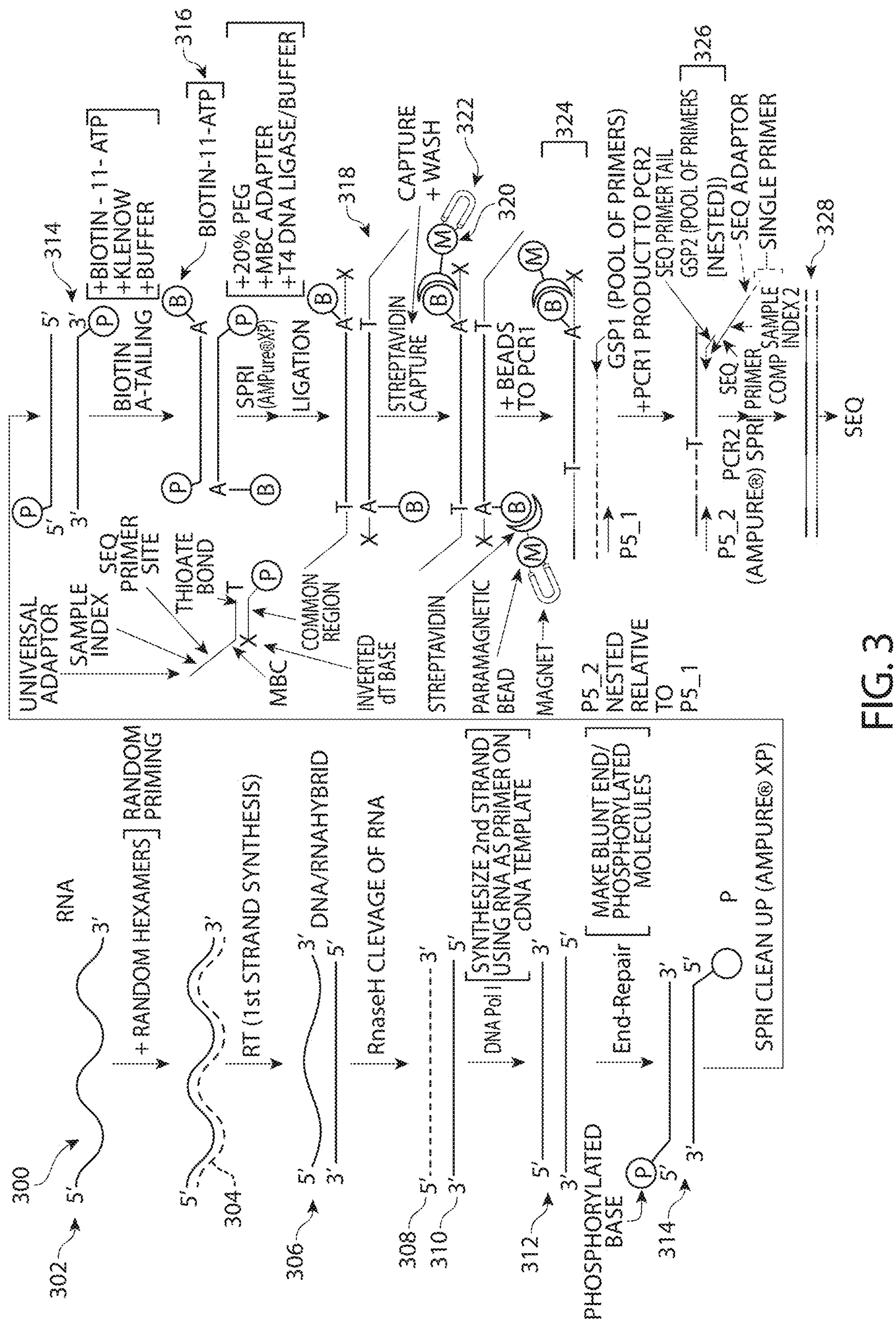
FIG. 3 depicts a process of generating a double-stranded cDNA sample using a template RNA strand.
Figure 4:
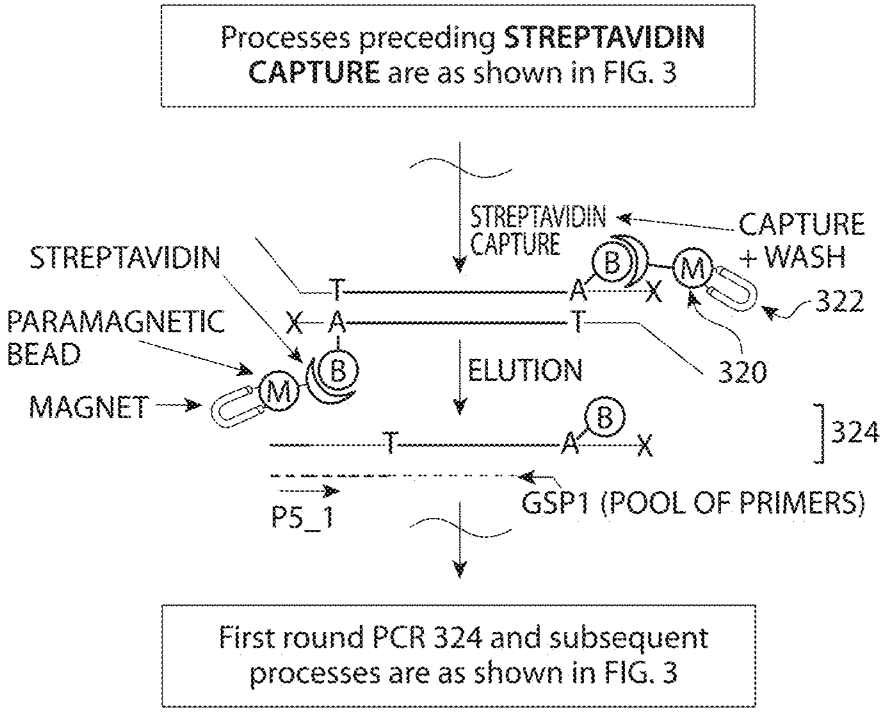
FIG. 4 depicts a process of generating a double-stranded cDNA sample using a template RNA strand, where captured ligation product is eluted from magnetic beads prior to amplification.
Figure 5:
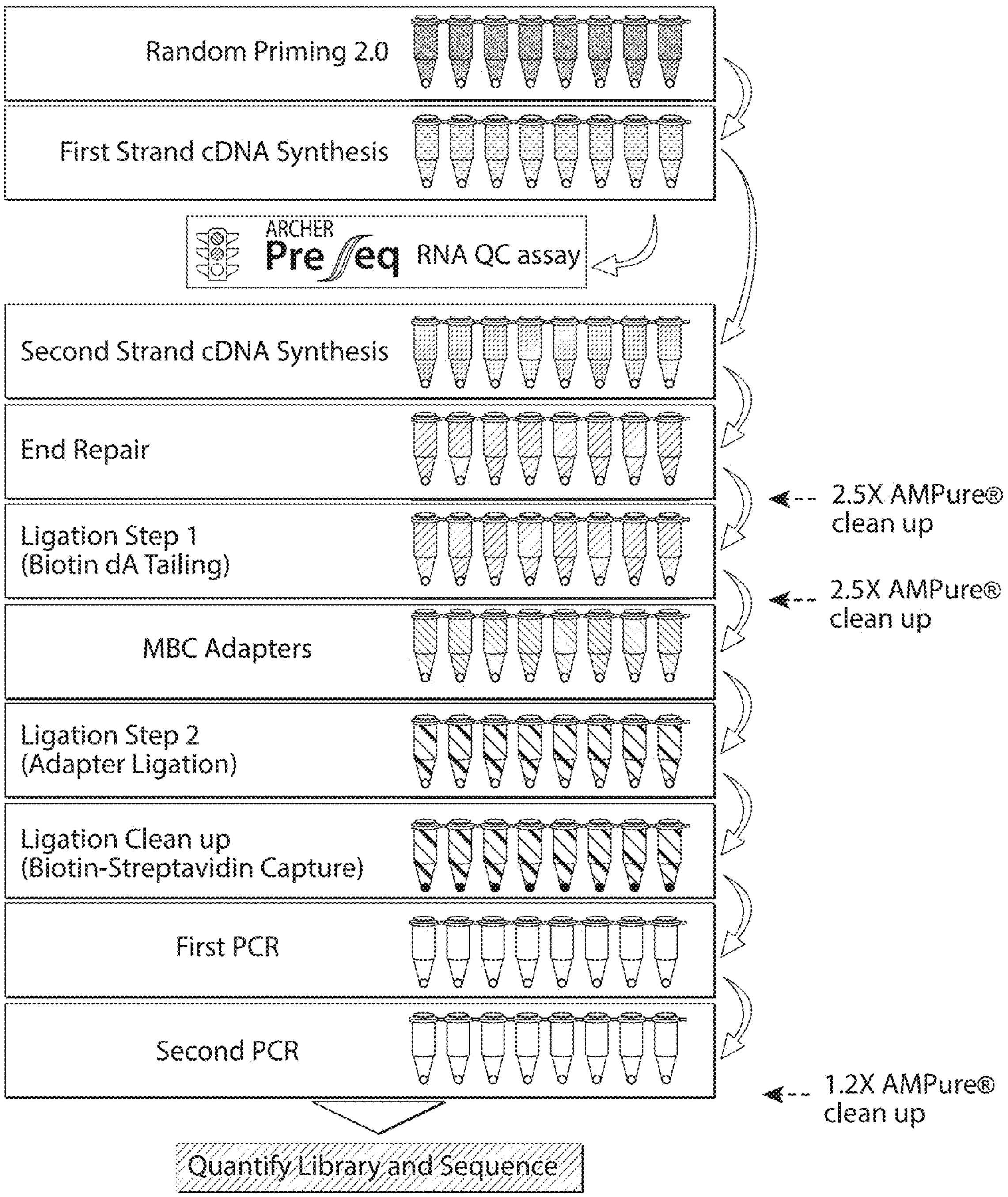
FIG. 5 is a depiction of a workflow for a method of preparing a high-fidelity nucleic acid sample for analysis.

As shown in FIG. 3, in some embodiments, the captured adapter-ligated nucleic acid is subjected to a first round of PCR 324 in the form of a bead-immobilized product. In yet other embodiments, as shown in FIG. 4, the captured adapter-ligated nucleic acid is eluted from the paramagnetic bead 320 prior to first round PCR 324. Elution of captured adapter-ligated nucleic acids from the beads can be performed, by way of example and not limitation, using a chemical reagent and/or heat. In some embodiments, the chemical reagent is a base (e.g., NaOH). In some embodiments, captured adapter-ligated nucleic acid is eluted with a low concentration (e.g., less than 1 M, less than 0.5 M, less than 0.1 M, less than 0.05 M, less than 0.01 M, less than 0.001 M, less than 0.0001 M) of NaOH. In some embodiments, captured adapter-ligated nucleic acid is eluted with a low concentration of NaOH and heat.

The immobilized (e.g., as in FIG. 3) or eluted (e.g., as in FIG. 4) adapter-ligated nucleic acid is subjected to a first round of PCR 324 using a first gene-specific primer ("GSP1") that specifically anneals to the target nucleotide sequence and a first adapter primer ("P5_1") that specifically anneals to a complementary sequence of the adapter nucleic acid. In this way, P5_1 primes off of the strand generated by GSP1. As shown, in some embodiments, GSP1 (e.g., a first target-specific primer) is tailed with a 5' region that does not hybridize with the target nucleotide sequence. In some embodiments, a 5' tail region can prevent primer dimers, e.g., by having a sequence content that minimizes the occurrence of primer dimers. In some embodiments, GSP1 is not tailed with the 5' tailed region. As further shown in FIG. 3, a second round of PCR 326 is conducted using a second gene-specific primer ("GSP2") and a second adapter primer ("P5_2"). As shown, GSP2 is nested relative to GSP1. Also as shown, GSP2 is tailed with a 5' region that does not hybridize with the target nucleotide sequence. In a similar fashion to the first round of PCR, P5_2 primes off of the strand generated by GSP2. In this second round of PCR, an additional primer ("SINGLE PRIMER") is included that contains (i) a 3' region that is identical to at least a portion of the tailed 5' region of GSP2 and (ii) a 5' region that contains additional elements useful for sequencing, such as a sequencing primer binding site and a sample index. After P5_2 generates a sense strand from the complementary strand generated by GSP2, the additional primer then primes off of the now complementary sequence of the GSP2 tailed region to generate the sequencing-ready product 328.

In some embodiments, the techniques described herein allow for the enrichment of target nucleotide sequences from a nucleic acid sample. In some embodiments, the nucleic acid sample comprises genomic DNA. In some embodiments, the nucleic acid sample comprises cDNA. In some embodiments, cDNA may be prepared by conducting a first strand synthesis reaction using a capture moiety modified primer that anneals to a target nucleic acid and conducting a second strand synthesis reaction using a fragment of the target nucleic acid as a primer.

Adding Capture Moiety in Strand Synthesis

As described herein, a target nucleic acid molecule (e.g., mRNA) comprising a known target nucleotide sequence is contacted with a target-specific primer and extended in a first strand synthesis reaction using the nucleic acid molecule as a template. In some embodiments, the first strand synthesis reaction may be conducted such that a product of the first strand synthesis reaction comprises a capture moiety, and a binding partner of the capture moiety can be used to capture (e.g., isolate) the product. Accordingly, aspects of the disclosure provide techniques useful for enriching for the product of the first strand synthesis that is complementary to the initial input comprising the target nucleic acid molecule (e.g., mRNA).

In some aspects, the disclosure relates to the recognition that incorporation of a capture moiety into a first strand synthesized from a target nucleic acid molecule (e.g., RNA) during library preparation minimizes the presence of non-target nucleic acids during enrichment for nucleic acids comprising a target nucleotide sequence. This may be particularly advantageous when preparing nucleic acid libraries for immune repertoire sequencing. For example, although TCR and BCR genomic sequences will be present in all cells, the TCR and BCR mRNA will only be expressed in T cells and B cells, respectively. Evaluation of the immune repertoire relies on analyzing these genes after processing (e.g., recombination, splicing, etc.) to evaluate the sequence landscape present in a system. Accordingly, in some embodiments, techniques provided herein permit selective capture of mRNAs expressed from recombined immune loci. For example, as described herein, when a first strand is synthesized directly from a target nucleic acid, the capture moiety allows for enrichment of the desired product while minimizing non-target nucleic acid carryover.

In some aspects, the disclosure provides a method of preparing nucleic acids for analysis, comprising synthesizing a first nucleic acid strand using a capture moiety modified primer and a nucleic acid molecule comprising a target nucleotide sequence as a template, ligating an adapter nucleic acid to the first nucleic acid strand, and capturing the adapter-ligated first nucleic acid strand with a binding partner of the capture moiety.

Figure 41:
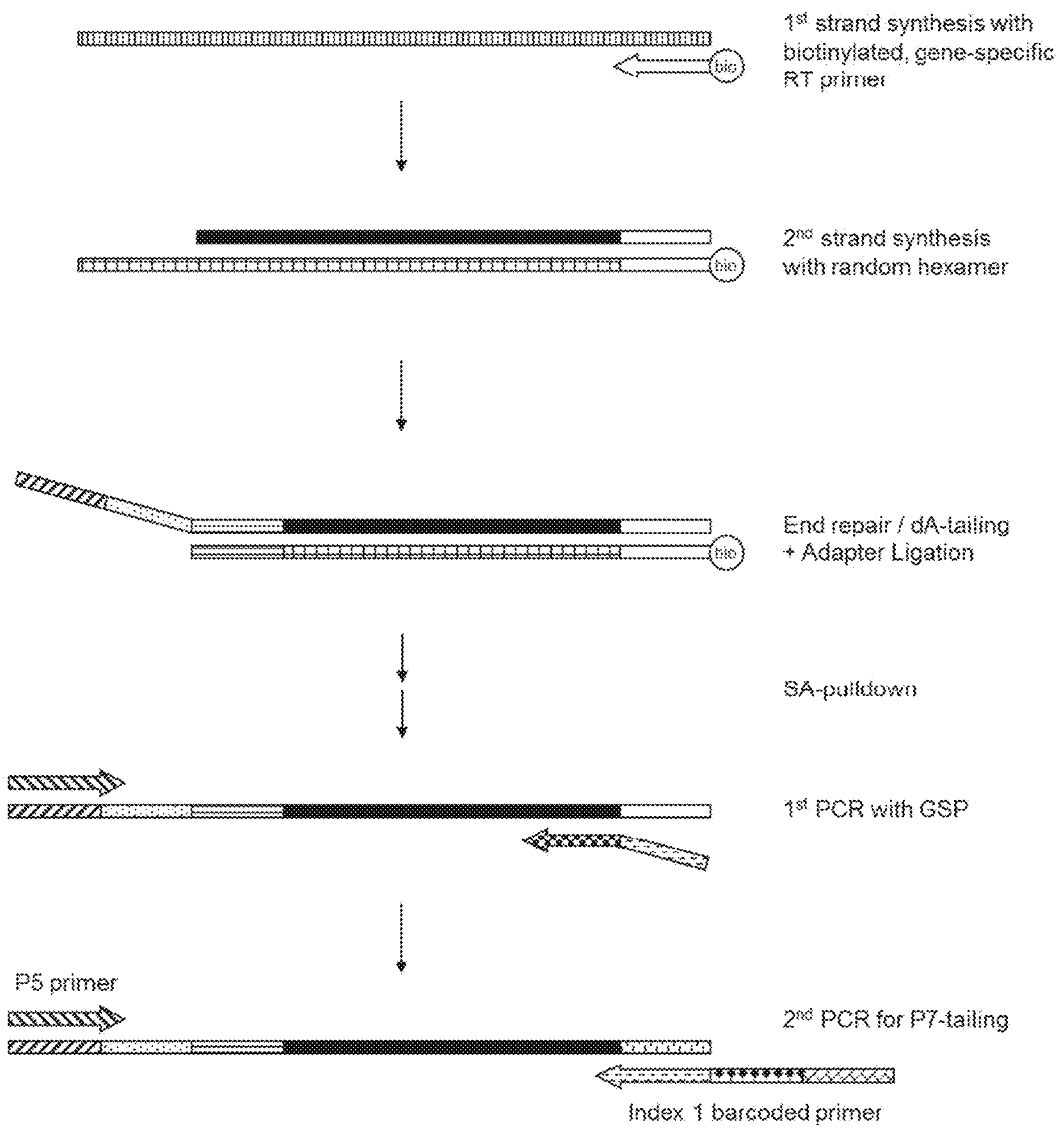
FIG. 41 is an illustration of a strategy for preparing a nucleic acid molecule for analysis using a capture moiety modified primer.

In some embodiments, the capture moiety modified primer is a biotin moiety modified primer. A depiction of this method is shown in FIG. 41, which provides a non-limiting example of a method involving a biotin moiety modified primer. In this embodiment, an RNA molecule (e.g., mRNA) is annealed with a DNA primer that is modified to comprise a biotin moiety. The biotin moiety modified primer is extended in a first strand synthesis reaction to generate a DNA/RNA hybrid. The RNA of the DNA/RNA hybrid is subjected to degradation via the action of a ribonuclease, and the RNA fragments that remain annealed to the DNA serve as primers in a second strand synthesis reaction to generate a double-stranded cDNA. In some embodiments, the second strand synthesis reaction of may be primed by any nucleic acid fragment present in a sample comprising the nucleic acid molecule. For example, in some embodiments, the sample comprises a complex mixture of nucleic acids that are capable of dissociating from a complementary strand and re-annealing to a different strand present within the mixture. The double-stranded cDNA is subjected to end repair and dA-tailing to generate 3' overhangs suitable for a ligation reaction. Following ligation of an adapter nucleic acid to the double-stranded cDNA, these library molecules are captured, or isolated, from unligated adapter using a streptavidin-coated substrate (e.g., a paramagnetic substrate).

In some embodiments, following the capture, a first round of PCR amplification of the substrate-immobilized, captured adapter-ligated double-stranded cDNA is conducted. In yet other embodiments, the captured adapter-ligated double-stranded cDNA is eluted from the paramagnetic substrate prior to first round PCR. Elution of captured adapter-ligated nucleic acids from paramagnetic substrates can be performed, by way of example and not limitation, using a chemical reagent and/or heat. In some embodiments, the chemical reagent is a base (e.g., NaOH). In some embodiments, captured adapter-ligated double-stranded cDNA is eluted with a low concentration (e.g., less than 1 M, less than 0.5 M, less than 0.1 M, less than 0.05 M, less than 0.01 M, less than 0.001 M, less than 0.0001 M) of NaOH. In some embodiments, captured adapter-ligated double-stranded cDNA is eluted with a low concentration of NaOH and heat.

The immobilized or eluted adapter-ligated double-stranded cDNA is subjected to a first round of PCR amplification using a first adapter primer that anneals to a complement of the adapter and a target specific primer that hybridizes to a target nucleotide sequence and has a non-hybridized tail region comprising a common sequence. In this way, the first adapter primer primes off of the strand generated by the target specific primer. A second round of PCR amplification is conducted using a tail primer that anneals to a complement of the common sequence and a second adapter primer that anneals to a complement of the adapter. As shown, the tail primer includes an index 1 barcoded primer. In some embodiments, the tail primer includes an index 2 barcoded primer. In some embodiments, the adapter nucleic acid includes an index 1 primer and the tail primer includes an index 2 primer.

In some aspects, the disclosure provides a method of preparing nucleic acids for analysis, comprising contacting a primer-hybridized nucleic acid molecule comprising a target nucleotide sequence with a capture moiety modified nucleotide for incorporation into a newly synthesized strand, subjecting the mixture to extension conditions to synthesize a first nucleic acid strand comprising at least one capture moiety modified nucleotide, ligating an adapter nucleic acid to the first nucleic acid strand, and capturing the adapter-ligated first nucleic acid strand with a binding partner of the capture moiety.

Figure 42:
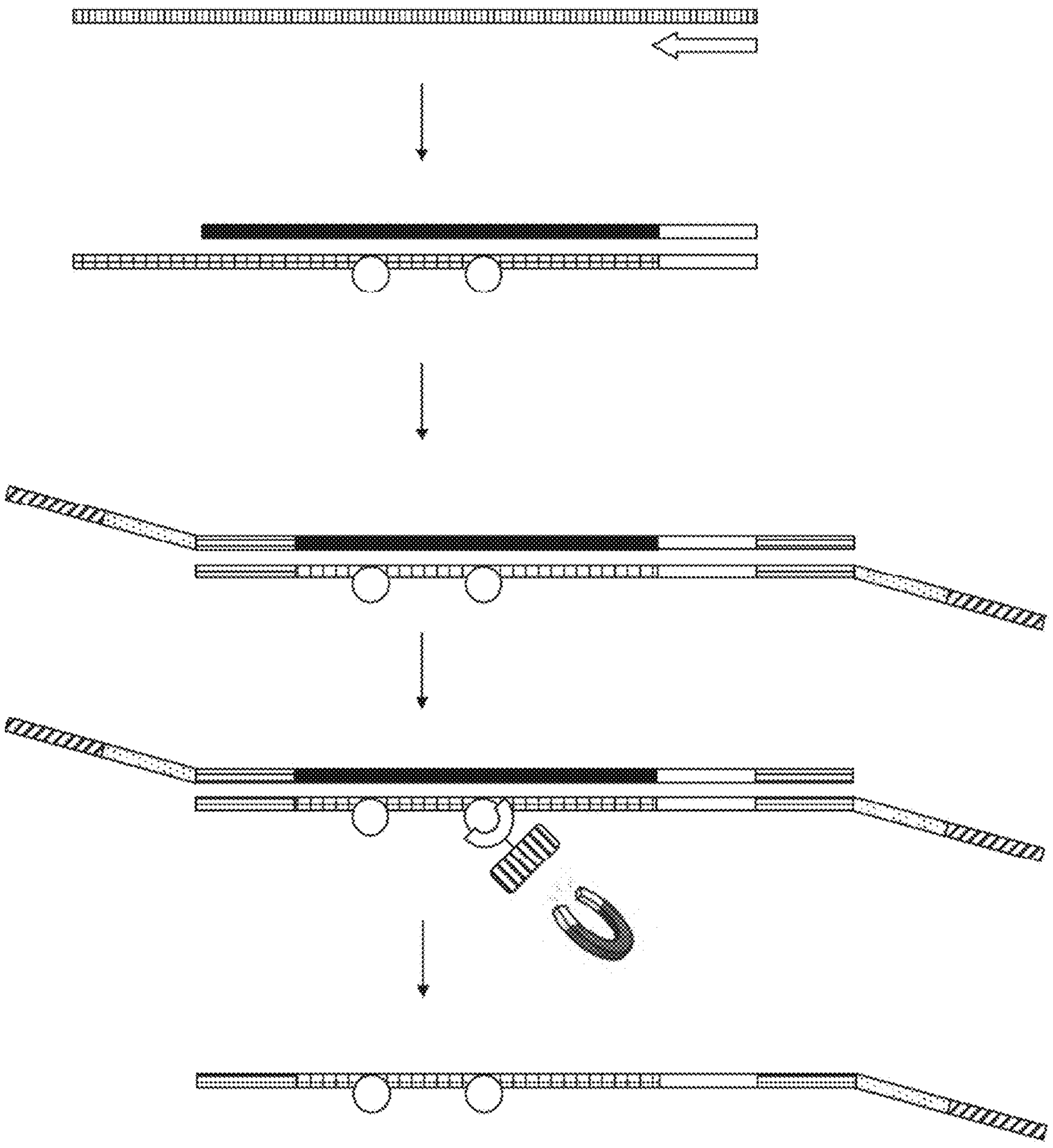
FIG. 42 is an illustration of a strategy for preparing a nucleic acid molecule for analysis using capture moiety modified nucleotides.

In some embodiments, the capture moiety of the capture moiety modified nucleotide is a biotin moiety. For example, FIG. 42 depicts a non-limiting embodiment of a method involving the use of biotin-modified nucleotides. In this embodiment, an RNA molecule (e.g., mRNA) is annealed with a DNA primer. A first strand synthesis reaction is conducted using biotinylated nucleotides to generate a biotinylated DNA/RNA hybrid. The RNA of the DNA/RNA hybrid is subjected to degradation via the action of a ribonuclease, and the RNA fragments that remain annealed to the DNA serve as primers in a second strand synthesis reaction to generate a double-stranded cDNA. In some embodiments, the second strand synthesis reaction of may be primed by any nucleic acid fragment present in a sample comprising the nucleic acid molecule. For example, in some embodiments, the sample comprises a complex mixture of nucleic acids that are capable of dissociating from a complementary strand and re-annealing to a different strand present within the mixture. The double-stranded cDNA is subjected to end repair and dA-tailing to generate 3' overhangs suitable for a ligation reaction. Following ligation of an adapter nucleic acid to the double-stranded cDNA, these library molecules are captured, or isolated, from unligated adapter using a streptavidin coated paramagnetic bead.

Figure 43:
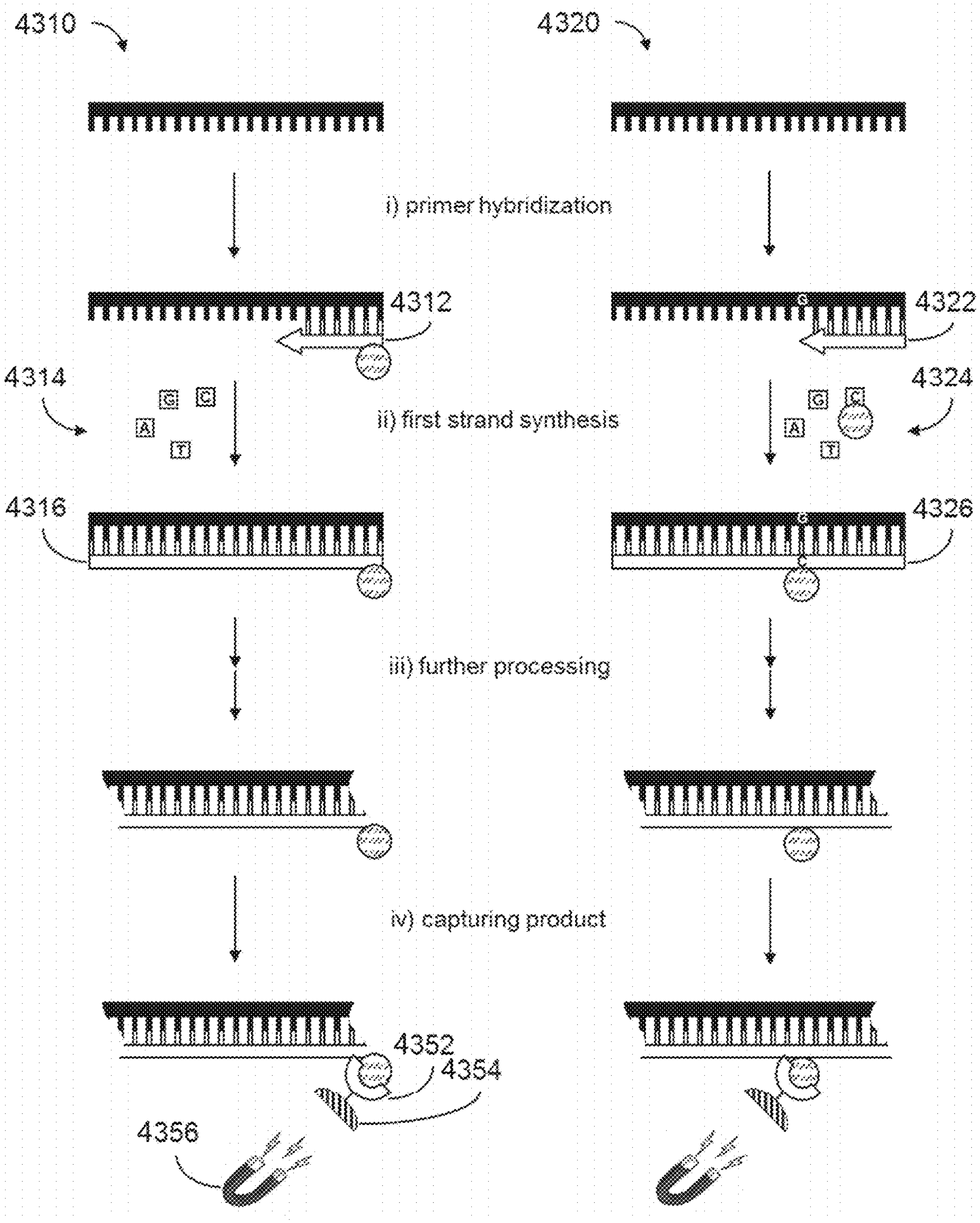
FIG. 43 illustrates a comparison of nucleic acid preparation strategies using either a capture moiety modified primer or capture moiety modified nucleotides.

As described in the foregoing, aspects of the disclosure provide techniques for preparing a nucleic acid molecule for analysis which can involve the use of a capture moiety to capture a nucleic acid product generated during a preparative process. FIG. 43 is an illustration that compares different strategies for nucleic acid preparation using capture moieties. Selected preparation steps are shown for a first process 4310 which incorporates a capture moiety into a nucleic acid product using a capture moiety modified primer (e.g., as illustrated in FIG. 41) and for a second process 4320 which incorporates a capture moiety into a nucleic acid product using capture moiety modified nucleotides (e.g., as illustrated in FIG. 42). In each of the first process 4310 and second process 4320, a nucleic acid molecule is exposed to a target specific primer under conditions to promote primer hybridization (step i). As shown, the target specific primer of the first process 4310 is a capture moiety modified primer 4312, while the target specific primer of the second process 4320 utilizes a first target specific primer 4322 that does not include a capture moiety modification.

Following primer hybridization, a first strand synthesis reaction (step ii) is performed in the first process 4310 using a plurality of types of nucleotides 4314 for incorporation into a newly synthesized first strand 4316 using the nucleic acid molecule as a template. By comparison, a first strand synthesis reaction (step ii) is performed in the second process 4320 using a plurality of types of nucleotides 4324, of which at least one of the plurality is a capture moiety modified nucleotide. By way of example and not limitation, a C nucleotide is shown having a capture moiety modification. In this way, during first strand synthesis using the nucleic acid molecule as a template, the capture moiety modified nucleotide is incorporated into the newly synthesized first strand 4326 at a position complementary to a G nucleotide in the nucleic acid molecule.

Following first strand synthesis in either of the first process 4310 or second process 4320, a nucleic acid comprising the capture moiety is optionally subjected to further processing (step iii) that involves additional modifications to the nucleic acid. Examples of further processing can include, without limitation, second strand synthesis, end-repair, adapter ligation, and other processing steps described elsewhere herein. Following the optional further processing in either of the first process 4310 or second process 4320, a nucleic acid product comprising the capture moiety is contacted with a binding partner of the capture moiety for the purpose of capturing the nucleic acid product (step iv) generated from either process. As shown, product capture can be performed using a binding partner 4352 of the capture moiety, which is optionally immobilized to a substrate 4354. Where the substrate 4354 is a paramagnetic substrate, the nucleic acid product can be isolated by exposure to a magnetic field 4356.

In some aspects, the disclosure provides a method of preparing a nucleic acid library for analysis of an immune repertoire. For example, in some embodiments, the nucleic acid library is prepared from a sample comprising a nucleic acid sequence encoding an immune receptor (e.g., a TCR), an immunoglobulin (e.g., a BCR), or a mixture thereof.

Cell-Free DNA

Among other aspects, the disclosure relates to the preparation of cell-free DNA for analysis. Cell-free DNA (cfDNA) is DNA circulating freely in bodily fluids such as circulating blood, urine, lymph, interstitial fluid, etc. In some embodiments, cfDNA may be extracted from bodily fluids, such as blood, plasma, and urine. In some embodiments, cfDNA may be arise from apoptotic cells, necrotic cells, and intact cells that are released into the bloodstream or other bodily fluid and eventually lysed.

In some embodiments, preparative techniques described herein may be useful for analysis and sequencing of cfDNA, e.g., in connection with screening tests. In some embodiments, cell-free DNA screening tests can also be used to screen for tumor DNA, for example, as present in the blood of a cancer patient. Analyzing the fraction of mutant-alleles from cell-free tumor DNA (ctDNA) compared to normal alleles from the patient's genome provides opportunities for minimally-invasive cancer diagnosis, prognosis, and tumor monitoring. Furthermore, cfDNA in serum and plasma is usually composed primarily of cell-free DNA fragments derived from healthy cells. In cancer patients, ctDNA can be detected with a higher signal-to-noise ratio than whole blood for non-invasive diagnostics.

In some embodiments, suitable protocols for extraction of cfDNA from bodily fluids may be used to obtain a cfDNA sample to be used in preparative methods described herein. For example, in some embodiments, a suitable protocol for isolation of cfDNA from blood may include centrifugation of a blood, serum or plasma sample, followed by isolation and purification of cell-free DNA from the sample. In some embodiments, similar steps may be performed for analyzing cell-free tumor DNA, in which blood may be processed, e.g., by centrifugation, to remove all cells, and the remaining sample may be processed to obtain cfDNA and/or further analyzed.

In some embodiments, techniques described herein may be useful for evaluating tumor DNA and mutation detection. In some embodiments, tumor tissue may be evaluated to detect cell-free tumor DNA. Cell-free tumor DNA can be present in a wide range of cancers but occurs at different levels and mutant allele fractions. For example, it has been reported that cell-free tumor DNA is highly fragmented to around 170 bp. In some embodiments, it may be observed that platelets isolated from healthy individuals take up RNA-containing membrane vesicles from cancer cells. In some embodiments, cell-free tumor DNA molecules are released by tumor cells and circulate in the blood of cancer patients. In some embodiments, assays using these molecules can be used for early tumor detection, monitoring, or detection of resistance mutations.

In some embodiments, cell-free fetal DNA (cffDNA) originates in trophoblasts, which may be found, e.g., in placenta. Thus, in some embodiments, non-invasive prenatal testing (NIPT) may be used to screen for fetal abnormalities in the X and Y chromosomes and to determine if a woman is at high risk of having a fetus with Down's syndrome (trisomy 21), trisomy 18, or trisomy 13. In some embodiments, techniques described herein may be useful for preparing samples of fetal DNA and mutation detection. For example, studies generally focus on detecting paternally inherited sequences to detect fetal DNA. This can be conducted, in some embodiments, using primers that have been designed to target the Y chromosome of male fetuses for polymerase chain reaction (PCR).

In some embodiments, differences in gene activation between maternal DNA and fetal DNA can be exploited. In some embodiments, epigenetic modifications may be made to detect cell-free fetal DNA. In some embodiments, a hypermethylated RASSFIA promoter can be used as a universal fetal marker to confirm the presence of cell-free fetal DNA.

In some embodiments, mRNA transcripts from genes expressed in the placenta are detectable in maternal plasma. In some embodiments, isolating a cfDNA sample comprises centrifuging the mixture of plasma and transferring the aqueous layer. In some embodiments, RNA is extracted and RT-PCR is set up for selected RNA expression. In some embodiments, hPL and beta-hCG mRNA are stable in maternal blood. In some embodiments, the presence of fetal DNA in the maternal plasma may be determined by any suitable means. In some embodiments, cfDNA samples are evaluated to detect target sequences for one or more of the following genes: AKTI, ALK, BRAF, CTNBB1, DDR2, EGFR, ERBB2, ESR1, FGFR1, HRAS, IDH1, IDH2, KIT, KRAS, MAP2K1, MAP2K2, MET, NRAS, NTRK1, NTRK3, PDGFRA, PIK3CA, RET, ROS1, SMAD4, and TP53. However, it should be appreciated that any gene of a genome may be targeted for analysis.

Immune Repertoire

As the adaptive immune system functions in part by clonal expansion of cells expressing unique antigen binding molecules, accurately measuring the changes in total abundance of each T cell or B cell clone is important to understanding the dynamics of an adaptive immune response. Utilizing advances in high-throughput sequencing, a new field of molecular immunology has recently emerged to profile the vast TCR and BCR repertoires. In some embodiments, techniques described herein are useful for analyzing an immune cell clonotype.

As used herein, a "clonotype" refers to a successfully recombined nucleotide sequence that arises during a rearrangement process for one or more genes that encode an immune receptor chain or a portion thereof. In some embodiments, a "successfully recombined nucleotide sequence" refers to a nucleotide sequence that is comprised by mRNA and has undergone genetic recombination to produce a unique clonotype. Accordingly, in some embodiments, techniques provided in the present disclosure may be useful for detecting a successful rearrangement of an IR loci that is expressed as mRNA, but not an IR rearrangement per se. In some embodiments, a clonotype refers to a nucleotide sequence that corresponds to an mRNA encoding a single receptor chain. In some embodiments, techniques provided in the present disclosure may be useful for detecting one or more somatic hypermutations. In some embodiments, techniques provided in the present disclosure may be useful for detecting TCR and/or BCR isotypes (e.g., A, D, E, G, and M IgH isotypes, and select subclasses thereof). In some embodiments, a clonotype is a recombined nucleotide sequence of a T cell or B cell. In some embodiments, a clonotype encodes a TCR or BCR, or a portion thereof. In some embodiments, clonotypes may encode all or a portion of a VDJ rearrangement of IgH, a DJ rearrangement of IgH, a VJ rearrangement of IgK, a VJ rearrangement of IgL, a VDJ rearrangement of TCR β, a DJ rearrangement of TCR β, a VJ rearrangement of TCR α, a VJ rearrangement of TCR γ, a VDJ rearrangement of TCR δ, a VD rearrangement of TCR δ, a kappa deleting element (KDE) rearrangement, or the like. In some embodiments, clonotypes have sequences that are sufficiently long to represent or reflect the diversity of the immune molecules from which they are derived. Accordingly, in some embodiments, clonotypes may vary widely in length. In some embodiments, methods of the disclosure are useful for determining a clonotype profile.

As used herein, a "clonotype profile" refers to a listing of distinct clonotypes and their relative abundances that are derived from a population of lymphocytes. In some embodiments, the population of lymphocytes is obtained from a tissue sample. A clonotype profile is related to the immunology concept of "immune repertoire." In some embodiments, a clonotype profile includes a wide variety of lists and abundances of rearranged immune receptor-encoding nucleic acids, which may be derived from selected subsets of lymphocytes (e.g. tissue-infiltrating lymphocytes, immunophenotypic subsets, or the like), or which may encode portions of immune receptors that have reduced diversity as compared to full immune receptors. In some embodiments, clonotype profiles may comprise at least $10^3$ distinct clonotypes, at least $10^4$ distinct clonotypes, at least $10^5$ distinct clonotypes, at least $10^6$ distinct clonotypes, or at least $10^7$ distinct clonotypes. In some embodiments, clonotype profiles may comprise between about 1 and 500,000 distinct clonotypes. In some embodiments, clonotypes may comprise between about 1 and 1,000,000 distinct clonotypes (e.g., between about 1 and about 100,000, between about 100,000 and about 200,000, between about 200,000 and about 300,000, between about 300,000 and about 400,000, between about 400,000 and about 500,000, between about 500,000 and about 600,000, between about 600,000 and about 700,000, between about 700,000 and about 800,000, between about 800,000 and about 900,000, between about 900,000 and about 1,000,000 distinct clonotypes). In some embodiments, such clonotype profiles may further comprise abundances or relative frequencies of each of the distinct clonotypes. In one aspect, a clonotype profile is a set of distinct recombined nucleotide sequences (with their abundances) that encode TCRs or BCRs, or fragments thereof, respectively, in a population of lymphocytes of an individual, wherein the nucleotide sequences of the set have a one-to-one correspondence with distinct lymphocytes or their clonal subpopulations for substantially all of the lymphocytes of the population. In one aspect, nucleic acid segments defining clonotypes are selected so that their diversity (e.g., the number of distinct nucleic acid sequences in the set) is large enough so that substantially every T cell or B cell or clone thereof in an individual carries a unique nucleic acid sequence of such repertoire. That is, preferably each different clone of a sample has different clonotype. In other aspects, the population of lymphocytes corresponding to a repertoire may be circulating B cells, or may be circulating T cells, or may be subpopulations of either of the foregoing populations, including but not limited to, CD4+ T cells, or CD8+ T cells, or other subpopulations defined by cell surface markers, or the like. In some embodiments, such subpopulations may be acquired by taking samples from particular tissues, e.g. bone marrow, or lymph nodes, or the like, or by sorting or enriching cells from a sample (such as peripheral blood) based on one or more cell surface markers, size, morphology, or the like. In still other aspects, the population of lymphocytes corresponding to a repertoire may be derived from disease tissues, such as a tumor tissue, an infected tissue, or the like. In some embodiments, a clonotype profile comprising nucleic acids corresponding to TCR and/or BCR chains or fragments thereof comprises a number of distinct nucleotide sequences in the range of from about 1 to about 25, about 25 to about 50, about 50 to about 100, about 11 to about 250, about 250 to about 500, about 500 to about 1000, about 1000 to about 2500, about 2500 to about 5000, about 5000 to about 7500, about 7500 to about 10000, about 10000 to about 25000, about 25000 to about 50000, about 50000 to about 100000, about 100000 to about 250000, about 250000 to about 500000, about 500000 to about 750000, about 750000 to about 1000000.

In some embodiments, a clonotype profile comprises a set of nucleotide sequences encoding substantially all segments of the V(D)J region of a BCR (e.g., an IgH chain). In one aspect, "substantially all" as used herein means every segment having a relative abundance of 0.0001 percent or higher, 0.0005 percent or higher, 0.001 percent or higher, 0.005 percent or higher, 0.01 percent or higher, 0.05 percent or higher, or 0.1 percent or higher; or in another aspect, "substantially all" as used herein means every segment having a relative abundance of 0.0001 percent or higher. In some embodiments, not all V, D, and J segments are represented. In another embodiment, a clonotype profile comprises a set of nucleotide sequences that encodes substantially all segments of the V(D)J region of a TCR (e.g., TCR β chain, TCR δ chain). In another embodiment, a clonotype profile comprises a set of nucleotide sequences having lengths in the range of from 1-25, 1-50, 1-100, 1-200, 1-300, 1-400, 1-450, 1-500, 25-100, 25-200, 25-300, 25-400, 25-450, 25-500, 100-200, 100-300, 100-400, 100-450, 100-500, 200-300, 200-400, 200-450, 200-500, 300-400, 300-450, 300-500, 400-450, 400-500, 450-500, or more nucleotides and including segments of the V, D, and J regions of a TCR (e.g., TCR β chain, TCR δ chain). In another embodiment, a clonotype profile comprises a set of nucleotide sequences having lengths in the range of from 1-25, 1-50, 1-100, 1-200, 1-300, 1-400, 1-450, 1-500, 25-100, 25-200, 25-300, 25-400, 25-450, 25-500, 100-200, 100-300, 100-400, 100-450, 100-500, 200-300, 200-400, 200-450, 200-500, 300-400, 300-450, 300-500, 400-450, 400-500, 450-500, or more nucleotides and including segments of the V. D, and J regions of a BCR (e.g., an IgH chain). In another embodiment, a clonotype profile comprises a number of distinct nucleotide sequences that is substantially equivalent to the number of lymphocytes expressing a distinct BCR (e.g., IgH chain, Ig light chain, e.g., IgK (kappa) chain, IgL (lambda) chain). In another embodiment, a clonotype profile comprises a number of distinct nucleotide sequences that is substantially equivalent to the number of lymphocytes expressing a distinct TCR (e.g., TCR β chain, TCR δ chain, TCR α chain, TCR γ chain). In still another embodiment, "substantially equivalent" means that with 99 percent probability a clonotype profile will include a nucleotide sequence encoding a BCR (e.g., IgH, IgK, IgL) or TCR (e.g., TCR β, TCR δ, TCR α, TCR γ) or portion thereof carried or expressed by every lymphocyte of a population of an individual. In still another embodiment, "substantially equivalent" means that with 99 percent probability a repertoire of nucleotide sequences will include a nucleotide sequence encoding a BCR (e.g., IgH, IgK, IgL) or TCR (e.g., TCR β, TCR δ, TCR α, TCR γ) or portion thereof carried or expressed by every lymphocyte present in a sample.

In some embodiments, clonotype profiles are obtained from samples of immune cells, which are present in a wide variety of tissues. In some embodiments, immune cells of interest include T cells and/or B cells. In some embodiments, T cells (T lymphocytes) include, for example, cells that express TCRs. In some embodiments, B cells (B lymphocytes) include, for example, cells that express BCRs. In some embodiments, T-cells include helper T cells (effector T cells or Th cells), cytotoxic T cells (CTLs), memory T cells, and regulatory T cells, which may be distinguished by cell surface markers. In some embodiments, a sample of immune cells may also comprise B cells. In some embodiments, B cells include, for example, plasma B cells, memory B cells, B1 cells, B2 cells, marginal-zone B cells, and follicular B cells. B cells can express immunoglobulins (also referred to herein as antibodies or B cell receptors).

T-Cell Receptors

The adaptive immune system employs several strategies to generate a repertoire of T and B cell antigen receptors (e.g., adaptive immune receptors) with sufficient diversity to recognize the universe of potential pathogens. The ability of T cells to recognize the universe of antigens associated with various cancers or infectious organisms is conferred by its TCR, which is a heterodimer of an a (alpha) chain from the TCRA locus and β (beta) chain from the TCRB locus, or a heterodimer of a γ (gamma) chain from the TCRG locus and a δ (delta) chain from the TCRD locus. The proteins which make up these chains are encoded by DNA, which in lymphoid cells employs a unique rearrangement mechanism for generating the tremendous diversity of the TCR. This multi-subunit immune recognition receptor associates with the CD3 complex and binds to peptides presented by either the major histocompatibility complex (MHC) class I or MHC class II proteins on the surface of antigen-presenting cells (APCs). Binding of TCR to the antigenic peptide on the APC is the central event in T cell activation, which occurs at an immunological synapse at the point of contact between the T cell and the APC.

Each TCR peptide contains variable complementarity determining regions (CDRs), as well as framework regions (FRs) and a constant region. The sequence diversity of αßT cells is largely determined by the amino acid sequence of the third complementarity-determining region (CDR3) loops of the α and β chain variable domains, which diversity is a result of recombination between variable (Vβ), diversity (Dβ), and joining (Jβ) gene segments in the β chain locus, and between analogous Jα and Jα gene segments in the α chain locus, respectively. The existence of multiple such gene segments in the TCR α and β chain loci allows for a large number of distinct CDR3 sequences to be encoded. CDR3 sequence diversity is further increased by independent addition and deletion of nucleotides at the Vβ-Dβ, Dβ-Jβ, and Vα-Jα junctions during the process of TCR gene rearrangement. In this respect, immunocompetence is derived from the diversity of TCRs.

The γδ TCR heterodimer is distinctive from the αβ TCR in that it encodes a receptor that interacts closely with the innate immune system, and recognizes antigen in a non-HLA-dependent manner. TCR γδ is expressed early in development, and has specialized anatomical distribution, unique pathogen and small-molecule specificities, and a broad spectrum of innate and adaptive cellular interactions. A biased pattern of TCRγ V and J segment expression is established early in ontogeny. Consequently, the diverse TCRγ repertoire in adult tissues is the result of extensive peripheral expansion following stimulation by environmental exposure to pathogens and toxic molecules.

Processes for generating diversity of a TCR are similar to those described for immunoglobulins. The TCR α chain is generated by VJ recombination, while the β chain is generated by V(D)J recombination. Similarly, generation of the TCR γ chain involves VJ recombination, while generation of the TCR δ chain occurs by V(D)J recombination. The intersection of these specific regions (V and J for the α or γ chain, V D and J for the β or δ chain) corresponds to the CDR3 region that is important for antigen-MHC recognition. It is the unique combination of the segments at this region, along with palindromic and random N- and P-nucleotide additions, which accounts for the TCR binding repertoire. Additionally, the CDR3 region begins with the second conserved cysteine in the 3' region of the vβ gene and ends with the conserved phenylalanine encoded by the 5' region of the Iβ gene. Thus, amplified sequences can be informatically translated to locate the conserved cysteine, obtain the intervening peptide sequence, and tabulate counts of each unique clone in the sample.

B-Cell Receptors

Immunoglobulins (Igs), also referred to herein as B cell receptors (BCR), are proteins expressed by B cells consisting of four polypeptide chains, two heavy chains (H chains) from the IGH locus and two light chains (L chains) from either the IGK or the IGL locus, forming an H2L2 structure. H and L chains each contain three CDRs involved in antigen recognition, as well as framework regions and a constant domain, analogous to TCR. The H chains of Igs are initially expressed as membrane-bound isoforms using either the IGM or IGD constant region exons, but after antigen recognition the constant region can class-switch to several additional isotypes, including IGG, IGE and IGA. As with TCR, the diversity of naïve Igs within an individual is mainly determined by the hypervariable CDRs. Similar to TCRB, the CDR3 domain of H chains is created by the combinatorial joining of the VH, DH, and JH gene segments. Hypervariable domain sequence diversity is further increased by independent addition and deletion of nucleotides at the VH-DH, DH-JH, and VH-JH junctions during the process of Ig gene rearrangement. Distinct from TCR, Ig sequence diversity is further augmented by somatic hypermutation (SHM) throughout the rearranged IG gene after a naïve B cell initially recognizes an antigen. The process of SHM is not restricted to CDR3, and therefore can introduce changes to the germline sequence in framework regions, CDR1 and CDR2, as well as in the somatically rearranged CDR3.

In some aspects, the DNA and RNA analyzed in the methods described herein can correspond to sequences encoding heavy chain immunoglobulins (IgH) with constant regions (α, δ, ε, γ, or μ) or light chain immunoglobulins (IgK or IgL) with constant regions (λ or κ). Each antibody has two identical light chains and two identical heavy chains. Each chain is composed of a constant (C) and a variable region. For the heavy chain, the variable region is composed of variable (V), diversity (D), and joining (J) segments. Several distinct sequences coding for each type of these segments are present in the genome. A specific VDJ recombination event occurs during the development of a B-cell, marking that cell to generate a specific heavy chain. Diversity in the light chain is generated in a similar fashion except that there is no D region so there is only VJ recombination. Somatic mutation often occurs close to the site of the recombination, causing the addition or deletion of several nucleotides, further increasing the diversity of heavy and light chains generated by B-cells. The possible diversity of the antibodies generated by a B-cell is then the product of the different heavy and light chains. The variable regions of the heavy and light chains contribute to form the antigen recognition (or binding) region or site. Added to this diversity is a process of somatic hypermutation which can occur after a specific response is mounted against some epitope.

In some embodiments, antibodies are produced by recombined genomic Ig sequences in B lineage cells. Immunoglobulin light chains are derived from either κ or λ genes. The λ genes are comprised of four constant (C) genes and approximately thirty variable (V) genes. In contrast, the κ genes are comprised of one C gene and 250 V genes. The heavy chain gene family is comprised of several hundred V genes, fifteen D genes, and four joining (J) genes. Somatic recombination during B cell differentiation randomly chooses one V-D-J combination in the heavy chain and one V-J combination in either κ or λ light chain. Because there are so many genes, millions of unique combinations are possible. The V genes also undergo somatic hypermutation after recombination, generating further diversity. Despite this underlying complexity, it is possible to use dozens of primers targeting conserved sequences to sequence the full heavy and light chain complement in several multiplexed reactions.

Immune Repertoire Analysis

In some aspects, techniques described herein may be used to determine the presence of a condition of interest. In some embodiments, determination of the presence of a condition of interest can relate to diagnostic applications, where a subject has or is suspected of having the condition. In some embodiments, determination of the presence of a condition of interest can be useful for predictive measures for the purpose of preventative treatment. In some embodiments, analysis of an immune repertoire can indicate the presence of a condition of interest. For example, in some embodiments, a history of cancer may be reflected in the presence of immune receptor sequences that bind to one or more cancer antigens. In some embodiments, the presence of autoimmune disease may be reflected in the presence of immune receptor sequences that bind to autoantigens. In some embodiments, conditions related to autoimmunity may be evaluated at a particular point in time or tracked over a period of time using techniques described herein. In some embodiments, conditions related to autoimmunity include multiple sclerosis (MS), celiac disease, diabetes mellitus type 1, sarcoidosis, systemic lupus erythematosus (SLE), Sjögren's syndrome, eosinophilic granulomatosis with polyangiitis. Hashimoto's thyroiditis, Graves' disease, idiopathic thrombocytopenia purpura, Addison's disease, rheumatoid arthritis (RA), ankylosing spondylitis, polymyositis (PM), and dermatomyositis (DM). Accordingly, in some embodiments, methods described herein may be used to determine whether treatment of a condition is appropriate. For example, in some embodiments, the abundance of malignant T cell and B cell may be tracked over time via specific CDR3 sequences.

In some aspects, methods provided by the disclosure may be used to determine an optimal therapeutic treatment. In some embodiments, an optimal therapeutic treatment can be determined by analyzing the immune repertoire in a sample, and based on that information, selecting an appropriate therapy, dose, or treatment modality that is optimal for stimulating or suppressing a targeted immune response while minimizing undesirable toxicity. In some embodiments, a treatment is optimized by selection for a treatment that minimizes undesirable toxicity while providing for effective activity. For example, in some embodiments, a subject (e.g., a patient) may be assessed for the immune repertoire relevant to an autoimmune disease, and a systemic or targeted immunosuppressive regimen may be selected based on that information.

In some aspects, techniques provided by the disclosure may be used to assess the progression of a condition in a subject. For example, in some embodiments, analysis of an immune repertoire can be used to assess the progression, stagnation, or regression of a condition. In such embodiments, the immune repertoire can be advantageously assessed before, during, and/or after treatment with a therapeutic to assess the effectiveness of the therapeutic in treating the condition. For example, in some embodiments, methods described herein can be useful for detecting the earliest changes along a disease pathway (e.g., a carcinogenesis pathway, inflammatory pathway, etc.), and/or to monitor the efficacy of various therapies and preventive interventions.

In some aspects, the methods disclosed herein can also be utilized to analyze the effects of agents on cells of the immune system. For example, in some embodiments, analysis of changes in immune repertoire following exposure to one or more test compounds can performed to analyze the effect(s) of the test compounds on an individual. In such embodiments, these analyses can be useful for multiple purposes, for example in the development of immunosuppressive or immune enhancing therapies. In some embodiments, agents to be analyzed for potential therapeutic value can be any compound, small molecule, protein, lipid, carbohydrate, nucleic acid, or other agent appropriate for therapeutic use. In some embodiments, tests are performed in vivo, e.g. using an animal model, to determine effects on the immune repertoire.

In some embodiments, analysis of an immune repertoire can be used to determine the effects of an antigen challenge in an organism. In some embodiments, nucleic acids are obtained from an organism after the organism has been challenged with an antigen (e.g., following vaccination). In some embodiments, nucleic acids are obtained from an organism before the organism has been challenged with an antigen. In some embodiments, comparing the diversity of the immune repertoire present before and after challenge may assist the analysis of the organism's response to the challenge.

Capture Moiety

Aspects of the techniques described herein relate to the use of a capture moiety to isolate a molecule of interest (e.g., a nucleic acid, a ligation product, etc.). As used herein, a "capture moiety" refers to a moiety that is configured to selectively interact with a binding partner for the purpose of capturing (e.g., isolating/purifying) the molecule of interest.

A capture moiety and a binding partner of the capture moiety may comprise any suitable binding pair. In some embodiments, a binding pair can selectively interact through covalent or non-covalent binding. In some embodiments, a binding pair can selectively interact by hybridization, ionic bonding, hydrogen bonding, van der Waals interactions, or any combination of these forces. In some embodiments, a capture moiety and/or binding partner can comprise, for example, biotin, avidin, streptavidin, digoxigenin, inosine, avidin, GST sequences, modified GST sequences, biotin ligase recognition (BiTag) sequences, S tags, SNAP-tags, enterokinase sites, thrombin sites, antibodies or antibody domains, antibody fragments, antigens, receptors, receptor domains, receptor fragments, or combinations thereof.

In some embodiments, a capture moiety comprises a biotin moiety. In some embodiments, techniques described herein are useful in preparing nucleic acid samples for analysis. Accordingly, in some embodiments, a nucleic acid molecule comprises a biotinylated capture moiety. In some embodiments, the nucleic acid molecule comprises at least one capture moiety modified nucleotide comprising a biotin moiety. In some embodiments, the capture moiety modified nucleotide comprises the general structure of formula (I):

(I)

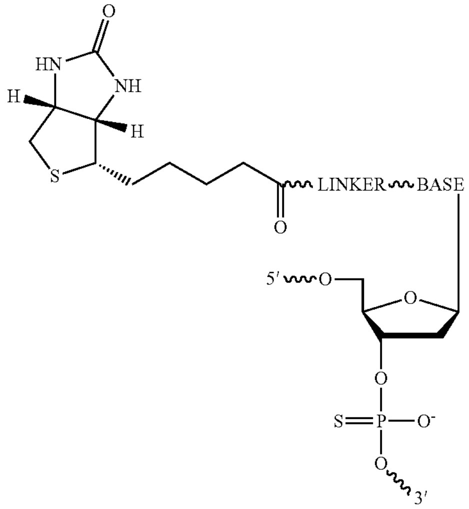

As shown in formula (I), a capture moiety modified nucleotide may comprise a biotin moiety attached to a nucleobase of a nucleotide. For example, in some embodiments, the biotin moiety comprises biotin-triethylene glycol, bis-biotin, photocleavable biotin, desthiobiotin, desthiobiotin-triethylene glycol, or biotin azide. Non-limiting examples of capture moiety modified nucleotides are shown in Table 1.

TABLE 1

| Example structures of capture moiety modified nucleotides |
| --- |
| 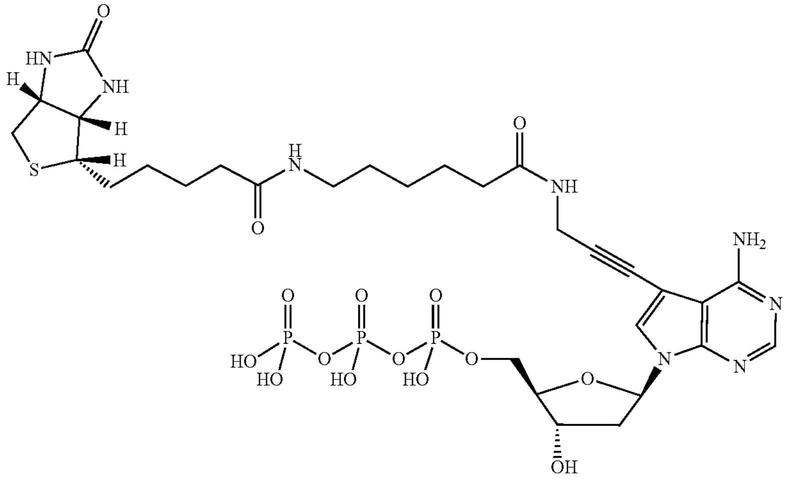 |
| Biotin-11-dATP |

TABLE 1-continued
| Example structures of capture moiety modified nucleotides |
| --- |
| 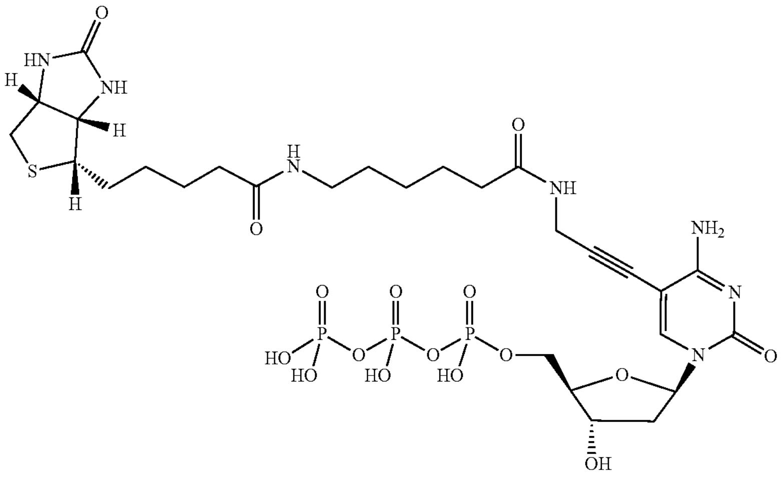 Biotin-11-dCTP |
| 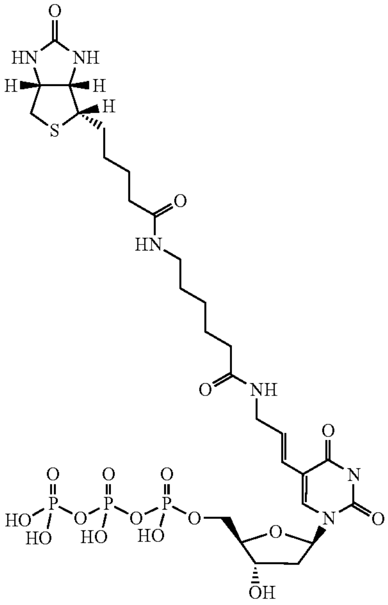 Biotin-11-dUTP |

TABLE 1-continued
| Example structures of capture moiety modified nucleotides |
| --- |
$C_{30}H_{45}N_8O_{16}P_3S$
898
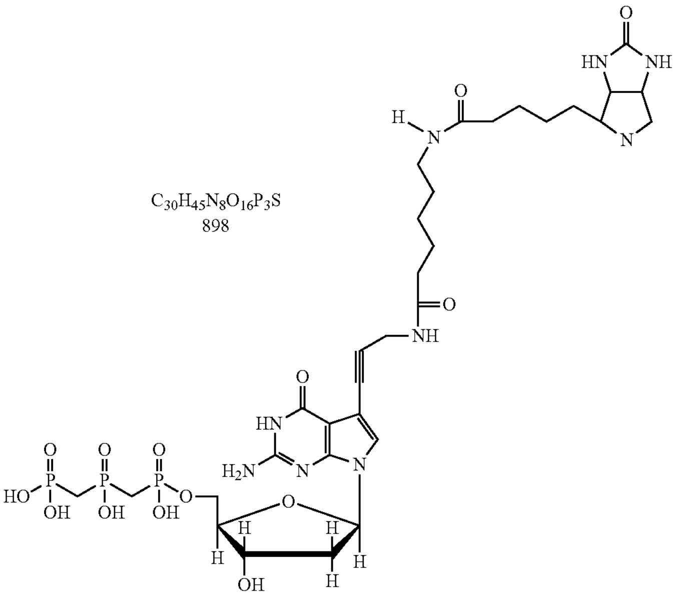
Biotin-11-dGTP
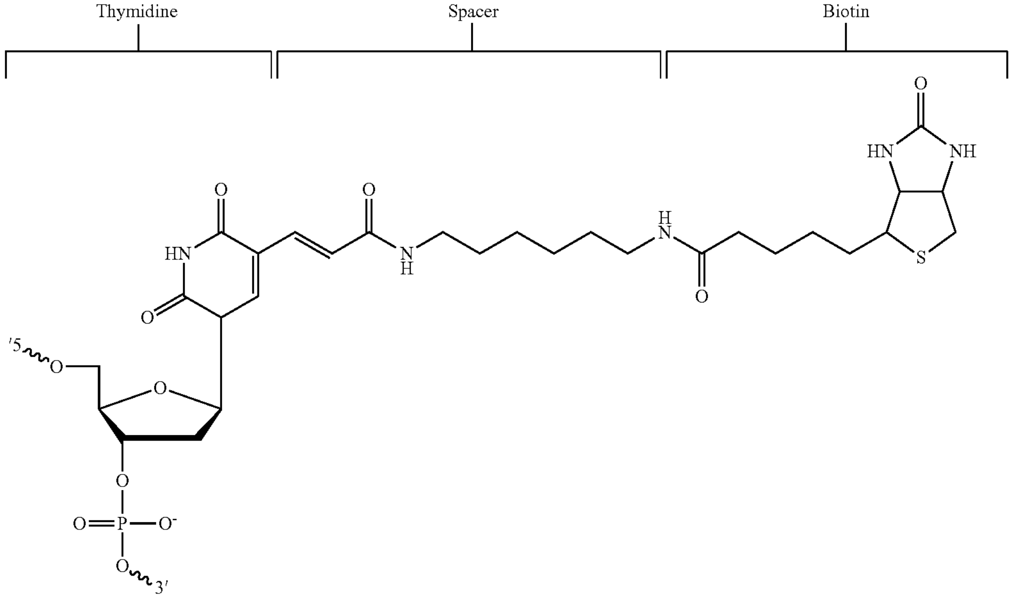

TABLE 1-continued

| Example structures of capture moiety modified nucleotides |
| --- |
| 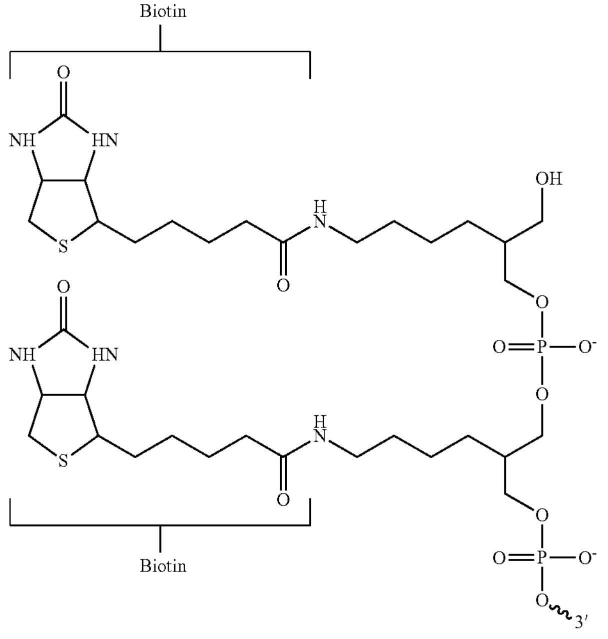 |
| 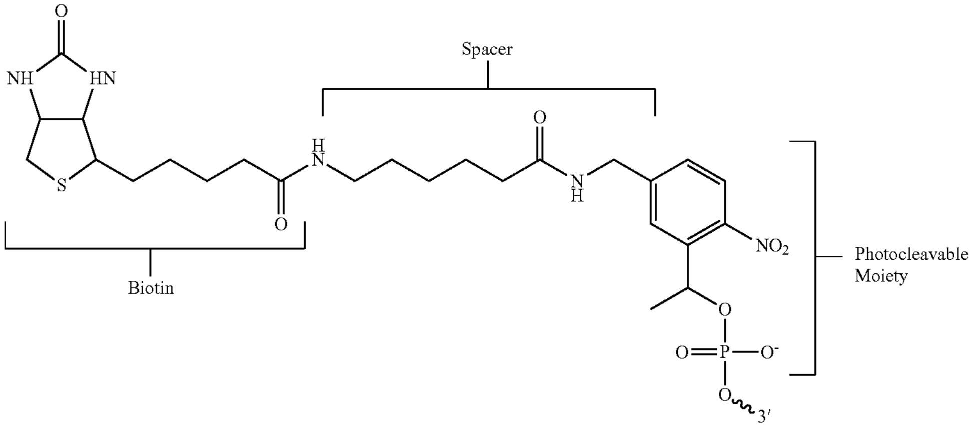 |

In some embodiments, a capture moiety modified nucleotide comprises a linker between the capture moiety and a nucleobase of the nucleotide. In some embodiments, the capture moiety is covalently linked to the nucleobase via a linker of any suitable length. In some embodiments, the capture moiety is covalently linked to the nucleobase via a linker of 5 to 20 atoms in length. In some embodiments, the linker comprises an aliphatic chain. In some embodiments a linker comprises $-(CH_2)n-$, wherein n is an integer from 1 to 20, inclusive. In some embodiments, n is an integer from 1 to 10, inclusive. In certain embodiments, a linker comprises a heteroaliphatic chain. In some embodiments, a linker comprises a polyethylene glycol moiety. In some embodiments, a linker comprises a polypropylene glycol moiety. In some embodiments, a linker comprises $-(CH_2CH_2O)n-$, wherein n is an integer from 1 to 20, inclusive. In some embodiments, a linker comprises $-(CH_2CH_2O)n-$, wherein n is an integer from 1 to 10, inclusive. In certain embodiments, a linker comprises one or more arylenes. In some embodiments, a linker comprises one or more phenylenes (e.g., para-substituted phenylene). In certain embodiments, a linker comprises a chiral center. In certain embodiments, a linker comprises one or more phosphates, an aliphatic chain, a heteroaliphatic chain, and one or more amides (e.g., —C(═O) NH—).

In some embodiments, a capture moiety modified nucleotide is biotin-n-dNTP, wherein n is an integer from 5 to 20 representing the number of linker atoms between a carbonyl-group of the biotin moiety and the position of attachment on a nucleobase of the NTP.

In some embodiments, a binding partner is attached to an insoluble support. Thus, in some embodiments, the molecule of interest may be immobilized on an insoluble support through a selective binding interaction formed between a capture moiety and a binding partner of the capture moiety attached to the insoluble support.

In some embodiments, the insoluble support comprises a bead or other solid surface. For example, in some embodiments, the bead is a paramagnetic bead. The use of beads for isolation is well known in the art, and any suitable bead isolation method can be used with the techniques described herein. In some embodiments, beads can be useful for isolation in that molecules of interest can be attached to the beads, and the beads can be washed to remove solution components not attached to the beads, allowing for purification and isolation. In some embodiments, the beads can be separated from other components in the solution based on properties such as size, density, or dielectric, ionic, and magnetic properties.

In some embodiments, the insoluble support is a magnetic bead. Use of beads allows the derivatized nucleic acid capture moiety to be separated from a reaction mixture by centrifugation or filtration, or, in the case of magnetic beads, by application of a magnetic field. In some embodiments, magnetic beads can be introduced, mixed, removed, and released into solution using magnetic fields. In some embodiments, processes utilizing magnetic beads may be automated. In some embodiments, the beads can be functionalized using well known chemistry to provide a surface having suitable functionalization for attaching a binding partner of a capture moiety. Derivatization of surfaces to allow binding of the capture moiety is conventional in the art. For example, coating of surfaces with streptavidin allows binding of a biotinylated capture moiety. Coating of surfaces with streptavidin has been described in, for example, U.S. Pat. No. 5,374,524 to Miller. In some embodiments, solid surfaces other than beads may be used. In some embodiments, the solid surfaces can be planar surfaces, such as those used for hybridization microarrays, or the solid surfaces can be the packing of a separation column.

In some embodiments, a binding partner of a capture moiety may be attached to an insoluble support before, simultaneous with, or after binding the capture moiety. In some embodiments, it may be preferable to contact a capture moiety with a binding partner of the capture moiety while both are in solution. In such embodiments, the capture moiety:binding partner complex can then be immobilized on an insoluble support by contacting the complex with an appropriately derivatized surface. Thus, in some embodiments, the molecule of interest may be isolated through a complex formed between a capture moiety attached to the molecule of interest and a binding partner of the capture moiety.

In some embodiments, it may be desirable to attach the capture moiety to a nucleobase of a nucleotide. In this manner, the 3' end remains free to be optionally ligated to an adapter nucleic acid while the capture moiety is available to be captured by a binding partner. In some embodiments, the capture moiety modified nucleotide comprises a nucleobase selected from the group consisting of adenine, guanine, thymine, uracil, and cytosine, or a derivative thereof. For example, in some embodiments, the capture moiety modified nucleotide comprises an adenine nucleobase or derivative thereof. In some embodiments, the capture moiety is covalently linked to the adenine nucleobase or derivative thereof at position 5, 6, 7 or 8. In some embodiments, the capture moiety is covalently linked to the adenine nucleobase at position 7. A numbering scheme for an adenine ring is depicted in formula (II):

(II)

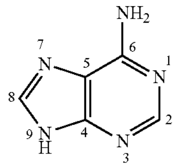

In some embodiments, it may be desirable to modify one or more positions on a nucleobase that is attached to a capture moiety. For example, in some embodiments, position 7 of the adenine nucleobase is a carbon atom. However, it should be appreciated that any atom capable of forming an additional covalent bond (e.g., C, O, N, S, etc.) may be substituted into a position on a nucleobase suitable for attachment of a capture moiety. In some embodiments, following capturing the adapter-ligated fragments, the library is subjected to amplification to enrich target nucleotide sequences.

Sample Purification

In some embodiments, target nucleic acids and/or amplification products thereof can be isolated from enzymes, primers, or buffer components before and/or after any appropriate step of a method. Any suitable methods for isolating nucleic acids may be used. In some embodiments, the isolation can comprise Solid Phase Reversible Immobilization (SPRI) cleanup. Methods for SPRI cleanup are well known in the art, e.g., Agencourt AMPure XP-PCR Purification (Cat No. A63880, Beckman Coulter; Brea, CA). In some embodiments, enzymes can be inactivated by heat treatment. In some embodiments, unlabeled dNTPs are removed by enzymatic treatment. In some embodiments, a cleanup step (e.g., an SPRI cleanup) is conducted to remove unextended or excess primers (e.g., capture moiety modified primers, target-specific primers, adapter primers, etc.).

In some embodiments, SPRI cleanup relates to the use of paramagnetic beads that bind DNA. For example, in some embodiments, SPRI cleanup utilizes beads having a polystyrene core surround by a thin layer of magnetite, which makes the beads paramagnetic (i.e., beads aggregate only when exposed to a magnetic field). In some embodiments, the bead is coated by molecules comprising carboxyl groups that provide charged groups for DNA binding. In some embodiments, SPRI cleanup is conducted in the presence of polyethylene glycol (PEG) and salt, which work together as crowding agents to activate the beads to reversibly bind DNA. In some embodiments, an SPRI comprises mixing a DNA sample with paramagnetic beads and allowing the beads to bind the DNA, applying a magnetic field to aggregate the DNA-bound beads, rinsing the beads with ethanol (e.g., 70% ethanol), and eluting the DNA from the paramagnetic beads.

In some embodiments, unhybridized primers can be removed from a nucleic acid preparation using appropriate methods (e.g., purification, digestion, etc.). In some embodiments, a nuclease (e.g., exonuclease I) is used to remove primers from a preparation. In some embodiments, such nucleases are heat inactivated subsequent to primer digestion. Once the nucleases are inactivated, a further set of primers may be added together with other appropriate components (e.g., enzymes, buffers) to perform a further amplification reaction.

In some embodiments, steps of the methods provided herein optionally comprise an intervening sample purification step. In some embodiments, a sample purification step comprises a wash step. In some embodiments, a sample purification step comprises SPRI cleanup (e.g., AMPure). For example, a method of preparing nucleic acids for analysis can comprise: (i) washing a substrate immobilized nucleic acid; and (ii) releasing the washed immobilized nucleic acid from the paramagnetic substrate or surface.

As another example, a method of preparing nucleic acids for analysis can comprise: (a) preparing a cDNA by conducting a randomly-primed first strand synthesis reaction using an RNA preparation as a template and a second strand synthesis reaction using a product of the randomly-primed first strand synthesis reaction as a template, wherein the RNA preparation comprises a target nucleotide sequence: (b) end repairing the cDNA to produce a blunt-ended, double-stranded nucleic acid comprising the target nucleotide sequence; (c) immobilizing the blunt-ended, double-stranded nucleic acid on a paramagnetic substrate or surface; (d) washing the immobilized blunt-ended, double-stranded nucleic acid: (e) releasing the washed immobilized blunt-ended, double-stranded nucleic acid from the paramagnetic substrate or surface: (f) adding one or more nucleotides to the 3' end of the released blunt-ended, double-stranded nucleic acid; (g) ligating an adapter that comprises a ligatable duplex portion and an overhang sequence to the nucleic acid produced in step (f) to produce a ligation product, wherein the overhang sequence is complementary with the one or more nucleotides; (h) without washing the ligation product, amplifying the ligation product by polymerase chain reaction using a first target-specific primer that specifically anneals to the target nucleotide sequence and a first adapter primer that specifically anneals to a complementary sequence of the adapter nucleic acid; (i) amplifying an amplification product of step (h) by polymerase chain reaction using a second adapter primer and a second target-specific primer, wherein the second target-specific primer is nested relative to the first target-specific primer; (j) immobilizing the amplification product of step (i) to a paramagnetic substrate or surface; (k) washing the immobilized amplification product; and (l) releasing the washed immobilized amplification product from the paramagnetic substrate or surface. In some embodiments, steps of the methods provided herein optionally comprise adding one or more nucleotides to a nucleic acid, wherein at least one of the one or more nucleotides comprises a capture moiety, and capturing the nucleic acid via an interaction between the capture moiety and a binding partner of the capture moiety. For example, a method of preparing nucleic acids for analysis can comprise: (a) preparing a cDNA by conducting a randomly-primed first strand synthesis reaction using a nucleic acid preparation as a template and a second strand synthesis reaction using a product of the randomly-primed first strand synthesis reaction as a template, wherein the nucleic acid preparation comprises a target nucleotide sequence: (b) end repairing the cDNA to produce a blunt-ended, double-stranded nucleic acid comprising the target nucleotide sequence: (c) washing the blunt-ended, double-stranded nucleic acid; (d) adding one or more nucleotides to the 3' end of the nucleic acid washed in step (c), optionally wherein at least one of the one or more nucleotides is a capture moiety modified nucleotide; (e) washing the nucleic acid produced in step (d); (f) ligating an adapter nucleic acid that comprises a ligatable duplex portion and an overhang sequence to the nucleic acid washed in step (e) to produce a ligation product, wherein the overhang sequence is complementary with the one or more nucleotides; (g) amplifying the ligation product by polymerase chain reaction using a first target-specific primer that specifically anneals to the target nucleotide sequence and a first adapter primer that specifically anneals to a complementary sequence of the adapter nucleic acid: (h) amplifying an amplification product of step (g) by polymerase chain reaction using a second adapter primer and a second target-specific primer, wherein the second target-specific primer is nested relative to the first target-specific primer; and (j) washing the amplification product of step (h).

Nucleic Acid Adapter

As used herein, the term "adapter nucleic acid," "nucleic acid adapter" or "adapter" refers to a nucleic acid molecule that may be ligated to a nucleic acid comprising a target nucleotide sequence to provide one or more elements useful during amplification and/or sequencing of the target nucleotide sequence. In some embodiments, an adapter is single-stranded. In some embodiments, an adapter is double-stranded. In some embodiments, a double-stranded adapter comprises a first ligatable duplex end and a second unpaired end. In some embodiments, an adapter comprises an amplification strand and a blocking strand. In some embodiments, the amplification strand comprises a 5' unpaired portion and a 3' duplex portion. In some embodiments, the amplification strand further comprises a 3' overhang. In some embodiments, the 3' overhang is a 3'T overhang. In some embodiments, the amplification strand comprises nucleotide sequences identical to a first and second adapter primer. In some embodiments, the blocking strand of the adapter comprises a 5' duplex portion and a non-extendable 3' portion. In some embodiments, the blocking strand further comprises a 3' unpaired portion. In some embodiments, the duplex portions of the amplification strand and the blocking strand are substantially complementary and the duplex portion is of sufficient length to remain in duplex form at the ligation temperature.

In some embodiments, the portion of the amplification strand that comprises a nucleotide sequence identical to a first and second adapter primer can be comprised, at least in part, by the 5' unpaired portion of the amplification strand.

In some embodiments, the adapter can have a "Y" shape, i.e., the second unpaired end comprises a 5' unpaired portion of an amplification strand and a 3' portion of a blocking strand. The 3' unpaired portion of the blocking strand can be shorter than, longer than, or equal in length to the 5' unpaired portion of the amplification strand. In some embodiments, the 3' unpaired portion of the blocking strand can be shorter than the 5' unpaired portion of the amplification strand. Y-shaped adapters have the advantage that the unpaired portion of the blocking strand will not be subject to 3' extension during a PCR regimen.

In some embodiments, the blocking strand of the adapter can further comprise a 3' unpaired portion that is not substantially complementary to the 5' unpaired portion of the amplification strand, wherein the 3' unpaired portion of the blocking strand is not substantially complementary to or substantially identical to any of the primers. In some embodiments, the blocking strand can further comprise a 3' unpaired portion that does not specifically anneal to the 5' unpaired portion of the amplification strand at the annealing temperature, wherein the 3' unpaired portion of the blocking strand will not specifically anneal to any of the primers or the complements thereof at the annealing temperature. In some embodiments, an adapter nucleic acid comprises, at a minimum, a sample index sequence for multiplexing. However, in some embodiments, the adapter nucleic further comprises a random molecular barcode.

Amplification

Aspects of the present disclosure relate to techniques that may comprise one or more rounds of amplification. In some embodiments, a first round of amplification is conducted using a first target-specific primer and a first adapter primer.

As used herein, a "first target-specific primer" is an oligonucleotide comprising a nucleic acid sequence that can specifically anneal, under suitable annealing conditions, to a target nucleotide sequence of a template nucleic acid. During amplification, the first target-specific primer generates a strand that is complementary to its template, and this complementary strand is capable of being hybridized with a first adapter primer.

As used herein, a "first adapter primer" is an oligonucleotide comprising a nucleic acid sequence that can specifically anneal, under suitable annealing conditions, to a complementary sequence of an adapter nucleic acid. As the first adapter primer is therefore identical to at least a portion of the adapter, it anneals to the complementary strand generated by the first target specific-primer to allow amplification to proceed.

In some embodiments, in the first PCR amplification cycle of the first amplification step, a first target-specific primer can specifically anneal to a template strand of a nucleic acid comprising a target nucleotide sequence. In some embodiments, depending upon the orientation with which the first target-specific primer was designed, a sequence upstream or downstream of the target nucleotide sequence will be synthesized as a strand complementary to the template strand. In some embodiments, if, during the extension phase of PCR, the 5' end of a template strand terminates in a ligated adapter, the 3' end of the newly synthesized complementary strand will comprise sequence capable of hybridizing with a first adapter primer. In subsequent PCR amplification cycles, both the first target-specific primer and the first adapter primer will be able to specifically anneal to the appropriate strands of the target nucleic acid sequence and the sequence between the known nucleotide target sequence and the adapter can be amplified. In some embodiments, a second round of amplification is conducted using a second target-specific primer and a second adapter primer.

As used herein, a "second target-specific primer" is an oligonucleotide comprising a nucleic acid sequence that can specifically anneal, under suitable annealing conditions, to a portion of the target nucleotide sequence comprised by the amplicon resulting from a preceding amplification step. During amplification, the second target-specific primer generates a strand that is complementary to its template, and this complementary strand is capable of being hybridized with a second adapter primer.

As used herein, a "second adapter primer" is an oligonucleotide comprising a nucleic acid sequence that can specifically anneal, under suitable annealing conditions, to a complementary sequence of an adapter nucleic acid. As the first adapter primer is therefore identical to at least a portion of the adapter, it anneals to the complementary strand generated by the second target specific-primer to allow amplification to proceed.

In some embodiments, a second target-specific primer is nested relative to a first target-specific primer. In some embodiments, the use of nested adapter primers eliminates the possibility of producing final amplicons that are amplifiable (e.g., during bridge PCR or emulsion PCR) but cannot be sequenced, a situation that can arise during hemi-nested methods. In other situations, hemi-nested approaches using a primer identical to a sequencing primer can result in the carry-over of undesired amplification products from the first PCR step to the second PCR step and would ultimately yield artificial sequencing reads. In some embodiments, a second target-specific primer is nested with respect to a first target-specific primer by at least 1 nucleotide, e.g., by 1, 2, 3, 4, 5, 6, 7, 8, 9, 10, or more nucleotides. In some embodiments, a second target-specific primer is nested with respect to a first target-specific primer by about 5 nucleotides to about 10 nucleotides, by about 10 nucleotides to about 15 nucleotides, by about 15 nucleotides to about 20 nucleotides, or by about 20 nucleotides or more.

Among other aspects, techniques described herein may involve the use of one or more nested primers. In some embodiments, the use of nested primers may reduce non-specific binding in PCR products due to the amplification of unexpected primer binding sites. As used herein, the term "nested" is used to describe a positional relationship between the annealing site of a primer of a primer pair and the annealing site of another primer of another primer pair. For example, in some embodiments, a second primer is nested by 1, 2, 3 or more nucleotides relative to a first primer, meaning that it binds to a site on the template strand that is frame-shifted by 1, 2, 3 or more nucleotides.

In some embodiments, a second target-specific primer comprises a 3' portion that specifically anneals to a target nucleotide sequence and a 5' tail that does not anneal to the target nucleotide sequence. In some embodiments, the 5' tail comprises a nucleic acid sequence that is identical to a second sequencing primer. In some embodiments, multiple primers (e.g., one or more target specific primers and/or one or more adapter primers) present in a reaction can comprise identical 5' tail sequence portions.

In some embodiments, a 5' tail can be a GC-rich sequence. In some embodiments, a 5' tail sequence may comprise at least 50% GC content, at least 55% GC content, at least 60% GC content, at least 65% GC content, at least 70% GC content, at least 75% GC content, at least 80% GC content, or higher GC content. In some embodiments, a 5' tail sequence may comprise at least 60% GC content. In some embodiments, a 5' tail sequence may comprise at least 65% GC content.

In some embodiments, a second round of amplification includes a second target-specific primer comprising a 5' tail, a first adapter primer, and an additional primer. In some embodiments, the additional primer comprises a 3' portion that is identical to the 5' tail of the second target-specific primer. In some embodiments, the additional primer may comprise additional sequences 5' to the hybridization sequence that may include barcode, index, adapter sequences, or sequencing primer sites. In some embodiments, the additional primer is a generic sequencing adapter/index primer.

In some embodiments, the first and second target-specific primers are substantially complementary to the same strand of the target nucleic acid. In some embodiments, the portions of the first and second target-specific primers that specifically anneal to the known target sequence can comprise a total of at least 20 unique bases of the known target nucleotide sequence, e.g., 20 or more unique bases, 25 or more unique bases, 30 or more unique bases, 35 or more unique bases, 40 or more unique bases, or 50 or more unique bases. In some embodiments, the portions of the first and second target-specific primers that specifically anneal to the known target sequence can comprise a total of at least 30 unique bases of the known target nucleotide sequence.

In some embodiments, the first adapter primer can comprise a nucleic acid sequence identical to about the 20 5'-most bases of the amplification strand of the adapter and the second adapter primer can comprise a nucleic acid sequence identical to about 30 bases of the amplification strand of the adapter, with a 5' base that is at least 1 nucleotide 3' of the 5' terminus of the amplification strand.

In some embodiments, an adapter ligated nucleic acid (e.g., a ligation product) is minimal. In such embodiments, a first adapter primer may be used that contains a portion of the adapter nucleic sequence at its 3' end and then additional sequencer-important information at its 5' end. In such embodiments, a second adapter primer may be used that contains, at its 3' end, the 5' end of the first adapter primer. In such embodiments, the second adapter primer may also have a nucleotide sequence that permits sequencing at its 5' end. In such embodiments, it is possible to produce, using PCR, a library that is sequencer compatible.

Extension and Amplification

Aspects of the present disclosure relate to techniques that may comprise one or more extension reactions (e.g., first strand synthesis, second strand synthesis) and/or one or more rounds of amplification. As described herein, extension reactions and amplification may be conducted using one or more target-specific primers.

As used herein, a "target-specific primer" refers to a primer comprising a sequence that is complementary to a target nucleotide sequence. In some embodiments, a target-specific primer is used to prime a first strand synthesis reaction. For example, in some embodiments, the target-specific primer is a reverse transcriptase primer that anneals to an mRNA molecule comprising a target nucleotide sequence. In some embodiments, as described herein, a capture moiety modified primer is a target-specific primer that may be used to prime a first strand synthesis reaction. In some embodiments, a target-specific primer is used to prime an amplification reaction. For example, in some embodiments, methods described herein may include a step of amplification that uses a target-specific primer that comprises a 3' portion that specifically anneals to the target nucleotide sequence. In some embodiments, the disclosure provides methods that may include the use of target-specific primers (e.g., identical or different target-specific primers) in more than one step.

Accordingly, in some embodiments of the methods described herein, where the term target-specific primer appears in more than one step and refers to separate primers, additional terminology may be included for clarification. For example, in some embodiments, an initial target-specific primer may be used in a first strand synthesis reaction to generate a cDNA that is subsequently amplified using a disparate target-specific primer. In such embodiments, the initial target-specific primer may be referred to as a "capture moiety modified primer" while the latter target-specific primer may be referred to as a "target-specific primer." Alternatively, in some embodiments, the initial target-specific primer and the latter target-specific primer may be referred to as a "first" and "second" target-specific primer, respectively.

It should be appreciated that, in some embodiments, use of the terms "first," "second." "third." etc. may be used relatively, such that these terms may be refer to different classes of primers depending on the context of the technique being described. For example, in some embodiments, a target-specific reverse transcriptase primer is used with an mRNA molecule to generate a cDNA, which is further subjected to PCR reactions using additional target-specific primers. In such embodiments, the target-specific reverse transcriptase primer may be referred to as a "first target-specific primer" with subsequent PCR primers binding to a known target sequence referred to as a "second target-specific primer." "third target-specific primer." etc. In some embodiments, a plurality of random reverse transcriptase primers are used with an mRNA molecule to generate a cDNA, which is further subjected to PCR reactions using target-specific primers. In such embodiments, the plurality of random primers are not referred to as being "target-specific"; accordingly, if subsequent PCR reactions utilize target-specific primers, the terms "first target-specific primer," "second target-specific primer," etc. may be used according to distinct reactions (e.g., in a method of preparing nucleic acids for sequencing).

In some aspects, the disclosure provides methods that may include conducting a first strand synthesis reaction using a first target-specific primer (e.g., a capture moiety modified primer). In some embodiments, a first round of amplification is conducted using a second target-specific primer (e.g., a target-specific primer) and a first adapter primer.

In some embodiments, a "target-specific primer" is an oligonucleotide comprising a nucleic acid sequence that can specifically anneal, under suitable annealing conditions, to a target nucleotide sequence of a nucleic acid molecule (e.g., a template nucleic acid). In some embodiments, ordinal terms (e.g., first, second, third) may be used to distinguish one target-specific primer from another used in different steps of a multi-step method. For example, in some embodiments, a second target-specific primer is a target specific primer for use in an amplification reaction in a process comprising a prior first strand synthesis involving use of a first target-specific primer. In such embodiments, during amplification, the second target-specific primer generates a strand that is complementary to its template, and this complementary strand is capable of being hybridized with a first adapter primer.

As used herein, an "adapter primer" is an oligonucleotide comprising a nucleic acid sequence that can specifically anneal, under suitable annealing conditions, to a complementary sequence of an adapter nucleic acid. In some embodiments, an adapter primer (e.g., a first adapter primer) is identical to at least a portion of the adapter, and it anneals to the complementary strand generated by a target-specific primer (e.g., a second target-specific primer) to allow amplification to proceed.

In some embodiments, in the first PCR amplification cycle of the first amplification step, a second target-specific primer can specifically anneal to a template strand of a nucleic acid comprising a target nucleotide sequence. In some embodiments, depending upon the orientation with which the second target-specific primer was designed, a sequence upstream or downstream of the target nucleotide sequence will be synthesized as a strand complementary to the template strand. In some embodiments, if, during the extension phase of PCR, the 5' end of a template strand terminates in a ligated adapter, the 3' end of the newly synthesized complementary strand will comprise sequence capable of hybridizing with a first adapter primer. In subsequent PCR amplification cycles, both the second target-specific primer and the first adapter primer will be able to specifically anneal to the appropriate strands of the target nucleic acid sequence and the sequence between the known nucleotide target sequence and the adapter can be amplified. In some embodiments, a second target-specific primer comprises a 5' tail portion that does not specifically anneal to the target nucleotide sequence. For example, in some embodiments, a 5' tail portion may comprise a region that provides a primer-binding site for subsequent extension reactions (e.g., during amplification). In some embodiments, a second round of amplification is conducted using a tail primer and a second adapter primer.

As used herein, a "tail primer" is an oligonucleotide comprising a nucleic acid sequence that comprises a 3' portion that can specifically anneal, under suitable annealing conditions, to a complementary sequence of the 5' tail portion of a target-specific primer (e.g., second target-specific primer) comprised by the amplicon resulting from a preceding amplification step. In some embodiments, a tail primer comprises a 5' portion that does not specifically anneal to the complementary sequence of the 5' tail portion of the target-specific primer. In some embodiments, the 5' portion of the tail primer comprises at least one of a sample index region, a PCR primer-binding region, a molecular barcode region, and a sequencing primer site region. Although a tail primer, as used herein, generally relates to a primer that is used in a second round of PCR, it should be appreciated that the term may be used to refer to any primer that hybridizes with a sequence that is complementary to a 5' tail portion of a primer used in a preceding reaction.

In some embodiments, an adapter primer (e.g., a second adapter primer) is identical to at least a portion of the adapter, and it anneals to the complementary strand generated by the tail primer to allow amplification to proceed.

In some embodiments, a second adapter primer is nested relative to a first adapter primer. In some embodiments, the use of nested adapter primers eliminates the possibility of producing final amplicons that are amplifiable (e.g., during bridge PCR or emulsion PCR) but cannot be sequenced, a situation that can arise during hemi-nested methods. In other situations, hemi-nested approaches using a primer identical to a sequencing primer can result in the carry-over of undesired amplification products from the first PCR step to the second PCR step and would ultimately yield artificial sequencing reads. In some embodiments, a second adapter primer is nested with respect to a first adapter primer by at least 1 nucleotide, e.g., by 1, 2, 3, 4, 5, 6, 7, 8, 9, 10, or more nucleotides. In some embodiments, a second adapter primer is nested with respect to a first adapter primer by about 5 nucleotides to about 10 nucleotides, by about 10 nucleotides to about 15 nucleotides, by about 15 nucleotides to about 20 nucleotides, or by about 20 nucleotides or more.

Among other aspects, techniques described herein may involve the use of one or more nested primers. In some embodiments, the use of nested primers may reduce non-specific binding in PCR products due to the amplification of unexpected primer binding sites. As used herein, the term "nested" is used to describe a positional relationship between the annealing site of a primer of a primer pair and the annealing site of another primer of another primer pair. For example, in some embodiments, a second primer is nested by 1, 2, 3 or more nucleotides relative to a first primer, meaning that it binds to a site on the template strand that is frame-shifted by 1, 2, 3 or more nucleotides.

In some embodiments, a target-specific primer (e.g., a second target-specific primer) comprises a 3' portion that specifically anneals to a target nucleotide sequence and a 5' tail that does not anneal to the target nucleotide sequence. In some embodiments, the 5' tail comprises a nucleic acid sequence that is identical to a 3' portion of a tail primer. In some embodiments, multiple primers (e.g., one or more target specific primers and/or one or more adapter primers) present in a reaction can comprise identical 5' tail sequence portions.

In some embodiments, a 5' tail can be a GC-rich sequence. In some embodiments, a 5' tail sequence may comprise at least 50% GC content, at least 55% GC content, at least 60% GC content, at least 65% GC content, at least 70% GC content, at least 75% GC content, at least 80% GC content, or higher GC content. In some embodiments, a 5' tail sequence may comprise at least 60% GC content. In some embodiments, a 5' tail sequence may comprise at least 65% GC content.

In some embodiments, a first round of amplification includes a second target-specific primer comprising a 5' tail, a first adapter primer, and an additional primer. In some embodiments, the additional primer comprises a 3' portion that is identical to the 5' tail of the second target-specific primer. In some embodiments, the additional primer may comprise additional sequences 5' to the hybridization sequence that may include barcode, index, adapter sequences, or sequencing primer sites. In some embodiments, the additional primer is a generic sequencing adapter/index primer.

In some embodiments, two target-specific primers (e.g., first and second target-specific primers) are substantially complementary to the same strand of the target nucleic acid. In some embodiments, the portions of the first and second target-specific primers that specifically anneal to the known target sequence can comprise a total of at least 20 unique bases of the known target nucleotide sequence, e.g., 20 or more unique bases, 25 or more unique bases, 30 or more unique bases, 35 or more unique bases, 40 or more unique bases, or 50 or more unique bases. In some embodiments, the portions of the first and second target-specific primers that specifically anneal to the known target sequence can comprise a total of at least 30 unique bases of the known target nucleotide sequence.

In some embodiments, the first adapter primer can comprise a nucleic acid sequence identical to about the 20 5'-most bases of the amplification strand of the adapter and the second adapter primer can comprise a nucleic acid sequence identical to about 30 bases of the amplification strand of the adapter, with a 5' base that is at least 1 nucleotide 3' of the 5' terminus of the amplification strand.

In some embodiments, an adapter ligated nucleic acid (e.g., a ligation product) is minimal. In such embodiments, a first adapter primer may be used that contains a portion of the adapter nucleic sequence at its 3' end and then additional sequencer-important information at its 5' end. In such embodiments, a second adapter primer may be used that contains, at its 3' end, the 5' end of the first adapter primer. In such embodiments, the second adapter primer may also have a nucleotide sequence that permits sequencing at its 5' end. In such embodiments, it is possible to produce, using PCR, a library that is sequencer compatible.

Primers

In general, a primer comprising a sequence that is complementary to a sequence of interest (e.g., a target sequence or an adapter sequence) can either consist of only a complementary sequence or also can include an additional sequence that is not complementary to the sequence of interest (e.g., a tail sequence, an adapter sequence, an index sequence, etc.). In some embodiments, a primer can also include non-nucleotide moieties (e.g., capture moieties, etc.).

In some embodiments, primers (e.g., first and second target-specific primers, first and second adapter primers, tail primers, capture moiety modified primers) are designed such that they will specifically anneal to their complementary sequences at an annealing temperature of from about 61 to 72° C., e.g., from about 61 to 69° C., from about 63 to 69° C., from about 63 to 67° C., from about 64 to 66° C. In some embodiments, primers are designed such that they will specifically anneal to their complementary sequences at an annealing temperature of less than 72° C. In some embodiments, primers are designed such that they will specifically anneal to their complementary sequences at an annealing temperature of less than 70° C. In some embodiments, primers are designed such that they will specifically anneal to their complementary sequences at an annealing temperature of less than 68° C. In some embodiments, primers are designed such that they will specifically anneal to their complementary sequences at an annealing temperature of about 65° C. In some embodiments, systems provided herein are configured to alter vessel temperature (e.g., by cycling between different temperature ranges) to facilitate primer annealing.

In some embodiments, the portions of the target-specific primers that specifically anneal to the target nucleotide sequence (e.g., known target nucleotide sequence) will anneal specifically at a temperature of about 61 to 72° C., e.g., from about 61 to 69° C., from about 63 to 69° C., from about 63 to 67° C., from about 64 to 66° C. In some embodiments, the portions of the target-specific primers that specifically anneal to the known target nucleotide sequence will anneal specifically at a temperature of about 65° C. in a PCR buffer.

In some embodiments, primers (e.g., random primers, target-specific primers) described herein comprise reverse transcriptase primers. In some embodiments, reverse transcriptase primers specifically anneal to an mRNA molecule at a temperature of about 50 to 52° C., from about 51 to 53° C., from about 52 to 54° C., from about 53 to 55° C., from about 54 to 56° C., from about 55 to 57° C., from about 56-58° C., from about 57 to 59° C., from about 58 to 60° C. For example, in some embodiments, reverse transcriptase primers have an annealing temperature of about 53° C., about 53.5° C., about 54° C., about 54.5° C., about 56° C. In some embodiments, reverse transcriptase primers comprise one or more capture moieties (e.g., as described herein). In some embodiments, the one or more capture moieties may be attached to a reverse transcriptase primer at the 5' end of the primer nucleic acid. In some embodiments, reverse transcriptase primers comprise a phosphorothioate bond linking the 5'-most base to the adjacent 5'-penultimate base.

Nucleic Acid Extension, Amplification, and PCR

In some embodiments, methods described herein comprise an extension regimen or step. In such embodiments, extension may proceed from one or more hybridized random primers, using the nucleic acid molecules which the primers are hybridized to as templates. Extension steps are described herein. In some embodiments, one or more random primers can hybridize to substantially all of the nucleic acids in a sample, many of which may not comprise a target nucleotide sequence. Accordingly, in some embodiments, extension of random primers may occur due to hybridization with templates that do not comprise a target nucleotide sequence.

In some embodiments, methods described herein may involve a polymerase chain reaction (PCR) amplification regimen, involving one or more amplification cycles. Amplification steps of the methods described herein can each comprise a PCR amplification regimen, i.e., a set of polymerase chain reaction (PCR) amplification cycles. As used herein, the term "amplification regimen" refers to a process of specifically amplifying (increasing the abundance of) a nucleic acid of interest. In some embodiments, exponential amplification occurs when products of a previous polymerase extension serve as templates for successive rounds of extension. In some embodiments, a PCR amplification regimen according to methods disclosed herein may comprise at least one, and in some cases at least 5 or more iterative cycles. In some embodiments, each iterative cycle comprises steps of: 1) strand separation (e.g., thermal denaturation); 2) oligonucleotide primer annealing to template molecules; and 3) nucleic acid polymerase extension of the annealed primers. In should be appreciated that any suitable conditions and times involved in each of these steps may be used. In some embodiments, conditions and times selected may depend on the length, sequence content, melting temperature, secondary structural features, or other factors relating to the nucleic acid template and/or primers used in the reaction. In some embodiments, an amplification regimen according to methods described herein is performed in a thermal cycler, many of which are commercially available. In some embodiments, methods described herein can comprise linear amplification. For example, in some embodiments, amplification steps performed using nested primers may be performed using linear amplification. In some embodiments, amplification may be conducted using nucleic acid sequence-based amplification (NASBA). For example, in some embodiments, amplification comprises a T7-mediated NASBA reaction.

In some embodiments, a nucleic acid extension reaction involves the use of a nucleic acid polymerase. As used herein, the phrase "nucleic acid polymerase" refers to an enzyme that catalyzes the template-dependent polymerization of nucleoside triphosphates to form primer extension products that are complementary to the template nucleic acid sequence. A nucleic acid polymerase enzyme initiates synthesis at the 3' end of an annealed primer and proceeds in the direction toward the 5' end of the template. Numerous nucleic acid polymerases are known in the art and are commercially available. One group of nucleic acid polymerases are thermostable, i.e., they retain function after being subjected to temperatures sufficient to denature annealed strands of complementary nucleic acids, e.g., 94° C., or sometimes higher. A non-limiting example of a protocol for amplification involves using a polymerase (e.g., Phoenix Taq, VeraSeq) under the following conditions: 98° C. for 30 s, followed by 14-22 cycles comprising melting at 98° C. for 10 s, followed by annealing at 68° C. for 30 s, followed by extension at 72° C. for 3 min, followed by holding of the reaction at 4° C. However, other appropriate reaction conditions may be used. In some embodiments, annealing/extension temperatures may be adjusted to account for differences in salt concentration (e.g., 3° C. higher to higher salt concentrations). In some embodiments, slowing the ramp rate (e.g., 1° C./s, 0.5° C./s, 0.28° C./s, 0.1° C./s or slower), for example, from 98° C. to 65° C., improves primer performance and coverage uniformity in highly multiplexed samples. In some embodiments, systems provided herein are configured to alter vessel temperature (e.g., by cycling between different temperature ranges, having controlled ramp up or down rates) to facilitate amplification.

In some embodiments, a nucleic acid polymerase is used under conditions in which the enzyme performs a template-dependent extension. In some embodiments, the nucleic acid polymerase is DNA polymerase I, Taq polymerase, Phoenix Taq polymerase, Phusion polymerase, T4 polymerase, T7 polymerase, Klenow fragment, Klenow exo-, phi29 polymerase, AMV reverse transcriptase, M-MuLV reverse transcriptase, HIV-1 reverse transcriptase, VeraSeq ULtra polymerase, VeraSeq HF 2.0 polymerase, EnzScript, or another appropriate polymerase. In some embodiments, a nucleic acid polymerase is not a reverse transcriptase. In some embodiments, a nucleic acid polymerase acts on a DNA template. In some embodiments, the nucleic acid polymerase acts on an RNA template. In some embodiments, an extension reaction involves reverse transcription performed on an RNA to produce a complementary DNA molecule (RNA-dependent DNA polymerase activity). In some embodiments, a reverse transcriptase is a mouse moloney murine leukemia virus (M-MLV) polymerase, AMV reverse transcriptase, RSV reverse transcriptase, HIV-1 reverse transcriptase, HIV-2 reverse transcriptase, or another appropriate reverse transcriptase.

In some embodiments, a nucleic acid amplification reaction involves cycles including a strand separation step generally involving heating of the reaction mixture. As used herein, the term "strand separation" or "separating the strands" means treatment of a nucleic acid sample such that complementary double-stranded molecules are separated into two single strands available for annealing to an oligonucleotide primer. In some embodiments, strand separation according to methods described herein is achieved by heating the nucleic acid sample above its melting temperature ($T_m$). In some embodiments, for a sample containing nucleic acid molecules in a reaction preparation suitable for a nucleic acid polymerase, heating to 94° C. is sufficient to achieve strand separation. In some embodiments, a suitable reaction preparation contains one or more salts (e.g., 1 to 100 mM KCl, 0.1 to 10 mM $MgCl_2$), at least one buffering agent (e.g., 1 to 20 mM Tris-HCl), and a carrier (e.g., 0.01 to 0.5% BSA). A non-limiting example of a suitable buffer comprises 50 mM KCl, 10 mM Tris-HCl (pH 8.8 at 25° C.), 0.5 to 3 mM $MgCl_2$, and 0.1% BSA. A further non-limiting example of a suitable buffer comprises 50 mM KCl, 10 mM Tris-HCl (pH 8.8 at 25° C.), 0.5 to 5 mM (e.g., approximately 0.5 mM, approximately 1 mM, approximately 2 mM, approximately 3 mM, approximately 4 mM, approximately 5 mM) $MgCl_2$, and 0.1% BSA.

In some embodiments, a nucleic acid amplification involves annealing primers to nucleic acid templates having a strands characteristic of a target nucleic acid. In some embodiments, a strand of a target nucleic acid can serve as a template nucleic acid. As used herein, the term "anneal" refers to the formation of one or more complementary base pairs between two nucleic acids. In some embodiments, annealing involves two complementary or substantially complementary nucleic acid strands hybridizing together. In some embodiments, in the context of an extension reaction, annealing involves the hybridization of primer to a template such that a primer extension substrate for a template-dependent polymerase enzyme is formed. In some embodiments, conditions for annealing (e.g., between a primer and nucleic acid template) may vary based of the length and sequence of a primer. In some embodiments, conditions for annealing are based upon a $T_m$ (e.g., a calculated $T_m$) of a primer. In some embodiments, an annealing step of an extension regimen involves reducing the temperature following a strand separation step to a temperature based on the $T_m$ (e.g., a calculated $T_m$) for a primer, for a time sufficient to permit such annealing. In some embodiments, a $T_m$ can be determined using any of a number of algorithms (e.g., OLIGO™ (Molecular Biology Insights Inc. Colorado) primer design software and VENTRO NTI™ (Invitrogen, Inc. California) primer design software and programs available on the internet, including Primer3, Oligo Calculator, and NetPrimer (Premier Biosoft; Palo Alto, CA; and freely available on the world wide web (e.g., at premierbiosoft-.com/netprimer/netprlaunch/Help/xnetprlaunch.html)). In some embodiments, the $T_m$ of a primer can be calculated using the following formula, which is used by NetPrimer software and is described in more detail in Frieir, et al. PNAS 1986 83:9373-9377 which is incorporated by reference herein in its entirety.

$$T_m = \Delta H/(\Delta S + R*In(C/4)) + 16.6\ \log([K^+]/(1+0.7[K^+])) - 273.15$$

wherein: ΔH is enthalpy for helix formation; ΔS is entropy for helix formation; R is molar gas constant (1.987 cal/° C.*mol); C is the nucleic acid concentration; and $[K^+]$ is salt concentration. For most amplification regimens, the annealing temperature is selected to be about 5° C. below the predicted $T_m$, although temperatures closer to and above the $T_m$ (e.g., between 1° C. and 5° C. below the predicted $T_m$ or between 1° C. and 5° C. above the predicted $T_m$) can be used, as can, for example, temperatures more than 5° C. below the predicted $T_m$ (e.g., 6° C. below, 8° C. below, 10° C. below or lower). In some embodiments, the closer an annealing temperature is to the $T_m$, the more specific is the annealing. In some embodiments, the time used for primer annealing during an extension reaction (e.g., within the context of a PCR amplification regimen) is determined based, at least in part, upon the volume of the reaction (e.g., with larger volumes involving longer times). In some embodiments, the time used for primer annealing during an extension reaction (e.g., within the context of a PCR amplification regimen) is determined based, at least in part, upon primer and template concentrations (e.g., with higher relative concentrations of primer to template involving less time than lower relative concentrations). In some embodiments, depending upon volume and relative primer/template concentration, primer annealing steps in an extension reaction (e.g., within the context of an amplification regimen) can be in the range of 1 second to 5 minutes, 10 seconds to 2 minutes, or 30 seconds to 2 minutes. As used herein, "substantially anneal" refers to an extent to which complementary base pairs form between two nucleic acids that, when used in the context of a PCR amplification regimen, is sufficient to produce a detectable level of a specifically amplified product.

As used herein, the term "polymerase extension" refers to template-dependent addition of at least one complementary nucleotide, by a nucleic acid polymerase, to the 3' end of a primer that is annealed to a nucleic acid template. In some embodiments, polymerase extension adds more than one nucleotide, e.g., up to and including nucleotides corresponding to the full length of the template. In some embodiments, conditions for polymerase extension are based, at least in part, on the identity of the polymerase used. In some embodiments, the temperature used for polymerase extension is based upon the known activity properties of the enzyme. In some embodiments, in which annealing temperatures are below the optimal temperatures for the enzyme, it may be acceptable to use a lower extension temperature. In some embodiments, enzymes may retain at least partial activity below their optimal extension temperatures. In some embodiments, a polymerase extension (e.g., performed with thermostable polymerases such as Taq polymerase and variants thereof) is performed at 65° C. to 75° C. or 68° C. to 72° C. In some embodiments, methods provided herein involve polymerase extension of primers that are annealed to nucleic acid templates at each cycle of a PCR amplification regimen. In some embodiments, a polymerase extension is performed using a polymerase that has relatively strong strand displacement activity. In some embodiments, polymerases having strong strand displacement are useful for preparing nucleic acids for purposes of detecting fusions (e.g., 5' fusions). In some embodiments, polymerases having 5'→3' exonuclease activity (e.g., Taq polymerase) are useful for producing long library fragments.

In some embodiments, primer extension is performed under conditions that permit the extension of annealed oligonucleotide primers. As used herein, the term "conditions that permit the extension of an annealed oligonucleotide such that extension products are generated" refers to the set of conditions (e.g., temperature, salt and co-factor concentrations, pH, and enzyme concentration) under which a nucleic acid polymerase catalyzes primer extension. In some embodiments, such conditions are based, at least in part, on the nucleic acid polymerase being used. In some embodiments, a polymerase may perform a primer extension reaction in a suitable reaction preparation.

In some embodiments, a suitable reaction preparation contains one or more salts (e.g., 1 to 100 mM KCl, 0.1 to 10 mM $MgCl_2$), at least one buffering agent (e.g., 1 to 20 mM Tris-HCl), a carrier (e.g., 0.01 to 0.5% BSA), and one or more NTPs (e.g., 10 to 200 M of each of dATP, dTTP, dCTP, and dGTP). A non-limiting set of conditions is 50 mM KCl, 10 mM Tris-HCl (pH 8.8 at 25° C.), 0.5 to 3 mM $MgCl_2$, 200 μM each dNTP, and 0.1% BSA at 72° C., under which a polymerase (e.g., Taq polymerase) catalyzes primer extension.

In some embodiments, a suitable reaction preparation contains one or more salts (e.g., 1 to 100 mM KCl, 0.5 to 5 mM $MgCl_2$), at least one buffering agent (e.g., 1 to 20 mM Tris-HCl), a carrier (e.g., 0.01 to 0.5% BSA), and one or more NTPs (e.g., 50 to 350 M of each of dATP, dTTP, dCTP, and dGTP). A non-limiting set of conditions is 50 mM KCl, 10 mM Tris-HCl (pH 8.8 at 25° C.), 3 mM $MgCl_2$, 200 UM each dNTP, and 0.1% BSA at 72° C., under which a polymerase (e.g., Taq polymerase) catalyzes primer extension. A further non-limiting set of conditions is 50 mM KCl, 10 mM Tris-HCl (pH 8.8 at 25° C.), 3 mM $MgCl_2$, 266 μM dATP, 200 μM dCTP, 133 μM dGTP, 200 UM dTTP, and 0.1% BSA at 72° C., under which a polymerase (e.g., Taq polymerase) catalyzes primer extension.

In some embodiments, conditions for initiation and extension may include the presence of one, two, three or four different deoxyribonucleoside triphosphates (e.g., selected from dATP, dTTP, dCTP, and dGTP) and a polymerization-inducing agent such as DNA polymerase or reverse transcriptase, in a suitable buffer. In some embodiments, a "buffer" may include solvents (e.g., aqueous solvents) plus appropriate cofactors and reagents which affect pH, ionic strength, etc. In some embodiments, the two, three or four different deoxyribonucleoside triphosphates are present in equimolar, or approximately equimolar, concentrations. In some embodiments, the two, three or four different deoxyribonucleoside triphosphates are present in different concentrations, which have been experimentally determined to be suitable to a particular implementation of the technology.

In some embodiments, nucleic acid amplification involves up to 5, up to 10, up to 20, up to 30, up to 40 or more rounds (cycles) of amplification. In some embodiments, nucleic acid amplification may comprise a set of cycles of a PCR amplification regimen from 5 cycles to 20 cycles in length. In some embodiments, an amplification step may comprise a set of cycles of a PCR amplification regimen from 10 cycles to 20 cycles in length. In some embodiments, each amplification step can comprise a set of cycles of a PCR amplification regimen from 12 cycles to 16 cycles in length. In some embodiments, an annealing temperature can be less than 70° C. In some embodiments, an annealing temperature can be less than 72° C. In some embodiments, an annealing temperature can be about 65° C. In some embodiments, an annealing temperature can be from about 61 to about 72° C.

In various embodiments, methods and compositions described herein relate to performing a PCR amplification regimen with one or more of the types of primers described herein. As used herein, "primer" refers to an oligonucleotide capable of specifically annealing to a nucleic acid template and providing a 3' end that serves as a substrate for a template-dependent polymerase to produce an extension product which is complementary to the template. In some embodiments, a primer is single-stranded, such that the primer and its complement can anneal to form two strands. Primers according to methods and compositions described herein may comprise a hybridization sequence (e.g., a sequence that anneals with a nucleic acid template) that is less than or equal to 300 nucleotides in length, e.g., less than or equal to 300, or 250, or 200, or 150, or 100, or 90, or 80, or 70, or 60, or 50, or 40, or 30 or fewer, or 20 or fewer, or 15 or fewer, but at least 6 nucleotides in length. In some embodiments, a hybridization sequence of a primer may be 6 to 50 nucleotides in length, 6 to 35 nucleotides in length, 6 to 20 nucleotides in length, 10 to 25 nucleotides in length.

Any suitable method may be used for synthesizing oligonucleotides and primers. In some embodiments, commercial sources offer oligonucleotide synthesis services suitable for providing primers for use in methods and compositions described herein (e.g., INVITROGEN™ Custom DNA Oligos (Life Technologies, Grand Island, NY) or custom DNA Oligos from Integrated DNA Technologies (Coralville, IA)).

Target Nucleic Acid

As used herein, the terms "target nucleic acid," "nucleic acid molecule comprising a target nucleotide sequence." and "nucleic acid comprising a target nucleotide sequence" refer to a nucleic acid molecule of interest (e.g., a nucleic acid to be prepared for analysis). In some embodiments, a target nucleic acid comprises both a target nucleotide sequence (e.g., a known or predetermined nucleotide sequence) and an adjacent nucleotide sequence that is to be determined (which may be referred to as an unknown sequence). A target nucleic acid can be of any appropriate length. In some embodiments, a target nucleic acid is double-stranded. In some embodiments, a target nucleic acid is DNA. In some embodiments, a target nucleic acid comprises genomic or chromosomal DNA (gDNA). In some embodiments, a target nucleic acid comprises complementary DNA (cDNA). In some embodiments, a target nucleic acid is single-stranded. In some embodiments, a target nucleic acid comprises RNA (e.g., mRNA, rRNA, tRNA, cfDNA, cfRNA, long non-coding RNA, microRNA).

Many of the sequencing methods suitable for use in the methods described herein provide sequencing runs with optimal read lengths of tens to hundreds of nucleotide bases (e.g., Ion Torrent technology can produce read lengths of 200-400 bp). Target nucleic acids comprised, for example, by genomic DNA or mRNA, can be comprised by nucleic acid molecules which are substantially longer than this optimal read length. In order for the amplified nucleic acid portion resulting from the second amplification step to be of a suitable length (e.g., up to 100 bp, 200 bp, 300 bp, 400 bp, 500 bp, 1 kb, 2 kb) for use in a particular sequencing technology, the average distance between the known target nucleotide sequence and an end of the target nucleic acid to which the adapter can be ligated should be as close to the optimal read length of the selected technology as possible. For example, if the optimal read-length of a given sequencing technology is 200 bp, then the nucleic acid molecules amplified in accordance with the methods described herein should have an average length of about 400 bp or less. However, it should be appreciated that, in some embodiments, techniques described herein may be implemented when nucleic acid molecules exceed 400 bp in length. For example, in some embodiments, nucleic acid fragments can be approximately 400 or more nucleotides, 500 or more nucleotides, 600 or more nucleotides, 700 or more nucleotides, 800 or more nucleotides, 900 or more nucleotides, 1000 or more nucleotides, 1500 or more nucleotides, 2000 or more nucleotides, 2500 or more nucleotides, 3000 or more nucleotides, 4000 or more nucleotides, 5000 or more nucleotides, 10000 or more nucleotides. Target nucleic acids comprised by, e.g., genomic DNA or mRNA, can be sheared, e.g., mechanically or enzymatically sheared, to generate fragments of any desired size. Non-limiting examples of mechanical shearing processes include sonication, nebulization, and AFA™ shearing technology available from Covaris (Woburn, MA). In some embodiments, a target nucleic acid comprised by genomic DNA can be mechanically sheared by sonication.

In some embodiments, when the target nucleic acid is comprised by RNA, the sample can be subjected to a reverse transcriptase regimen to generate a DNA template. In some embodiments, the DNA template can then be sheared. In some embodiments, the DNA template is not sheared. For example, in some embodiments, the concentration of primers used during a reverse transcriptase regimen can be adjusted such that the product cDNA is of an appropriate "fragmented" length. In some embodiments, target RNA can be sheared before performing the reverse transcriptase regimen. In some embodiments, a sample comprising target RNA can be used in the methods described herein using total nucleic acids extracted from either fresh or degraded specimens; without the need of genomic DNA removal for cDNA sequencing; without the need of ribosomal RNA depletion for cDNA sequencing; without the need of mechanical or enzymatic shearing in any of the steps; by subjecting the RNA for double-stranded cDNA synthesis using random hexamers; and by subjecting the nucleic acid to end-repair, phosphorylation, and adenylation.

In some embodiments, a target nucleotide sequence can be comprised by a gene rearrangement. The methods described herein are suited for determining the presence and/or identity of a gene rearrangement as the identity of only one half of the gene rearrangement must be previously known (i.e., the half of the gene rearrangement which is to be targeted by the gene-specific primers). In some embodiments, the gene rearrangement can comprise an oncogene. In some embodiments, the gene rearrangement can comprise a fusion oncogene. In some embodiments, the gene rearrangement can comprise a V(D)J recombination product.

As used herein, the term "known target nucleotide sequence" or "target nucleotide sequence" refers to a portion of a target nucleic acid for which the sequence (e.g., the identity and order of the nucleotide bases of the nucleic acid) is known. For example, in some embodiments, a known target nucleotide sequence is a nucleotide sequence of a nucleic acid that is known or that has been determined in advance of an interrogation of an adjacent unknown sequence of the nucleic acid. A known target nucleotide sequence can be of any appropriate length.

In some embodiments, a target nucleotide sequence (e.g., a known target nucleotide sequence) has a length of 10 or more nucleotides, 30 or more nucleotides, 40 or more nucleotides, 50 or more nucleotides, 100 or more nucleotides, 200 or more nucleotides, 300 or more nucleotides, 400 or more nucleotides, 500 or more nucleotides, 600 or more nucleotides, 700 or more nucleotides, 800 or more nucleotides, 900 or more nucleotides, 1000 or more nucleotides, 1500 or more nucleotides, 2000 or more nucleotides, 2500 or more nucleotides, 3000 or more nucleotides, 4000 or more nucleotides, 5000 or more nucleotides, 10000 or more nucleotides. In some embodiments, a target nucleotide sequence (e.g., a known target nucleotide sequence) has a length in the range of 10 to 100 nucleotides, 10 to 500 nucleotides, 10 to 1000 nucleotides, 100 to 500 nucleotides, 100 to 1000 nucleotides, 500 to 1000 nucleotides, 500 to 5000 nucleotides.

In some embodiments, methods are provided herein for determining sequences of contiguous (or adjacent) portions of a nucleic acid. As used herein, the term "nucleotide sequence contiguous to" refers to a nucleotide sequence of a nucleic acid molecule (e.g., a target nucleic acid) that is immediately upstream or downstream of another nucleotide sequence (e.g., a known nucleotide sequence). In some embodiments, a nucleotide sequence contiguous to a known target nucleotide sequence may be of any appropriate length. In some embodiments, a nucleotide sequence contiguous to a known target nucleotide sequence comprises 1 kb or less of nucleotide sequence, e.g., 1 kb or less of nucleotide sequence, 750 bp or less of nucleotide sequence, 500 bp or less of nucleotide sequence, 400 bp or less of nucleotide sequence, 300 bp or less of nucleotide sequence, 200 bp or less of nucleotide sequence, 100 bp or less of nucleotide sequence. In some embodiments, in which a sample comprises different target nucleic acids comprising a known target nucleotide sequence (e.g., a cell in which a known target nucleotide sequence occurs multiple times in its genome, or on separate, non-identical chromosomes), there may be multiple sequences which comprise "a nucleotide sequence contiguous to" the known target nucleotide sequence. As used herein, the term "determining a (or the)nucleotide sequence," refers to determining the identity and relative positions of the nucleotide bases of a nucleic acid.

In some embodiments, a known target nucleic acid can contain a fusion sequence resulting from a gene rearrangement. In some embodiments, methods described herein are suited for determining the presence and/or identity of a gene rearrangement. In some embodiments, the identity of one portion of a gene rearrangement is previously known (e.g., the portion of a gene rearrangement that is to be targeted by the gene-specific primers) and the sequence of the other portion may be determined using methods disclosed herein. In some embodiments, a gene rearrangement can involve an oncogene. In some embodiments, a gene rearrangement can comprise a fusion oncogene.

Molecular Barcodes and Index Sequences

In some embodiments, primers and/or adapters may contain additional sequences such as an identifier sequence (e.g., a barcode, an index), sequencing primer hybridization sequences (e.g., Rd1), and adapter sequences. In some embodiments the adapter sequences are sequences used with a next generation sequencing system. In some embodiments, the adapter sequences are P5 and P7 sequences for Illumina-based sequencing technology. In some embodiments, the adapter sequence are PI and A compatible with Ion Torrent sequencing technology.

In some embodiments, as used herein, "barcode," "molecular barcode," and "molecular barcode tag" may be used interchangeably, and generally refer to a region of an adapter nucleic acid that is useful as an identifier for the specific nucleic acid to which it is ligated. In some embodiments, a molecular barcode comprises a randomized nucleic acid sequence that provides a unique identifier for the nucleic acid to which it is ligated. In some embodiments, a molecular barcode may be used to identify unique fragments and "de-duplicate" the sequencing reads from a sample. In some embodiments, a molecular barcode may be used to identify and remove PCR duplicates. In some embodiments, a molecular barcode may be 2 to 25 nucleotides in length, 2 to 15 nucleotides in length, 2 to 10 nucleotides in length, 2 to 6 nucleotides in length. In some embodiments, a molecular barcode comprises at least 2, 3, 4, 5, 6, 7, 8, 9, 10, 11, 12, 13, 14, 15, 16, 17, 18, 19, 20, 21, 22, 23, 24, or at least 25 nucleotides. In some embodiments, a molecular barcode comprises 8 nucleotides.

In some embodiments, as used herein, "index." "index sequence," "index region," and "sample index" may be used interchangeably, and generally refer to a region of an adapter nucleic acid that is useful as an identifier for the population to which the ligated nucleic acid belongs. In some embodiments, an index comprises a fixed nucleic acid sequence that may be used to identify a collection of sequences belonging to a common library. For example, an index may be used to identify a sample that corresponds to a nucleic acid. In some embodiments, an index may be used, for example, as a source identifier, location identifier, date or time identifier (e.g., date or time of sampling or processing), or other identifier of a nucleic acid relating to a shared or common property (e.g., common among other nucleic acids of a library). In some embodiments, such index sequences are useful for identifying different aspects of a nucleic acid that are present in a population of nucleic acids. In some embodiments, index sequences may provide a source or location identifier for a target nucleic acid. For example, an index sequence may serve to identify a patient from whom a nucleic acid is obtained. In some embodiments, index sequences enable sequencing of multiple different samples on a single reaction (e.g., performed in a single flow cell). In some embodiments, an index sequence can be used to orientate a sequence imager for purposes of detecting individual sequencing reactions. In some embodiments, an index sequence may be 2 to 25 nucleotides in length, 2 to 15 nucleotides in length, 2 to 10 nucleotides in length, 2 to 6 nucleotides in length. In some embodiments, an index comprises at least 2, 3, 4, 5, 6, 7, 8, 9, 10, 11, 12, 13, 14, 15, 16, 17, 18, 19, 20, 21, 22, 23, 24, or at least 25 nucleotides.

In some embodiments, when a population of tailed random primers is used in accordance with methods described herein, multiple distinguishable amplification products can be present after amplification. In some embodiments, because tailed random primers hybridize at various positions throughout nucleic acid molecules of a sample, a set of target-specific primers can hybridize (and amplify) the extension products created by more than 1 hybridization event, e.g., one tailed random primer may hybridize at a first distance (e.g., 100 nucleotides) from a target-specific primer hybridization site, and another tailed random primer can hybridize at a second distance (e.g., 200 nucleotides) from a target-specific primer hybridization site, thereby resulting in two amplification products (e.g., a first amplification product comprising about 100 bp and a second amplification product comprising about 200 bp). In some embodiments, these multiple amplification products can each be sequenced using next generation sequencing technology. In some embodiments, sequencing of these multiple amplification products is advantageous because it provides multiple overlapping sequence reads that can be compared with one another to detect sequence errors introduced during amplification or sequencing processes. In some embodiments, individual amplification products (e.g., derived from a single molecule) can be aligned and where they differ in the sequence present at a particular base, an artifact or error of PCR and/or sequencing may be present.

DNA Shearing/Fragmentation

The nucleic acid molecules described herein can be sheared (e.g., mechanically or enzymatically sheared, sheared via nebulizer) to generate fragments of any desired size. Non-limiting examples of mechanical shearing processes include sonication, nebulization, and AFA™ shearing technology available from Covaris (Woburn, MA). In some embodiments, a nucleic acid can be mechanically sheared by sonication. In some embodiments, a target nucleic acid is not sheared or digested. In some embodiments, nucleic acid products of preparative steps (e.g., extension products, amplification products) are not sheared or enzymatically digested.

In some embodiments, when a target nucleotide sequence comprises RNA, the sample can be subjected to a reverse transcriptase regimen to generate a DNA template and the DNA template can then be sheared. In some embodiments, target RNA can be sheared before performing a reverse transcriptase regimen. In some embodiments, a sample comprising target RNA can be used in methods described herein using total nucleic acids extracted from either fresh or degraded specimens; without the need of genomic DNA removal for cDNA sequencing; without the need of ribosomal RNA depletion for cDNA sequencing; without the need of mechanical or enzymatic shearing in any of the steps: by subjecting the RNA for double-stranded cDNA synthesis using random hexamers.

Sequencing

In some aspects, the technology described herein relates to methods of enriching nucleic acid samples for oligonucleotide sequencing. In some embodiments, the sequencing can be performed by a next-generation sequencing method. As used herein, "next-generation sequencing" refers to oligonucleotide sequencing technologies that have the capacity to sequence oligonucleotides at speeds above those possible with conventional sequencing methods (e.g., Sanger sequencing), due to performing and reading out thousands to millions of sequencing reactions in parallel. Non-limiting examples of next-generation sequencing methods/platforms include Massively Parallel Signature Sequencing (Lynx Therapeutics); 454 pyro-sequencing (454 Life Sciences/Roche Diagnostics); solid-phase, reversible dye-terminator sequencing (Solexa/Illumina); SOLID technology (Applied Biosystems); Ion semiconductor sequencing (ION Torrent); DNA nanoball sequencing (Complete Genomics); and technologies available from Pacific Biosciences, Intelligen Biosystems, and Oxford Nanopore Technologies. In some embodiments, the sequencing primers can comprise portions compatible with the selected next-generation sequencing method. Next-generation sequencing technologies and the constraints and design parameters of associated sequencing primers are well known in the art (see, e.g., Shendure, et al., "Next-generation DNA sequencing," Nature, 2008, vol. 26, No. 10, 1135-1145; Mardis, "The impact of next-generation sequencing technology on genetics." Trends in Genetics, 2007, vol. 24, No. 3, pp. 133-141; Su, et al., "Next-generation sequencing and its applications in molecular diagnostics" Expert Rev Mol Diagn, 2011, 11 (3): 333-43; Zhang et al., "The impact of next-generation sequencing on genomics". J Genet Genomics, 2011, 38 (3): 95-109; (Nyren, P. et al. Anal Biochem 208:17175 (1993); Bentley, D. R. Curr Opin Genet Dev 16:545-52 (2006); Strausberg, R. L., et al. Drug Disc Today 13:569-77 (2008); U.S. Pat. Nos. 7,282,337; 7,279,563; 7,226,720; 7,220,549; 7,169,560; 6,818,395; 6,911,345; US Pub. Nos. 2006/0252077; 2007/0070349; and 20070070349; which are incorporated by reference herein in their entireties).

In some embodiments, the sequencing step relies upon the use of a first and second sequencing primer. In some embodiments, the first and second sequencing primers are selected to be compatible with a next-generation sequencing method as described herein.

Methods of aligning sequencing reads to known sequence databases of genomic and/or cDNA sequences are well known in the art, and software is commercially available for this process. In some embodiments, reads (less the sequencing primer and/or adapter nucleotide sequence) which do not map, in their entirety, to wild-type sequence databases can be genomic rearrangements or large indel mutations. In some embodiments, reads (less the sequencing primer and/or adapter nucleotide sequence) comprising sequences which map to multiple locations in the genome can be genomic rearrangements. In some embodiments, a de novo assembly of reads overlapping into contiguous sequences, or "contigs," may be built and utilized in the alignment of sequencing reads. In some embodiments, a hot spot reference may be utilized that does not rely on a publicly accessible genomics database.

Samples

In some embodiments, a nucleic acid (e.g., target nucleic acid, nucleic acid comprising a target nucleotide sequence) is present in or obtained from an appropriate sample (e.g., a food sample, environmental sample, biological sample e.g., blood sample, etc.). In some embodiments, the target nucleic acid is a biological sample obtained from a subject. In some embodiments a sample can be a diagnostic sample obtained from a subject. In some embodiments, a sample can further comprise proteins, cells, fluids, biological fluids, preservatives, and/or other substances. By way of non-limiting example, a sample can be a cheek swab, blood, serum, plasma, sputum, cerebrospinal fluid, urine, tears, alveolar isolates, pleural fluid, pericardial fluid, cyst fluid, tumor tissue, tissue, a biopsy, saliva, an aspirate, or combinations thereof. In some embodiments, a sample can be obtained by resection or biopsy.

In some embodiments, the sample can be obtained from a subject in need of treatment for a disease associated with a genetic alteration, e.g., cancer or a hereditary disease. In some embodiments, a known target sequence is present in a disease-associated gene.

In some embodiments, a sample is obtained from a subject in need of treatment for cancer. In some embodiments, the sample comprises a population of tumor cells, e.g., at least one tumor cell. In some embodiments, the sample comprises a tumor biopsy, including but not limited to, untreated biopsy tissue or treated biopsy tissue (e.g., formalin-fixed and/or paraffin-embedded biopsy tissue).

In some embodiments, the sample is freshly collected. In some embodiments, the sample is stored prior to being used in methods and compositions described herein. In some embodiments, the sample is an untreated sample. As used herein, "untreated sample" refers to a biological sample that has not had any prior sample pre-treatment except for dilution and/or suspension in a solution. In some embodiments, a sample is obtained from a subject and preserved or processed prior to being utilized in methods and compositions described herein. By way of non-limiting example, a sample can be embedded in paraffin wax, refrigerated, or frozen. A frozen sample can be thawed before determining the presence of a nucleic acid according to methods and compositions described herein. In some embodiments, the sample can be a processed or treated sample. Exemplary methods for treating or processing a sample include, but are not limited to, centrifugation, filtration, sonication, homogenization, heating, freezing and thawing, contacting with a preservative (e.g., anti-coagulant or nuclease inhibitor) and any combination thereof. In some embodiments, a sample can be treated with a chemical and/or biological reagent. Chemical and/or biological reagents can be employed to protect and/or maintain the stability of the sample or nucleic acid comprised by the sample during processing and/or storage. In addition, or alternatively, chemical and/or biological reagents can be employed to release nucleic acids from other components of the sample. By way of non-limiting example, a blood sample can be treated with an anti-coagulant prior to being utilized in methods and compositions described herein. Suitable methods and processes for processing, preservation, or treatment of samples for nucleic acid analysis may be used in the method disclosed herein. In some embodiments, a sample can be a clarified fluid sample. In some embodiments, a sample can be clarified by low-speed centrifugation (e.g., 3,000×g or less) and collection of the supernatant comprising the clarified fluid sample.

In some embodiments, a nucleic acid present in a sample can be isolated, enriched, or purified prior to being utilized in methods and compositions described herein. Suitable methods of isolating, enriching, or purifying nucleic acids from a sample may be used. For example, kits for isolation of genomic DNA from various sample types are commercially available (e.g., Catalog Nos. 51104, 51304, 56504, and 56404; Qiagen; Germantown, MD). In some embodiments, methods described herein relate to methods of enriching for target nucleic acids, e.g., prior to a sequencing of the target nucleic acids. In some embodiments, a sequence of one end of the target nucleic acid to be enriched is not known prior to sequencing. In some embodiments, methods described herein relate to methods of enriching specific nucleotide sequences prior to determining the nucleotide sequence using a next-generation sequencing technology. In some embodiments, methods of enriching specific nucleotide sequences do not comprise hybridization enrichment.

Target genes and Therapeutic Applications

Aspects of the disclosure may be useful in the genetic analysis of an immune system. However, it should be appreciated that the techniques described herein may be applied to any target gene or nucleic acid of interest. In some embodiments of techniques described herein, a determination of the sequence contiguous to a known oligonucleotide target sequence can provide information relevant to treatment of disease. Thus, in some embodiments, methods disclosed herein can be used to aid in treating disease. In some embodiments, a sample can be from a subject in need of treatment for a disease associated with a genetic alteration. In some embodiments, a known target sequence is a sequence of a disease-associated gene, e.g., an oncogene. In some embodiments, a sequence contiguous to a known oligonucleotide target sequence and/or the known oligonucleotide target sequence can comprise a mutation or genetic abnormality which is disease-associated, e.g., a SNP, an insertion, a deletion, and/or a gene rearrangement. In some embodiments, a sequence contiguous to a known target sequence and/or a known target sequence present in a sample comprised sequence of a gene rearrangement product. In some embodiments, a gene rearrangement can be an oncogene, e.g., a fusion oncogene.

Certain treatments for cancer are particularly effective against tumors comprising certain oncogenes, e.g., a treatment agent which targets the action or expression of a given fusion oncogene can be effective against tumors comprising that fusion oncogene but not against tumors lacking the fusion oncogene. Methods described herein can facilitate a determination of specific sequences that reveal oncogene status (e.g., mutations, SNPs, and/or rearrangements). In some embodiments, methods described herein can further allow the determination of specific sequences when the sequence of a flanking region is known, e.g., methods described herein can determine the presence and identity of gene rearrangements involving known genes (e.g., oncogenes) in which the precise location and/or rearrangement partner are not known before methods described herein are performed.

In some embodiments, a subject is in need of treatment for lung cancer (e.g., with EGFR-TKI, a targeted cancer therapy). In some embodiments, e.g., when the sample is obtained from a subject in need of treatment for lung cancer, the known target sequence can comprise a sequence from a gene selected from the group of ALK, ROS1, and RET. Accordingly, in some embodiments, gene rearrangements result in fusions involving the ALK, ROS1, or RET. Non-limiting examples of gene arrangements involving ALK, ROS1, or RET are described in, e.g., Soda et al. Nature 2007 448561-6: Rikova et al. Cell 2007 131:1190-1203; Kohno et al. Nature Medicine 2012 18:375-7; Takouchi et al. Nature Medicine 2012 18:378-81; which are incorporated by reference herein in their entireties. However, it should be appreciated that the precise location of a gene rearrangement and the identity of the second gene involved in the rearrangement may not be known in advance. Accordingly, in methods described herein, the presence and identity of such rearrangements can be detected without having to know the location of the rearrangement or the identity of the second gene involved in the gene rearrangement.

In some embodiments, the known target sequence can comprise sequence from a gene selected from the group of: ALK, ROS1, and RET.

In some embodiments, the presence of a gene rearrangement of ALK in a sample obtained from a tumor in a subject can indicate that the tumor is susceptible to treatment with a treatment selected from the group consisting of: an ALK inhibitor; EGFR; crizotinib (PF-02341066); AP26113; LDK378; 3-39; AF802; IPI-504; ASP3026; AP-26113; X-396; GSK-1838705A; CH5424802; diamino and aminopyrimidine inhibitors of ALK kinase activity such as NVP-TAE684 and PF-02341066 (see, e.g., Galkin et al., Proc Natl Acad Sci USA, 2007, 104:270-275; Zou et al., Cancer Res, 2007, 67:4408-4417; Hallberg and Palmer F1000 Med Reports 2011 3:21; Sakamoto et al., Cancer Cell 2011 19:679-690; and molecules disclosed in WO 04/079326). All of the foregoing references are incorporated by reference herein in their entireties. An ALK inhibitor can include any agent that reduces the expression and/or kinase activity of ALK or a portion thereof, including, e.g., oligonucleotides, small molecules, and/or peptides that reduce the expression and/or activity of ALK or a portion thereof. As used herein "anaplastic lymphoma kinase" or "ALK" refers to a transmembrane tyrosine kinase typically involved in neuronal regulation in the wildtype form. The nucleotide sequence of the ALK gene and mRNA are known for a number of species, including human (e.g., as annotated under NCBI Gene ID: 238).

In some embodiments, the presence of a gene rearrangement of ROS1 in a sample obtained from a tumor in a subject can indicate that the tumor is susceptible to treatment with a treatment selected from the group consisting of: a ROS1 inhibitor and an ALK inhibitor as described herein above (e.g., crizotinib). A ROS1 inhibitor can include any agent that reduces the expression and/or kinase activity of ROS1 or a portion thereof, including, e.g., oligonucleotides, small molecules, and/or peptides that reduce the expression and/or activity of ROS1 or a portion thereof. As used herein "c-ros oncogene 1" or "ROS1" (also referred to in the art as ros-1) refers to a transmembrane tyrosine kinase of the sevenless subfamily and which interacts with PTPN6. Nucleotide sequences of the ROS1 gene and mRNA are known for a number of species, including human (e.g., as annotated under NCBI Gene ID: 6098).

In some embodiments, the presence of a gene rearrangement of RET in a sample obtained from a tumor in a subject can indicate that the tumor is susceptible to treatment with a treatment selected from the group consisting of: a RET inhibitor; DP-2490, DP-3636, SU5416; BAY 43-9006, BAY 73-4506 (regorafenib), ZD6474, NVP-AST487, sorafenib, RPI-1, XL184, vandetanib, sunitinib, imatinib, pazopanib, axitinib, motesanib, gefitinib, and withaferin A (see, e.g., Samadi et al., Surgery 2010 148:1228-36; Cuccuru et al., JNCI 2004 13:1006-1014; Akeno-Stuart et al., Cancer Research 2007 67:6956; Grazma et al., J Clin Oncol 2010 28: 15s 5559; Mologni et al., J Mol Endocrinol 2006 37:199-212; Calmomagno et al., Journal NCI 2006 98:326-334; Mologni, Curr Med Chem 2011 18:162-175; and the compounds disclosed in WO 06/034833; US Patent Publication 2011/0201598 and U.S. Pat. No. 8,067,434). All of the foregoing references are incorporated by reference herein in their entireties. A RET inhibitor can include any agent that reduces the expression and/or kinase activity of RET or a portion thereof, including, e.g., oligonucleotides, small molecules, and/or peptides that reduce the expression and/or activity of RET or a portion thereof. As used herein, "rearranged during transfection" or "RET" refers to a receptor tyrosine kinase of the cadherin superfamily which is involved in neural crest development and recognizes glial cell line-derived neurotrophic factor family signaling molecules. Nucleotide sequences of the RET gene and mRNA are known for a number of species, including human (e.g., as annotated under NCBI Gene ID: 5979).

In some embodiments, the known target sequence can comprise a gene selected from Table 2.

TABLE 2

Known target sequences

| GENE | TRANSCRIPT NCBI Reference Sequence (RefSeq) | EXONS | DIRECTION | TYPE |
|---|---|---|---|---|
| AKT3 | NM_005465 | 1, 2, 3 | 5' | Fusion |
| ALK | NM_004304 | 19, (intron 19), 20, 21, 22 | 5' | Fusion |
| ARHGAP26 | NM_015071 | 2, 10, 11, 12 | 5' | Fusion |
| AXL | NM_021913 | 19, 20 | 3' | Fusion |
| BRAF | NM_004333 | 7, 8 | 3' | Fusion |
| BRAF | NM_004333 | 7, 8, 9, 10, 11, 12 | 5' | Fusion |
| BRAF | NM_004333 | 15 | 5' | Fusion |
| BRAF | NM_004333 | V600E | n/a | Mutation |
| BRD3 | NM_007371 | 9, 10, 11, 12 | 3' | Fusion |
| BRD4 | NM_014299 | 10, 11 | 3' | Fusion |
| EGFR | NM_005228 | 7, 9, 16, 20 | 5' | Fusion |
| EGFR | NM_005228 | 8 (2-7 exon skipping event) | n/a | Mutation |
| EGFR | NM_005228 | 24, 25 | 3' | Fusion |
| ERG | NM_004449 | 2, 3, 4, 5, 6, 7, 8, 9, 10, 11 | 5' | Fusion |
| ESR1 | NM_001122742 | 3, 4, 5, 6 | 3' | Fusion |
| ETV1 | NM_004956 | 3, 4, 5, 6, 7, 8, 9, 10, 11, 12, 13 | 5' | Fusion |
| ETV4 | NM_001986 | 2, 4, 5, 6, 7, 8, 9, 10 | 5' | Fusion |
| ETV5 | NM_004454 | 2, 3, 7, 8, 9 | 5' | Fusion |

TABLE 2-continued

| Known target sequences | | | | |
|---|---|---|---|---|
| GENE | TRANSCRIPT NCBI Reference Sequence (RefSeq) | EXONS | DIRECTION | TYPE |
| ETV6 | NM_001987 | 1, 2, 3, 4, 5, 6 | 3' | Fusion |
| ETV6 | NM_001987 | 2, 3, 5, 6, 7 | 5' | Fusion |
| EWSR1 | NM_005243 | 4, 5, 6, 7, 8, 9, 10, 11, 12, 13, 14 | 3' | Fusion |
| FGFR1 | NM_015850 | 2, 8, 9, 10, 17 | 5' | Fusion |
| FGFR2 | NM_000141 | 2, 8, 9, 10 | 5' | Fusion |
| FGFR2 | NM_000141 | 17 | 3' | Fusion |
| FGFR3 | NM_000142 | 17, Intron 17 | 3' | Fusion |
| FGFR3 | NM_000142 | 8, 9, 10 | 5' | Fusion |
| FGR | NM_005248 | 2 | 5' | Fusion |
| INSR | NM_000208 | 20, 21, 22 | 3' | Fusion |
| INSR | NM_000208 | 12, 13, 14, 15, 16, 17, 18, 19 | 5' | Fusion |
| MAML2 | NM_032427 | 2, 3 | 5' | Fusion |
| MAST1 | NM_014975 | 7, 8, 9, 18, 19, 20, 21 | 5' | Fusion |
| MAST2 | NM_015112 | 2, 3, 5, 6 | 5' | Fusion |
| MET | NM_000245 | 13 | 3' | Fusion |
| MET | NM_000245 | 13, 15 (exon 14 skipping event) | n/a | Mutation |
| MSMB | NM_002443 | 2, 3, 4 | 3' | Fusion |
| MUSK | NM_005592 | 7, 8, 9, 11, 12, 13, 14 | 5' | Fusion |
| MYB | NM_001130173 | 7, 8, 9, 11, 12, 13, 14, 15, 16 | 3' | Fusion |
| NOTCH1 | NM_017617 | 2, 4, 29, 30, 31 | 3' | Fusion |
| NOTCH1 | NM_017617 | 26, 27, 28, 29 (internal exon 3-27 deletion) | 5' | Fusion |
| NOTCH2 | NM_024408 | 5, 6, 7 | 3' | Fusion |
| NOTCH2 | NM_024408 | 26, 27, 28 | 5' | Fusion |
| NRG1 | NM_004495 | 1, 2, 3, 6 | 5' | Fusion |
| NTRK1 | NM_002529 | 8, 10, 11, 12, 13 | 5' | Fusion |
| NTRK2 | NM_006180 | 11, 12, 13, 14, 15, 16, 17 | 5' | Fusion |
| NTRK3 | NM_002530 | 13, 14, 15, 16 | 5' | Fusion |
| NTRK3 | NM_001007156 | 15 | 5' | Fusion |
| NUMBL | NM_004756 | 3 | 5' | Fusion |
| NUTM1 | NM_175741 | 3 | 5' | Fusion |
| PDGFRA | NM_006206 | 7 (exon 8 deletion) | n/a | Mutation |
| PDGFRA | NM_006206 | 10, 11, 12, 13, 14, | 5' | Fusion |
| PDGFRA | NM_006206 | T674I, D842V | n/a | Mutation |
| PDGFRB | NM_002609 | 8, 9, 10, 11, 12, 13, 14 | 5' | Fusion |
| PIK3CA | NM_006218 | 2 | 5' | Fusion |
| PKN1 | NM_002741 | 10, 11, 12, 13 | 5' | Fusion |
| PPARG | NM_015869 | 1, 2, 3 | 5' | Fusion |
| PRKCA | NM_002737 | 4, 5, 6 | 5' | Fusion |
| PRKCB | NM_002738 | 3 | 5' | Fusion |
| RAF1 | NM_002880 | 4, 5, 6, 7, 9 | 3' | Fusion |
| RAF1 | NM_002880 | 4, 5, 6, 7, 9, 10, 11, 12 | 5' | Fusion |
| RELA | NM_021975 | 3, 4 | 5' | Fusion |
| RET | NM_020630 | 8, 9, 10, 11, 12, 13 | 5' | Fusion |
| ROS1 | NM_002944 | 31, 32, 33, 34, 35, 36, 37 | 5' | Fusion |
| RSPO2 | NM_178565 | 1, 2 | 5' | Fusion |
| RSPO3 | NM_032784 | 2 | 5' | Fusion |
| TERT | NM_198253 | 2 | 5' | Fusion |
| TFE3 | NM_006521 | 2, 3, 4, 5, 6 | 3' | Fusion |
| TFE3 | NM_006521 | 2, 3, 4, 5, 6, 7, 8 | 5' | Fusion |
| TFEB | NM_007162 | 1, 2 | 5' | Fusion |
| THADA | NM_022065 | 28 | 3' | Fusion |
| TMPRSS2 | NM_005656 | 1, 2, 3, 4, 5, 6 | 3' | Fusion |
| TMPRSS2 | NM_001135099 | 1 | 3' | Fusion |

Further non-limiting examples of applications of methods described herein include detection of hematological malignancy markers and panels thereof (e.g., including those to detect genomic rearrangements in lymphomas and leukemias), detection of sarcoma-related genomic rearrangements and panels thereof; and detection of IGH/TCR gene rearrangements and panels thereof for lymphoma testing.

In some embodiments, methods described herein relate to treating a subject having or diagnosed as having, e.g., cancer with a treatment for cancer. Subjects having cancer can be identified by a physician using current methods of diagnosing cancer. For example, symptoms and/or complications of lung cancer which characterize these conditions and aid in diagnosis are well known in the art and include but are not limited to, weak breathing, swollen lymph nodes above the collarbone, abnormal sounds in the lungs, dullness when the chest is tapped, and chest pain. Tests that may aid in a diagnosis of, e.g., lung cancer include, but are not limited to, x-rays, blood tests for high levels of certain substances (e.g., calcium), CT scans, and tumor biopsy. A family history of lung cancer, or exposure to risk factors for lung cancer (e.g., smoking or exposure to smoke and/or air pollution) can also aid in determining if a subject is likely to have lung cancer or in making a diagnosis of lung cancer. Cancer can include, but is not limited to, carcinoma, including adenocarcinoma, lymphoma, blastoma, melanoma, sarcoma, leukemia, squamous cell cancer, small-cell lung cancer, non-small cell lung cancer, gastrointestinal cancer, Hodgkin's and non-Hodgkin's lymphoma, pancreatic cancer, glioblastoma, basal cell carcinoma, biliary tract cancer, bladder cancer, brain cancer including glioblastomas and medulloblastomas; breast cancer, cervical cancer, choriocarcinoma; colon cancer, colorectal cancer, endometrial carcinoma, endometrial cancer; esophageal cancer, gastric cancer; various types of head and neck cancers, intraepithelial neoplasms including Bowen's disease and Paget's disease; hematological neoplasms including acute lymphocytic and myelogenous leukemia; Kaposi's sarcoma, hairy cell leukemia; chronic myelogenous leukemia, AIDS-associated leukemias and adult T-cell leukemia lymphoma; kidney cancer such as renal cell carcinoma, T-cell acute lymphoblastic leukemia/lymphoma, lymphomas including Hodgkin's disease and lymphocytic lymphomas; liver cancer such as hepatic carcinoma and hepatoma, Merkel cell carcinoma, melanoma, multiple myeloma; neuroblastomas; oral cancer including squamous cell carcinoma; ovarian cancer including those arising from epithelial cells, sarcomas including leiomyosarcoma, rhabdomyosarcoma, liposarcoma, fibrosarcoma, and osteosarcoma; pancreatic cancer; skin cancer including melanoma, stromal cells, germ cells and mesenchymal cells; prostate cancer, rectal cancer; vulval cancer, renal cancer including adenocarcinoma: testicular cancer including germinal tumors such as seminoma, non-seminoma (teratomas, choriocarcinomas), stromal tumors, and germ cell tumors; thyroid cancer including thyroid adenocarcinoma and medullar carcinoma; esophageal cancer, salivary gland carcinoma, and Wilms' tumors. In some embodiments, the cancer can be lung cancer.

Multiplex Methods

Methods described herein can be employed in a multiplex format. In embodiments of methods described herein, multiplex applications can include determining the nucleotide sequence contiguous to one or more known target nucleotide sequences. As used herein, "multiplex amplification" refers to a process that involves simultaneous amplification of more than one target nucleic acid in one or more reaction vessels. In some embodiments, methods involve subsequent determination of the sequence of the multiplex amplification products using one or more sets of primers. Multiplex can refer to the detection of between about 2-1,000 different target sequences in a single reaction. In some embodiments, however, multiplex can refer to the detection of between about 1,000-10,000 different target sequences in a single reaction. In some embodiments, multiplex can refer to the detection of between about 10,000-100,000 different target sequences in a single reaction. As used herein, multiplex refers to the detection of any range between 2-1,000, e.g., between 5-500, 25-1,000, or 10-100 different target sequences in a single reaction, etc. The term "multiplex" as applied to PCR implies that there are primers specific for at least two different target sequences in the same PCR reaction.

In some embodiments, target nucleic acids in a sample, or separate portions of a sample, can be amplified with a plurality of primers (e.g., a plurality of first and second target-specific primers). In some embodiments, the plurality of primers (e.g., a plurality of first and second target-specific primers) can be present in a single reaction mixture, e.g., multiple amplification products can be produced in the same reaction mixture. In some embodiments, the plurality of primers (e.g., a plurality of sets of first and second target-specific primers) can specifically anneal to known target sequences comprised by separate genes. In some embodiments, at least two sets of primers (e.g., at least two sets of first and second target-specific primers) can specifically anneal to different portions of a known target sequence. In some embodiments, at least two sets of primers (e.g., at least two sets of first and second target-specific primers) can specifically anneal to different portions of a known target sequence comprised by a single gene. In some embodiments, at least two sets of primers (e.g., at least two sets of first and second target-specific primers) can specifically anneal to different exons of a gene comprising a known target sequence. In some embodiments, the plurality of primers (e.g., first target-specific primers) can comprise identical 5' tag sequence portions.

In embodiments of methods described herein, multiplex applications can include determining the nucleotide sequence contiguous to one or more known target nucleotide sequences in multiple samples in one sequencing reaction or sequencing run. In some embodiments, multiple samples can be of different origins, e.g., from different tissues and/or different subjects. In such embodiments, primers (e.g., tailed random primers) can further comprise a barcode portion. In some embodiments, a primer (e.g., a tailed random primer) with a unique barcode portion can be added to each sample and ligated to the nucleic acids therein; the samples can subsequently be pooled. In such embodiments, each resulting sequencing read of an amplification product will comprise a barcode that identifies the sample containing the template nucleic acid from which the amplification product is derived.

EXAMPLES

The following examples are intended to illustrate certain embodiments described herein, including certain aspects of the present invention, but do not exemplify the full scope of the invention.

Example 1: Design of Technology Specific Adapter Nucleic Acids

Adapter nucleic acids and corresponding adapter primers suitable for use in various next-generation sequencing technologies were designed and generated.

An example of an adapter nucleic acid and adapter primers that can be used in Illumina specific applications is shown below:

Illumina Specific Adapter Nucleic Acid and Adapter Primers

Top (amplification) strand (5'→3'): AATGATACGGCGACCACCGAGATCTACACATCCGTACACACTCTTTCCCTACACG ACGCTCTTCCGATCTNNNNNNNNAACCGCCAGGAG*T (SEQ ID NO: 1), where "N" represents a nucleotide of a molecular barcode sequence, and "*T" represents a T having a phosphothioate bond.

Bottom (blocking) strand (5'→3'): 5phosCTCCTGGCGGTTt (SEQ ID NO: 2), where "t" represents a modified thymine nucleobase (e.g., an inverted thymine)

```
First adapter primer (5'→3'):
                                        (SEQ ID NO: 3)
AATGATACGGCGACCACCGAGATCTA

Second adapter primer (5'→3'):
                                        (SEQ ID NO: 4)
ATGATACGGCGACCACCGAGATCTACAC
```

As shown, the first and second adapter primers contain sequences that are identical to a portion of the top (amplification) strand. As a result of this design, each primer is able to prime off of complementary strands generated by a first and second target-specific primer during a first and second PCR step, respectively. The second adapter primer in this example contains two additional nucleotides and is nested relative to the first adapter primer.

An example of an adapter nucleic acid and adapter primers that can be used in Ion semiconductor specific applications is shown below:

Ion Specific Adapter Nucleic Acid and Adapter Primers

Top (amplification) strand (5'→3'): CCATCTCATCCCTGCGTGTCTCCGACTCAGCTAAGGTAACNNNNNNNNGCTCTTC CGATC*T (SEQ ID NO: 5), where "N" represents a nucleotide of a molecular barcode sequence, and "*T" represents a T having a phosphothioate bond.

Bottom (blocking) strand (5'→3'): 5phosGATCGGAAGAGCt (SEQ ID NO: 6), where "t" represents a modified thymine nucleobase (e.g., an inverted thymine)

```
First adapter primer (5'→3'):
                                        (SEQ ID NO: 7)
CCATCTCATCCCTGCGTGTC

Second adapter primer (5'→3'):
                                        (SEQ ID NO: 8)
CCATCTCATCCCTGCGTGTCTCCGACTCAG
```

As shown, the first and second adapter primers contain sequences that are identical to a portion of the top (amplification) strand. As a result of this design, each primer is able to prime off of complementary strands generated by a first and second target-specific primer during a first and second PCR step, respectively. The second adapter primer in this example contains ten additional nucleotides and is nested relative to the first adapter primer.

Example 2: Preparing a Nucleic Acid Sample for Analysis

An example of a workflow that illustrates a method of preparing a nucleic acid sample for analysis is shown in FIG.

5. A sample of RNA molecules is annealed with random primers. This annealing can be achieved, for example, by the addition of random hexamers to the sample, followed by heating at 65° C. for 5 minutes. Following annealing, first strand cDNA synthesis is achieved by primer extension (e.g., at room temperature) using a reverse transcriptase enzyme to generate a DNA/RNA hybrid.

At this point, a "PreSeq" RNA QC assay may be performed to assess library complexity. In this assay, the use of 600 ng of random hexamers (annealed at 65° C. for 5 minutes) was compared to the use of 100 ng of random hexamers (annealed at 65° C. for 5 minutes). The determination of a "Ct" value provides an indication of library complexity and a prediction of the likelihood of molecular barcode inflation during later steps. Generally, a threshold Ct of 28 is used as a benchmark, with values below this threshold being most desirable. It was found that increasing random primer concentration advantageously minimizes Ct.

Following the optional PreSeq assay, RNA of the DNA/RNA hybrid is cleaved, for example, by treating the sample with RnaseH. The resulting fragments of RNA that remain hybridized to the DNA serve as primers for second strand cDNA synthesis. This is achieved using DNA PolI and incubating the sample, e.g., at 16° C. for 60 minutes. Following this period, DNA PolI is inactivated by heat (e.g., by incubating the sample at 75° C. for 20 minutes). It was found that heat inactivation of DNA PolI greatly increased the sample integrity in subsequent sample preparation steps.

Figure 6:
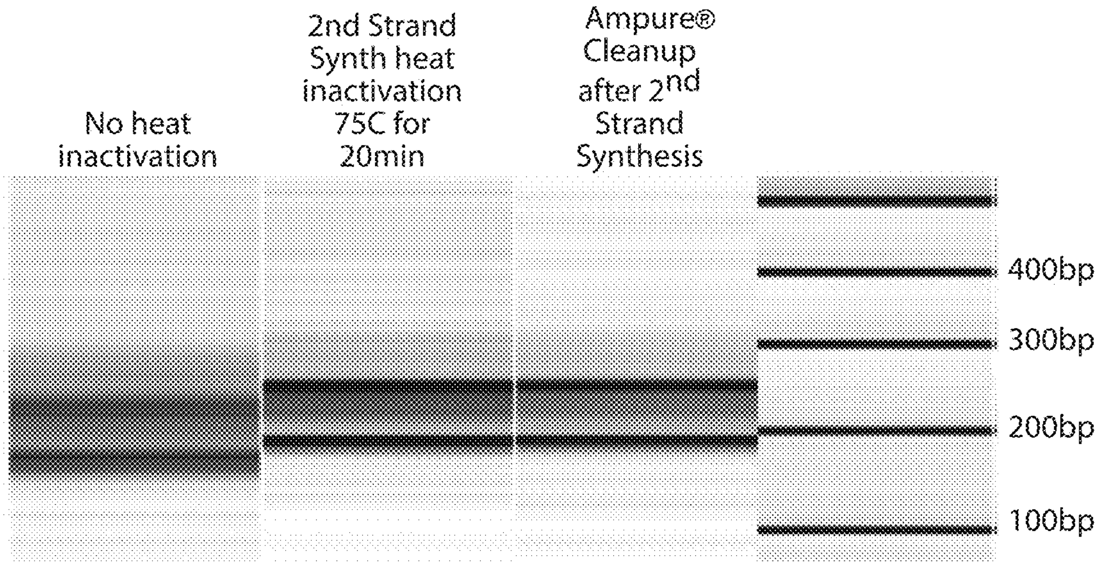
FIG. 6 is an image representation of a gel that depicts a library sample that has been end repaired without polymerase inactivation and a library sample that has been end repaired following heat inactivation of polymerase.

As shown in FIG. 6, heat inactivation of DNA PolI produced samples showing much cleaner bands by gel chromatography following second strand synthesis when compared to no heat inactivation. It is postulated that DNA PolI becomes active during end repair and is damaging fragments due to its 5'→3' and/or 3'→5' exonuclease activity-heat inactivation of DNA PolI following second strand synthesis prevents this from occurring.

The double-stranded cDNA sample is subjected to end repair to blunt end the cDNA and phosphorylate 5' ends. In this step, an excess of T4 DNA Polymerase and T4 Polynucleotide Kinase is added to the sample along with sufficient dNTPs and allowed to incubate (e.g., for 30 minutes at 25° C.). An AMPure cleanup (2.5×) following this period is critical, as it removes residual dATP from the library preparation before tailing with biotin-labeled dATP. This cleanup step prevents the labeling of library fragments with dATP instead of biotin-dATP, which would result in loss of the mislabeled fragments during the capture step.

The library fragments are A-tailed at 3'ends with biotin-labeled dATP in a first ligation step using Klenow Fragment (3'-5' exo-). This can be achieved, for example, by incubating the sample and the necessary components at 37° C. for 15 minutes. An AMPure cleanup (2.5×) following A-tailing is critical, as it removes residual biotin-labeled dATP from the library preparation before the capturing step. This cleanup prevents free biotin-dATP from saturating streptavidin binding sites, resulting in loss of library fragments during capture.

Figure 7:
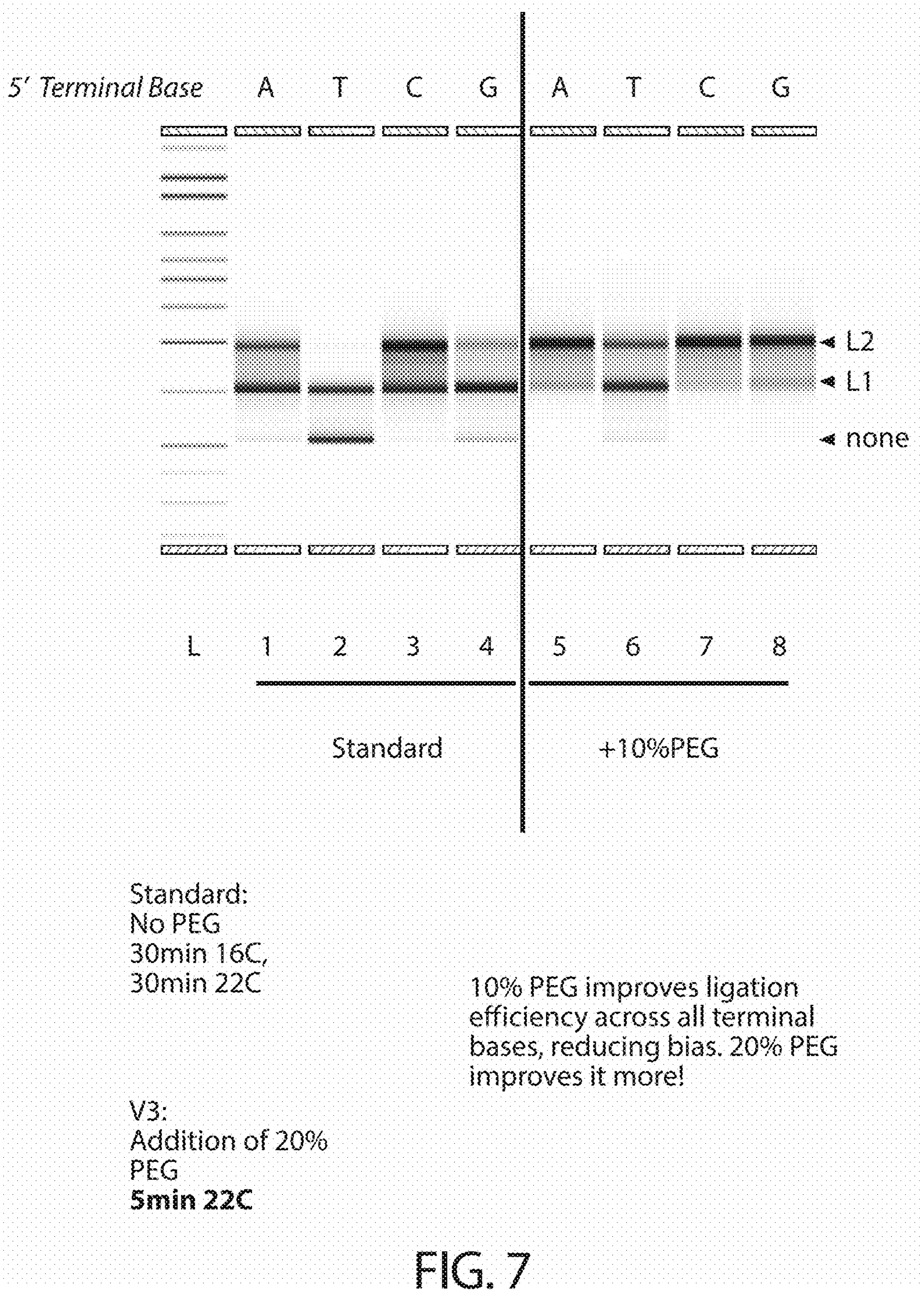
FIG. 7 is an image representation of a gel that depicts adapter ligation efficiencies of samples ligated in the absence or presence of a crowding agent.

In a second ligation step, adapter nucleic acids are ligated to the biotin-A-tailed library fragments using DNA ligase. Interestingly, it was found that the addition of a crowding agent to the ligation mixture greatly improved ligation efficiency across all terminal bases. As shown in FIG. 7, regardless of 5' terminal base, the inclusion of 10% PEG further minimized non-ligated fragments (none) and singly-ligated fragments (L1) while concomitantly increasing doubly-ligated fragments (L2). Moreover, adapter ligation with 10% PEG was achieved in 5 minutes compared to the "Standard" protocol that was performed in 60 minutes. Further data has shown that 20% PEG improves ligation efficiency even further (not shown).

Figure 8A:
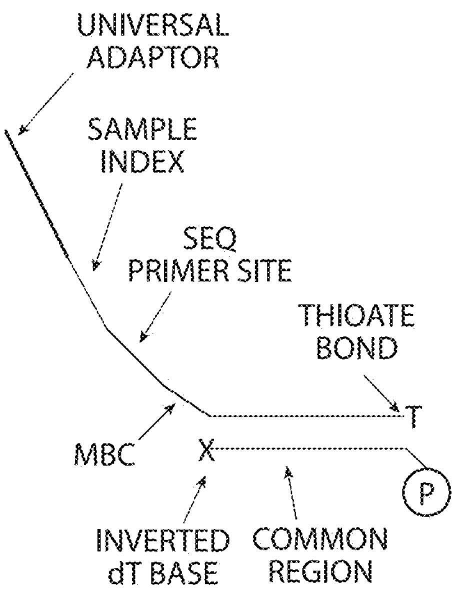
FIG. 8A is a diagram illustrating the components that may comprise an adapter nucleic acid.

FIG. 8A depicts a nucleic acid adapter used in these experiments. As shown, the top strand (amplification strand) contains, in 5'→3', a universal adapter primer site region, a sample index region, a sequencing primer site region, a molecular barcode region, a 3' duplex portion, and a 3' T overhang. The bottom strand (blocking strand) contains a common region that is duplexed with the 3' duplex portion of the top strand, a 5' phosphorylated end, and an inverted dT base that prevents extension of the strand.

Following adapter ligation, ligation cleanup is conducted by capture of library fragments via streptavidin-coated beads. This is performed using M-280 streptavidin dynabeads (10 mg/mL concentration stored in PBS+0.1% BSA+0.02% Azide). The storage buffer is exchanged with ligation cleanup buffer (1 M NaCl, 1 mM EDTA, 0.1% Tween, 10 mM Tris pH 8) prior to adding the beads to the sample. The ligated DNA product (50 μL) is mixed with ligation cleanup beads (50 μL for a total of 100 μL). A magnetic field is subsequently applied to the sample to capture library fragments, and the supernatant is removed. Library-bound beads are then transferred to a separate mixture of components for a first PCR step.

A first round of PCR is performed using a first target-specific primer and a first adapter primer. The first adapter primer is identical to at least a portion of the amplification strand, such that it anneals to the complementary strand generated by the first target-specific primer. A second round of PCR is conducted using a second target-specific primer and a second adapter primer, the latter of which is similarly identical to a portion of the amplification strand. The second target-specific primer is nested relative to the first target-specific primer and is further contacted by an additional primer.

Figure 8B:
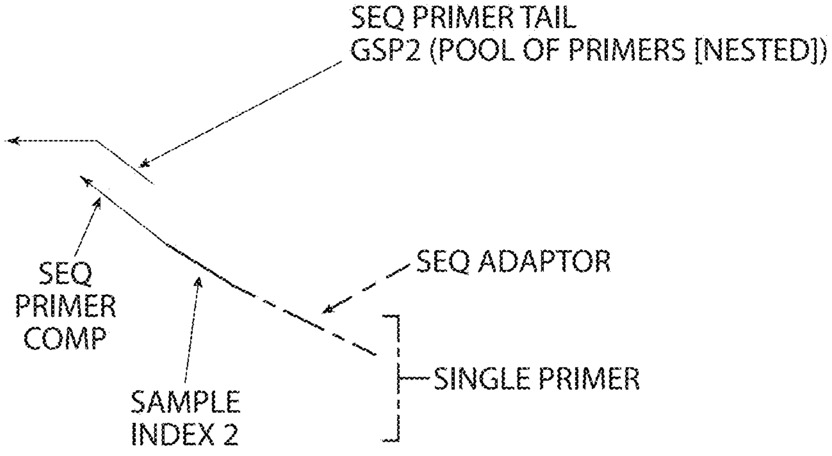
FIG. 8B is a diagram illustrating the components that may comprise a second target-specific primer.

As shown in FIG. 8B, the second target-specific primer contains a 5' tail that does not hybridize to the target-specific region. An additional primer is included that contains a region that is identical to the 5' tail along with a second sample index region and a sequencing adapter region. In this way, the second target-specific primer primes off of the template strand to generate a complement strand having an uncommon tailed region. As in the first round of PCR, the second adapter primes off of this complementary strand to generate a copy of the template strand. As this copy of the template strand will contain a region that is complementary to the 5' tail sequence, the additional primer containing the second sample index region and sequencing adapter region will prime off of this sequence to generate a bottom strand that is ready for sequencing.

Example 3: Preparing a Cell-Free Nucleic Acid Sample for Analysis

Anchored Multiplex PCR (AMP) Method

Figure 9:
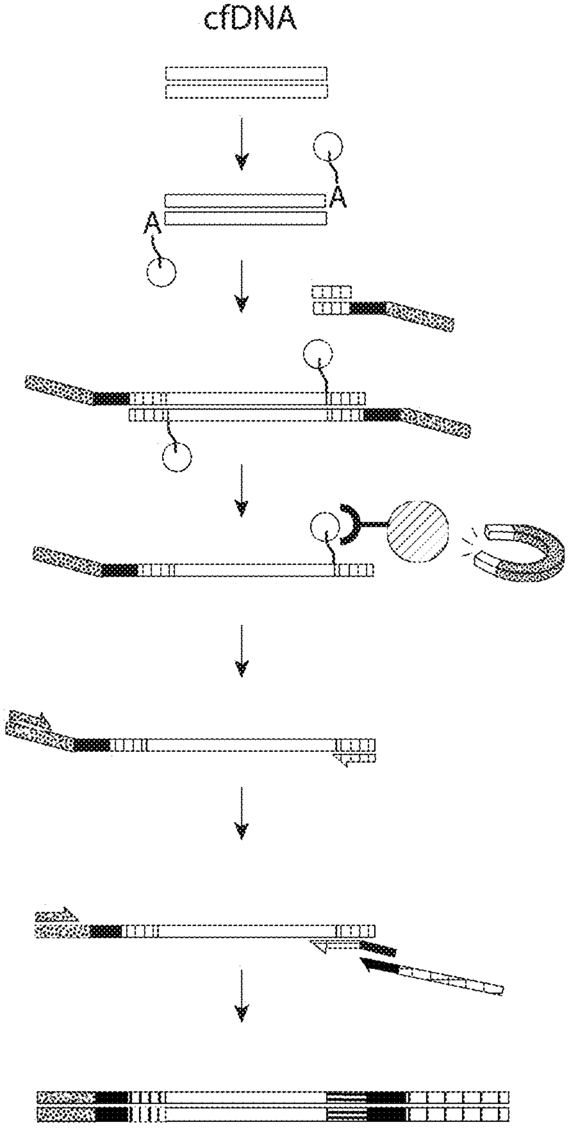
FIG. 9 shows an overall method of generating target-enriched libraries for next generation sequencing (NGS) using anchored multiplex PCR (AMP).

The anchored multiplex PCR method is performed with the unidirectional gene-specific primer and a common adaptor sequence primer to amplify the region of interest. The PCR product is optionally purified using solid phase reversible mobilization (SPRI). Alternatively, a small portion of the PCR product following the first amplification is added directly to a nested PCR, which is performed with a second set of primers. The PCR product is again purified using SPRI for use in a next-generation sequencing (FIG. 9).

Sensitivity for Ultra-Low AF Variants

Figure 10:
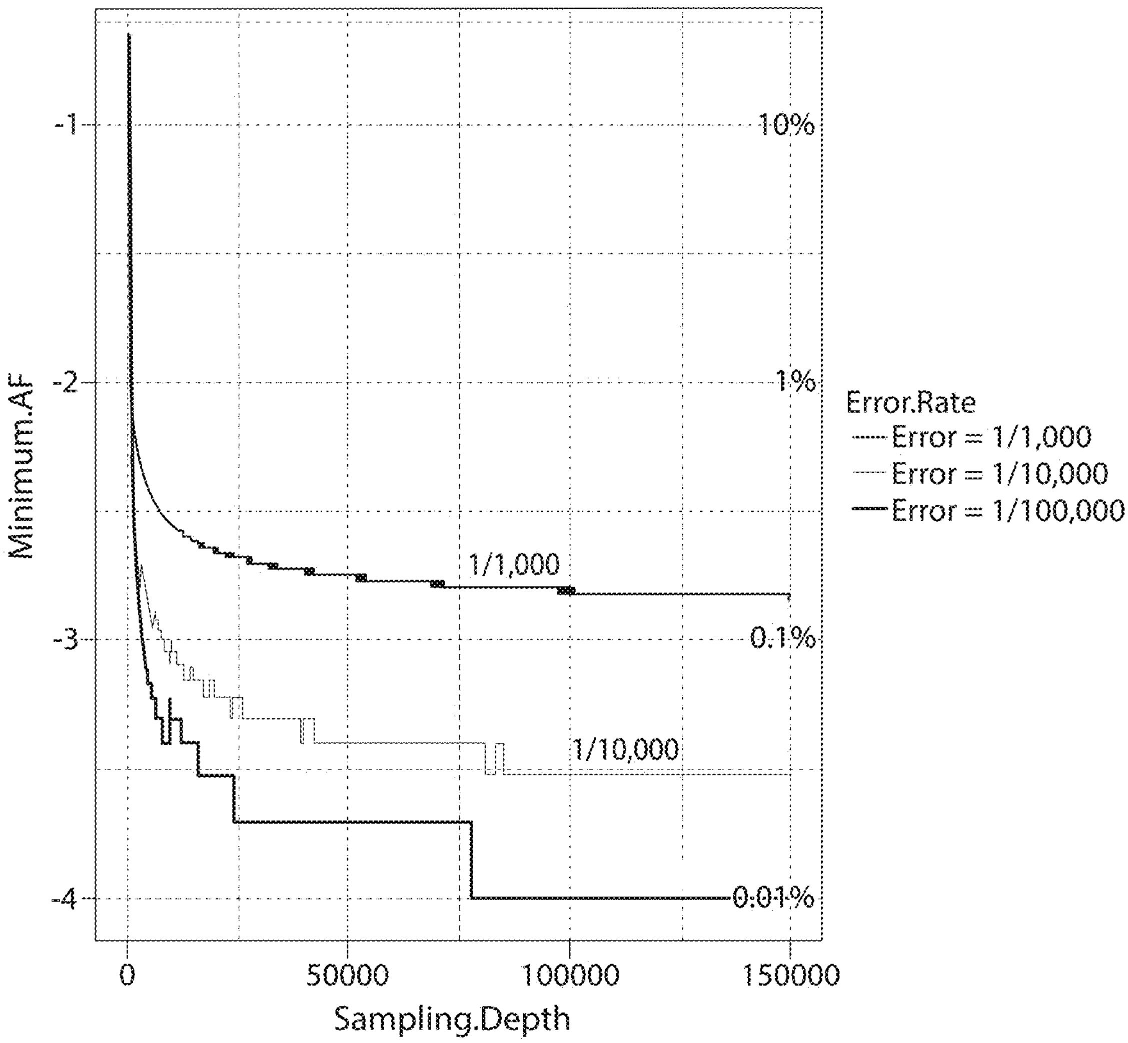
FIG. 10 is a graph showing the theoretical sensitivity for ultra-low allele frequency (AF) variants.
Figure 11:
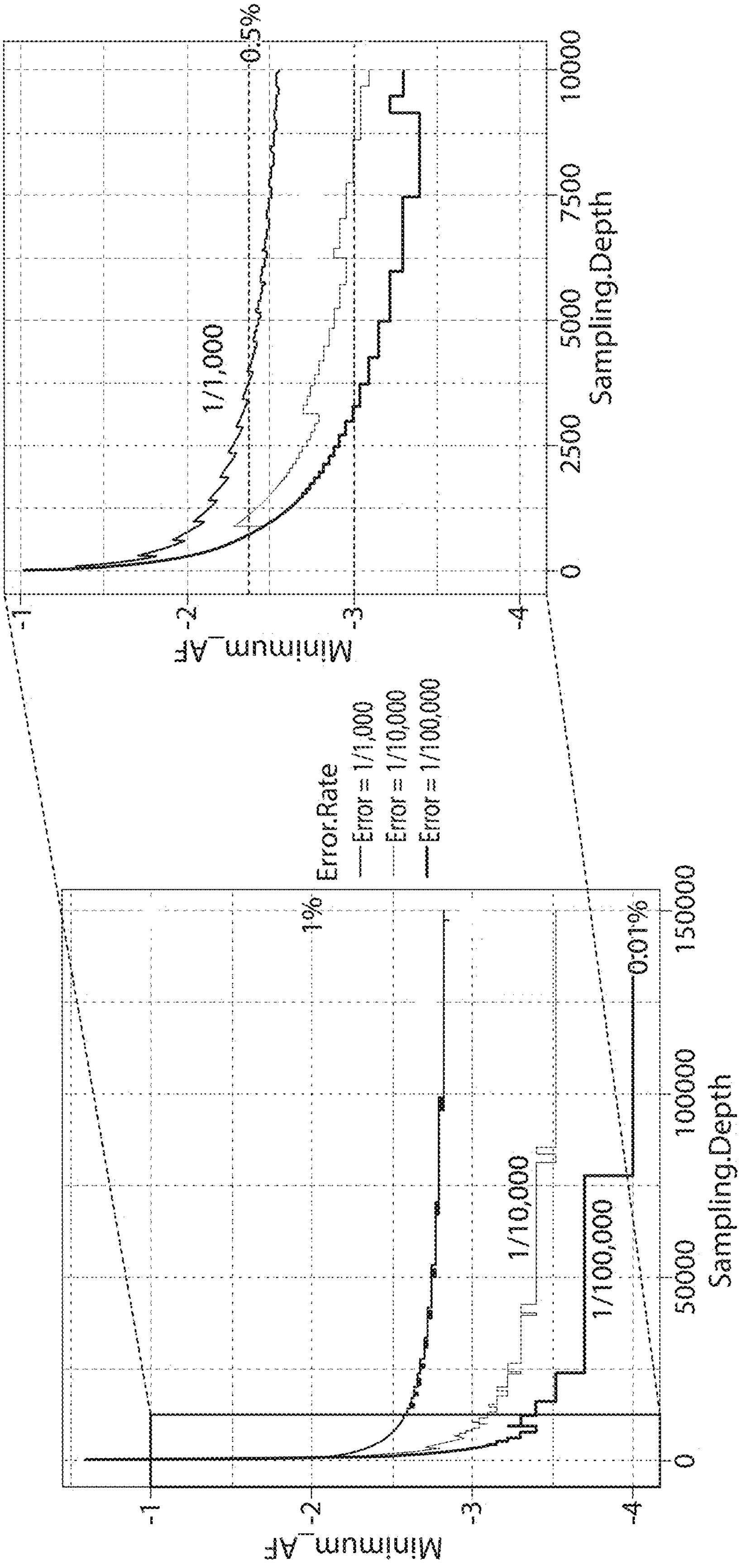
FIG. 11 are graphs showing a more in depth view of the minimum AF between a sampling depth of 0 and 10,000.

Variant detection sensitivity is a function of depth of interrogation and signal-to-noise ratio. FIG. 10 shows minimum AF detectable with 95% sensitivity. In these experiments, the detection threshold was set as the expected number of miscalled bases+3 standard deviations. Error correction and identification of unique molecules is a necessity for low AF variant detection. FIG. 11 shows the initial drop in error rate between a sampling depth of 0 and 10,000, illustrating the limitation of sequencing error rate.

Fragmented Material

Figure 12:
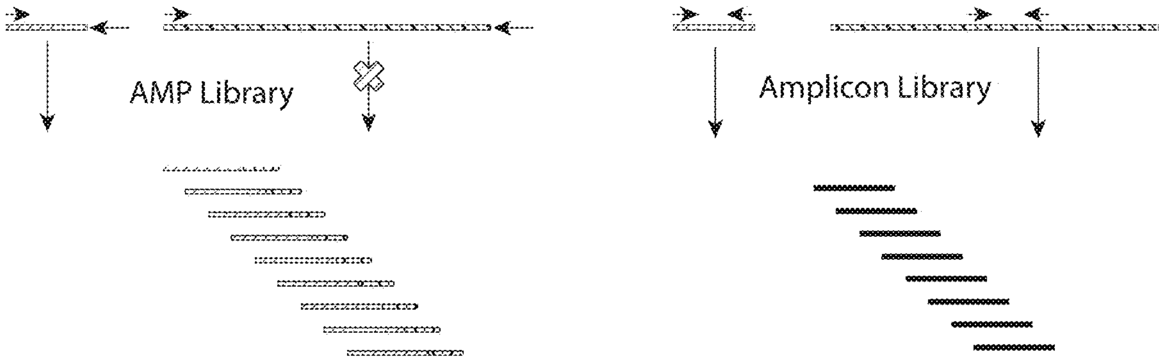
FIG. 12 is a schematic showing highly fragmented material enriched by ligation-based capture using the AMP method versus traditional methods.
Figure 13:
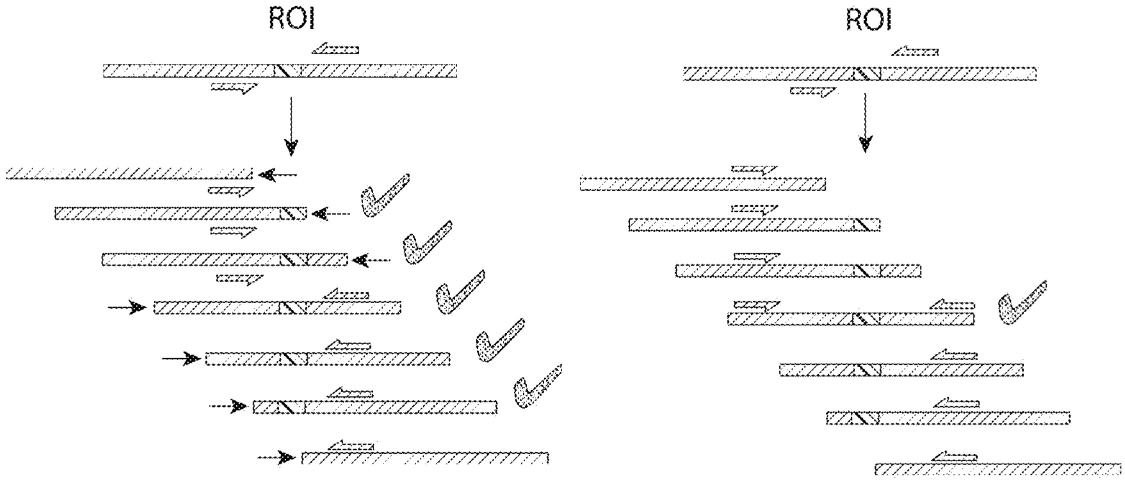
FIG. 13 is a schematic showing independent observations facilitated using the AMP method versus observations resulting from traditional methods.

Using the multiplex polymerase chain reaction assay AMP, detection of single nucleotide variants, insertions/deletions, copy number changes, and rearrangements is possible (FIG. 12, left panel, FIG. 13, left panel). Using this method, the assay may be performed with low amounts of RNA or DNA in a one- or two-tube format using commercially available reagents, custom primers, and standard library preparation instrumentation.

Amplicon sequencing is a targeted approach for analyzing genetic variation in specific genomic regions (FIG. 12, right panel). The sequencing of amplicons allows for variant identification and characterization. Using this method, cfDNA and other DNA fragments are equally amplifiable, making them indistinguishable after amplification (FIG. 13, right panel). Further, background signal is increased, requiring greater sequencing depth to find the same variant.

Analysis of Material

Figure 14:
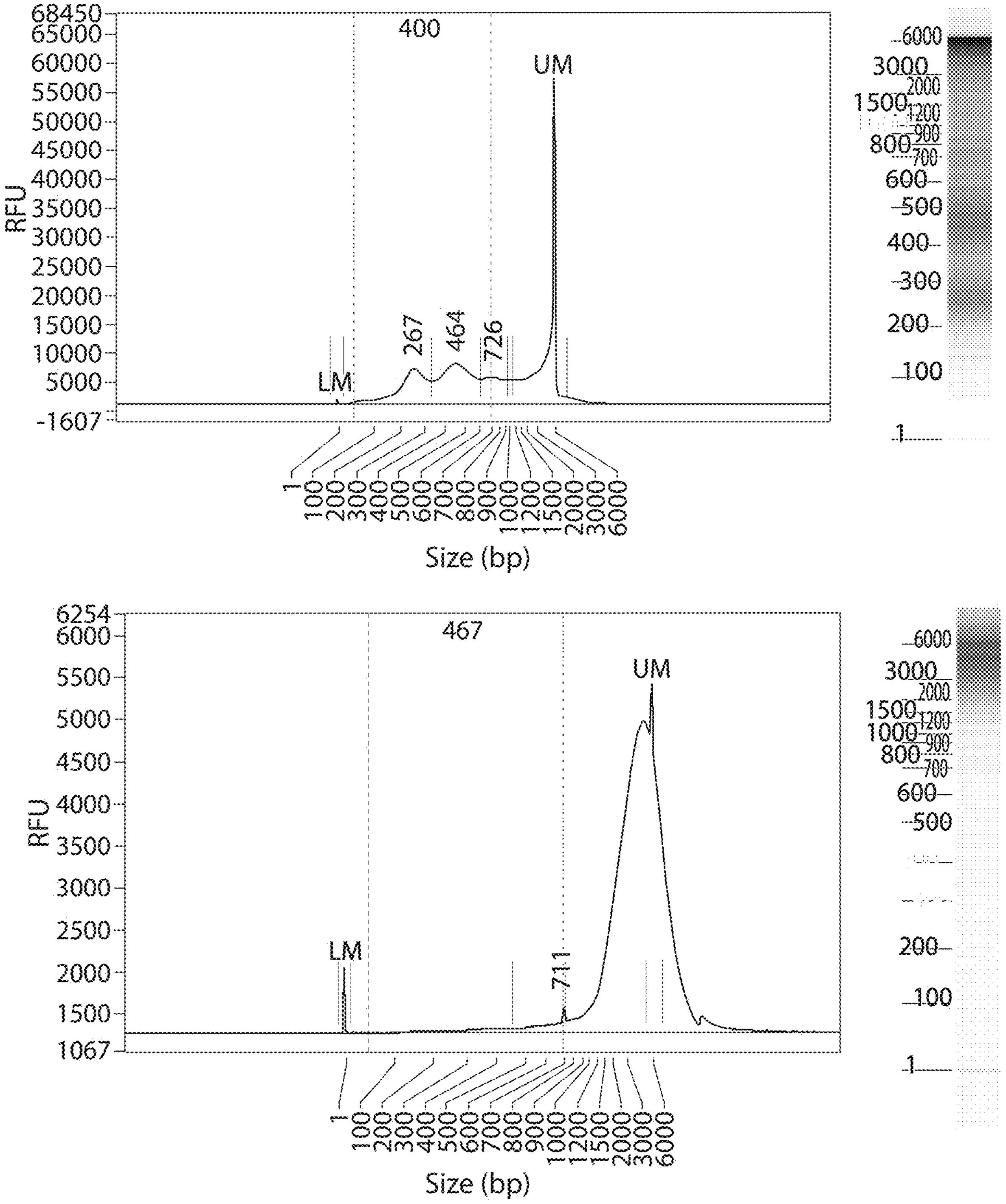
FIG. 14 shows mass spectrometry analysis of cfDNA in the urine comparing individuals with recurrent bladder cancer versus those without.

Capillary electrophoresis can be used to analyze cfDNA passed from blood through the kidney barrier to the urine. Using the AMP method, cfDNA is shown at higher levels in patients with recurrent bladder cancer (FIG. 14, top panel) than those without cancer (FIG. 14, bottom panel).

Figure 15:
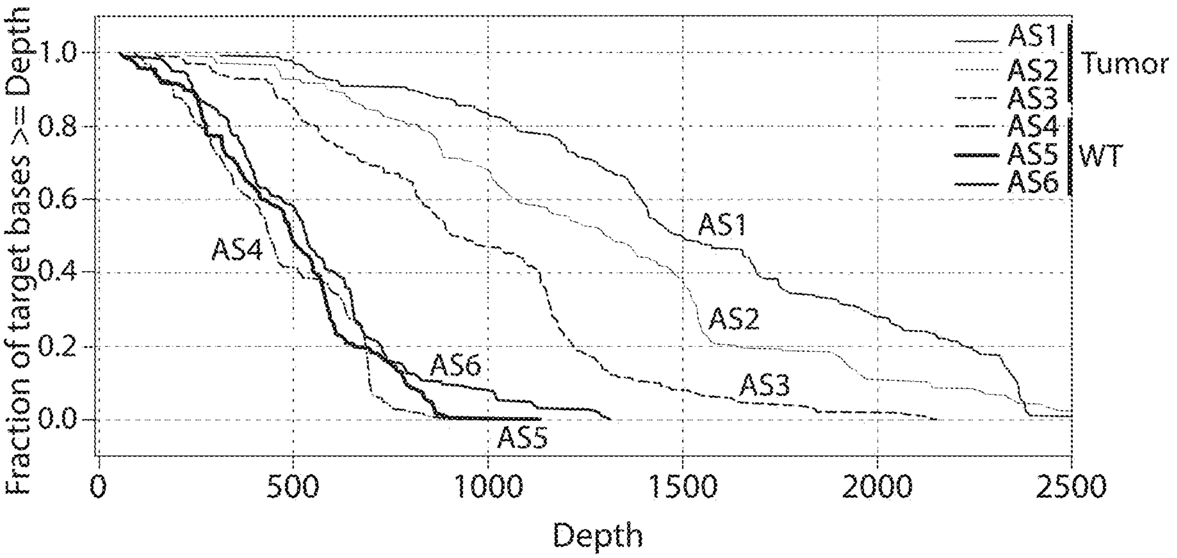
FIG. 15 is a graph showing high-coverage libraries produced by fragmented inputs

The unique coverage depth is shown to at least double for DNA extracted from tumor bearing individuals (FIG. 15).

Optimized Capture

Figure 16:
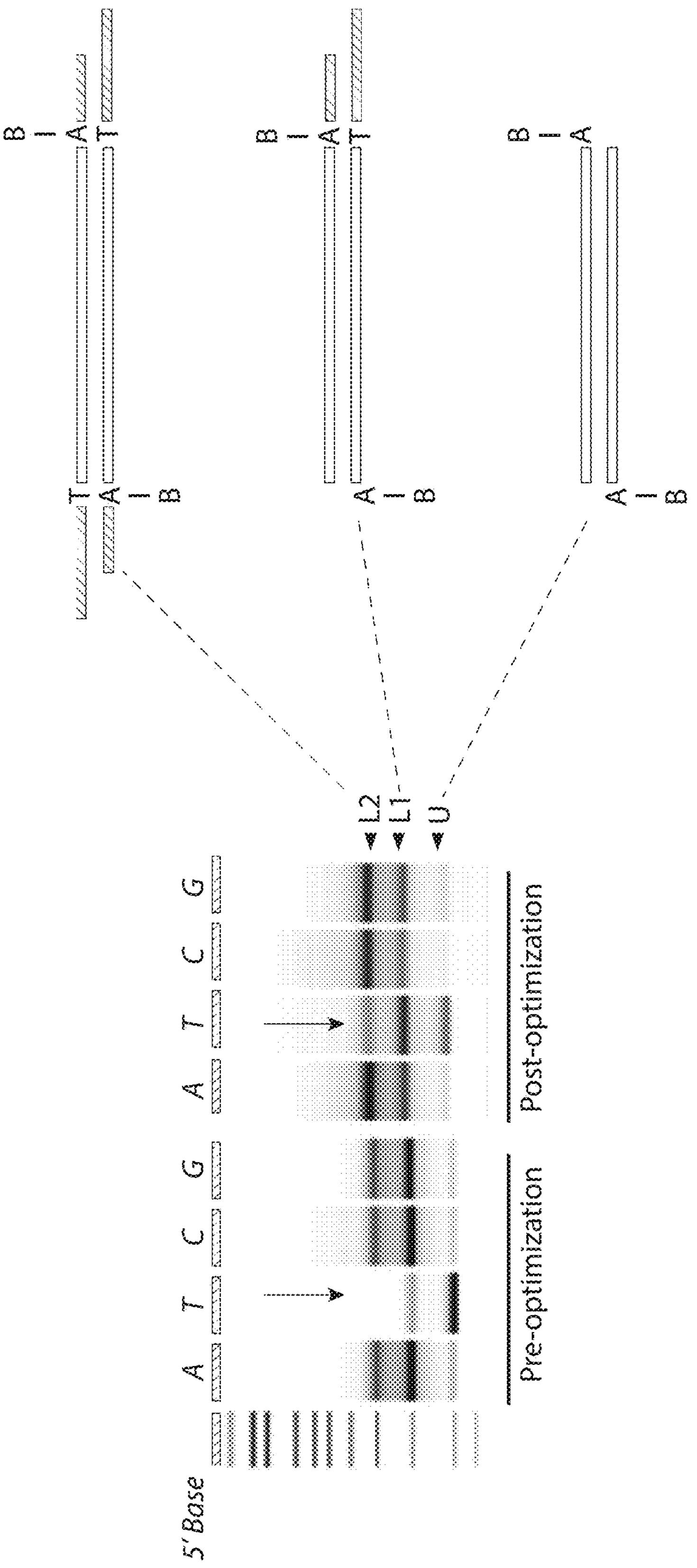
FIG. 16 shows the optimization of front-end ligation capture using synthetic DNA report assay
Figure 17:
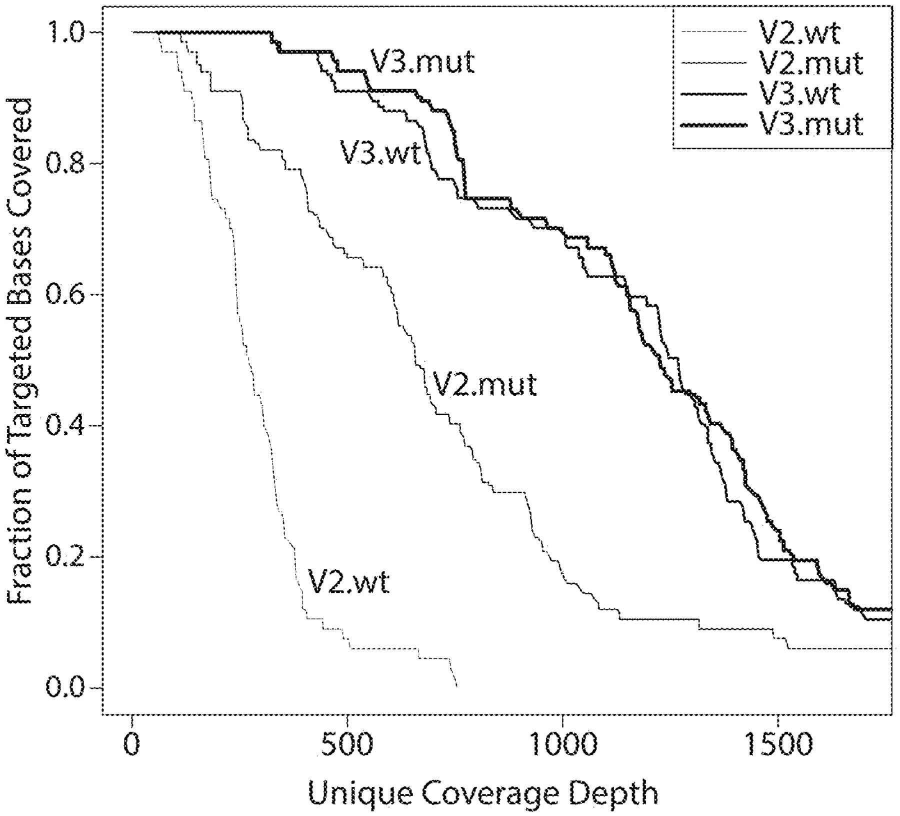
FIG. 17 is a graph showing that the optimized capture chemistry yields significantly more coverage than traditional methods.

Optimization of adapter nucleic acid ligation resulted in several modifications to existing protocols, including the addition of a crowding agent, which vastly improved ligation efficiency (FIG. 16). Consistent with the results visualized by gel chromatography, the optimized ligation protocol yielded significantly more coverage (FIG. 17).

Depth at Targeted Loci

Figure 18:
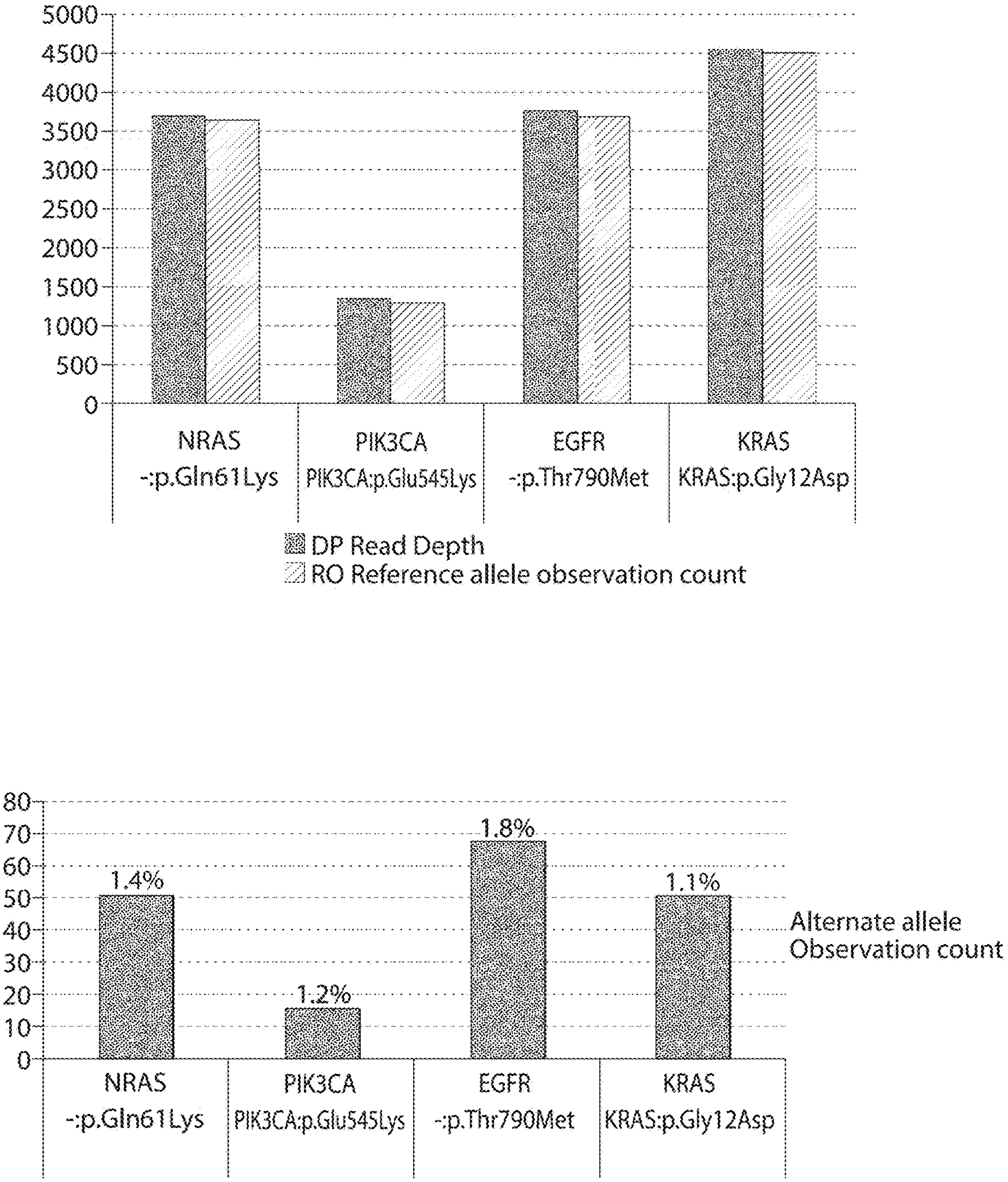
FIG. 18 shows graphs depicting high-depth, unique coverage at targeted loci using Horizon cfDNA material.

Earlier experiments used Horizon cfDNA material, which is extracted using liquid biopsy, as a control to compare the sensitivity, specificity, and accuracy of the wild-type cfDNA assay and platform. In this instance, the DNA QC assay revealed that less 50% DNA mass is amplifiable in a 115 bp amplicon (FIG. 18).

Figure 19:
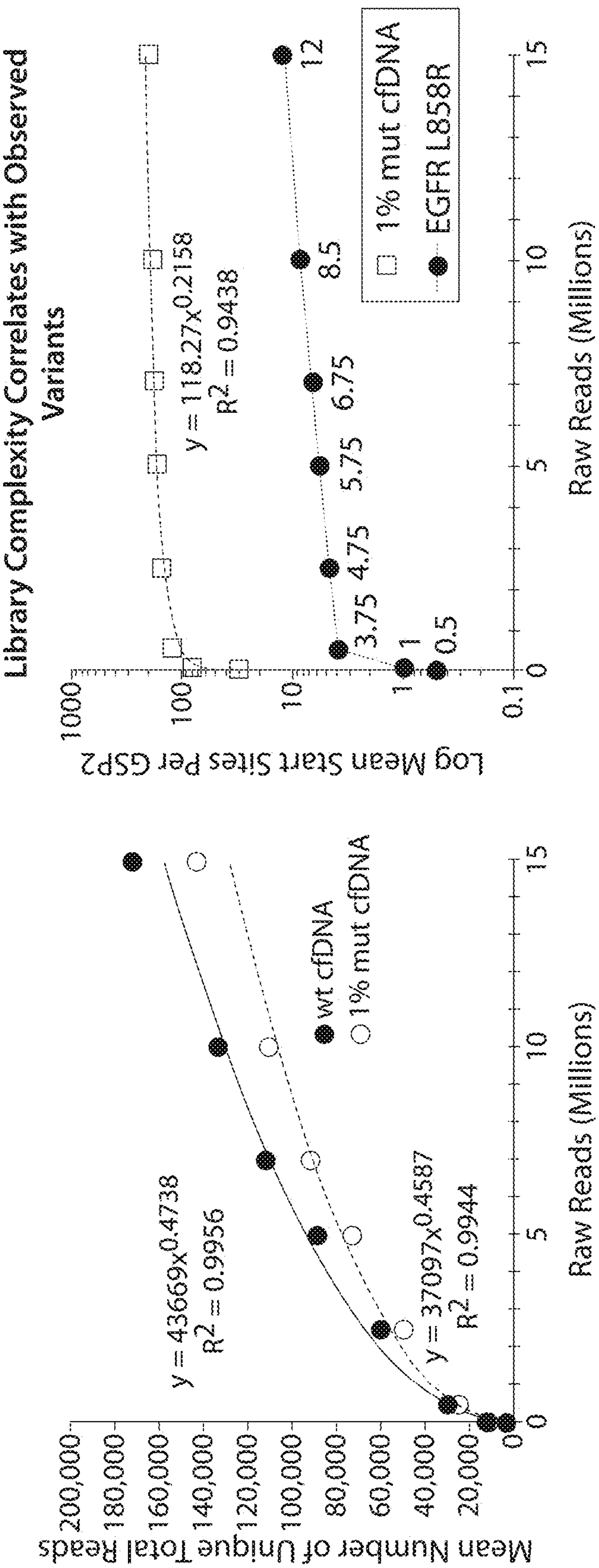
FIG. 19 shows graphs depicting ROI curves of sequencing depth.

Current experiments are focused on improvements to PCR uniformity. The goal is to mitigate the bin-depth, as ROI curves of sequencing depth suggest bin-depth uniformity hinders complexity (FIG. 19).

T-Cell and B-Cell Receptors

Figure 20:
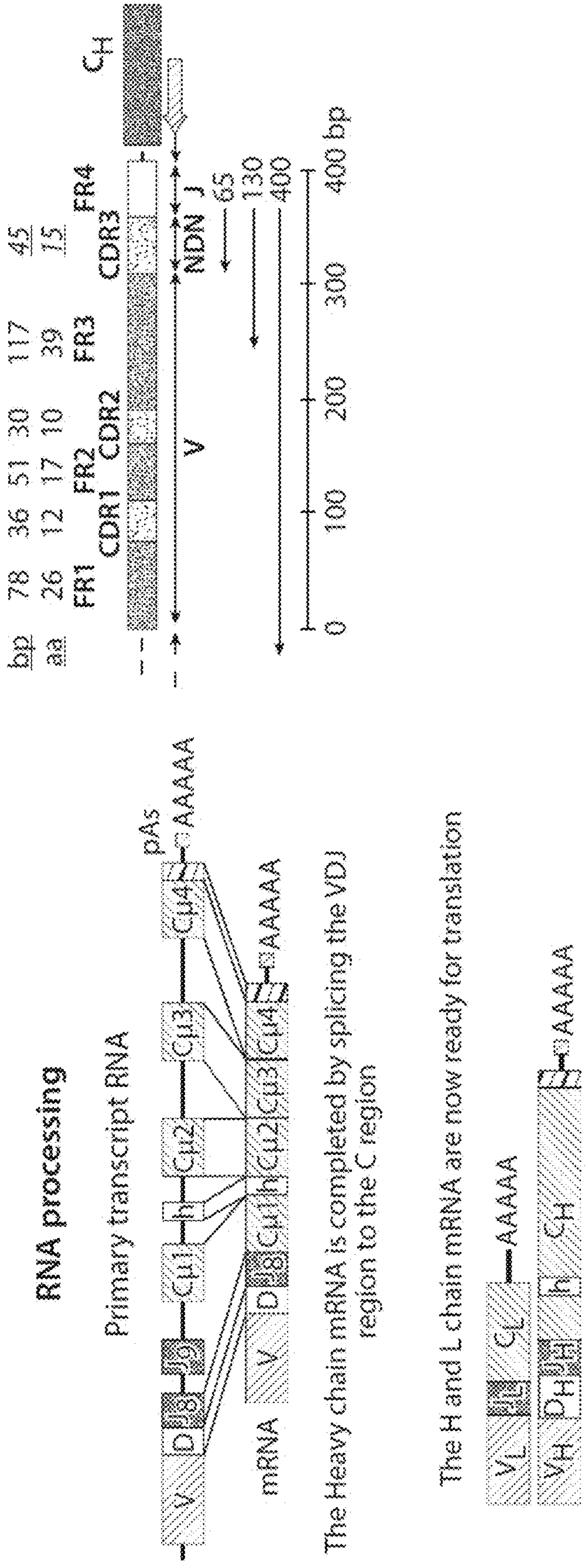
FIG. 20 depicts a RNA immune repertoire sequencing strategy.

It was sought to design mRNA-specific primers to the constant region of T-cell receptors and to immunoglobulin heavy and light chain constant regions (FIG. 20, left panel). A generic structure of a locus encoding the variable region of a TCRB or IGH chain after V-D-J rearrangement, illustrating the intervals that encode the 4 framework (FR1-FR4) and 3 complementarity-determining (CDR1-CDR3) regions, the portions contributed by the V. D. and J gene segments, and the "N" nucleotides inserted at the V-D and D-J junctions. The maximum length of FR1-FR3, CDR1, and CDR2, and the modal length of CDR3, in base pairs (bp) and amino acids (aa), are indicated by the numbers at the top of FIG. 20, right panel. The left-pointing arrows below the block structure indicate the approximate fraction of the locus that would be sequenced with reads of the indicated length (65, 130, or ≥400 bp) initiated by sequencing primers annealing to the 5' region of the J gene segment, typical of current deep-sequencing protocols. The scale bar at the bottom of the figure indicates the length of the generic locus in base pairs.

Figure 21:
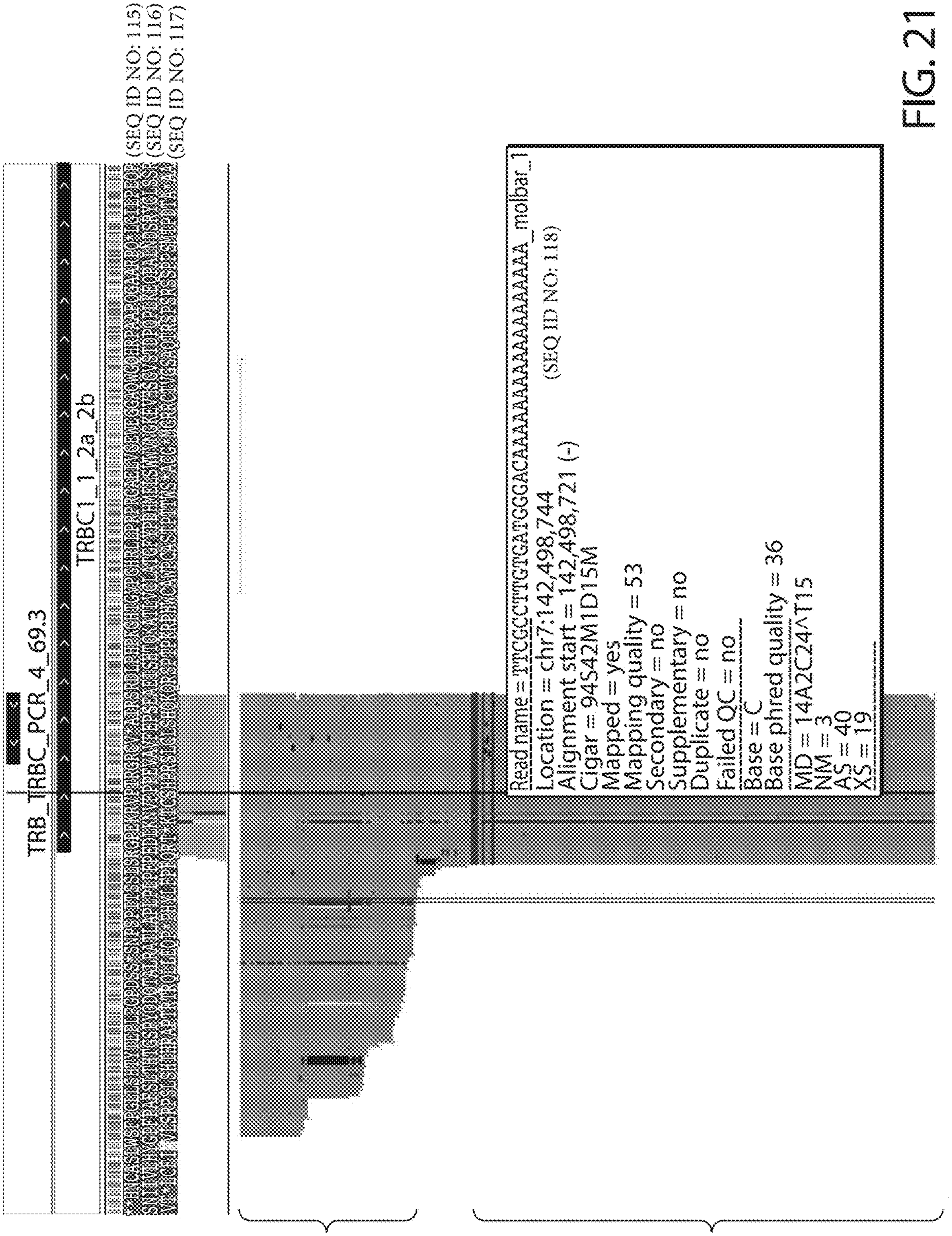
FIG. 21 depicts the mapping of TCRB-derived reads generating typical AMP data.
Figure 22:
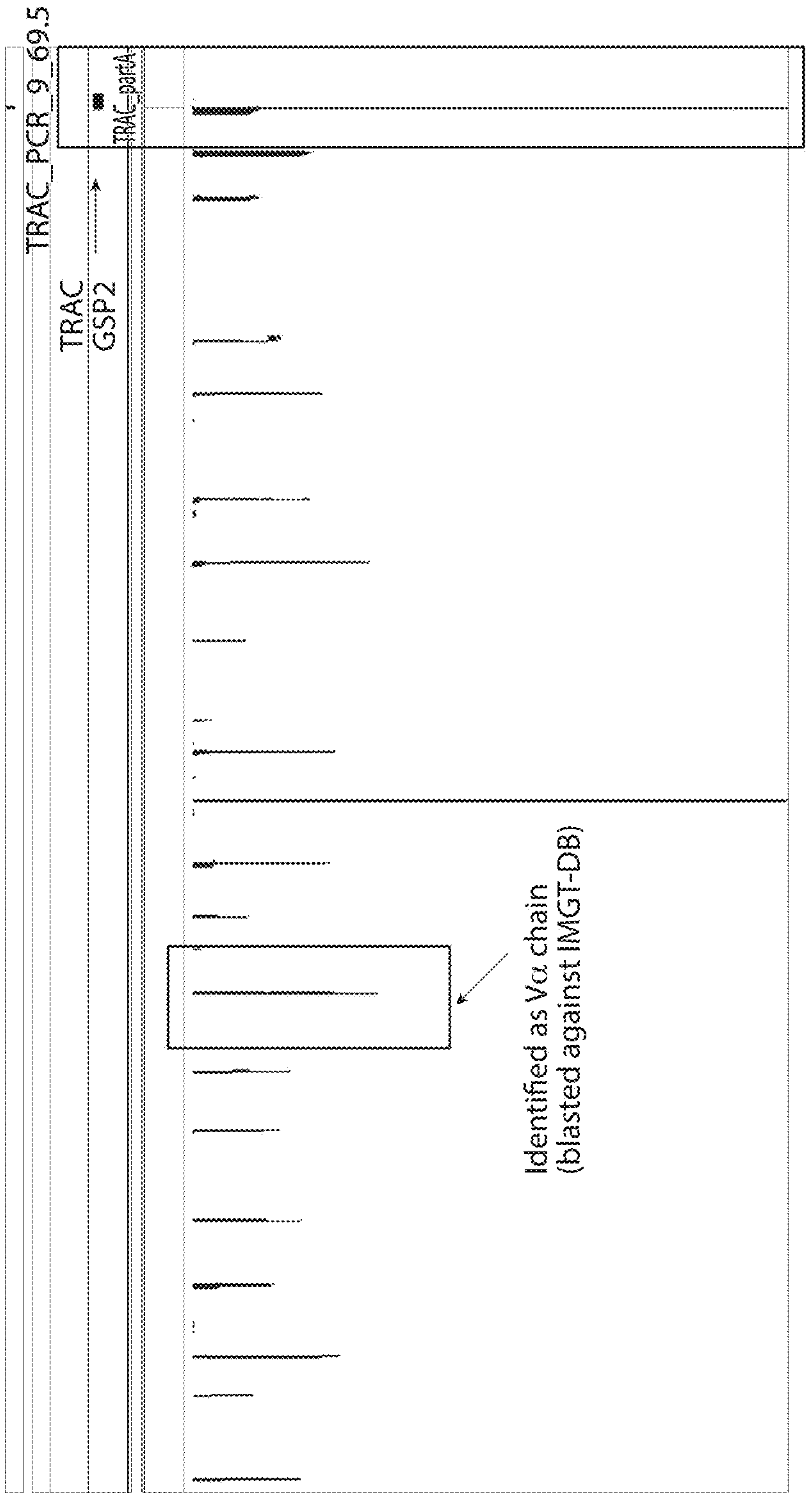
FIG. 22 depicts empirically derived V and J segments from TCRA.

Presented here is typical AMP data generated from the mapping of TCRB-derived reads. Results show thousands of RNA-derived reads and some DNA-derived reads. The DNA reads show low-complexity samples as a control for primer functionality. RNA reads are soft-clipped on the 5'-end of the exon, as reads jumped to the J-segment (FIG. 21). Also, presented here are updated hg19 immune loci annotations which have been aided by V- and J-segments derived from TCRA (FIG. 22).

Figure 23A:
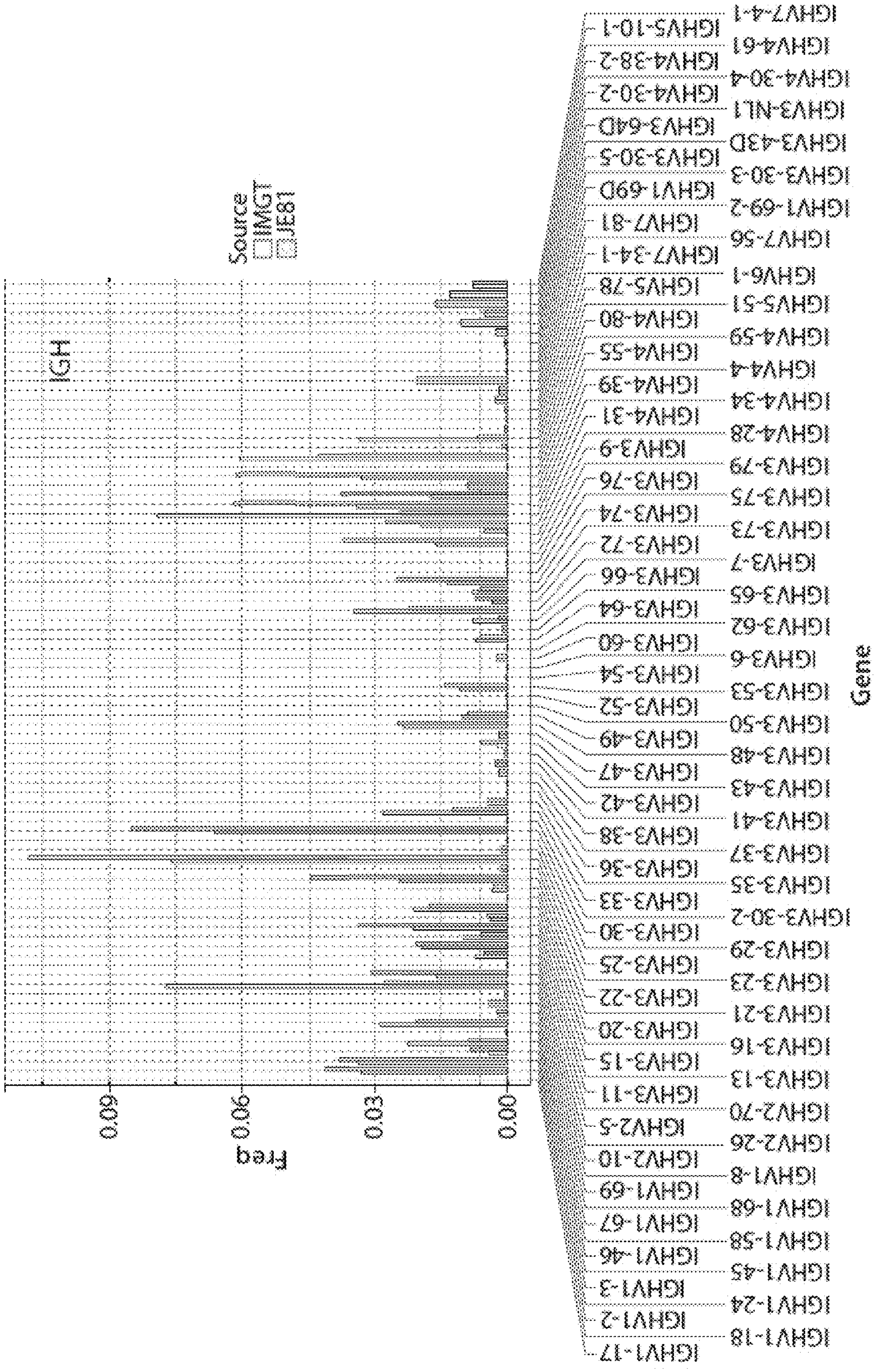
FIGS. 23A, 23B, and 23C show graphs depicting BCR V-segment usage.
Figure 23B:
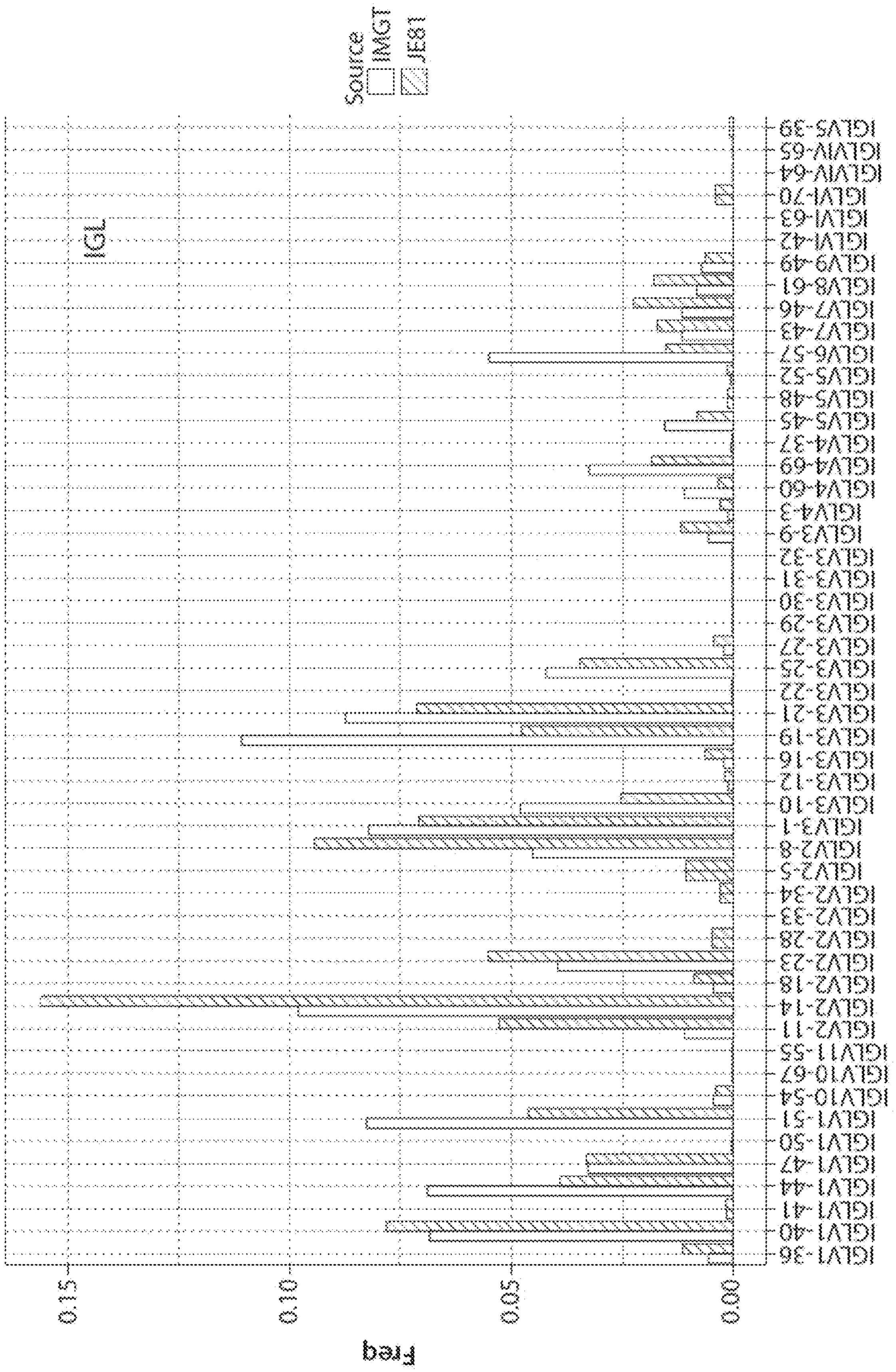
Figure 23C:
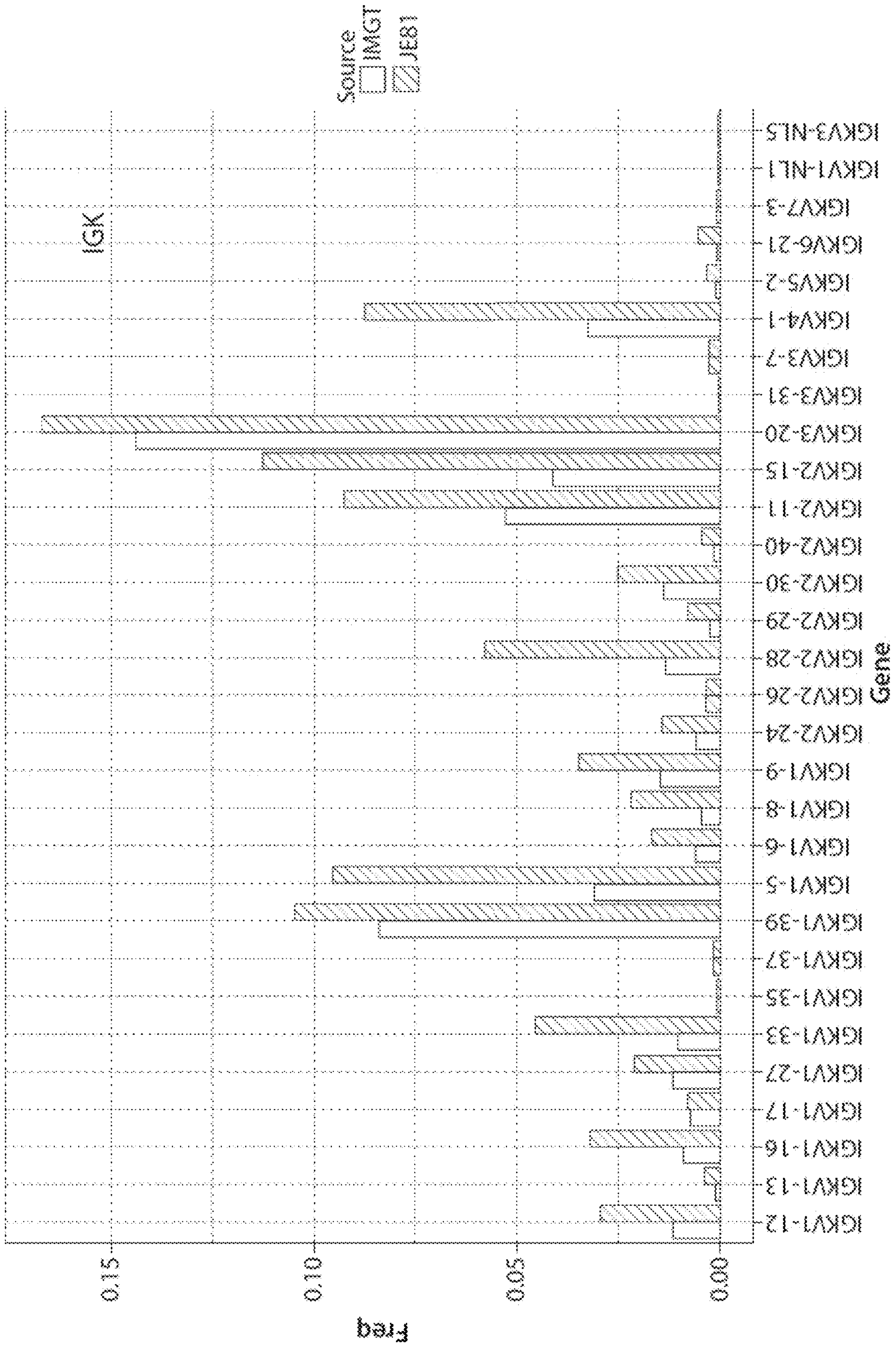

Using the ImMunoGeneTics (IMGT) information system, one is able to access to all nucleotide, protein, genetic, and structural immunogenetics data for sequenced material. The results presented here have determined that B-cell receptor V-segment usage in peripheral blood leukocytes correlates closely with the segment usage reported in IMGT (FIG. 23).

Figure 24:
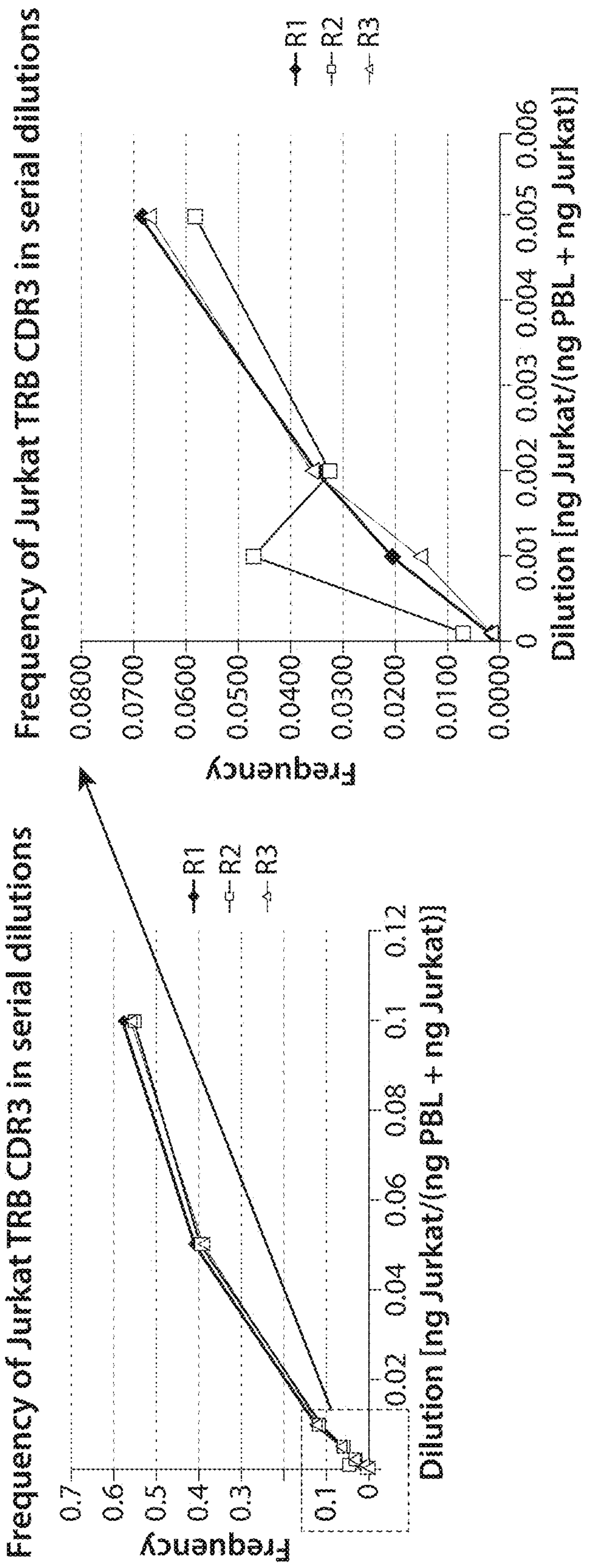
FIG. 24 show graphs depicting the frequency of Jurkat TRB CDR3 in serial dilutions.

Using the methods presented here, a TRB assay was also shown to enable quantitative clone tracking, except for the outliers in replicate R2 (FIG. 24 and Table 3).

TABLE 3

| Frequency of TRB clones | | | | | |
|---|---|---|---|---|---|
| Ratio | Dilution | R1 | R2 | R3 | Avg |
| 1:10 | 0.1 | 0.58 | 0.55 | 0.56 | 0.56 |
| 1:20 | 0.05 | 0.41 | 0.39 | 0.39 | 0.40 |
| 1:100 | 0.01 | 0.12 | 0.12 | 0.12 | 0.12 |
| 1:200 | 0.005 | 0.07 | 0.06 | 0.07 | 0.06 |
| 1:500 | 0.002 | 0.03 | 0.03 | 0.04 | 0.03 |
| 1:1000 | 0.001 | 0.02 | 0.05 | 0.02 | 0.03 |
| 1:10000 | 0.0001 | 0.0015 | 0.0068 | 0.0015 | 0.0033 |

*Note:

Starting frequency of Jurkat TRB clones (1:10 dilution) to all PBL TRB clones is 0.56.

Figure 25:
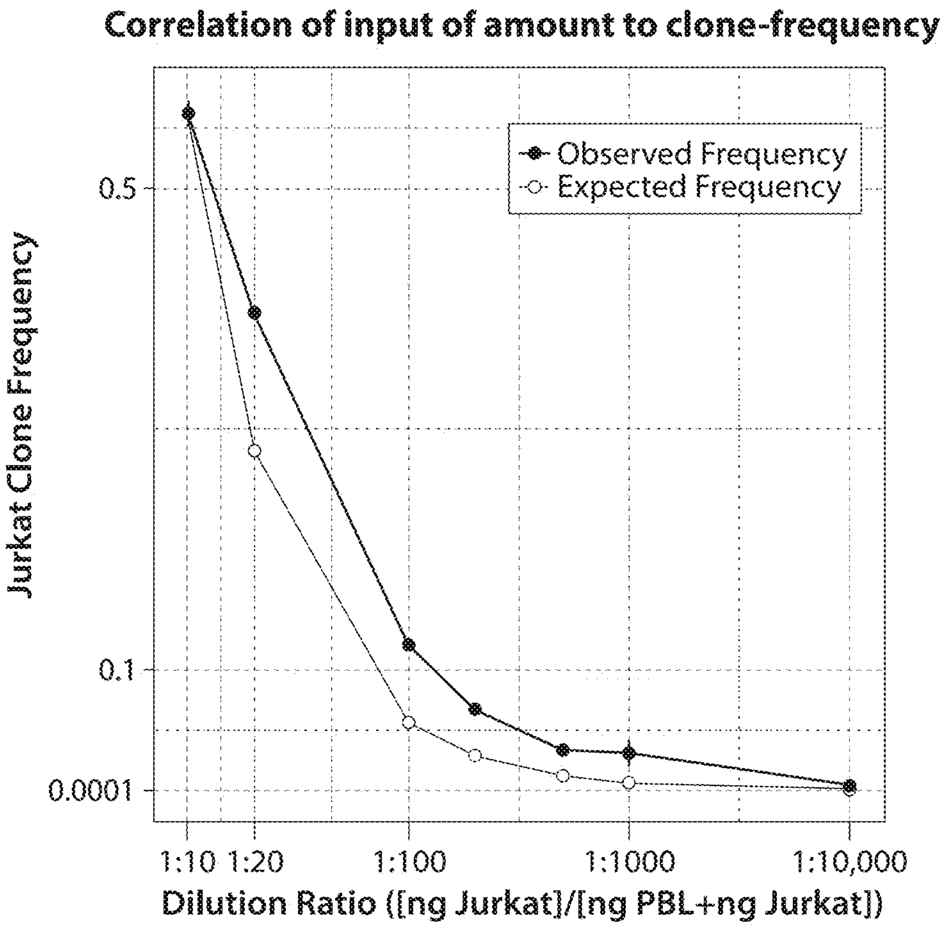
FIG. 25 shows the correlation of the Jurkat clone frequency as compared to the dilution ratio.
Figure 26:
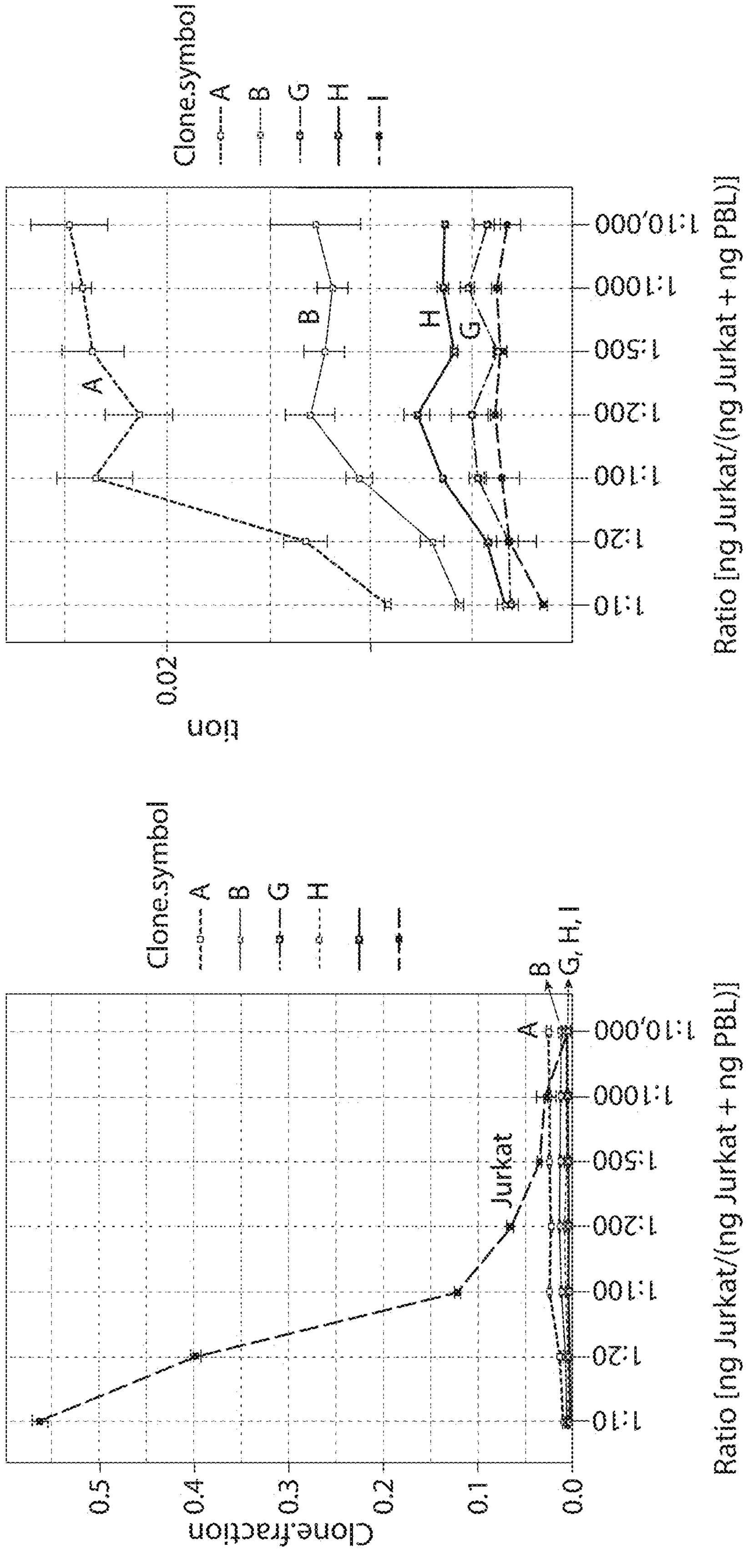
FIG. 26 shows the relationship of non-Jurkat clones versus Jurkat clones.

When reviewing the TRB clones, results showed a spike in Jurkat frequency over the expected frequency (FIG. 25). When comparing the five most frequent non-Jurkat clones to the Jurkat clones, it was reported that the non-Jurkat clones retain their relative frequency order across the samples (FIG. 26).

Example 4: cfDNA Assessment

Figure 27A:
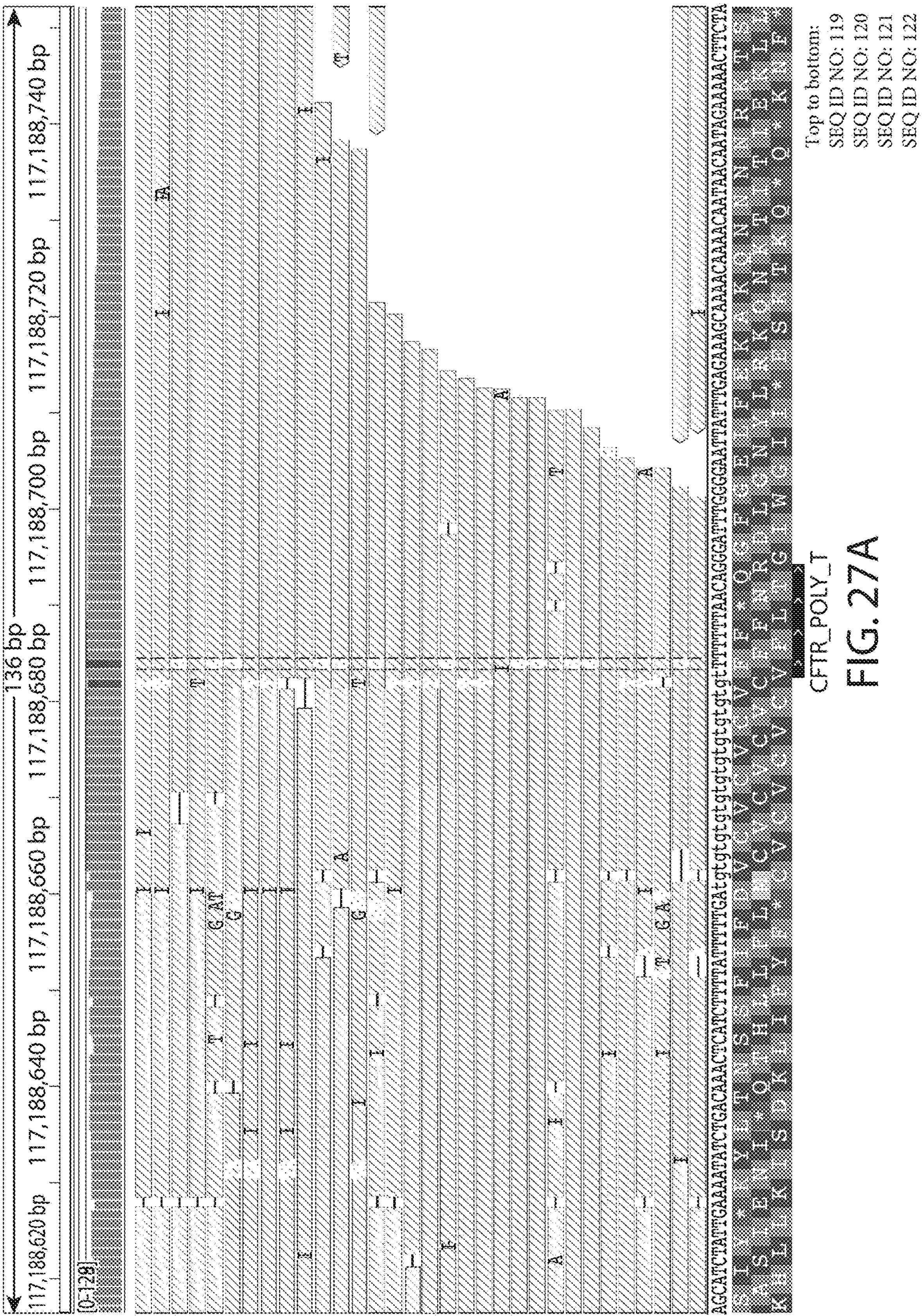
FIGS. 27A and 27B illustrate that molecular barcodes correct for both PCR- and sequencing-derived errors.
Figure 27:
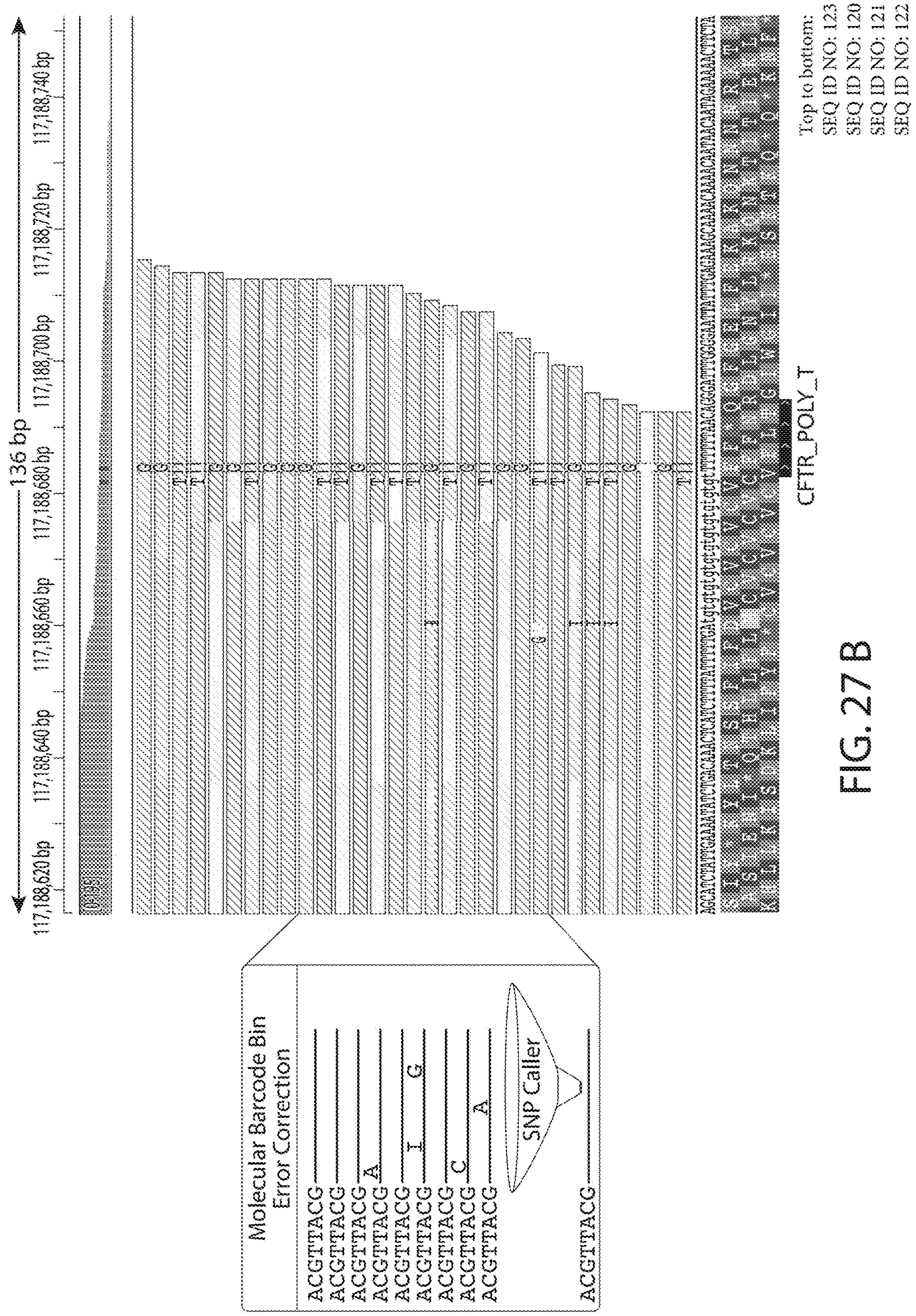
Figure 28:
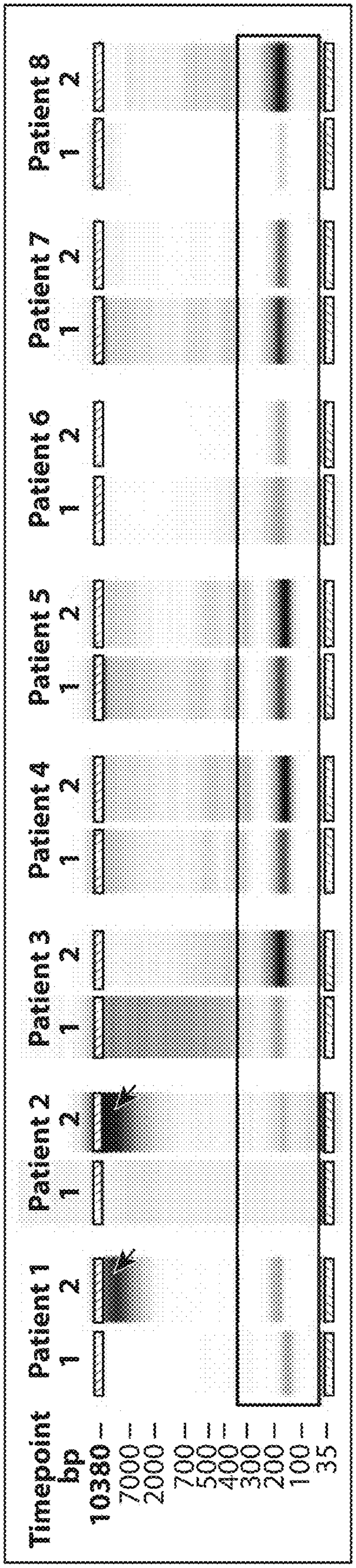
FIG. 28 shows microfluidic electrophoresis analysis of cfDNA fragment length.

Further assessment of cfDNA was performed. FIG. 27 illustrates that molecular barcodes correct for both PCR- and sequencing-derived errors. FIG. 28 shows microfluidic electrophoresis analysis of cfDNA fragment length. DNA size distribution between 35 bp and 10.4 kb was measured using High Sensitivity DNA chip. Samples were obtained prior to chemotherapy (time point 1) and after the first chemotherapy cycle (time point 2). Samples obtained at time point 2 from patients 1 and 2 contained substantially larger DNA fragments (arrows) with a size range of 200 bp-10.4 kb, consistent with necrosis as a source of cfDNA in these samples. Here, cfDNA is comprised of fragmented gDNA. Cancer cells undergo apoptosis or necrosis; small cfDNA fragments are derived from apoptosis, while large fragments (FIG. 28) come from necrotic cells.

Figure 29:
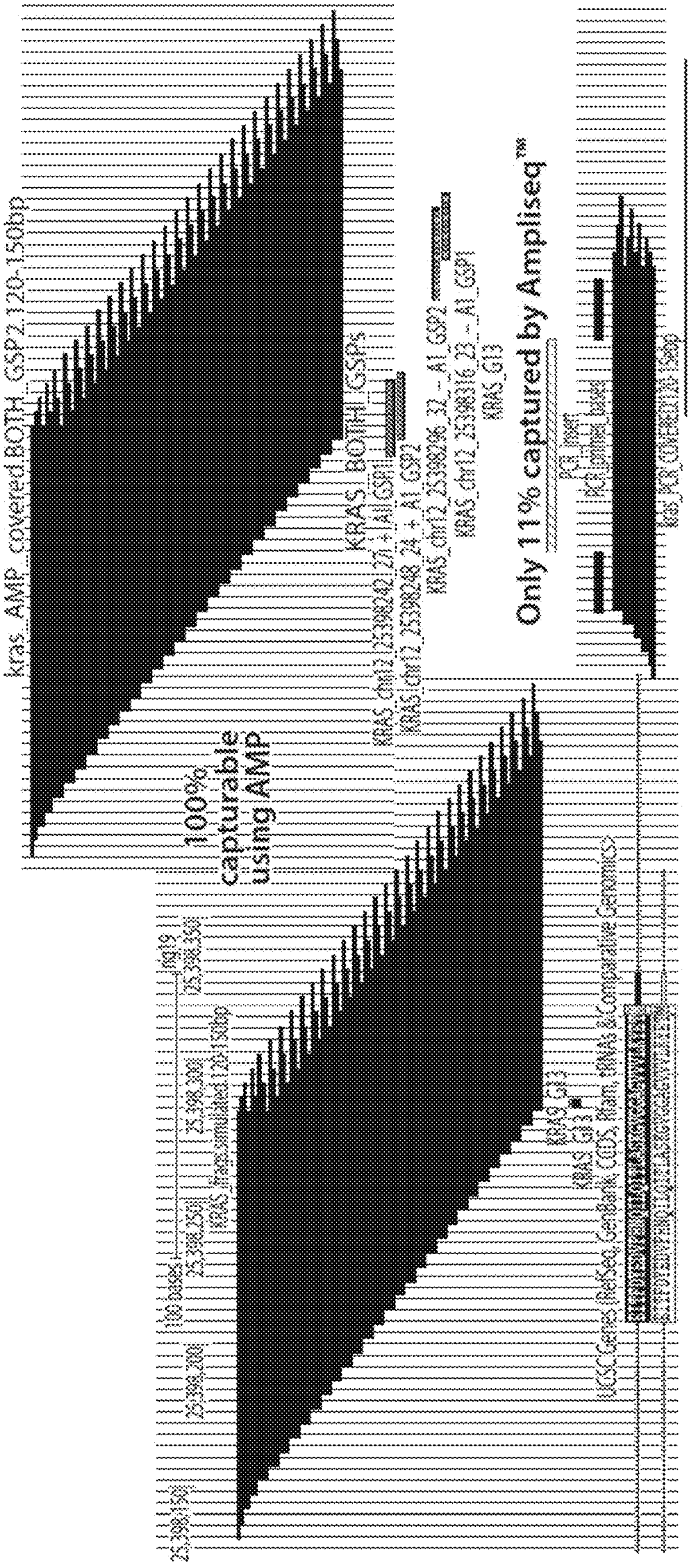
FIG. 29 shows the AMP advantage as compared to Ampliseq with cfDNA.
Figure 30:
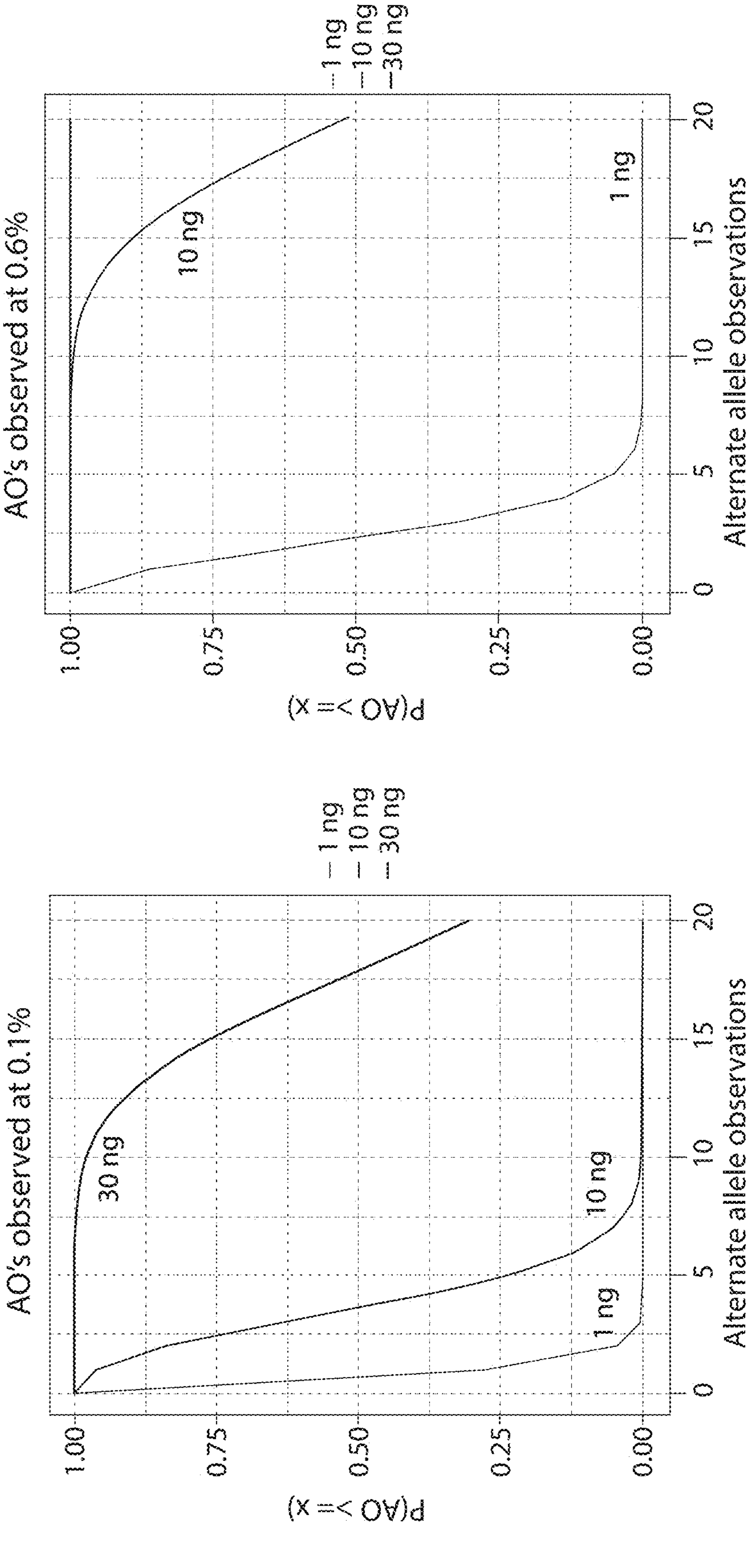
FIG. 30 shows that the assay input influences sensitivity.

FIG. 29 shows the AMP advantage as compared to Ampliseq. cfDNA is 100% capturable using AMP, while it is only 11% capturable by Ampliseq. FIG. 30 shows that the assay input influences sensitivity. A theoretical sensitivity of 330 genomes per ng and assuming 100% efficiency results in the following:

| AF | Number of AO's required to call variant | 1 ng | 10 ng | 30 ng |
|---|---|---|---|---|
| 0.1% | 1 A0 | 28.12% | 96.32% | 100.00% |
| | 2 AO | 4.38% | 84.15% | 100.00% |
| | 3 AO | 0.47% | 64.07% | 100.00% |
| | 4 AO | 0.04% | 41.97% | 100.00% |
| | 5 AO | 0.00% | 23.73% | 99.99% |
| 0.6% | 1 AO | 86.3% | 100.0% | 100.0% |
| | 2 AO | 58.9% | 100.0% | 100.0% |
| | 3 AO | 31.8% | 100.0% | 100.0% |
| | 4 AO | 13.9% | 100.0% | 100.0% |
| | 5 AO | 5.0% | 100.0% | 100.0% |

Figure 31:
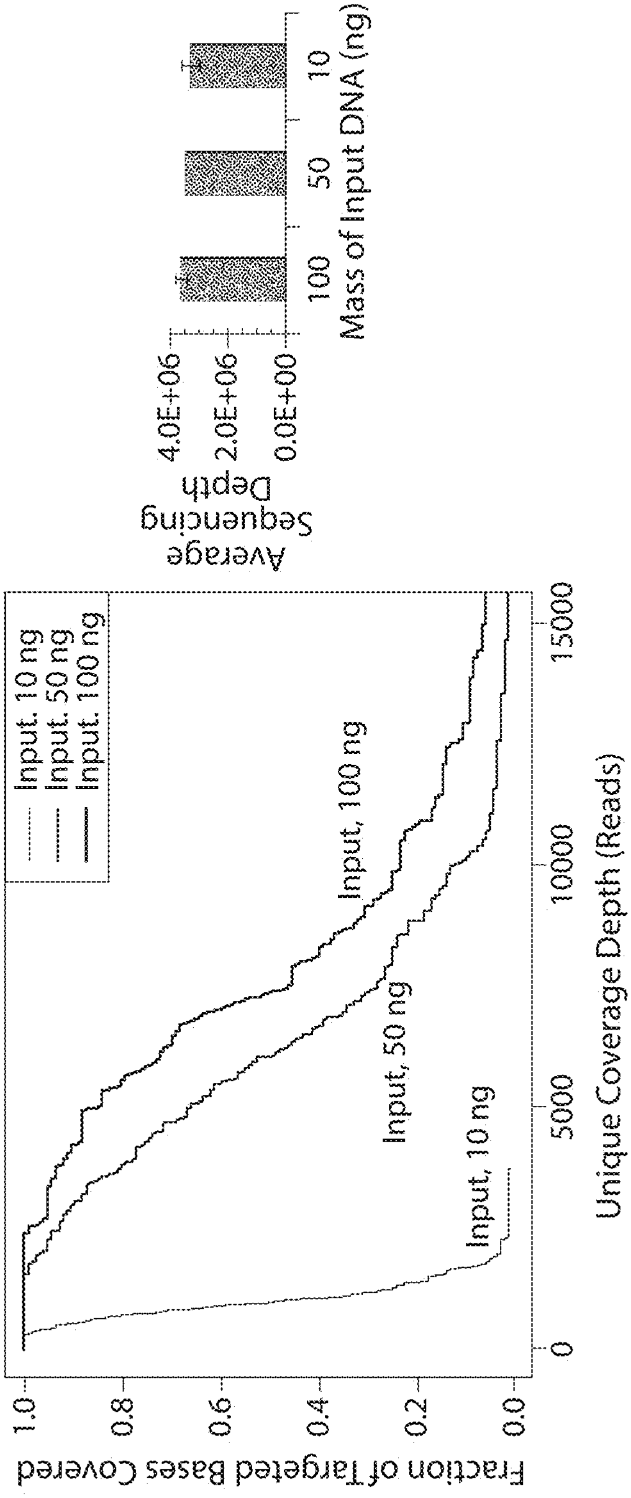
FIG. 31 illustrates a coverage comparison across varying cfDNA input quantities.
Figure 32:
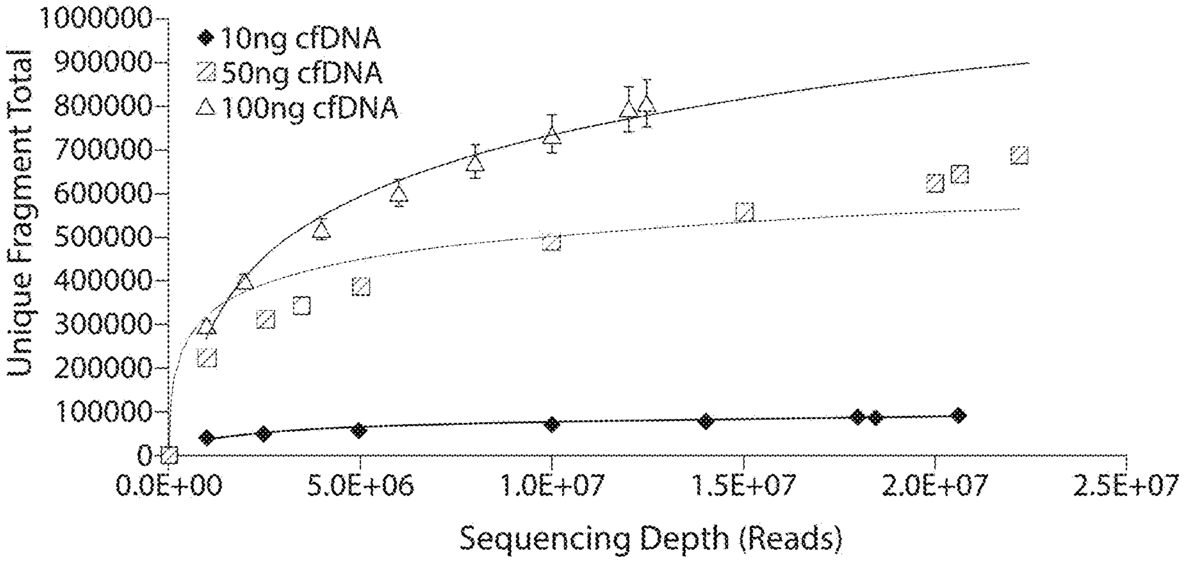
FIG. 32 is a graph demonstrates that input drives complexity and sensitivity.
Figure 33:
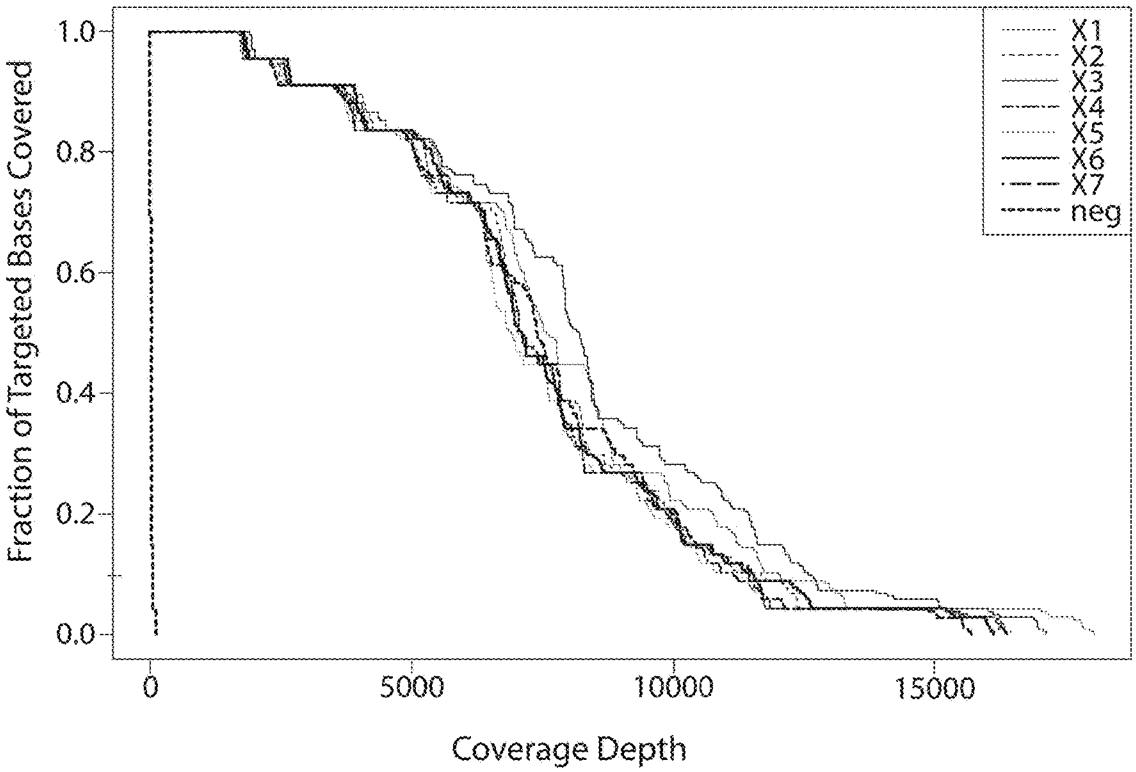
FIG. 33 is a graph showing the high coverage and reproducibility based on synthetic cfDNA input.
Figure 34:
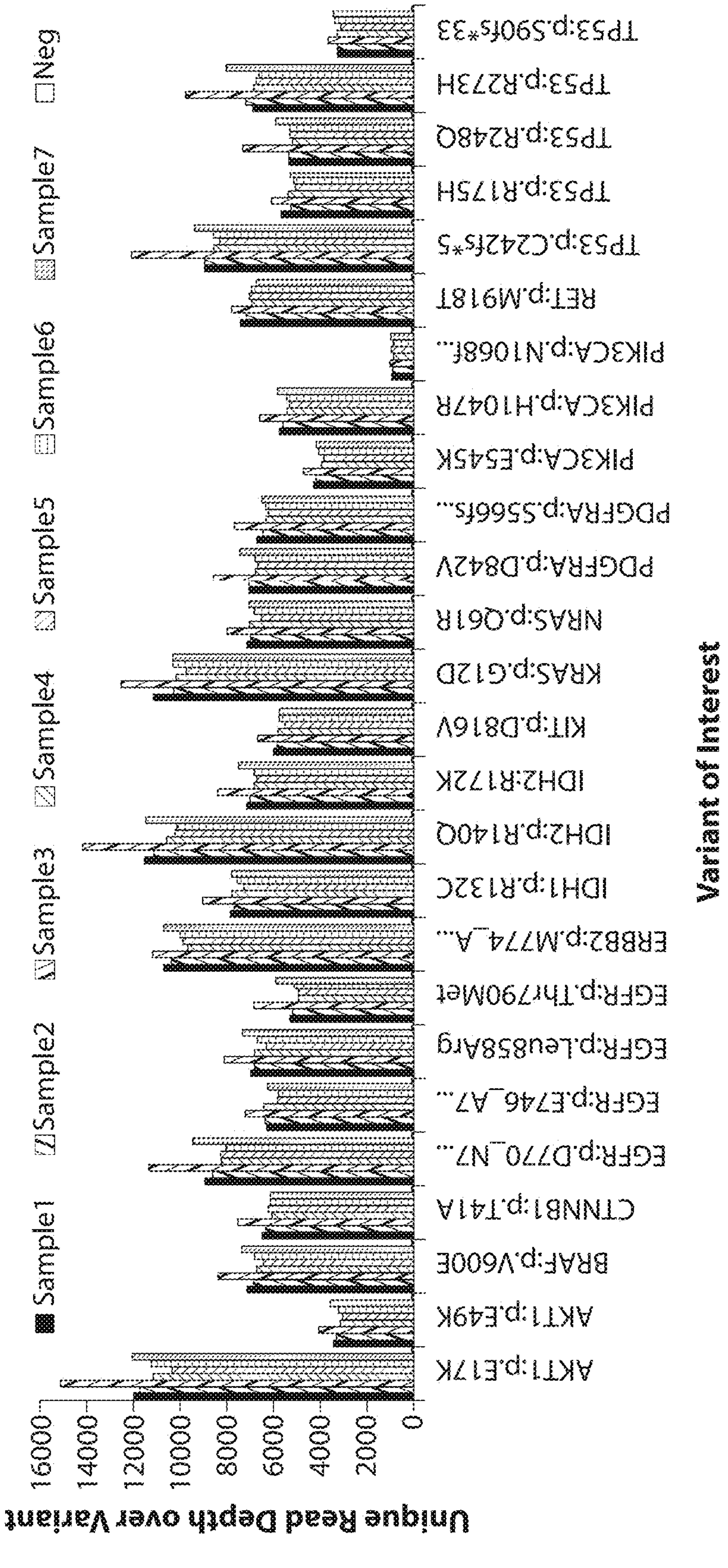
FIG. 34 shows the results of a panel assay.
Figure 35:
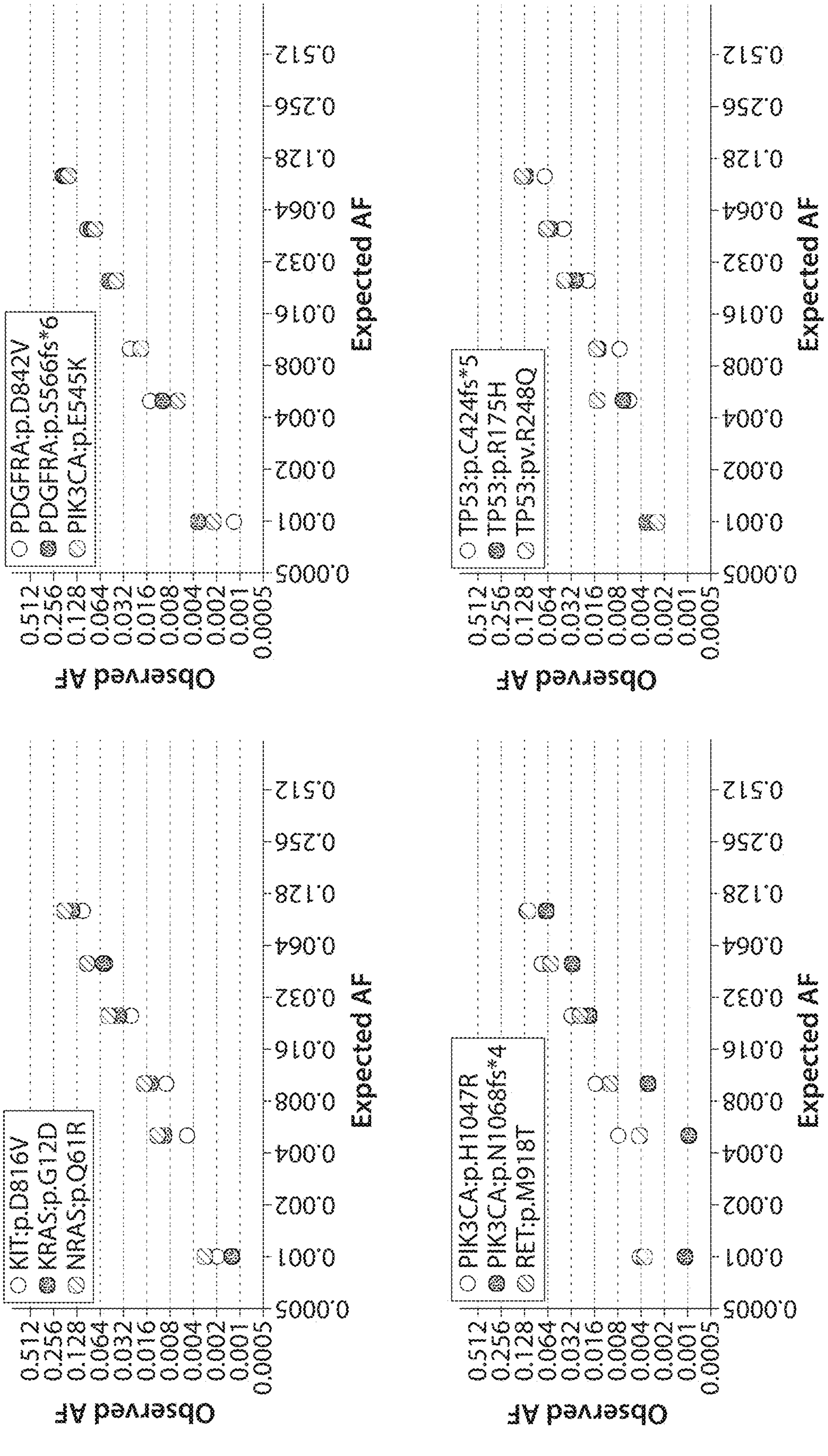
FIG. 35 is four graphs showing highly quantitative variant detection.
Figure 36:
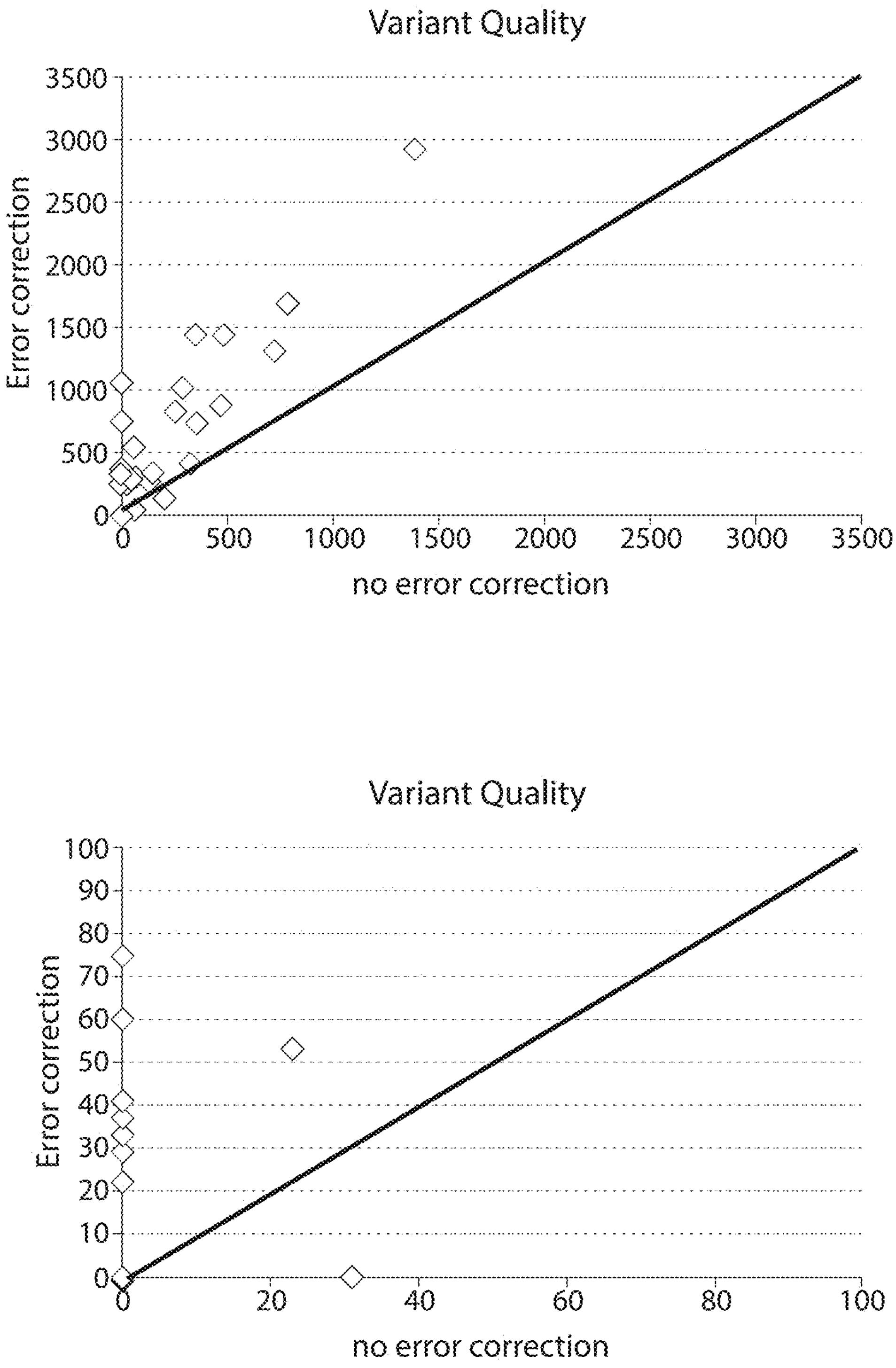
FIG. 36 shows error correction greatly enhances variant identification.
Figure 37:
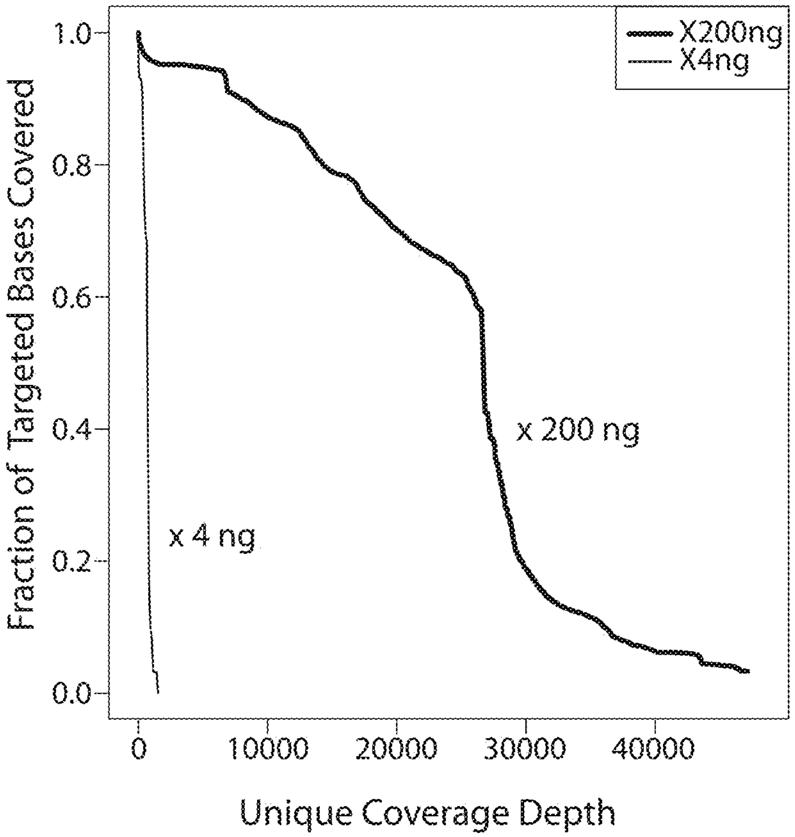
FIG. 37 presents a coverage comparison.

FIG. 31 illustrates a coverage comparison across varying cfDNA input quanitites. FIG. 32 is a graph demonstrates that input drives complexity and sensitivity. FIG. 33 is a graph showing the high coverage and reproducibility of 100 ng of synthetic cfDNA input. Approximately 4 million reads total were over 3.4 kb. FIG. 34 shows the results of a panel assayed using 100 ng synthetic cfDNA samples. FIG. 35 is four graphs showing highly quantitative variant detection down to AF=0.1%. The graphs depict representative variants and is not error-corrected. FIG. 36 shows error correction greatly enhances variant identification with AF=0.5% (top) and AF=0.1% (bottom). FIG. 37 presents a coverage comparison. Input mass strongly correlates with coverage depth, and high inputs enable detection down to 0.1% allele fraction:

| Variant Calling from 200 ng of Horizon cfDNA Input | | | | | | | | | | |
|---|---|---|---|---|---|---|---|---|---|---|
| annotation | type | Chr | position | reference | mutation | DP | RO | AO | AF | Exp. AF |
| EGFR:p.Leu858Arg | snp | chr7 | 55259515 | T | G | 27339 | 27214 | 35 | 0.0013 | 0.001 |
| EGFR:p.Thr790Met | snp | chr7 | 55249071 | C | T | 26538 | 26485 | 53 | 0.002 | 0.001 |
| KRAS:p.Gly12Asp | snp | chr12 | 25398284 | C | T | 30134 | 30055 | 74 | 0.0025 | 0.0013 |
| NRAS:p.Gln61Lys | snp | chr1 | 115256530 | G | T | 30533 | 30461 | 40 | 0.0013 | 0.0013 |
| NRAS:p.Ala59Thr | snp | chr1 | 115256536 | C | T | 29969 | 29925 | 40 | 0.0013 | 0.0013 |
| PIK3CA:p.Glu545Lys | snp | chr3 | 178936091 | G | A | 23797 | 23748 | 46 | 0.0019 | 0.0013 |
| EGFR:p.Val769_Asp770ins AlaSerVal | ins | chr7 | 55248998 | A | ATGGCCAGCG (SEQ ID NO: 9) | 31058 | 31022 | 18 | 0.0006 | 0.001 |
| EGFR:p.E746_A750delELR EA | del | chr7 | 55242464 | AGGAATTAA GAGAAGC (SEQ ID NO: 10) | A | 25138 | 25060 | 11 | 0.0004 | 0.001 |

Figure 38:
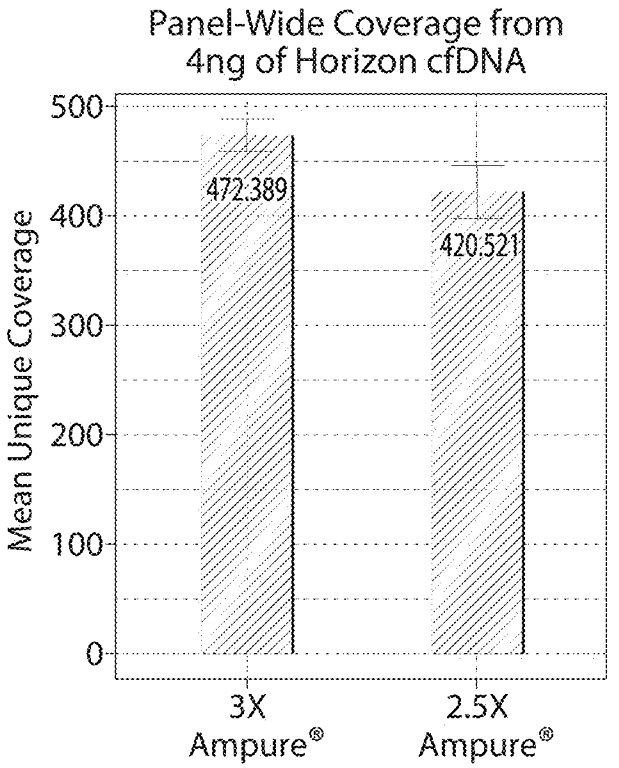
FIG. 38 demonstrates that the ctDNA panel yields over 400 times coverage with low input amounts.
Figure 39:
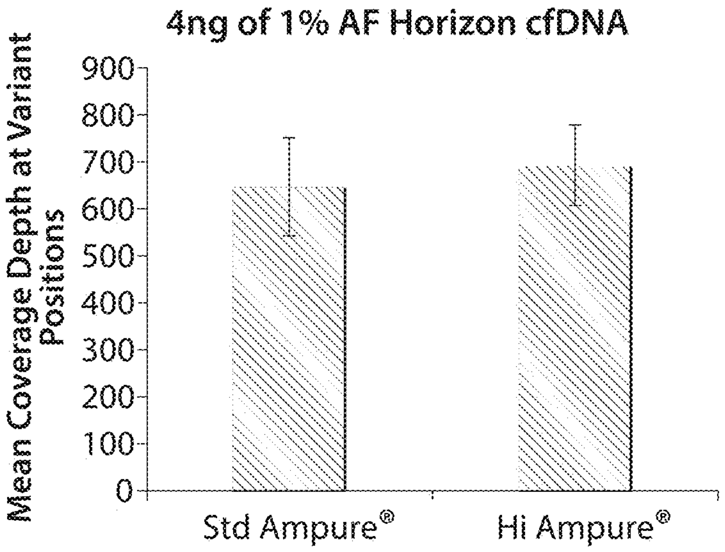
FIG. 39 shows variant calling data for cfDNA.
Figure 40:
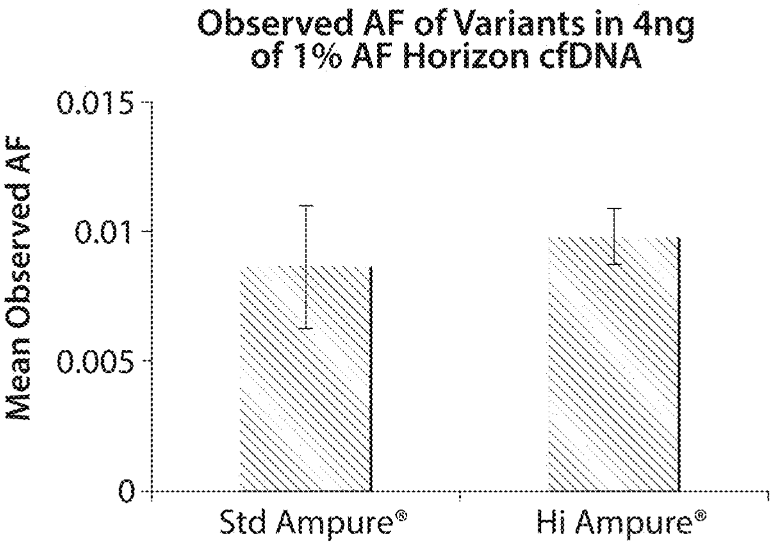
FIG. 40 shows sample variant calling data for cfDNA.

FIG. 38 demonstrates that the ctDNA panel yields over 400 times coverage with low (4 ng) input amounts. FIG. 39 shows variant calling from 4 ng of 1% AF Horizon cfDNA. FIG. 40 shows sample variant calling data for Horizon cfDNA. The raw data from the Horizon 1% AF sample is given below:

| 4 ng of Horizon cfDNA (1% AF) | | | | | | |
|---|---|---|---|---|---|---|
| chromosome | Depth | Ref. Obs | Alt. Obs | AF | annotation | Expected |
| chr1 | 724 | 715 | 8 | 0.0110 | NRAS:p.Gln61Lys | 0.013 |
| chr1 | 479 | 475 | 4 | 0.0084 | NRAS:p.Gly60Glu | 0.013 |
| chr3 | 601 | 595 | 6 | 0.0100 | PIK3CA:p.Glu545Lys | 0.013 |
| chr7 | 436 | 433 | 1 | 0.0023* | EGFR:p.Glu746_Ala750del | 0.01 |
| chr12 | 664 | 656 | 8 | 0.0120 | KRAS:p.Gly12Asp | 0.013 |
| chr7 | 537 | 532 | 5 | 0.0093 | EGFR:p.Thr790Met | 0.01 |
| chr7 | 603 | 588 | 15 | 0.0249 | EGFR:p.Leu858Arg | 0.01 |
| chr7 | 515 | 513 | 2 | 0.0039* | EGFR:p.Val769_Asp770insAlaSerVal | 0.01 |

Example 5: Nucleic Acid Sample Preparation

An example of a protocol that illustrates a method of preparing a nucleic acid sample for analysis is shown in FIG. 41.

A biotinylated receptor-specific primer is annealed with sample RNA. A thermal cycler is heated to 65° C. and purified total nucleic acid or RNA (20-250 ng) is combined with nuclease-free water while on ice before combining with receptor-specific primer. The sample is then transferred to the thermal cycler and incubated with a heated lid (≥100° C.) at 65° C. for 5 minutes and then held at 4° C. Once finished, the sample is placed on ice for at least 2 minutes.

Following annealing, the first strand cDNA is synthesized by extension of the receptor-specific primer by the action of a reverse transcriptase enzyme to generate a DNA/RNA hybrid. The sample is incubated in a thermal cycler with a heated lid (≥100° C.) at 50° C. for 30 minutes, followed by 20 minutes at 80° C., and then held at 4° C.

The RNA strand of the resulting DNA/RNA hybrid is partially degraded via the action of a ribonuclease, which leaves behind RNA fragments annealed to the first strand that serve as primers for a second strand synthesis reaction. The second strand cDNA is synthesized following incubation with DNA PolI in a thermal cycler with a heated lid (≥100° C.) at 16° C. for 60 minutes, followed by 20 minutes at 75° C., and then held at 4° C.

The double-stranded cDNA sample is subjected to end repair to blunt end the cDNA and phosphorylate the 5' ends. In this step, an excess of T4 DNA Polymerase and T4 Polynucleotide Kinase is added to the sample along with sufficient dNTPs and allowed to incubate for 30 minutes at 25° C. in a thermal cycler (without a heated lid). The DNA is subjected to a cleanup step using AMPure® XP beads (2.5×). The beads are completely re-suspended by vortexing and added to each reaction with mixing to ensure a homogenous mixture. The reaction is then incubated for 5 minutes at room temperature (20 to 25° C.). The tubes are then spun down and placed on a magnet for 4 minutes to ensure the beads are fully pelleted against the tube wall. The supernatant is discarded without disturbing the bead pellet and more magnification is used as necessary to re-pellet the beads. The beads are washed with 70% ethanol for 30 seconds while still on the magnet before the supernatant is discarded. The washing is repeated twice. After the final wash, the visible supernatant residue is completely removed and the beads are dried for 5 minutes at room temperature with open lids. The beads should not be over-dried as this significantly decreases the overall yield of nucleic acid. The DNA is eluted by re-suspending the beads in 10 mM Tris-HCl PH 8.0. The tubes are then placed back on the magnet for 2 minutes.

In a first ligation step, the purified DNA is then subjected to a dA-tailing reaction that incorporates dAMPs onto the 3' ends of the DNA strands during incubation in a thermal cycler with a heated lid (≥100° C.) for 15 minutes at 37° C. and then held at 4° C. The reaction is then spun down and placed on ice.

Following the A-tailing, the samples are cleaned using AMPure® XP beads (2.5×) following the same procedure described above. The DNA is eluted using nuclease-free water.

In a second ligation step, unique nucleotide sequences or molecular barcodes (MBCs) are ligated to the DNA via the action of DNA ligase following incubation in a thermal cycler (without a heated lid) for 15 minutes at 25° C. and then held at 4° C. The samples are then purified using streptavidin-coated beads. The samples are placed on a magnet for 1 minute or until the beads are pelleted. The supernatant is removed using a pipette without disturbing the bead pellet. The beads are then re-suspended in ligation cleanup buffer (1 M NaCl, 1 mM EDTA, 0.1% Tween, 10 mM Tris pH 8). The ligated DNA product (50 μL) is mixed with ligation cleanup beads (50 μL for a total of 100 μL) and the reaction is incubated at room temperature for 5 minutes, followed by mixing, and another 5 minutes of incubation. The samples are spun down and placed on a magnet for 1 minute to ensure the beads are fully pelleted against the tube wall. The supernatant is discarded without disturbing the beads and the beads are washed with ligation buffer and placed on a magnet for 1 minute. Once the slurry has cleared, the supernatant is discarded. The beads are then washed twice with buffer and then once with nuclease-free water. The MBC adapter-bound beads are then transferred to a separate mixture of components for a first PCR step.

A first round of PCR is performed using a first gene-specific primer and a first adapter primer. The reaction is kept on ice before performing the first PCR in a thermal cycler with a heated lid (≥100° C.) using the program described in Table 4. Once the reaction has reached 4° C., the reactions are briefly spun down and placed on ice.

TABLE 4

PCR Conditions for the First PCR Reaction.

| Step | Temperature (° C.) | Time (min) | Cycles |
|---|---|---|---|
| 1 | 95 | 3 min | 1 |
| 2 | 95 | 30 sec | 24 |
| 3 | 65 | 3 min<br>(100% ramp rate) | |
| 4 | 72 | 3 min | 1 |
| 5 | 4 | Hold | 1 |

The PCR reaction is then cleaned using AMPure® XP beads (1.2×) and incubated for 5 minutes at room temperature (20 to 25° C.). The tubes are then briefly spun down and placed on a magnet for 4 minutes to ensure that the beads are fully pelleted against the tube wall. The supernatant is discarded without disturbing the bead pellet. The tubes are then washed for 30 seconds with 70% ethanol while remaining on the magnet. The washing is repeated twice. After the final wash, the supernatant is removed with a pipette and the tubes are dried for 3 minutes at room temperature. The beads should not be over-dried as this significantly decreases the overall yield of nucleic acid. The DNA is eluted by re-suspending the beads in 10 mM Tris-HCl pH 8.0. The tubes are then placed on the magnet for 2 minutes before the supernatant is transferred to a separate mixture of components for a second PCR step.

A second round of PCR is performed using a second gene-specific primer and a second adapter primer. The second PCR step incorporates a P7-tail, which is incorporated as a 5' tailed region of the second gene-specific primer, as shown in FIG. 41. The sequences for Index 1 (P7) tags are shown in Table 5.

TABLE 5

Index 1 (P7) Sequence Table.

| Sample Number | Illumina Index 1 P7/i7 Sequence |
|---|---|
| 1 | TAAGGCGA |

TABLE 5-continued

| Index 1 (P7) Sequence Table. | |
|---|---|
| Sample Number | Illumina Index 1 P7/i7 Sequence |
| 2 | CGTACTAG |
| 3 | AGGCAGAA |
| 4 | TCCTGAGC |
| 5 | GGACTCCT |
| 6 | TAGGCATG |
| 7 | CTCTCTAC |
| 8 | CAGAGAGG |

The purified library DNA from the first PCR is mixed with the second gene-specific primer and second adapter primer and PCR components, and the second PCR is performed in the thermal cycler with a heated lid (≥100° C.) using the program described in Table 6. Once the reaction has reached 4° C., the reactions are briefly spun down and placed on ice.

TABLE 6

| PCR Conditions for the Second PCR Reaction. | | | |
|---|---|---|---|
| Step | Temperature (° C.) | Time | Cycles |
| 1 | 95 | 3 min | 1 |
| 2 | 95 | 30 sec | 6 |
| 3 | 65 | 3 min (100% ramp rate) | |
| 4 | 72 | 3 min | 1 |
| 5 | 4 | Hold | 1 |

The PCR reaction is then cleaned using AMPure® XP beads (1.2×) following the same procedure outlined in the First PCR Reaction. The DNA is eluted by re-suspending the beads in 10 mM Tris-HCl pH 8.0 and incubating on a magnet for 2 minutes. The library-tagged DNA is then transferred to a new PCR tube for storage, quantification, or normalization and sequencing.

Example 6: Diversity and Reproducibility

Figure 44:
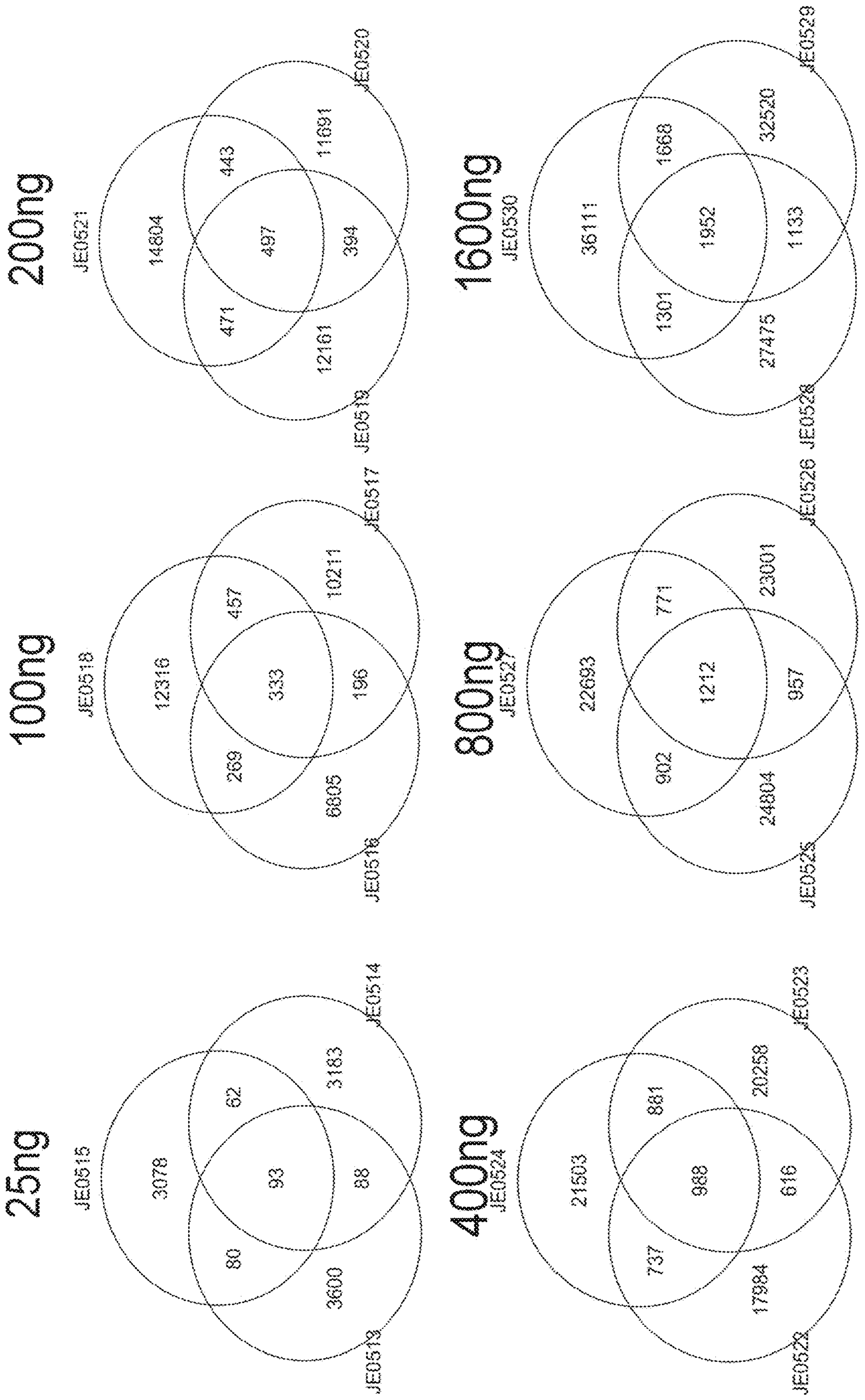
FIG. 44 is an illustration showing clonotype overlap between replicates in relation to input amount. The intersection of all samples yields sixty six overlapping clonotypes.
Figure 45:
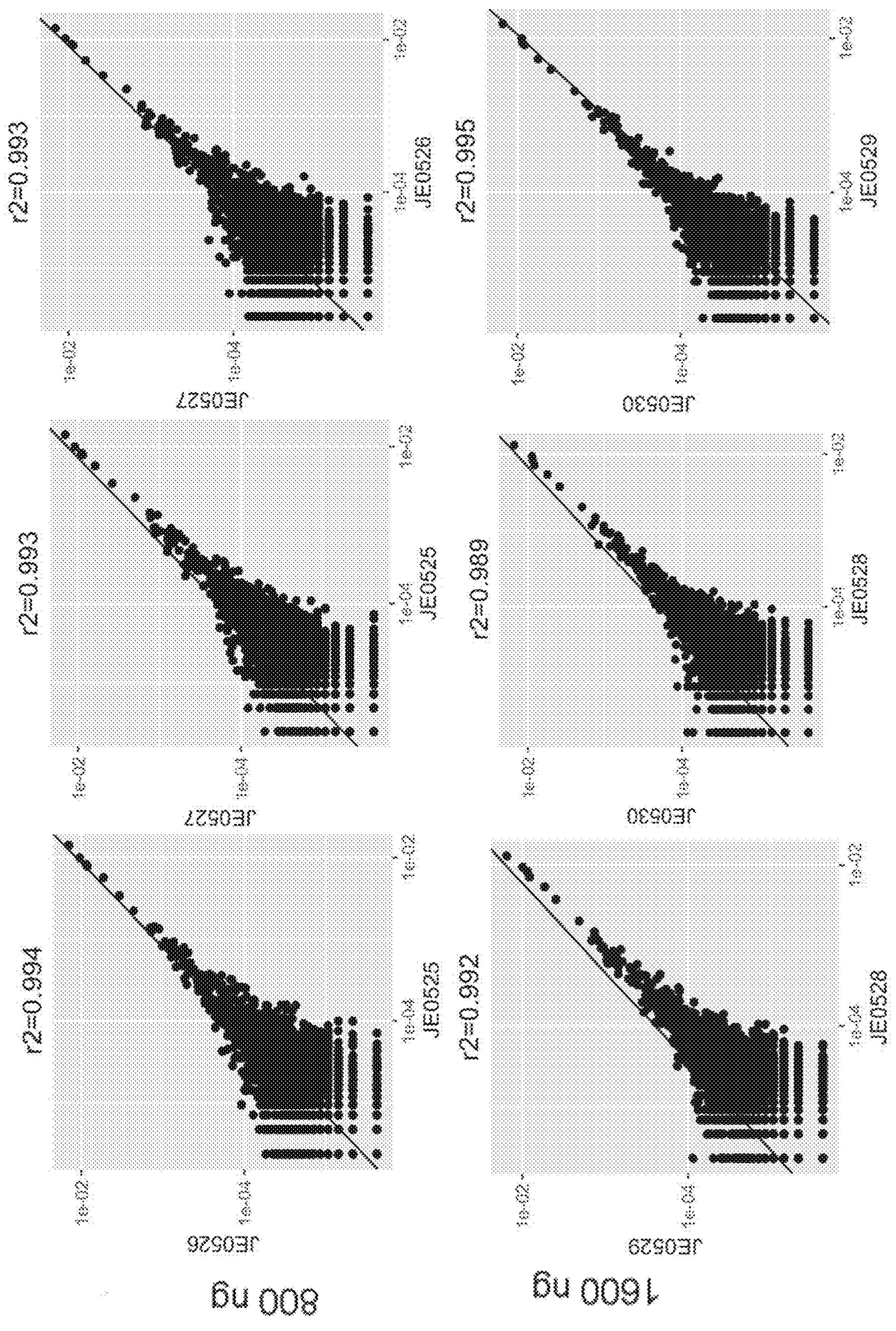
FIG. 45 is a chart illustrating that pairwise analysis of replicate samples demonstrates the highly reproducible nature of the assay.
Figure 46A:
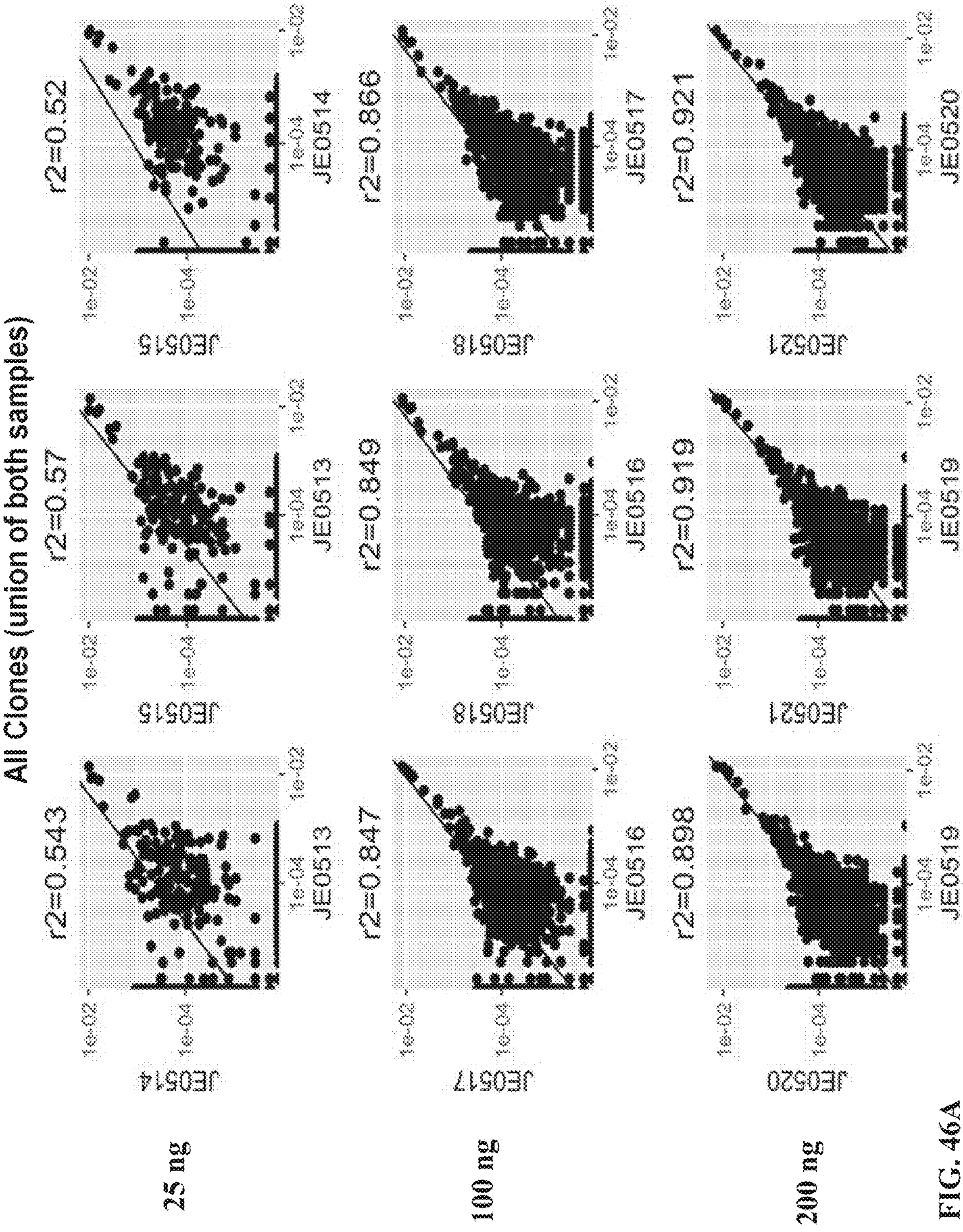
FIGS. 46A-46D depict a comparison between all clones (FIGS. 46A and 46B) and overlapping clones (FIGS. 46C and 46D).
Figure 46B:
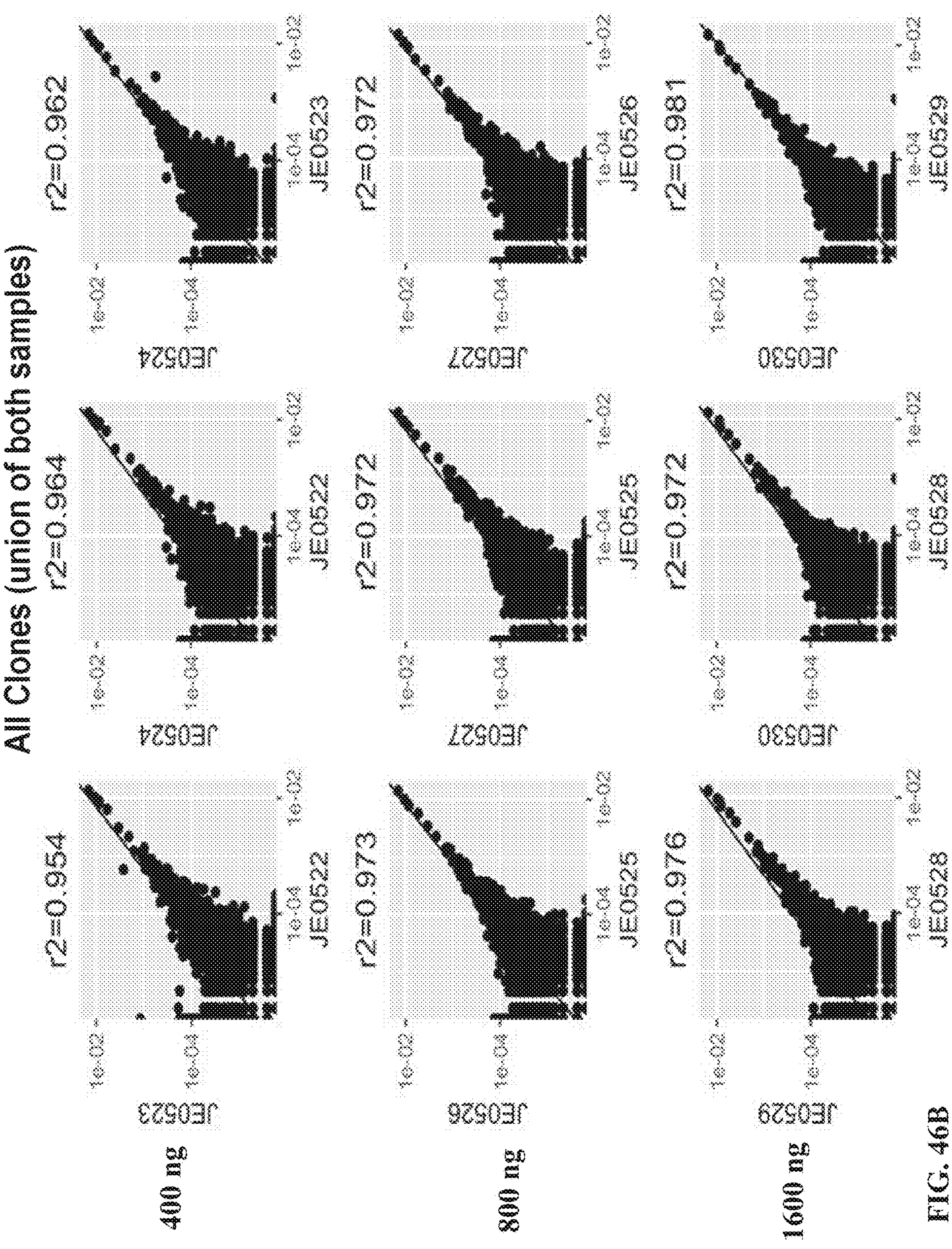
Figure 46C:
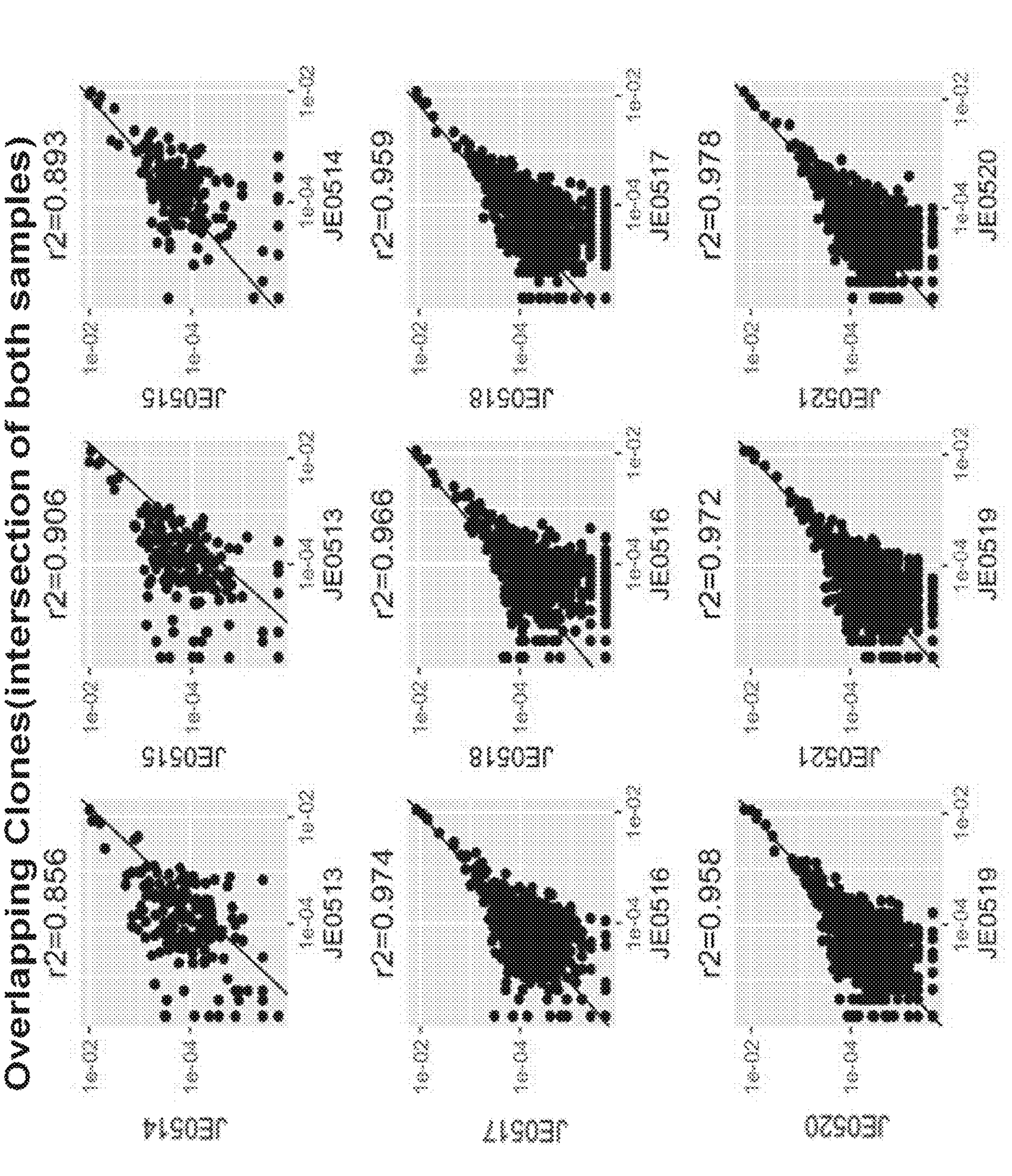
Figure 46D:
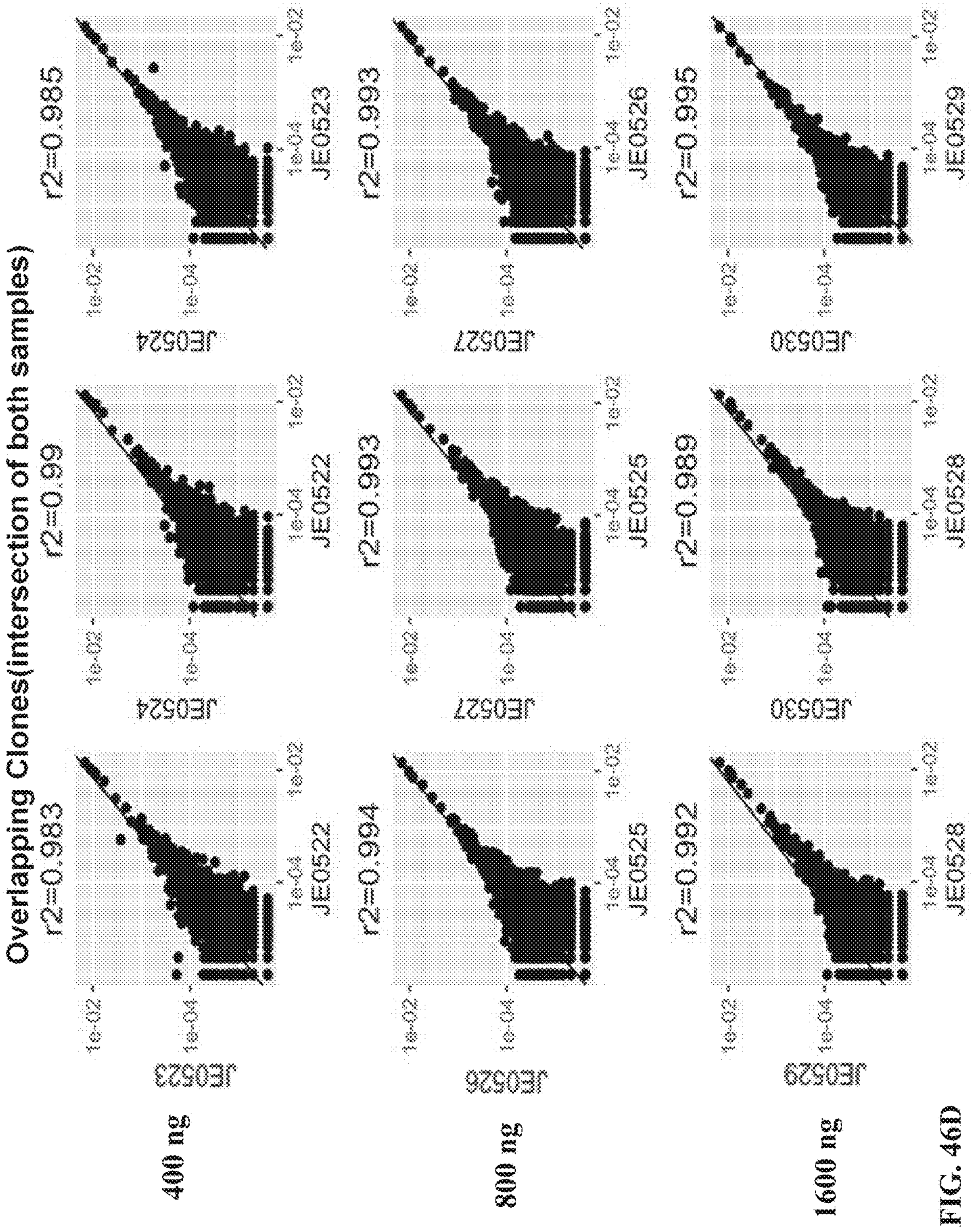
Figure 47:
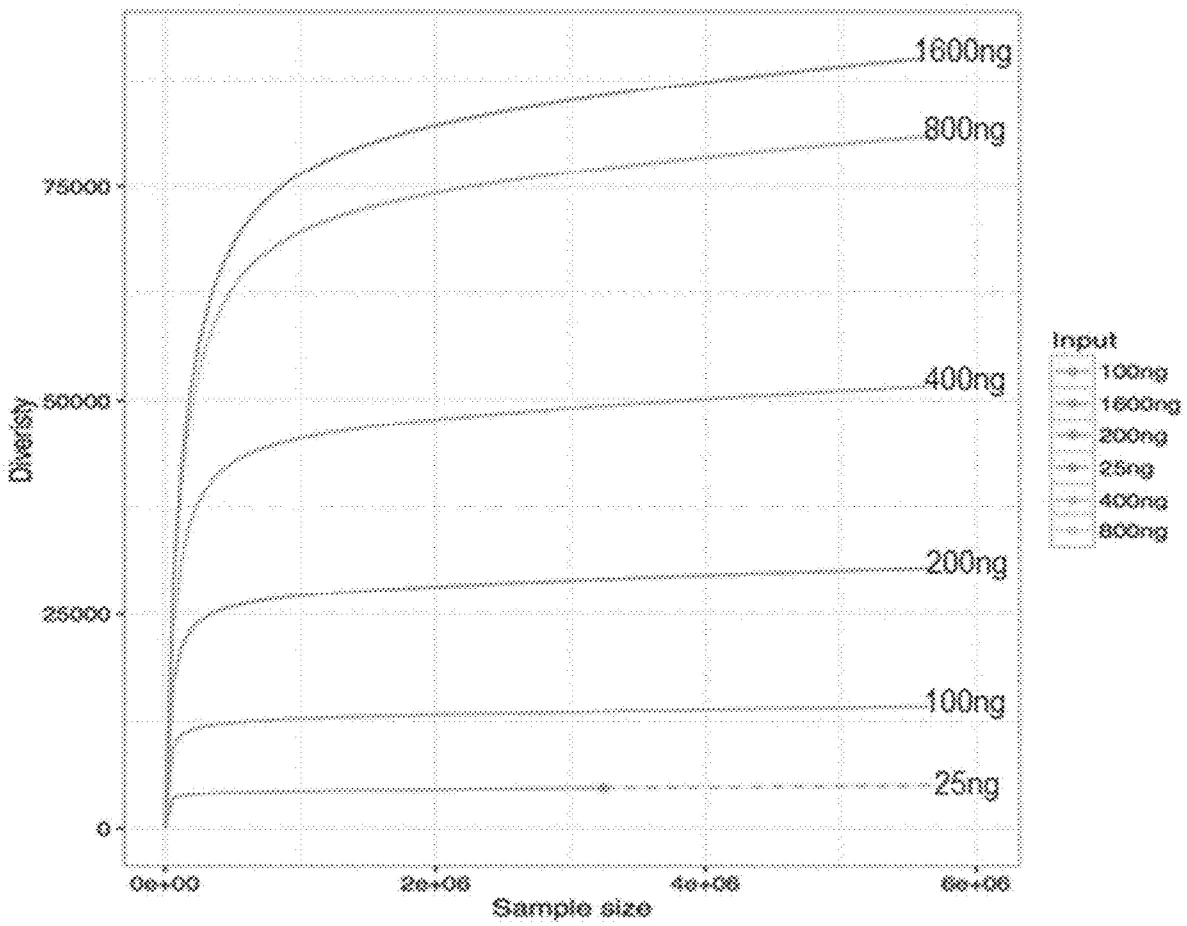
FIG. 47 illustrates that input quantity drives complexity and diversity of observation, with diversity in relation to sample size depicted at top and a chart depicting Shannon diversity index shown at bottom.
Figure 47:
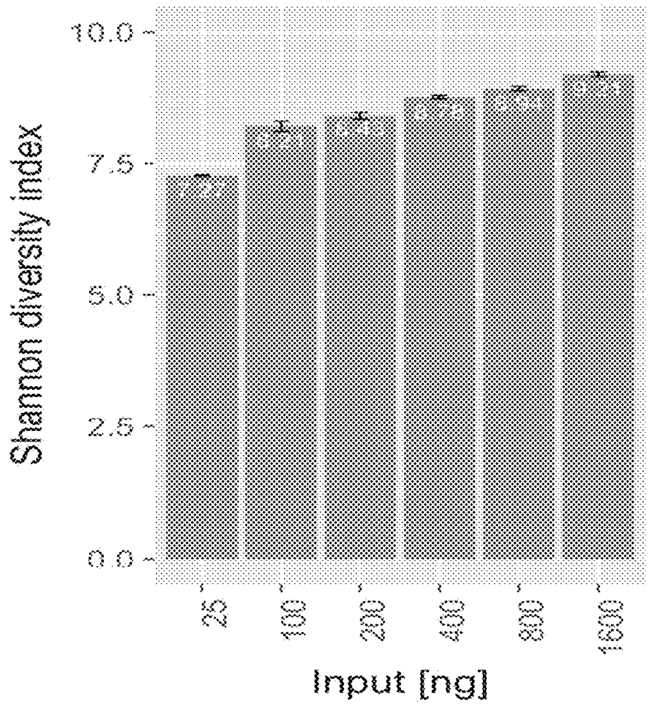

Sequencing information was obtained from samples of varied input amounts (25, 100, 200, 400, 800, and 1600 ng) across repeat experiments using the methods described above. As shown in FIG. 44, clonotype overlap between replicate experiments increases with input amount. A pair-wise analysis of replicate samples was further performed using data from 256,000 reads. The results, which demonstrated the highly reproducible nature of the assay, are shown for 800 and 1600 ng input samples in FIG. 45. FIGS. 46A and 46B depict the full side-by-side analysis of all clones (FIG. 46A) versus overlapping clones (FIG. 46B). FIG. 47 shows a plot of diversity versus sample size (top) and a chart of Shannon diversity index by input size (bottom), which show that input quantity drives complexity and diversity of observation.

Figure 48:
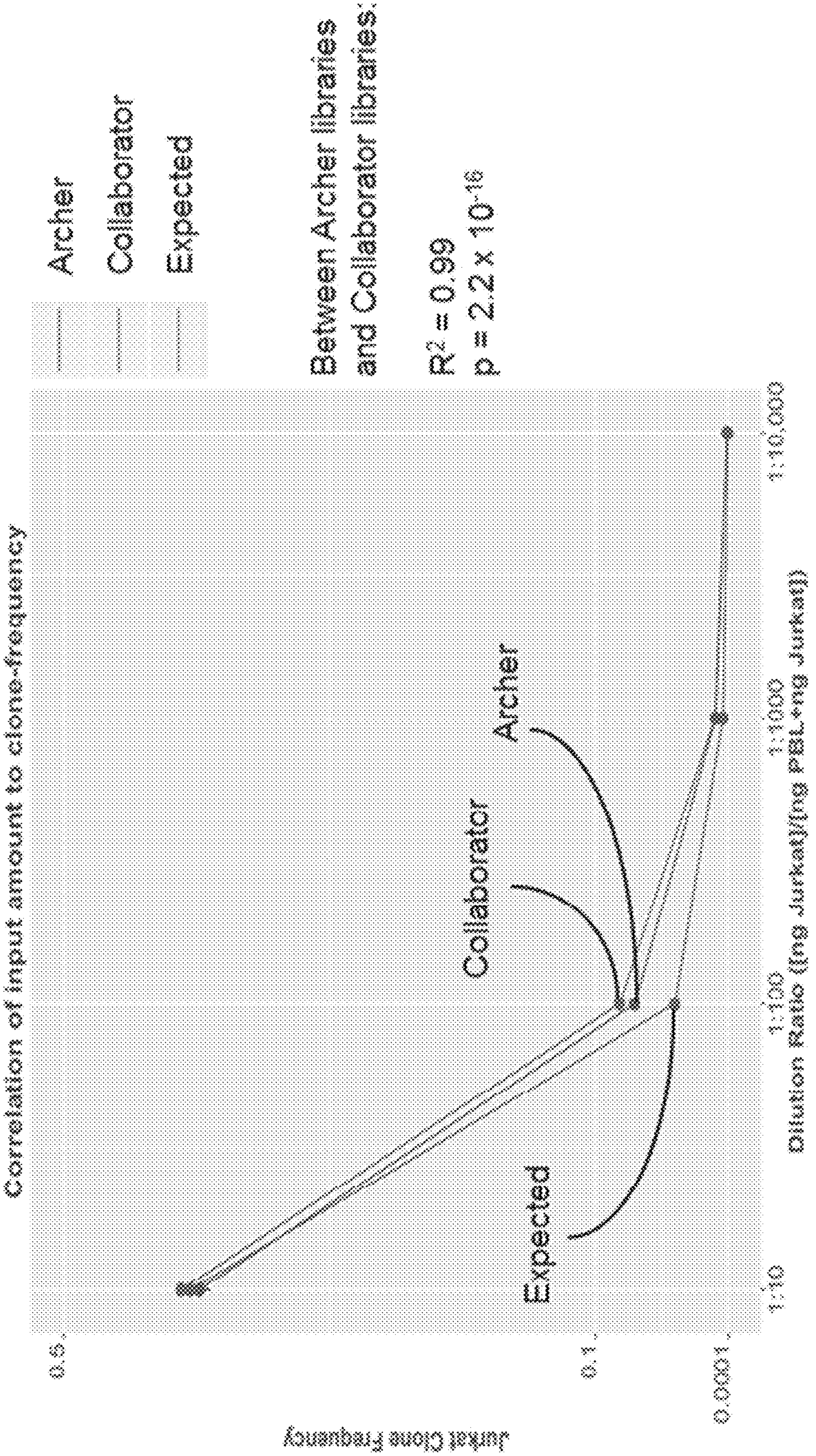
FIG. 48 is a graph demonstrating highly reproducible and quantitative clone tracking.
Figure 49:
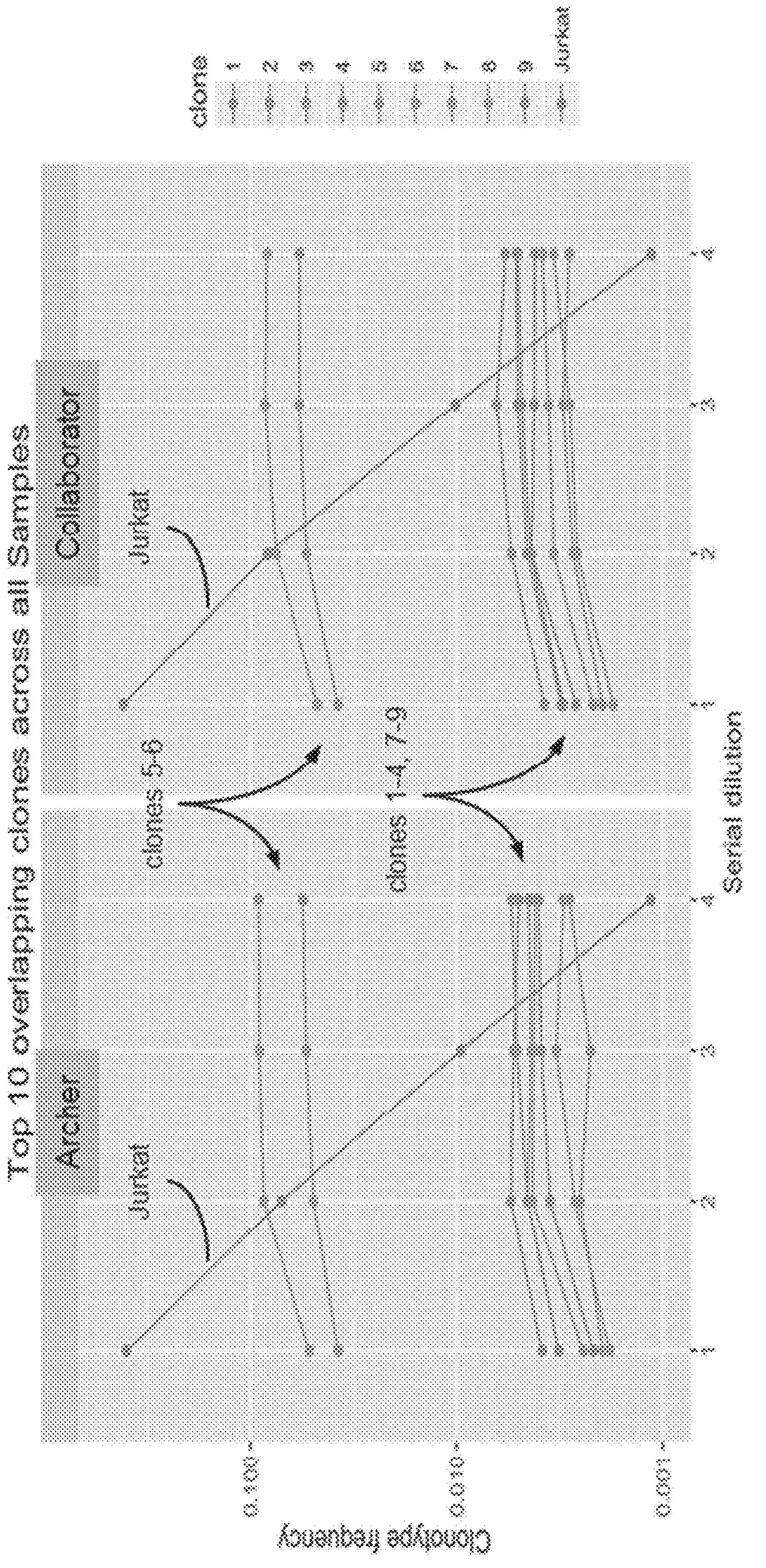
FIG. 49 illustrates that clonal tracking across dilutions is highly reproducible between independent laboratories.
Figure 50:
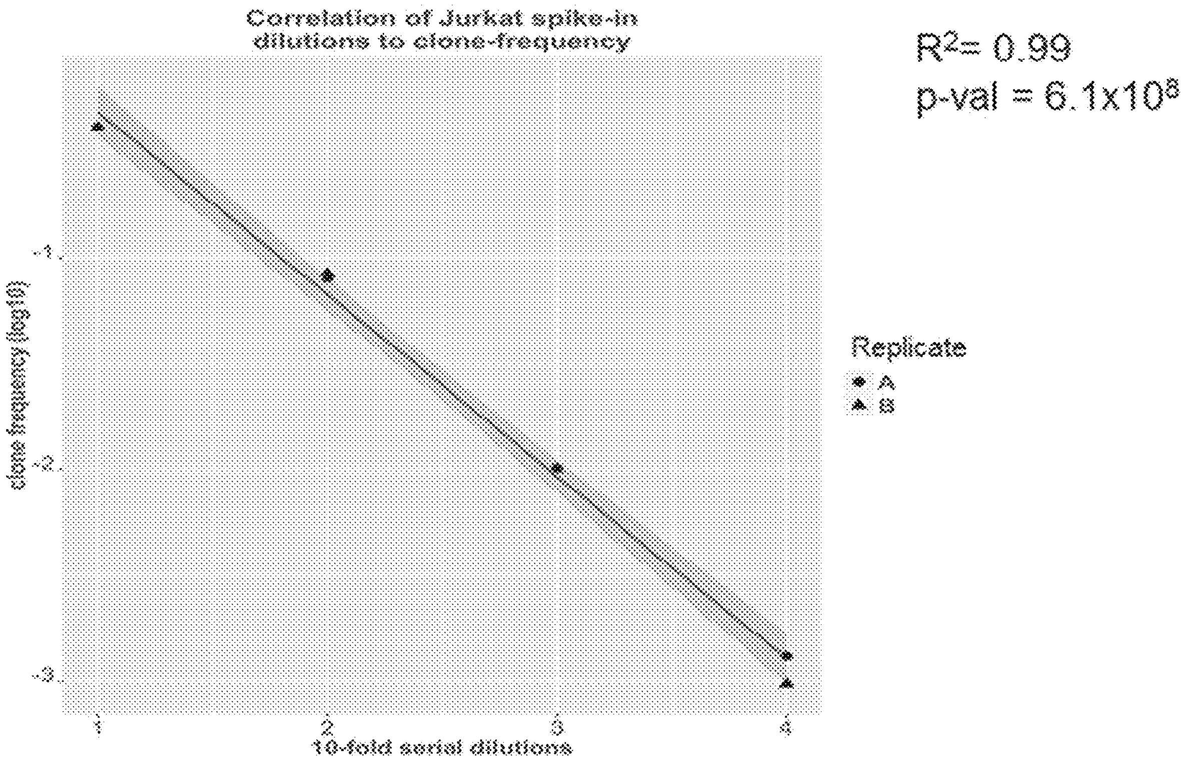
FIG. 50 is a graph depicting intra-laboratory reproducibility using a Jurkat sample dilution series.

As shown in FIGS. 48-50, a Jurkat dilution series was used to test intra- and inter-lab reproducibility. The Jurkat cell line expressing the TCRα:β receptor was spiked into healthy donor peripheral blood lymphocytes (PBL) RNA to determine limits of T cell receptor beta chain (TRB) detection and to assess inter-lab assay variation. A serial dilution of Jurkat total RNA into PBL RNA was performed ranging from 1:10 dilution to 1:10,000 [ng Jurkat/(ng Jurkat+ng PBL)] in duplicate.

Figure 51:
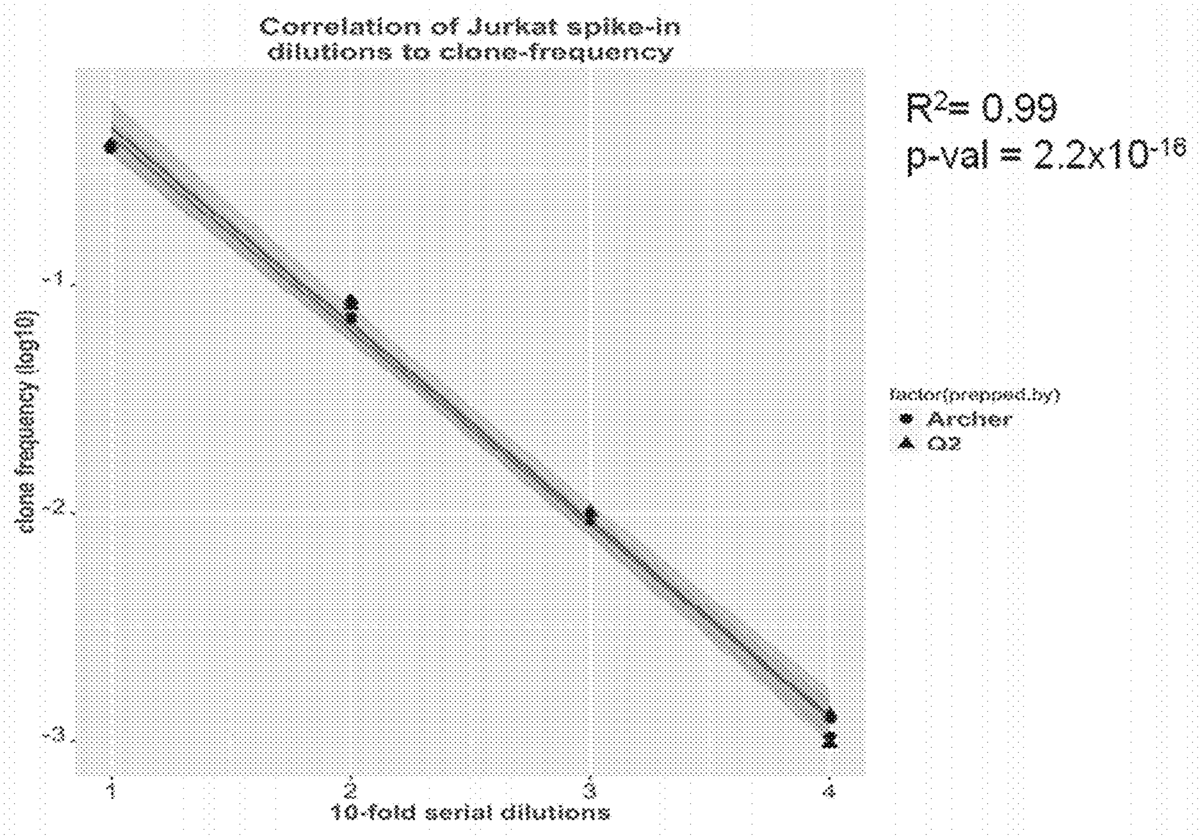
FIG. 51 is a graph depicting inter-laboratory reproducibility using the Jurkat sample dilution series.

The serial dilution was divided into two aliquots per dilution, and the libraries were prepared and sequenced. The results in FIG. 51 show a strong correlation between both labs.

All libraries were normalized to 600,000, deduplicated and error-corrected. The expected frequencies were determined by multiplying the clonotype frequencies of the 1:10 dilutions by 10 and dividing the resulting number by the respective dilution factors (e.g., factor=0.5 (1:10 dilution)×10=5.5/dilution factor=experimental frequency for given dilution factor).

Example 7: Primers

Figure 52:
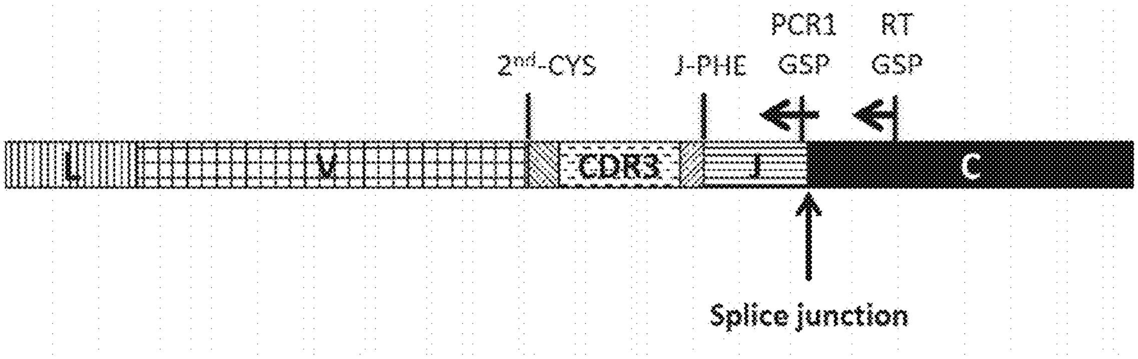
FIG. 52 is a schematic, not shown to scale, that generally depicts T cell receptor primer locations.

FIG. 52 depicts an FFPE-optimized strategy for analysis of TCR (β/γ) repertoire. As shown, the reverse transcriptase (RT) primer binding site corresponds to a 5' region of the constant domain exon. The first PCR gene-specific primers (GSPs) are designed to bind to a region that corresponds either to a 3' region of the J-segment or a region spanning the J-segment:C exon intersection. The average distance from the 5' end of the RT primer to the 5' end of CDR3 is less than 100 base pairs. Panels of primers were designed for immune repertoire sequencing of TCR (β/γ) and TCR (α/δ), listed in Table 7 and Table 8, respectively.

TABLE 7

| T Cell Receptor (β/γ) Primer Panel | |
|---|---|
| Reverse Transcriptase Primers | |
| Primer Name | Sequence (sequence with modified nucleotides shown beneath each) |
| TRAC_RT_19_60.7_BIOTIN_redesign | CACTGGATTTAGAGTCTCTCAGC (SEQ ID NO: 11)<br>/52-Bio/C*ACTGGATTTAGAGTCTCTCAGC (SEQ ID NO: 12) |
| TRBC1_RT_2_59.8_BIOTIN | GAACACCTTGTTCAGGTCCT (SEQ ID NO: 13)<br>/52-Bio/G*AACACCTTGTTCAGGTCCT (SEQ ID NO: 14) |
| TRBC2_RT_1_59.8_BIOTIN | GAACACGTTTTTCAGGTCCTC (SEQ ID NO: 15)<br>/52-Bio/G*AACACGTTTTTCAGGTCCTC (SEQ ID NO: 16) |
| TRDC_RT_37_59_BIOTIN | TCTTATATCCTTGGGGTAGAATTCC (SEQ ID NO: 17)<br>/52-Bio/T*CTTATATCCTTGGGGTAGAATTCC (SEQ ID NO: 18) |

TABLE 7-continued

| T Cell Receptor (β/γ) Primer Panel | |
|---|---|
| TRGC_RT_24_univ_60.6_BIOTIN | GGGAAACATCTGCATCAAGTTG (SEQ ID NO: 19)<br>/52-Bio/G*GGAAACATCTGCATCAAGTTG (SEQ ID NO: 20) |
| First PCR Gene-Specific Primers | |
| Primer Name | Sequence (sequence with tail shown beneath each) |
| TRBJ1-1*01_12_69.7 | CAGGTCCTCTACAACTGTGAGTCTGG (SEQ ID NO: 21)<br>AGACGTGTGCTCTTCCGATCTCAGGTCCTCTACAACTGTGAGTCTGG (SEQ ID NO: 22) |
| TRBJ1-2*01_3_70.1 | GGTCCTCTACAACGGTTAACCTGGTC (SEQ ID NO: 23)<br>AGACGTGTGCTCTTCCGATCTGGTCCTCTACAACGGTTAACCTGGTC (SEQ ID NO: 24) |
| TRBJ1-3*01_10_70.1 | GGTCCTCTACAACAGTGAGCCAACTT (SEQ ID NO: 25)<br>AGACGTGTGCTCTTCCGATCTGGTCCTCTACAACAGTGAGCCAACTT (SEQ ID NO: 26) |
| TRBJ1-4*01_11_70.1 | GGTCCTCCAAGACAGAGAGCTGG (SEQ ID NO: 27)<br>AGACGTGTGCTCTTCCGATCTGGTCCTCCAAGACAGAGAGCTGG (SEQ ID NO: 28) |
| TRBJ1-5*01_9_70.4 | GGTCCTCTAGGATGGAGAGTCGAGTC (SEQ ID NO: 29)<br>AGACGTGTGCTCTTCCGATCTGGTCCTCTAGGATGGAGAGTCGAGTC (SEQ ID NO: 30) |
| TRBJ1-6_7_70.5 | GGTCCTCTGTCACAGTGAGCCTG (SEQ ID NO: 31)<br>AGACGTGTGCTCTTCCGATCTGGTCCTCTGTCACAGTGAGCCTG (SEQ ID NO: 32) |
| TRBJ2-1*01_1_70.1 | TCTAGCACGGTGAGCCGTGT (SEQ ID NO: 33)<br>AGACGTGTGCTCTTCCGATCTTCTAGCACGGTGAGCCGTGT (SEQ ID NO: 34) |
| TRBJ2-2*01_6_70.0 | CAGTACGGTCAGCCTAGAGCCTTC (SEQ ID NO: 35)<br>AGACGTGTGCTCTTCCGATCTCAGTACGGTCAGCCTAGAGCCTTC (SEQ ID NO: 36) |
| TRBJ2-3*01_2_70.0 | TTCAGGTCCTCGAGCACTGTCAG (SEQ ID NO: 37)<br>AGACGTGTGCTCTTCCGATCTTTCAGGTCCTCGAGCACTGTCAG (SEQ ID NO: 38) |
| TRBJ2-4*01_2_69.5 | TTCAGGTCCTCCAGCACTGAGAG (SEQ ID NO: 39)<br>AGACGTGTGCTCTTCCGATCTTTCAGGTCCTCCAGCACTGAGAG (SEQ ID NO: 40) |
| TRBJ2-5*01_1_69.9 | CAGGTCCTCGAGCACCAGGA (SEQ ID NO: 41)<br>AGACGTGTGCTCTTCCGATCTCAGGTCCTCGAGCACCAGGA (SEQ ID NO: 42) |
| TRBJ2-6*01_1_69.5 | CAGCACGGTCAGCCTGCT (SEQ ID NO: 43)<br>AGACGTGTGCTCTTCCGATCTCAGCACGGTCAGCCTGCT (SEQ ID NO: 44) |
| TRBJ2-7*01_2_69.7 | TTCAGGTCCTCTGTGACCGTGAG (SEQ ID NO: 45)<br>AGACGTGTGCTCTTCCGATCTTTCAGGTCCTCTGTGACCGTGAG (SEQ ID NO: 46) |
| TRGJ1_2_C_Ex1_20_69.5 | ACATCTGCATCAAGTTGTTTATCTGTGACAAC (SEQ ID NO: 47)<br>AGACGTGTGCTCTTCCGATCTACATCTGCATCAAGTTGTTTATCTGTGACAAC (SEQ ID NO: 48) |
| TRGJP*01_C_Ex1_1_69.6 | TGTTTATCTGTAATGATAAGCTTTGTTCCGGGA (SEQ ID NO: 49)<br>AGACGTGTGCTCTTCCGATCTTGTTTATCTGTAATGATAAGCTTTGTTCCGGGA (SEQ ID NO: 50) |
| TRGJP1*01_C_Ex1_8_69.8 | TCAGGTGAAGTTACTATGAGCTTAGTCCCT (SEQ ID NO: 51)<br>AGACGTGTGCTCTTCCGATCTTCAGGTGAAGTTACTATGAGCTTAGTCCCT (SEQ ID NO: 52) |
| TRGJP2*01_C_Ex1_5_69.3 | GCGAAGTTACTATGAGCCTAGTCCCTT (SEQ ID NO: 53)<br>AGACGTGTGCTCTTCCGATCTGCGAAGTTACTATGAGCCTAGTCCCTT (SEQ ID NO: 54) |

TABLE 8

| T Cell Receptor (α/δ) Primer Panel | |
|---|---|
| **Reverse Transcriptase Primers** | |
| Primer Name | Sequence (sequence with modified nucleotides shown beneath each) |
| TRAC_RT_19_60.7_BIOTIN_redesign | CACTGGATTTAGAGTCTCTCAGC (SEQ ID NO: 11)<br>/52-Bio/C*ACTGGATTTAGAGTCTCTCAGC (SEQ ID NO: 12) |
| TRBC1_RT_2_59.8_BIOTIN | GAACACCTTGTTCAGGTCCT (SEQ ID NO: 13)<br>/52-Bio/G*AACACCTTGTTCAGGTCCT (SEQ ID NO: 14) |
| TRBC2_RT_1_59.8_BIOTIN | GAACACGTTTTTCAGGTCCTC (SEQ ID NO: 15)<br>/52-Bio/G*AACACGTTTTTCAGGTCCTC (SEQ ID NO: 16) |
| TRDC_RT_37_59_BIOTIN | TCTTATATCCTTGGGGTAGAATTCC (SEQ ID NO: 17)<br>/52-Bio/T*CTTATATCCTTGGGGTAGAATTCC (SEQ ID NO: 18) |
| TRGC_RT_24_univ_60.6_BIOTIN | GGGAAACATCTGCATCAAGTTG (SEQ ID NO: 19)<br>/52-Bio/G*GGAAACATCTGCATCAAGTTG (SEQ ID NO: 20) |
| **First PCR Gene-Specific Primers** | |
| Primer Name | Sequence (sequence with tail shown beneath each) |
| TRAC_PCR_9_69 | TCTCTCAGCTGGTACACGGCA (SEQ ID NO: 55)<br>AGACGTGTGCTCTTCCGATCTTCTCTCAGCTGGTACACGGCA (SEQ ID NO: 56) |
| TRDC_PCR_21_69 | TCACCAGACAAGCGACATTTGTTCC (SEQ ID NO: 57)<br>AGACGTGTGCTCTTCCGATCTTCACCAGACAAGCGACATTTGTTCC (SEQ ID NO: 58) |

Figure 53:
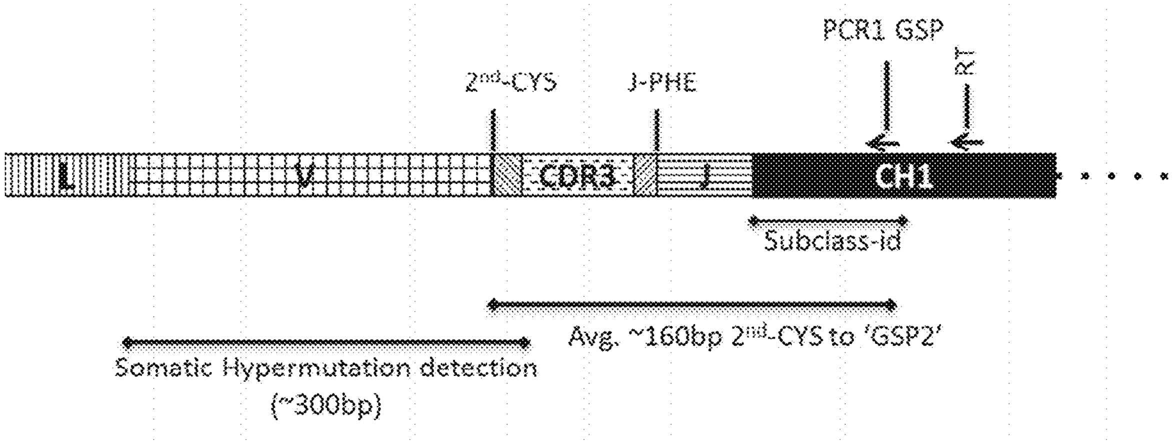
FIG. 53 is a schematic, not drawn to scale, that generally depicts immunoglobulin heavy chain (IgH) primer locations.

The BCR IgH primer panel has some additional requirements besides clonotype (CDR3) identification, compared to the TCR panels, since the IgH panel determines the isotype (A, D, E, G, M) and select subclasses. It also determines if the clone has undergone somatic hyper-mutation (V-segment analysis). The IgH primer locations are shown in FIG. 53. The RT primer and first PCR gene-specific primer bind to regions corresponding to the CH1 exon of the respective isotype constant region to distinguish select isotype subclasses. Panels of primers were designed for immune repertoire sequencing of BCR (IgH) and BCR (IgK/IgL), listed in Table 9 and Table 10, respectively

TABLE 9

| B Cell Receptor (IgH) Primer Panel | |
|---|---|
| Primer Name | Sequence (sequence with modified nucleotides shown beneath each) |
| **Reverse Transcriptase Primers** | |
| IGHA_RT_4_59_BIOTIN | GGCTCCTGGGGGAAGA (SEQ ID NO: 59)<br>/52-Bio/G*GCTCCTGGGGGAAGA (SEQ ID NO: 60) |
| IGHD_RT_40_59_BIOTIN | GTACCCAGTTATCAAGCATGC (SEQ ID NO: 61)<br>/52-Bio/G*TACCCAGTTATCAAGCATGC (SEQ ID NO: 62) |
| IGHE_RT_33_60_BIOTIN | AGTCACGGAGGTGGCAT (SEQ ID NO: 63)<br>/52-Bio/A*GTCACGGAGGTGGCAT (SEQ ID NO: 64) |
| IGHG_RT_18_59_BIOTIN | GACACCGTCACCGGTTC (SEQ ID NO: 65)<br>/52-Bio/G*ACACCGTCACCGGTTC (SEQ ID NO: 66) |
| IGM_RT_27_58_BIOTIN | GAAGGAAGTCCTGTGCGA (SEQ ID NO: 67)<br>/52-Bio/G*AAGGAAGTCCTGTGCGA (SEQ ID NO: 68) |
| IGLC_RT_72_major_60_BIOTIN | TTGACGGGGCTGCTATCT (SEQ ID NO: 69)<br>/52-Bio/T*TGACGGGGCTGCTATCT (SEQ ID NO: 70) |
| IGLC_RT_72_minor_59_BIOTIN | ACGGGGCTGCCATCT (SEQ ID NO: 71)<br>/52-Bio/A*CGGGGCTGCCATCT (SEQ ID NO: 72) |
| IGKC_RT_10_59_BIOTIN | CAGATTTCAACTGCTCATCAGA (SEQ ID NO: 73)<br>/52-Bio/C*AGATTTCAACTGCTCATCAGA (SEQ ID NO: 74) |

TABLE 9-continued

| B Cell Receptor (IgH) Primer Panel | |
|---|---|
| **Reverse Transcriptase Primers (Alternative Design 1)** | |
| IGHA_RT_4_59_BIOTIN | GGCTCCTGGGGGAAGA (SEQ ID NO: 59)<br>/52-Bio/G*GCTCCTGGGGGAAGA (SEQ ID NO: 60) |
| IGHD_RT_40_59_BIOTIN | GTACCCAGTTATCAAGCATGC (SEQ ID NO: 61)<br>/52-Bio/G*TACCCAGTTATCAAGCATGC (SEQ ID NO: 62) |
| IGHE_RT_33_60_BIOTIN | AGTCACGGAGGTGGCAT (SEQ ID NO: 63)<br>/52-Bio/A*GTCACGGAGGTGGCAT (SEQ ID NO: 64) |
| IGHG_PCR_4_58_BIOTIN | GGGAAGTAGTCCTTGACCA (SEQ ID NO: 75)<br>/52-Bio/G*GGAAGTAGTCCTTGACCA (SEQ ID NO 76) |
| IGM_RT_27_58_BIOTIN | GAAGGAAGTCCTGTGCGA (SEQ ID NO: 67)<br>/52-Bio/G*AAGGAAGTCCTGTGCGA (SEQ ID NO: 68) |
| IGLC_RT_72_major_60_BIOTIN | TTGACGGGGCTGCTATCT (SEQ ID NO: 69)<br>/52-Bio/T*TGACGGGGCTGCTATCT (SEQ ID NO: 70) |
| IGLC_RT_72_minor_59_BIOTIN | ACGGGGCTGCCATCT (SEQ ID NO: 71)<br>/52-Bio/A*CGGGGCTGCCATCT (SEQ ID NO: 72) |
| IGKC_RT_10_59_BIOTIN | CAGATTTCAACTGCTCATCAGA (SEQ ID NO: 73)<br>/52-Bio/C*AGATTTCAACTGCTCATCAGA (SEQ ID NO: 74) |
| **Primer Name** | **Sequence (sequence with tail shown beneath each)** |
| **First PCR Gene-Specific Primers** | |
| IGHA_PCR_4_69 | AGGCTCAGCGGGAAGACCT (SEQ ID NO: 77)<br>AGACGTGTGCTCTTCCGATCTAGGCTCAGCGGGAAGACCT (SEQ ID NO: 78) |
| IGHD_PCR_27_69 | CAGGGCTGTTATCCTTTGGGTGTC (SEQ ID NO: 79)<br>AGACGTGTGCTCTTCCGATCTCAGGGCTGTTATCCTTTGGGTGTC (SEQ ID NO: 80) |
| IGHE_PCR_24_68 | GAGGTGGCATTGGAGGGAATGT (SEQ ID NO: 81)<br>AGACGTGTGCTCTTCCGATCTGAGGTGGCATTGGAGGGAATGT (SEQ ID NO: 82) |
| IGHG_PCR_4_69 | TTCGGGGAAGTAGTCCTTGACCA (SEQ ID NO: 83)<br>AGACGTGTGCTCTTCCGATCTTTCGGGGAAGTAGTCCTTGACCA (SEQ ID NO: 84) |
| IGHG_PCR_4_minor_69 | GGTTCTGGGAAGTAGTCCTTGACCA (SEQ ID NO: 85)<br>AGACGTGTGCTCTTCCGATCTGGTTCTGGGAAGTAGTCCTTGACCA (SEQ ID NO: 86) |
| IGM_PCR_17_69 | TCGTATCCGACGGGGAATTCTCAC (SEQ ID NO: 87)<br>AGACGTGTGCTCTTCCGATCTTCGTATCCGACGGGGAATTCTCAC (SEQ ID NO: 88) |
| IGKC_PCR_22_70 | TGCTCATCAGATGGCGGGAAGAT (SEQ ID NO: 89)<br>AGACGTGTGCTCTTCCGATCTTGCTCATCAGATGGCGGGAAGAT (SEQ ID NO: 90) |
| IGLC_PCR_17_major_69 | CCTTGTTGGCTTGAAGCTCCTCA (SEQ ID NO: 91)<br>AGACGTGTGCTCTTCCGATCTCCTTGTTGGCTTGAAGCTCCTCA (SEQ ID NO: 92) |
| IGLC_PCR_17_minor_68 | CTTGTTGGCTTGGAGCTCCTCA (SEQ ID NO: 93)<br>AGACGTGTGCTCTTCCGATCTCTTGTTGGCTTGGAGCTCCTCA (SEQ ID NO: 94) |
| **First PCR Gene-Specific Primers (Alternative Design 1)** | |
| IGHA_PCR_4_69 | AGGCTCAGCGGGAAGACCT (SEQ ID NO: 77)<br>AGACGTGTGCTCTTCCGATCTAGGCTCAGCGGGAAGACCT (SEQ ID NO: 78) |
| IGHD_PCR_27_69 | CAGGGCTGTTATCCTTTGGGTGTC (SEQ ID NO: 79)<br>AGACGTGTGCTCTTCCGATCTCAGGGCTGTTATCCTTTGGGTGTC (SEQ ID NO: 80) |

TABLE 9-continued

| B Cell Receptor (IgH) Primer Panel | |
|---|---|
| IGHE_PCR_24_68 | GAGGTGGCATTGGAGGGAATGT (SEQ ID NO: 81)<br>AGACGTGTGCTCTTCCGATCTGAGGTGGCATTGGAGGGAATGT (SEQ ID NO: 82) |
| IGHG1_p38_70.2 | CCCAGAGGTGCTCTTGGAGGAG (SEQ ID NO: 95)<br>AGACGTGTGCTCTTCCGATCTCCCAGAGGTGCTCTTGGAGGAG (SEQ ID NO: 96) |
| IGHG2_4_p48_71.1 | GCTGTGCTCTCGGAGGTGCT (SEQ ID NO: 97)<br>AGACGTGTGCTCTTCCGATCTGCTGTGCTCTCGGAGGTGCT (SEQ ID NO: 98) |
| IGHG3_p40_70.6 | CGGAGGTGCTCCTGGAGCA (SEQ ID NO: 99)<br>AGACGTGTGCTCTTCCGATCTCGGAGGTGCTCCTGGAGCA (SEQ ID NO: 100) |
| IGM_PCR_17_69 | TCGTATCCGACGGGGAATTCTCAC (SEQ ID NO: 87)<br>AGACGTGTGCTCTTCCGATCTTCGTATCCGACGGGGAATTCTCAC (SEQ ID NO: 88) |
| First PCR Gene-Specific Primers (Alternative Design 2) | |
| IGHA_universal | GCGA/ideoxyI/GACCACGTTCCCATCT (SEQ ID NO: 101)<br>AGACGTGTGCTCTTCCGATCTGCGA/ideoxyI/GACCACGTTCCCATCT (SEQ ID NO: 102) |
| IGHA1_p54_69.0 | GCGATGACCACGTTCCCATCT (SEQ ID NO: 103)<br>AGACGTGTGCTCTTCCGATCTGCGATGACCACGTTCCCATCT (SEQ ID NO: 104) |
| IGHA1_p54_69.7 | GCGATGACCACGTTCCCATCTG (SEQ ID NO: 105)<br>AGACGTGTGCTCTTCCGATCTGCGATGACCACGTTCCCATCTG (SEQ ID NO: 106) |
| IGHA2_p54_71.1 | GCGACGACCACGTTCCCATCT (SEQ ID NO: 107)<br>AGACGTGTGCTCTTCCGATCTGCGACGACCACGTTCCCATCT (SEQ ID NO: 108) |
| IGHA2_p54_70 | GCGACGACCACGTTCCCATC (SEQ ID NO: 109)<br>AGACGTGTGCTCTTCCGATCTGCGACGACCACGTTCCCATC (SEQ ID NO: 110) |
| IGHA1_p43_70.1 | TTCCCATCTGGCTGGGTGCT (SEQ ID NO: 111)<br>AGACGTGTGCTCTTCCGATCTTTCCCATCTGGCTGGGTGCT (SEQ ID NO: 112) |
| IGHA2_p43_70.2 | TTCCCATCTTGGGGGGTGCT (SEQ ID NO: 113)<br>AGACGTGTGCTCTTCCGATCTTTCCCATCTTGGGGGGTGCT (SEQ ID NO: 114) |
| First PCR Gene-Specific Primers (Alternative Design 3) | |
| IGHD_PCR_27_69 | CAGGGCTGTTATCCTTTGGGTGTC (SEQ ID NO: 79)<br>AGACGTGTGCTCTTCCGATCTCAGGGCTGTTATCCTTTGGGTGTC (SEQ ID NO: 80) |
| IGHE_PCR_24_68 | GAGGTGGCATTGGAGGGAATGT (SEQ ID NO: 81)<br>AGACGTGTGCTCTTCCGATCTGAGGTGGCATTGGAGGGAATGT (SEQ ID NO: 82) |
| IGHG1_p38_70.2 | CCCAGAGGTGCTCTTGGAGGAG (SEQ ID NO: 95)<br>AGACGTGTGCTCTTCCGATCTCCCAGAGGTGCTCTTGGAGGAG (SEQ ID NO: 96) |
| IGHG2_4_p48_71.1 | GCTGTGCTCTCGGAGGTGCT (SEQ ID NO: 97)<br>AGACGTGTGCTCTTCCGATCTGCTGTGCTCTCGGAGGTGCT (SEQ ID NO: 98) |
| IGHG3_p40_70.6 | CGGAGGTGCTCCTGGAGCA (SEQ ID NO: 99)<br>AGACGTGTGCTCTTCCGATCTCGGAGGTGCTCCTGGAGCA (SEQ ID NO: 100) |
| IGM_PCR_17_69 | TCGTATCCGACGGGGAATTCTCAC (SEQ ID NO: 87)<br>AGACGTGTGCTCTTCCGATCTTCGTATCCGACGGGGAATTCTCAC (SEQ ID NO: 88) |

TABLE 10

| B Cell Receptor (IgK/IgL) Primer Panel | |
|---|---|
| Primer Name | Sequence (sequence with modified nucleotides shown beneath each) |
| Reverse Transcriptase Primers | |
| IGHA_RT_4_59_BIOTIN | GGCTCCTGGGGGAAGA (SEQ ID NO: 59)<br>/52-Bio/G*GCTCCTGGGGGAAGA (SEQ ID NO: 60) |
| IGHD_RT_40_59_BIOTIN | GTACCCAGTTATCAAGCATGC (SEQ ID NO: 61)<br>/52-Bio/G*TACCCAGTTATCAAGCATGC (SEQ ID NO: 62) |
| IGHE_RT_33_60_BIOTIN | AGTCACGGAGGTGGCAT (SEQ ID NO: 63)<br>/52-Bio/A*GTCACGGAGGTGGCAT (SEQ ID NO: 64) |
| IGHG_RT_18_59_BIOTIN | GACACCGTCACCGGTTC (SEQ ID NO: 65)<br>/52-Bio/G*ACACCGTCACCGGTTC (SEQ ID NO: 66) |
| IGM_RT_27_58_BIOTIN | GAAGGAAGTCCTGTGCGA (SEQ ID NO: 67)<br>/52-Bio/G*AAGGAAGTCCTGTGCGA (SEQ ID NO: 68) |
| IGLC_RT_72_major_60_BIOTIN | TTGACGGGGCTGCTATCT (SEQ ID NO: 69)<br>/52-Bio/T*TGACGGGGCTGCTATCT (SEQ ID NO: 70) |
| IGLC_RT_72_minor_59_BIOTIN | ACGGGGCTGCCATCT (SEQ ID NO: 71)<br>/52-Bio/A*CGGGGCTGCCATCT (SEQ ID NO: 72) |
| IGKC_RT_10_59_BIOTIN | CAGATTTCAACTGCTCATCAGA (SEQ ID NO: 73)<br>/52-Bio/C*AGATTTCAACTGCTCATCAGA (SEQ ID NO: 74) |
| Reverse Transcriptase Primers (Alternative Design 1) | |
| IGHA_RT_4_59_BIOTIN | GGCTCCTGGGGGAAGA (SEQ ID NO: 59)<br>/52-Bio/G*GCTCCTGGGGGAAGA (SEQ ID NO: 60) |
| IGHD_RT_40_59_BIOTIN | GTACCCAGTTATCAAGCATGC (SEQ ID NO: 61)<br>/52-Bio/G*TACCCAGTTATCAAGCATGC (SEQ ID NO: 62) |
| IGHE_RT_33_60_BIOTIN | AGTCACGGAGGTGGCAT (SEQ ID NO: 63)<br>/52-Bio/A*GTCACGGAGGTGGCAT (SEQ ID NO: 64) |
| IGHG_PCR_4_58_BIOTIN | GGGAAGTAGTCCTTGACCA (SEQ ID NO: 75)<br>/52-Bio/G*GGAAGTAGTCCTTGACCA (SEQ ID NO: 76) |
| IGM_RT_27_58_BIOTIN | GAAGGAAGTCCTGTGCGA (SEQ ID NO: 67)<br>/52-Bio/G*AAGGAAGTCCTGTGCGA (SEQ ID NO: 68) |
| IGLC_RT_72_major_60_BIOTIN | TTGACGGGGCTGCTATCT (SEQ ID NO: 69)<br>/52-Bio/T*TGACGGGGCTGCTATCT (SEQ ID NO: 70) |
| IGLC_RT_72_minor_59_BIOTIN | ACGGGGCTGCCATCT (SEQ ID NO: 71)<br>/52-Bio/A*CGGGGCTGCCATCT (SEQ ID NO: 72) |
| IGKC_RT_10_59_BIOTIN | CAGATTTCAACTGCTCATCAGA (SEQ ID NO: 73)<br>/52-Bio/C*AGATTTCAACTGCTCATCAGA (SEQ ID NO: 74) |
| First PCR Gene-Specific Primers | |
| Primer Name | Sequence (sequence with tail shown beneath each) |
| IGKC_PCR_22_70 | TGCTCATCAGATGGCGGGAAGAT (SEQ ID NO: 89)<br>AGACGTGTGCTCTTCCGATCTTGCTCATCAGATGGCGGGAAGAT (SEQ ID NO: 90) |
| IGLC_PCR_17_major_69 | CCTTGTTGGCTTGAAGCTCCTCA (SEQ ID NO: 91)<br>AGACGTGTGCTCTTCCGATCTCCTTGTTGGCTTGAAGCTCCTCA (SEQ ID NO: 92) |
| IGLC_PCR_17_minor_68 | CTTGTTGGCTTGGAGCTCCTCA (SEQ ID NO: 93)<br>AGACGTGTGCTCTTCCGATCTCTTGTTGGCTTGGAGCTCCTCA (SEQ ID NO: 94) |

Figure 54:
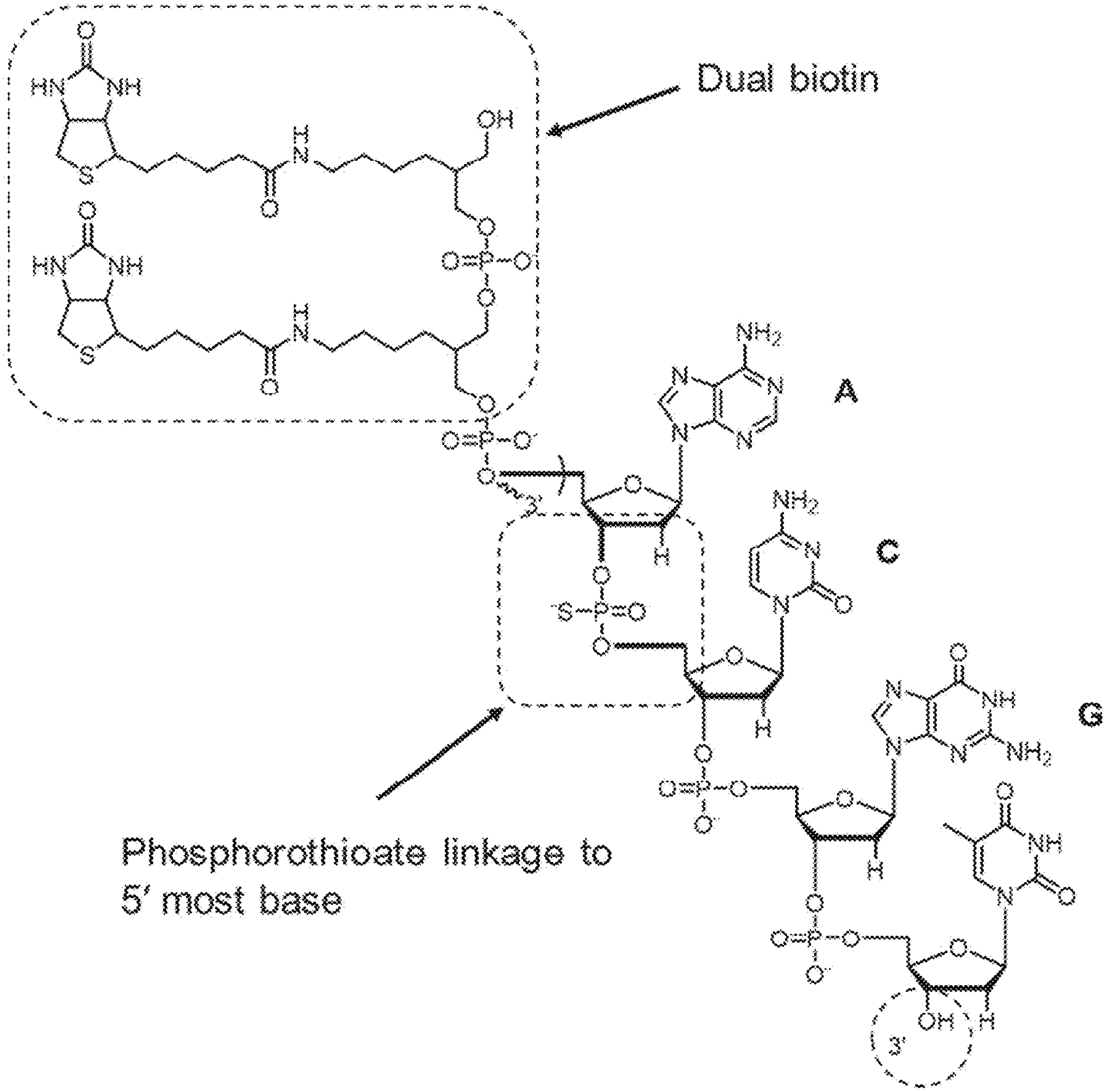
FIG. 54 is a schematic showing the structure of a reverse transcriptase (RT) primer.

The nucleotide sequences of the RT primers in Table 7-10 are alternatively listed with modifications shown with notation according to Integrated DNA Technologies (IDT) nomenclature—where "*" denotes a phosphorothioate bond between the nucleotide preceding "*" and the nucleotide following "*" in the sequence, and "/52-Biol" denotes a 5' dual biotin moiety. FIG. 54 shows an example of an RT primer having a 5' dual biotin moiety linked to the 5' most base ("A"), with a phosphorothioate bond between the 5' most base and the penultimate 5' most base ("C"). The dual biotin moiety allows selection of products of RT and ensures higher capture efficiency. However, it is possible to use a single biotin. The phosphorothioate linkage prevents degradation by exonuclease so as to ensure that the biotin-containing base is not removed.

ADDITIONAL EMBODIMENTS

A1. A method of preparing nucleic acids for analysis, the method comprising:

(a) adding one or more nucleotides to a 3' end of a double-stranded nucleic acid comprising a target nucleotide sequence, wherein at least one of the one or more nucleotides is a capture moiety modified nucleotide;

(b) ligating an adapter nucleic acid to the double-stranded nucleic acid to which the capture moiety modified nucleotide has been added to produce a ligation product, wherein a sequence of one or more nucleotides at a 3' end of the adapter nucleic acid is complementary with the one or more nucleotides added to the 3' end of the double-stranded nucleic acid in step (a);

(c) capturing the ligation product by contacting the ligation product with a binding partner of the capture moiety modified nucleotide; and (d) amplifying the ligation product by polymerase chain reaction using a first target-specific primer that specifically anneals to the target nucleotide sequence and a first adapter primer that specifically anneals to a complementary sequence of the adapter nucleic acid.

A2. The method of embodiment A1, wherein step (b) comprises combining the adapter nucleic acid, the double-stranded nucleic acid, and a ligase under conditions in which the ligase ligates the adapter nucleic acid to the double-stranded nucleic acid, wherein the adapter nucleic acid that is combined with the double-stranded nucleic acid comprises a duplex portion and an overhang sequence, wherein the overhang sequence comprises the sequence of one or more nucleotides at the 3' end of the adapter nucleic acid that is complementary with the one or more nucleotides added to the 3' end of the double stranded nucleic acid in step (a).

A3. The method of embodiment A1, wherein step (b) comprises combining the adapter nucleic acid, the double-stranded nucleic acid, and a ligase under conditions in which the ligase ligates the adapter nucleic acid to the double-stranded nucleic acid, wherein the adapter nucleic acid that is combined with the double-stranded nucleic acid is single-stranded.

A4. The method of embodiment A1 further comprising:

(e) amplifying an amplification product of step (d) by polymerase chain reaction using a second adapter primer and a second target-specific primer.

A5. The method of embodiment A4, wherein the second target-specific primer is nested relative to the first target-specific primer.

A6. The method of embodiment A4 or A5, wherein the second target-specific primer comprises a 5' tail that does not anneal to the target nucleotide sequence.

A7. The method of embodiment A6, further comprising adding an additional primer comprising a 3' portion that is identical to the 5' tail of the second target-specific primer.

A8. The method of any one of the preceding embodiments, wherein the capture moiety is a biotin moiety.

A9. The method of embodiment A8, wherein the biotin moiety comprises biotin-triethylene glycol, bis-biotin, photocleavable biotin, desthiobiotin, desthiobiotin-triethylene glycol, or biotin azide.

A10. The method of any one of the preceding embodiments, wherein the capture moiety modified nucleotide comprises a nucleobase selected from the group consisting of adenine, guanine, thymine, uracil, and cytosine, or derivative(s) thereof.

A11. The method of embodiment A10, wherein the capture moiety modified nucleotide comprises an adenine nucleobase or derivative thereof.

A12. The method of embodiment A11, wherein the capture moiety is covalently linked to the adenine nucleobase or derivative thereof at position 5, 6, 7 or 8.

A13. The method of embodiment A12, wherein the capture moiety is covalently linked to the adenine nucleobase at position 7.

A14. The method of embodiment A13, wherein position 7 of the adenine nucleobase is a carbon atom.

A15. The method of embodiment A10, wherein the biotin moiety is covalently linked to the nucleobase via a linker of 5 to 20 atoms in length.

A16. The method of any one of the preceding embodiments, wherein the capture moiety modified nucleotide is biotin-n-dNTP, wherein n is an integer from 5 to 20 representing the number of linker atoms between a carbonyl-group of the biotin moiety and the position of attachment on a nucleobase of the NTP.

A17. The method of any one of the preceding embodiments, wherein the binding partner is streptavidin.

A18. The method of embodiment A17, wherein the streptavidin is attached to a paramagnetic bead.

A19. The method of any one of the preceding embodiments, wherein, in step (a), one nucleotide is added to the 3' end of the double-stranded nucleic acid comprising the target nucleotide sequence.

A20. The method of any one of the preceding embodiments further comprising a washing step after step (b) and before step (c).

A21. The method of any one of the preceding embodiments further comprising, after step (c) and prior to step (d):

i) immobilizing the double-stranded nucleic acid, which comprises the capture moiety modified nucleotide, on a paramagnetic substrate or surface; and ii) washing the immobilized double-stranded nucleic acid.

A22. The method of embodiment A21 further comprising, after step (ii):

iii) releasing the washed immobilized double-stranded nucleic acid from the paramagnetic substrate or surface.

A23. The method of any one of the preceding embodiments further comprising, prior to step (a), 5' phosphorylating the double-stranded nucleic acid.

A24. The method of any one of the preceding embodiments further comprising, prior to step (a):

i) preparing cDNA by conducting a randomly-primed first strand synthesis reaction using an RNA preparation as a template and a second strand synthesis reaction using a product of the randomly-primed first strand synthesis reaction as a template; and ii) end repairing the cDNA to produce a blunt-ended, double-stranded nucleic acid.

A25. The method of embodiment A24 further comprising, after step ii):

iii) immobilizing the double-stranded nucleic acid, which comprises the capture moiety modified nucleotide, on a paramagnetic substrate or surface;

iv) washing the immobilized double-stranded nucleic acid; and v) releasing the washed immobilized double-stranded nucleic acid from the paramagnetic substrate or surface.

A26. The method of embodiment A25 further comprising a washing step after step (ii) and before step (iii).

A27. The method of any one of the preceding embodiments further comprising:

(f) immobilizing the amplification product of step (e) on a paramagnetic substrate or surface;

(g) washing the immobilized amplification product; and (h) releasing the washed immobilized amplification product from the paramagnetic substrate or surface.

A28. The method of embodiment A27, further comprising a washing step after step (e) and before step (f).

A29. The method of any one of the preceding embodiments, wherein, in step (b), the double-stranded nucleic acid is ligated to the adapter nucleic acid in the presence of a crowding agent.

A30. The method of embodiment A29, wherein the crowding agent is polyethylene glycol in an amount representing 5% to 50% of a ligation mixture.

A31. The method of any one of the preceding embodiments, wherein the double-stranded nucleic acid is blunt-ended.

A32. A method of preparing nucleic acids for analysis, the method comprising:

(a) preparing a cDNA by conducting a randomly-primed first strand synthesis reaction using an RNA preparation as a template and a second strand synthesis reaction using a product of the randomly-primed first strand synthesis reaction as a template, wherein the RNA preparation comprises a target nucleotide sequence;

(b) end repairing the cDNA to produce a blunt-ended, double-stranded nucleic acid comprising the target nucleotide sequence;

(c) immobilizing the blunt-ended, double-stranded nucleic acid on a paramagnetic substrate or surface;

(d) washing the immobilized blunt-ended, double-stranded nucleic acid;

(e) releasing the washed immobilized blunt-ended, double-stranded nucleic acid from the paramagnetic substrate or surface;

(f) adding one or more nucleotides to the 3' end of the released blunt-ended, double-stranded nucleic acid;

(g) ligating an adapter that comprises a ligatable duplex portion and an overhang sequence to the nucleic acid produced in step (f) to produce a ligation product, wherein the overhang sequence is complementary with the one or more nucleotides;

(h) without washing the ligation product, amplifying the ligation product by polymerase chain reaction using a first target-specific primer that specifically anneals to the target nucleotide sequence and a first adapter primer that specifically anneals to a complementary sequence of the adapter nucleic acid;

(i) amplifying an amplification product of step (h) by polymerase chain reaction using a second adapter primer and a second target-specific primer, wherein the second target-specific primer is nested relative to the first target-specific primer;

(j) immobilizing the amplification product of step (i) to a paramagnetic substrate or surface;

(k) washing the immobilized amplification product; and (l) releasing the washed immobilized amplification product from the paramagnetic substrate or surface.

A33. A method of preparing nucleic acids for analysis, the method comprising:

(a) preparing a cDNA by conducting a randomly-primed first strand synthesis reaction using a nucleic acid preparation as a template and a second strand synthesis reaction using a product of the randomly-primed first strand synthesis reaction as a template, wherein the nucleic acid preparation comprises a target nucleotide sequence;

(b) end repairing the cDNA to produce a blunt-ended, double-stranded nucleic acid comprising the target nucleotide sequence;

(c) washing the blunt-ended, double-stranded nucleic acid;

(d) adding one or more nucleotides to the 3' end of the nucleic acid washed in step (c), optionally wherein at least one of the one or more nucleotides is a capture moiety modified nucleotide;

(e) washing the nucleic acid produced in step (d);

(f) ligating an adapter nucleic acid that comprises a ligatable duplex portion and an overhang sequence to the nucleic acid washed in step (e) to produce a ligation product, wherein the overhang sequence is complementary with the one or more nucleotides;

(g) amplifying the ligation product by polymerase chain reaction using a first target-specific primer that specifically anneals to the target nucleotide sequence and a first adapter primer that specifically anneals to a complementary sequence of the adapter nucleic acid;

(h) amplifying an amplification product of step (g) by polymerase chain reaction using a second adapter primer and a second target-specific primer, wherein the second target-specific primer is nested relative to the first target-specific primer; and (j) washing the amplification product of step (h).

A34. The method of embodiment A33, wherein the washing steps are performed using a solid-phase reversible immobilization technique.

A35. The method of embodiment A34, wherein at least one of the one or more nucleotides is a capture moiety modified nucleotide, and wherein the method further comprises, following step (f) and before step (g), capturing the ligation product using an immobilized binding partner of the capture moiety of the capture moiety modified nucleotide; and cleaning the captured ligation product.

A36. The method of embodiment A35, wherein the capture moiety comprises a biotin moiety and wherein the binding partner comprises streptavidin.

A37. The method of embodiment A33, wherein the second adapter primer is nested relative to the first adapter primer.

A38. The method of embodiment A33, wherein the second adapter primer specifically anneals to a complementary sequence of the adapter nucleic acid.

B1. A method of preparing nucleic acids for analysis, the method comprising:

(a) adding one or more nucleotides to a 3' end of a double-stranded nucleic acid comprising a target nucleotide sequence, wherein at least one of the one or more nucleotides is a capture moiety modified nucleotide, wherein the double-stranded nucleic acid is obtained from cell-free DNA;

(b) ligating an adapter nucleic acid to the double-stranded nucleic acid to which the capture moiety modified nucleotide has been added to produce a ligation product, wherein a sequence of one or more nucleotides at a 3' end of the adapter nucleic acid is complementary with the one or more nucleotides added to the 3' end of the double-stranded nucleic acid in step (a); and (c) capturing the ligation product by contacting the ligation product with a binding partner of a capture moiety of the capture moiety modified nucleotide.

B2. The method of embodiment B1 further comprising:

(d) amplifying the ligation product by polymerase chain reaction using a first target-specific primer that specifically anneals to the target nucleotide sequence and a first adapter primer that specifically anneals to a complementary sequence of the adapter nucleic acid.

B3. The method of embodiment B1 or B2, wherein step (b) comprises combining the adapter nucleic acid, the double-stranded nucleic acid, and a ligase under conditions in which the ligase ligates the adapter nucleic acid to the double-stranded nucleic acid, wherein the adapter nucleic acid that is combined with the double-stranded nucleic acid comprises a duplex portion and an overhang sequence, wherein the overhang sequence comprises the sequence of one or more nucleotides at the 3' end of the adapter nucleic acid that is complementary with the one or more nucleotides added to the 3' end of the double stranded nucleic acid in step (a).

B4. The method of embodiment B1 or B2, wherein step (b) comprises combining the adapter nucleic acid, the double-stranded nucleic acid, and a ligase under conditions in which the ligase ligates the adapter nucleic acid to the double-stranded nucleic acid, wherein the adapter nucleic acid that is combined with the double-stranded nucleic acid is single-stranded.

B5. The method of embodiment B2 further comprising:

(e) amplifying an amplification product of step (d) by polymerase chain reaction using a second adapter primer and a second target-specific primer.

B6. The method of embodiment B5, wherein the second target-specific primer is nested relative to the first target-specific primer.

B7. The method of embodiment B5 or B6, wherein the second target-specific primer comprises a 5' tail that does not anneal to the target nucleotide sequence.

B8. The method of embodiment B7, further comprising adding an additional primer comprising a 3' portion that is identical to the 5' tail of the second target-specific primer.

B9. The method of any one of embodiments B1-B8, wherein the capture moiety is a biotin moiety.

B10. The method of embodiment B9, wherein the biotin moiety comprises biotin-triethylene glycol, bis-biotin, photocleavable biotin, desthiobiotin, desthiobiotin-triethylene glycol, or biotin azide.

B11. The method of any one of embodiments B1-B10, wherein the capture moiety modified nucleotide comprises a nucleobase selected from the group consisting of adenine, guanine, thymine, uracil, and cytosine, or a derivative thereof.

B12. The method of embodiment B11, wherein the capture moiety modified nucleotide comprises an adenine nucleobase or derivative thereof.

B13. The method of embodiment B12, wherein the capture moiety is covalently linked to the adenine nucleobase or derivative thereof at position 5, 6, 7 or 8.

B14. The method of embodiment B13, wherein the capture moiety is covalently linked to the adenine nucleobase at position 7.

B15. The method of embodiment B14, wherein position 7 of the adenine nucleobase is a carbon atom.

B16. The method of embodiment B9, wherein the biotin moiety is covalently linked to the nucleobase via a linker of 5 to 20 atoms in length.

B17. The method of any one of embodiments B1-B16, wherein the capture moiety modified nucleotide is biotin-n-dNTP, wherein n is an integer from 5 to 20 representing the number of linker atoms between a carbonyl-group of the biotin moiety and the position of attachment on a nucleobase of the NTP.

B18. The method of any one of embodiments B1-B17, wherein the binding partner is streptavidin.

B19. The method of embodiment B18, wherein the streptavidin is attached to a paramagnetic bead.

B20. The method of any one of embodiments B1-B19, wherein, in step (a), one nucleotide is added to the 3' end of the double-stranded nucleic acid comprising the target nucleotide sequence.

B21. The method of any one of embodiments B1-B20 further comprising a washing step after step (b) and before step (c).

B22. The method of any one of embodiments B2-B21 further comprising, after step (c) and prior to step (d):

i) immobilizing the double-stranded nucleic acid, which comprises the capture moiety modified nucleotide, on a paramagnetic surface; and ii) washing the immobilized double-stranded nucleic acid.

B23. The method of embodiment B22 further comprising, after step (ii):

iii) releasing the washed immobilized double-stranded nucleic acid from the paramagnetic surface.

B24. The method of any one of embodiments B1-B23 further comprising, prior to step (a), 5' phosphorylating the double-stranded nucleic acid.

B25. The method of any one of embodiments B1-B24 further comprising, prior to step (a):

i) preparing cDNA by conducting a randomly-primed first strand synthesis reaction using an RNA preparation as a template and a second strand synthesis reaction using a product of the randomly-primed first strand synthesis reaction as a template; and ii) end repairing the cDNA to produce a blunt-ended, double-stranded nucleic acid.

B26. The method of embodiment B25 further comprising, after step ii):

iii) immobilizing the double-stranded nucleic acid, which comprises the capture moiety modified nucleotide, on a paramagnetic surface;

iv) washing the immobilized double-stranded nucleic acid; and v) releasing the washed immobilized double-stranded nucleic acid from the paramagnetic surface.

B27. The method of embodiment B26 further comprising a washing step after step (ii) and before step (iii).

B28. The method of any one of embodiments B5 to B27 further comprising:

(f) immobilizing the amplification product of step (e) on a paramagnetic surface;

(g) washing the immobilized amplification product; and (h) releasing the washed immobilized amplification product from the paramagnetic surface.

B29. The method of embodiment B28, further comprising a washing step after step (e) and before step (f).

B30. The method of any one of embodiments B1-B29, wherein, in step (b), the double-stranded nucleic acid is ligated to the adapter nucleic acid in the presence of a crowding agent.

B31. The method of embodiment B30, wherein the crowding agent is polyethylene glycol in an amount representing 5% to 50% of a ligation mixture.

B32. The method of any one of embodiments B1-B31, wherein the double-stranded nucleic acid is blunt-ended.

B33. A method of preparing nucleic acids for analysis, the method comprising:

(a) preparing a cDNA by conducting a randomly-primed first strand synthesis reaction using an cell-free DNA preparation as a template and a second strand synthesis reaction using a product of the randomly-primed first strand synthesis reaction as a template, wherein the cell-free DNA preparation comprises a target nucleotide sequence;

(b) end repairing the cDNA to produce a blunt-ended, double-stranded nucleic acid comprising the target nucleotide sequence;

(c) immobilizing the blunt-ended, double-stranded nucleic acid on a paramagnetic surface;

(d) washing the immobilized blunt-ended, double-stranded nucleic acid;

(e) releasing the washed immobilized blunt-ended, double-stranded nucleic acid from the paramagnetic surface;

(f) adding one or more nucleotides to the 3' end of the released blunt-ended, double-stranded nucleic acid;

(g) ligating an adapter that comprises a ligatable duplex portion and an overhang sequence to the nucleic acid produced in step (f) to produce a ligation product, wherein the overhang sequence is complementary with the one or more nucleotides;

(h) without washing the ligation product, amplifying the ligation product by polymerase chain reaction using a first target-specific primer that specifically anneals to the target nucleotide sequence and a first adapter primer that specifically anneals to a complementary sequence of the adapter nucleic acid;

(i) amplifying an amplification product of step (h) by polymerase chain reaction using a second adapter primer and a second target-specific primer, wherein the second target-specific primer is nested relative to the first target-specific primer;

(j) immobilizing the amplification product of step (i) to a paramagnetic surface;

(k) washing the immobilized amplification product; and (l) releasing the washed immobilized amplification product from the paramagnetic surface.

B34. The method of any one of embodiments B1-B33, wherein the target sequence is within a sequence corresponding to a T-cell receptor constant region or to an immunoglobulin heavy or light chain constant region.

B35. A method of preparing nucleic acids for analysis, the method comprising:

(a) preparing a cDNA by conducting a randomly-primed first strand synthesis reaction using a cfDNA preparation as a template and a second strand synthesis reaction using a product of the randomly-primed first strand synthesis reaction as a template, wherein the cfDNA preparation comprises a target nucleotide sequence;

(b) end repairing the cDNA to produce a blunt-ended, double-stranded nucleic acid comprising the target nucleotide sequence;

(c) washing the blunt-ended, double-stranded nucleic acid;

(d) adding one or more nucleotides to the 3' end of the nucleic acid washed in step (c), optionally wherein at least one of the one or more nucleotides is a capture moiety modified nucleotide;

(e) washing the nucleic acid produced in step (d);

(f) ligating an adapter nucleic acid that comprises a ligatable duplex portion and an overhang sequence to the nucleic acid washed in step (e) to produce a ligation product, wherein the overhang sequence is complementary with the one or more nucleotides;

(g) amplifying the ligation product by polymerase chain reaction using a first target-specific primer that specifically anneals to the target nucleotide sequence and a first adapter primer that specifically anneals to a complementary sequence of the adapter nucleic acid;

(h) amplifying an amplification product of step (g) by polymerase chain reaction using a second adapter primer and a second target-specific primer, wherein the second target-specific primer is nested relative to the first target-specific primer; and (j) washing the amplification product of step (h).

B36. The method of embodiment B35, wherein the washing steps are performed using a solid-phase reversible immobilization technique.

B37. The method of embodiment B36, wherein at least one of the one or more nucleotides is a capture moiety modified nucleotide, and wherein the method further comprises, following step (f) and before step (g), capturing the ligation product using an immobilized binding partner of the capture moiety of the capture moiety modified nucleotide; and cleaning the captured ligation product.

B38. The method of embodiment B37, wherein the capture moiety comprises a biotin moiety and wherein the binding partner comprises streptavidin.

B39. The method of embodiment B35, wherein the second adapter primer is nested relative to the first adapter primer.

B40. The method of embodiment B35, wherein the second adapter primer specifically anneals to a complementary sequence of the adapter nucleic acid.

C1. A method of preparing nucleic acids for analysis, the method comprising:

(a) contacting a nucleic acid molecule comprising a target nucleotide sequence with a capture moiety modified primer that specifically anneals to the target nucleotide sequence under hybridization conditions;

(b) conducting a first strand synthesis reaction that is primed by a hybridized capture moiety modified primer and that uses the nucleic acid molecule as a template;

(c) conducting a second strand synthesis reaction that uses a product of the first strand synthesis reaction as a template to generate a double-stranded nucleic acid comprising a capture moiety;

(d) ligating an adapter nucleic acid to the double-stranded nucleic acid to produce a ligation product comprising the capture moiety;

(e) capturing the ligation product by contacting the ligation product with a binding partner of the capture moiety; and (f) amplifying the captured ligation product by polymerase chain reaction using a target-specific primer that comprises a 3' portion that specifically anneals to the target nucleotide sequence and a first adapter primer that specifically anneals to a complementary sequence of the adapter nucleic acid, wherein the target-specific primer comprises a 5' tail portion that does not specifically anneal to the target nucleotide sequence.

C2. The method of embodiment C1, further comprising:

(g) amplifying an amplification product of step (f) by polymerase chain reaction using a tail primer that comprises a 3' portion that specifically anneals to a complementary sequence of the 5' tail portion of the target-specific primer and a second adapter primer that specifically anneals to a complementary sequence of the adapter nucleic acid, wherein the tail primer comprises a 5' portion that does not specifically anneal to a complementary sequence of the target-specific primer.

C3. The method of embodiment C2, wherein the 5' portion of the tail primer comprises at least one of a sample index region, a molecular barcode region, and a sequencing primer site region.

C4. The method of any one of embodiments C1-C3, wherein step (d) comprises combining the adapter nucleic acid, the double-stranded nucleic acid, and a ligase under conditions in which the ligase ligates the adapter nucleic acid to the double-stranded nucleic acid, wherein the adapter nucleic acid that is combined with the double-stranded nucleic acid comprises a duplex portion and an overhang sequence, wherein the overhang sequence comprises a nucleotide sequence that is complementary to an overhang sequence at the 3' end of the double stranded nucleic acid.

C5. The method of any one of embodiments C1-C3, wherein step (d) comprises combining the adapter nucleic acid, the double-stranded nucleic acid, and a ligase under conditions in which the ligase ligates the adapter nucleic acid to the double-stranded nucleic acid, wherein the adapter nucleic acid that is combined with the double-stranded nucleic acid is single-stranded.

C6. The method of any one of embodiments C1-C5, wherein the capture moiety modified primer comprises at least one capture moiety modified nucleotide.

C7. The method of any one of embodiments C1-C5, wherein the capture moiety modified primer comprises a first chemical coupling group configured to bind a second chemical coupling group attached to a capture moiety.

C8. The method of any one of embodiments C1-C7, wherein the capture moiety is a biotin moiety.

C9. The method of embodiment C8, wherein the biotin moiety comprises biotin-triethylene glycol, bis-biotin, photocleavable biotin, desthiobiotin, desthiobiotin-triethylene glycol, or biotin azide.

C10. The method of any one of embodiments C1-C9, wherein the binding partner is streptavidin.

C11. The method of embodiment C10, wherein the streptavidin is attached to a substrate.

C12. The method of embodiment C11, wherein the substrate comprises a solid surface.

C13. The method of embodiment C12, wherein the solid surface comprises a paramagnetic bead.

C14. The method of any one of embodiments C1-C13 further comprising a washing step after step (d) and prior to step (e).

C15. The method of any one of embodiments C1-C14 further comprising, after step (e) and prior to step (f):

i) immobilizing the double-stranded nucleic acid, which comprises the capture moiety, on a paramagnetic substrate; and ii) washing the immobilized double-stranded nucleic acid.

C16. The method of embodiment C15 further comprising, after step ii):

iii) releasing the washed immobilized double-stranded nucleic acid from the paramagnetic substrate.

C17. The method of any one of embodiments C1-C16 further comprising, after step (c) and prior to step (d), 5' phosphorylating the double-stranded nucleic acid.

C18. The method of any one of embodiments C1-C17 further comprising, after step (c) and prior to step (d), end repairing the double-stranded nucleic acid to produce a blunt-ended, double-stranded nucleic acid.

C19. The method of embodiment C18, further comprising adding one or more nucleotides to a 3' end of the blunt-ended, double-stranded nucleic acid.

C20. The method of embodiment C19, wherein the one or more nucleotides comprise deoxyadenosine nucleotides.

C21. The method of embodiment C19, wherein the adapter nucleic acid comprises a nucleotide sequence at a 3' end comprising one or more nucleotides complementary to the one or more nucleotides added to the 3' end of the blunt-ended, double-stranded nucleic acid.

C22. The method of embodiment C21, wherein the nucleotide sequence at the 3' end of the adapter nucleic acid comprises one or more deoxythymidine nucleotides.

C23. The method of embodiment C21, wherein the adapter nucleic acid further comprises a blocking strand annealed to an amplification strand that comprises the nucleotide sequence at the 3' end, and wherein the nucleotide sequence at the 3' end is unpaired such that it forms an overhang sequence.

C24. The method of embodiment C18 further comprising, after end repair:

i) immobilizing the double-stranded nucleic acid, which comprises the capture moiety, on a paramagnetic substrate;

ii) washing the immobilized double-stranded nucleic acid; and iii) releasing the washed immobilized double-stranded nucleic acid from the paramagnetic substrate.

C25. The method of embodiment C18 further comprising, after end repair:

i) immobilizing the double-stranded nucleic acid, which comprises the capture moiety, on a paramagnetic substrate; and ii) washing the immobilized double-stranded nucleic acid.

C26. The method of embodiment C24 or embodiment C25 further comprising a washing step after end repair and prior to step i).

C27. The method of any one embodiments C2-C26 further comprising:

(h) immobilizing an amplification product of step (g) on a paramagnetic substrate;

(i) washing the immobilized amplification product; and (j) releasing the washed immobilized amplification product from the paramagnetic substrate.

C28. The method of embodiment C27, further comprising a washing step after step (g) and prior to step (h).

C29. The method of any one of embodiments C1-C28, wherein, in step (d), the double-stranded nucleic acid is ligated to the adapter nucleic acid in the presence of a crowding agent.

C30. The method of any one of embodiments C1-C29, further comprising, after step (b) and prior to step (c), contacting the nucleic acid molecule with a ribonuclease enzyme.

C31. The method of any one of embodiments C1-C30, wherein the second strand synthesis reaction is primed by a fragment of the nucleic acid molecule hybridized to the product of the first strand synthesis reaction.

C32. The method of any one of embodiments C1-C31, wherein the second strand synthesis is randomly primed using a plurality of random primers.

C33. The method of embodiment C32, wherein the plurality of random primers are between 6 bases in length and 15 bases in length.

C34. The method of any one of embodiments C1-C33, wherein the nucleic acid molecule comprises mRNA.

C35. The method of any one of embodiments C1-C34, wherein the nucleic acid molecule is obtained from a sample comprising a T cell, a B cell, or a mixture thereof.

C36. The method of embodiment C35, wherein the sample is obtained from a subject having, or suspected of having, a T cell malignancy or a B cell malignancy.

C37. The method of embodiment C36, wherein the T cell malignancy or the B cell malignancy is selected from the group consisting of lymphoma, multiple myeloma, acute lymphoblastic leukemia, and chronic lymphocytic leukemia.

C38. The method of any one of embodiments C35-C37, wherein the sample is obtained from a subject that has undergone or will undergo transplantation.

C39. The method of any one of embodiments C35-C37, wherein the sample is obtained from a subject whose immune response to a treatment is being evaluated.

C40. The method of any one of embodiments C35-C37, wherein the sample is obtained from a subject having, or suspected of having, a white blood cell malignancy.

C41. The method of any one of embodiments C36-C40, wherein the subject is a human.

C42. The method of any one of embodiments C36-C40, wherein the subject is a chordate.

C43. The method of any one of embodiments C1-C42, wherein the nucleic acid molecule is obtained from a sample comprising a leukocyte.

C44. The method of any one of embodiments C1-C43, wherein the target nucleotide sequence comprises a nucleotide sequence corresponding to a portion of a T cell receptor (TCR) gene or a B cell receptor (BCR) gene.

C45. The method of any one of embodiments C1-C44, wherein the capture moiety modified primer comprises a nucleotide sequence that is complementary to an immune receptor gene or an immunoglobulin gene.

C46. The method of embodiment C45, wherein the capture moiety modified primer specifically anneals to a constant region that is downstream of a complementarity determining region 3 (CDR3).

C47. The method of embodiment C45 or C46, wherein the target-specific primer specifically anneals to a constant region or a J-segment that is downstream of a CDR3.

C48. The method of embodiment C45 or C46, wherein the target-specific primer specifically anneals to an exon-exon junction formed between a constant region and a J-segment, and wherein the exon-exon junction is downstream of a CDR3.

C49. The method of any one of embodiments C2-C48, wherein the first adapter primer and the second adapter primer are the same.

C50. The method of any one of embodiments C2-C48, wherein the first adapter primer and the second adapter primer are different.

C51. The method of any one of embodiments C2-C48, wherein the second adapter primer is nested relative to the first adapter primer.

C52. A method of preparing nucleic acids for analysis, the method comprising:

(a) contacting a nucleic acid molecule comprising a known target nucleotide sequence and an unknown target nucleotide sequence with a capture moiety modified primer that specifically anneals to the known target nucleotide sequence under hybridization conditions;

(b) conducting a first strand synthesis reaction that is primed by a hybridized capture moiety modified primer and that uses the nucleic acid molecule as a template;

(c) conducting a second strand synthesis reaction that is primed by a fragment of the nucleic acid molecule and that uses a product of the first strand synthesis reaction as a template to generate a double-stranded nucleic acid comprising a capture moiety;

(d) end repairing the double-stranded nucleic acid to produce a blunt-ended, double-stranded nucleic acid comprising the capture moiety;

(e) ligating an adapter nucleic acid to the blunt-ended, double-stranded nucleic acid to produce a ligation product, wherein the ligation product comprises the unknown target nucleotide sequence flanked by the adapter nucleic acid and the capture moiety;

(f) capturing the ligation product by contacting the ligation product with an immobilized binding partner of the capture moiety;

(g) amplifying the ligation product by polymerase chain reaction using a target-specific primer that comprises a 3' portion that specifically anneals to the known target nucleotide sequence and a first adapter primer that specifically anneals to a complementary sequence of the adapter nucleic acid, wherein the target-specific primer comprises a 5' tail portion that does not specifically anneal to the known target nucleotide sequence;

(h) amplifying an amplification product of step (g) by polymerase chain reaction using a tail primer that specifically anneals to a complementary sequence of the 5' tail portion of the target-specific primer and a second adapter primer that specifically anneals to a complementary sequence of the adapter nucleic acid; and (i) washing an amplification product of step (h).

C53. A method of preparing nucleic acids for analysis, the method comprising:

(a) contacting a nucleic acid molecule comprising a target nucleotide sequence with a first target-specific primer that specifically anneals to the target nucleotide sequence under hybridization conditions;

(b) conducting a first strand synthesis reaction that is primed by a hybridized first target-specific primer and that uses the nucleic acid molecule as a template;

(c) conducting a second strand synthesis reaction that is primed by a hybridized fragment of the nucleic acid molecule and that uses a product of the first strand synthesis reaction as a template to generate a double-stranded nucleic acid;

(d) ligating an adapter nucleic acid to the double-stranded nucleic acid to produce a ligation product;

(e) amplifying the ligation product by polymerase chain reaction using a second target-specific primer that comprises a 3' portion that specifically anneals to the target nucleotide sequence and a first adapter primer that specifically anneals to a complementary sequence of the adapter nucleic acid, wherein the second target-specific primer comprises a 5' tail portion that does not specifically anneal to the target nucleotide sequence; and (f) amplifying an amplification product of step (e) by polymerase chain reaction using a tail primer that comprises a 3' portion that specifically anneals to a complementary sequence of the 5' tail portion of the second target-specific primer and a second adapter primer that specifically anneals to a complementary sequence of the adapter nucleic acid, wherein the tail primer comprises a 5' portion that does not specifically anneal to a complementary sequence of the second target-specific primer.

C54. The method of embodiment C53, wherein the first target-specific primer comprises a capture moiety.

C55. The method of embodiment C54, further comprising, after step (d) and prior to step (e), capturing the ligation product by contacting the ligation product with a binding partner of the capture moiety.

C56. The method of embodiment C53, wherein the first strand synthesis reaction is conducted using at least one type of capture moiety modified nucleotide, and wherein the product of the first strand synthesis reaction comprises at least one capture moiety.

C57. The method of embodiment C56, further comprising, after step (d) and prior to step (e), capturing the ligation product by contacting the ligation product with an immobilized binding partner of the at least one capture moiety.

C58. The method of embodiment C56, further comprising, after step (c) and prior to step (d), capturing the double-stranded nucleic acid by contacting the double-stranded nucleic acid with an immobilized binding partner of the at least one capture moiety.

C59. A method of determining an immune repertoire in a sample, the method comprising: (a) obtaining a sample comprising a nucleic acid molecule encoding at least one of an immune receptor and an immunoglobulin;

(b) contacting the nucleic acid molecule from the sample with a first target-specific primer that specifically anneals to a target nucleotide sequence of the nucleic acid molecule under hybridization conditions;

(c) conducting a first strand synthesis reaction that is primed by a hybridized first target-specific primer and that uses the nucleic acid molecule as a template;

(d) conducting a second strand synthesis reaction that uses a product of the first strand synthesis reaction as a template to generate a double-stranded nucleic acid;

(e) ligating an adapter nucleic acid to the double-stranded nucleic acid to produce a ligation product;

(f) amplifying the ligation product by polymerase chain reaction using a second target-specific primer that comprises a 3' portion that specifically anneals to the target nucleotide sequence and a first adapter primer that specifically anneals to a complementary sequence of the adapter nucleic acid, wherein the second target-specific primer comprises a 5' tail portion that does not specifically anneal to the target nucleotide sequence;

(g) amplifying an amplification product of step (f) by polymerase chain reaction using a tail primer that comprises a 3' portion that specifically anneals to a complementary sequence of the 5' tail portion of the second target-specific primer and a second adapter primer that specifically anneals to a complementary sequence of the adapter nucleic acid, wherein the tail primer comprises a 5' portion that does not specifically anneal to a complementary sequence of the second target-specific primer; and (h) sequencing an amplification product of step (g) using a first and second sequencing primer.

C60. The method of embodiment C59, wherein the immune receptor comprises a TCR, and wherein the immunoglobulin comprises a BCR.

C61. The method of embodiment C59, wherein the target nucleotide sequence corresponds to a genetically recombined sequence.

C62. The method of embodiment C59, wherein the sample comprises a T cell, a B cell, or a mixture thereof.

C63. The method of embodiment C62, wherein the sample is obtained from a subject.

C64. The method of embodiment C63, wherein the subject is a human.

C65. A method of preparing nucleic acids for analysis, the method comprising:

(a) contacting a nucleic acid molecule comprising a target nucleotide sequence with a first target-specific primer that specifically anneals to the target nucleotide sequence under conditions to generate a primer-hybridized nucleic acid molecule;

(b) contacting the primer-hybridized nucleic acid molecule with a plurality of types of nucleotides for incorporation into a first strand that is complementary to the nucleic acid molecule, wherein at least one of the plurality of types of nucleotides comprises a capture moiety;

(c) conducting a first strand synthesis reaction that is primed by the first target-specific primer of the primer-hybridized nucleic acid molecule and that uses the nucleic acid molecule of the primer-hybridized nucleic acid molecule as a template, wherein a product of the first strand synthesis reaction comprises at least one capture moiety;

(d) conducting a second strand synthesis reaction that is primed by a fragment of the nucleic acid molecule and that uses the product of the first strand synthesis reaction as a template to generate a double-stranded nucleic acid comprising the at least one capture moiety;

(e) ligating an adapter nucleic acid to the double-stranded nucleic acid to produce a ligation product comprising the at least one capture moiety; and (f) amplifying the ligation product by polymerase chain reaction using a second target-specific primer that comprises a 3' portion that specifically anneals to the target nucleotide sequence and a first adapter primer that specifically anneals to a complementary sequence of the adapter nucleic acid, wherein the second target-specific primer comprises a 5' tail portion that does not specifically anneal to the target nucleotide sequence.

C66. The method of embodiment C65, further comprising, after step (e) and prior to step (f), capturing the ligation product by contacting the ligation product with an immobilized binding partner of the capture moiety.

C67. The method of embodiment C65, further comprising, after step (d) and prior to step (e), capturing the double-stranded nucleic acid by contacting the double-stranded nucleic acid with an immobilized binding partner of the capture moiety.

C68. A method of preparing nucleic acids for analysis, the method comprising:

(a) contacting a nucleic acid molecule comprising a target nucleotide sequence with a capture moiety modified primer that comprises a 3' portion that specifically anneals to the target nucleotide sequence under hybridization conditions and a 5' tail portion that does not specifically anneal to the target nucleotide sequence;

(b) conducting a first strand synthesis reaction that is primed by a hybridized capture moiety modified primer and that uses the nucleic acid molecule as a template; (c) contacting a product of the first strand synthesis reaction with a plurality of random primers under hybridization conditions, wherein each of the plurality of random primers comprises a non-random 5' tail portion comprising a common sequence;

(d) conducting a second strand synthesis reaction that is primed by at least one of the plurality of random primers and that uses a product of the first strand synthesis reaction as a template to generate a double-stranded nucleic acid comprising the capture moiety;

(e) capturing the double-stranded nucleic acid comprising the capture moiety by contacting the double-stranded nucleic acid with a binding partner of the capture moiety;

(f) amplifying the double-stranded nucleic acid by polymerase chain reaction using a first tail primer and a first target-specific primer that specifically anneals to the target nucleotide sequence, wherein the first tail primer comprises a 3' portion that specifically anneals to a complement of the common sequence and a 5' tail portion that does not specifically anneal to a complement of the common sequence; and (g) amplifying an amplification product of step (f) by polymerase chain reaction using a second target-specific primer and a second tail primer that specifically anneals to a complement of the 5' tail portion of the first tail primer, wherein the second target-specific primer comprises a 3' portion that specifically anneals to the target nucleotide sequence and a 5' tail portion that does not specifically anneal to the target nucleotide sequence.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of." or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either." "one of," "only one of." or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A method of preparing nucleic acids for analysis, the method comprising:

(a) hybridizing a primer to a nucleic acid molecule comprising a target nucleotide sequence, wherein the nucleic acid molecule was obtained from cell-free DNA obtained from a subject having or suspected of having a cancer;

(b) generating a double stranded nucleic acid by a process comprising conducting a polymerase extension that is primed by the hybridized primer and that uses the nucleic acid molecule as a template, wherein the conducting of the polymerase extension comprises incorporating one or more capture moiety modified nucleotides into the double stranded nucleic acid, wherein each of the capture moiety modified nucleotides comprises a capture moiety;

(c) ligating an adapter nucleic acid to the double-stranded nucleic acid to produce a ligation product comprising the capture moiety;

(d) isolating the ligation product by a process comprising contacting the ligation product with a binding partner of the capture moiety; and (e) amplifying the isolated ligation product by a polymerase chain reaction using (i) a first adapter primer that specifically anneals to a sequence of the adapter nucleic acid and (ii) a target-specific primer that comprises a 3' portion that specifically anneals to the target nucleotide sequence and a 5' tail portion that does not specifically anneal to the target nucleotide sequence, thereby providing a first amplification product.

2. The method of claim 1, further comprising:

(f) amplifying the first amplification product by a polymerase chain reaction using a tail primer that comprises a 3' portion that specifically anneals to a complementary sequence of the 5' tail portion of the target-specific primer and a second adapter primer that specifically anneals to a portion of the adapter nucleic acid, wherein the tail primer comprises a 5' portion that does not specifically anneal to a complementary sequence of the target-specific primer.

3. The method of claim 1, wherein the one or more capture moiety modified nucleotides comprise biotin or a biotin moiety.

4. The method of claim 3, wherein the biotin moiety is selected from biotin-triethylene glycol, bis-biotin, photocleavable biotin, desthiobiotin, desthiobiotin-triethylene glycol, and biotin azide.

5. The method of claim 3, wherein the binding partner comprises streptavidin or streptavidin attached to a substrate.

6. The method of claim 1, wherein the nucleic acid molecule was derived from a cancer or tumor.

7. The method of claim 1, wherein the cell-free DNA comprises circulating tumor DNA.

8. The method of claim 1, wherein the cell free DNA was obtained from blood obtained from the subject.

9. The method of claim 6, wherein the cancer comprises a T cell malignancy or a B cell malignancy.

10. The method of claim 1, wherein the subject is a chordate or a human.

11. The method of claim 2, wherein:

the first adapter primer and the second adapter primer are different.

12. The method of claim 11, wherein the second adapter primer is nested relative to the first adapter primer.

13. The method of claim 2, wherein the 5' portion of the tail primer comprises a sample index region, a molecular barcode region, or a sequence identical to a portion of a sequencing primer.

14. The method of claim 2, wherein the first adapter primer and the second adapter primer are the same, and the amplifying of (d) and the amplifying of (e) takes place in a same reaction mixture or at the same time.

15. The method of claim 2 further comprising: after the amplifying of (f), determining a sequence of at least a portion of the target nucleic acid sequence.

16. The method of claim 15, further comprising detecting a tumor in the subject.

17. The method of claim 1, wherein the primer hybridized to the nucleic acid molecule in (a) comprises a capture moiety modified nucleotide.

18. The method of claim 1, wherein the primer that hybridizes to the nucleic acid molecule in (a) is a first target specific primer, or wherein the primer that hybridizes to the nucleic acid molecule in (a) is one of a population of random primers.

19. The method of claim 1, wherein the isolating of (d) comprises:

i) immobilizing the ligation product, which comprises the capture moiety, on a substrate comprising the binding partner;

ii) washing the immobilized ligation product; and iii) releasing the washed ligation product from the substrate.

20. A method of preparing nucleic acids for analysis, the method comprising:

(a) hybridizing a plurality of different target-specific primers to a population of nucleic acid molecules comprising a plurality of different target nucleotide sequences, wherein the population of nucleic acid molecules was obtained from cell-free DNA obtained from a human subject having or suspected of having a cancer;

(b) generating a plurality of double stranded nucleic acids by a process comprising conducting a polymerase extension that is primed by each of the plurality of different target-specific primers, wherein the conducting of the polymerase extension comprises incorporating one or more capture moiety modified nucleotides into the double stranded nucleic acids, and wherein each of the capture moiety modified nucleotides comprises a capture moiety;

(c) ligating an adapter nucleic acid to each of the plurality of double-stranded nucleic acids to produce a plurality of ligation products, each comprising at least one of the capture moiety;

(d) isolating the plurality of ligation products by a process comprising contacting the plurality of ligation products with a substrate or plurality of beads comprising a binding partner of the capture moiety;

(e) amplifying the isolated ligation products by a polymerase chain reaction using (i) a first adapter primer that specifically anneals to a sequence of the adapter nucleic acid and (ii) a plurality of different target-specific primers, each comprising a 3' portion that specifically anneals to one of the plurality of different target nucleotide sequences and a substantially identical 5' tail portion that does not specifically anneal to a target nucleotide sequence, thereby providing a plurality of first amplification products; and (f) amplifying the plurality of first amplification products by a polymerase chain reaction using (i) a tail primer that comprises a 3' portion that specifically anneals to a complementary sequence of the 5' tail portion of the plurality of different target-specific primers and (ii) a second adapter primer that specifically anneals to a portion of the adapter nucleic acid, thereby providing a plurality of second amplification products.

* * * * *